(12) United States Patent
Date et al.

(10) Patent No.: US 8,921,124 B2
(45) Date of Patent: Dec. 30, 2014

(54) PYRAZOLE-BASED CYANINE DYE

(75) Inventors: Matsuhiro Date, Hyogo (JP); Satoshi Hasaba, Hyogo (JP); Naoyuki Yamamoto, Hyogo (JP)

(73) Assignee: Wako Pure Chemical Industries, Ltd., Osaka-shi (JP)

( * ) Notice: Subject to any disclaimer, the term of this patent is extended or adjusted under 35 U.S.C. 154(b) by 1308 days.

(21) Appl. No.: 12/295,189

(22) PCT Filed: Mar. 30, 2007

(86) PCT No.: PCT/JP2007/057312
§ 371 (c)(1),
(2), (4) Date: Sep. 29, 2008

(87) PCT Pub. No.: WO2007/114398
PCT Pub. Date: Oct. 11, 2007

(65) Prior Publication Data
US 2009/0069546 A1    Mar. 12, 2009

(30) Foreign Application Priority Data

Mar. 31, 2006  (JP) .................................. 2006-098409
Apr. 27, 2006  (JP) ................................. 2006-123105

(51) Int. Cl.
| G01N 33/533 | (2006.01) |
| C09B 23/06 | (2006.01) |
| C07D 487/02 | (2006.01) |
| G01N 33/58 | (2006.01) |
| C07D 403/06 | (2006.01) |
| C07D 403/14 | (2006.01) |
| C07D 487/04 | (2006.01) |
| C07D 487/14 | (2006.01) |
| C09B 23/08 | (2006.01) |

(52) U.S. Cl.
CPC .............. *C09B 23/06* (2013.01); *G01N 33/582* (2013.01); *G01N 33/533* (2013.01); *C07D 403/06* (2013.01); *C07D 403/14* (2013.01); *C07D 487/04* (2013.01); *C07D 487/14* (2013.01); *C09B 23/083* (2013.01)
USPC ....................... 436/546; 548/356.1; 548/358.1

(58) Field of Classification Search
CPC . G01N 33/533; G01N 33/582; C07D 487/04; C07D 487/14; C07D 403/14; C07D 403/06; C09B 23/06; C09B 23/083
See application file for complete search history.

(56) References Cited

U.S. PATENT DOCUMENTS

| 5,268,486 | A | 12/1993 | Waggoner et al. |
| 5,486,616 | A | 1/1996 | Waggoner et al. |
| 5,569,587 | A | 10/1996 | Waggoner |
| 5,569,766 | A | 10/1996 | Waggoner et al. |
| 5,571,388 | A | 11/1996 | Patonay et al. |
| 5,627,027 | A | 5/1997 | Waggoner |
| 5,800,995 | A | 9/1998 | Patonay et al. |
| 6,403,807 | B1 | 6/2002 | Singh et al. |
| 2003/0113755 | A1 | 6/2003 | Nishigaki et al. |

FOREIGN PATENT DOCUMENTS

| GB | 730 489 A | 5/1955 |
| JP | 2-191674 A | 7/1990 |
| JP | 2003-34696 A | 2/2003 |
| JP | 2003-34697 A | 2/2003 |
| WO | 01/23374 A1 | 1/2001 |

OTHER PUBLICATIONS

Kendall et al. Cyanine and merocyanine dyes containing a pyrazolenine ring. 1955, GB 730489: CAPLUS Accession # 1955:83002 and Document # 49:83002. RN # 857394-71-9 & 857395-36-9.*
Mujumdar et al. Cyanine dye labeling reagenst: sulfoindocyanine succinimidyl esters. Bioconjugate Chemistry 1993, vol. 4, No. 2, pp. 105-111.*
Southwick et al. Cyanine dye labeling reagents-carboxymethylindocyanine succinimidyl esters. Cytochemistry 1990, vol. 11, pp. 418-430.*
Kendall et al (1995): STN International HCAPLUS database, (Columbus, Ohio), Accession No. 1995:83002, Document No. 49:83002. Attached pp. 1-4.*
International Search Report of PCT/JP2007/057312, date of mailing May 1, 2007.

* cited by examiner

*Primary Examiner* — Shafiqul Haq
(74) *Attorney, Agent, or Firm* — Westerman, Hattori, Daniels & Adrian, LLP

(57) ABSTRACT

PROBLEM
Provided is a novel cyanine dye derivative with a pyrazole skeleton and an indole skeleton, having high sensitivity performance in a shorter wavelength region as compared with a conventional optical system, and showing high water solubility.
SOLUTION
The invention provides (1) a compound represented by the following general formula [50] and a salt thereof:

[50]

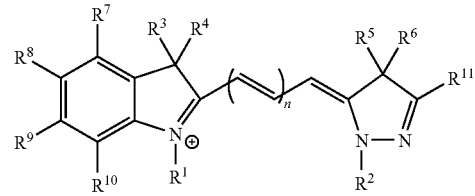

[wherein $R^1$ to $R^6$ each independently represent a substituted or unsubstituted alkyl group which may have an amide bond; $R^7$ to $R^{10}$ each independently represent alkyl group, alkenyl group, alkynyl group, aryl group, alkoxy group, aryloxy group, alkylthio group, arylthio group, alkylsulfonyl group, arylsulfonyl group, carbamoyl group, sulfamoyl group, ure ido group or amino group, those groups being able to have substituents; a group represented by the general formula [2]:

$$—COOR^{12} \quad [2]$$

(wherein $R^{12}$ represents hydrogen atom, $C_1$ to $C_{10}$ alkyl group, alkali metal atom, organic ammonium ion, ammonium ion or anion); a group represented by the general formula [3]:

$$—SO_3R^{13} \quad [3]$$

(wherein $R^{13}$ represents hydrogen atom, alkali metal atom, organic ammonium ion, ammonium ion or anion), halogen atom, aromatic heterocyclic thio group, hydrogen atom, hydroxyl group, cyano group, formyl group, thiol group or nitro group; $R^{11}$ represents hydrogen atom, or alkyl group, alkenyl group, alkynyl group or aryl group, those groups being able to have substituents; and n represents an integer of from 0 to 3, provided that any of $R^1$ and $R^2$, $R^4$ and $R^5$, $R^1$ and $R^6$, and $R^2$ and $R^4$ may form a bivalent group with a group selected from —O— group, —S— group, —COO— group and groups represented by the general formulae [52] to [54]:

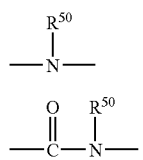

[52]

[53]

-continued

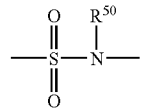

[54]

(wherein $R^{50}$ represents hydrogen atom, alkyl group, alkenyl group or aryl group, those groups being able to have substituents), and substituted or unsubstituted alkylene group; and in the case where said bivalent group is formed, at least one of $R^1$ to $R^{11}$, along with the bivalent group formed by any of $R^1$ and $R^2$, $R^4$ and $R^5$, $R^1$ and $R^6$, and $R^2$ and $R^4$, has the group represented by the general formula [2], the group represented by the general formula [3], amino group, hydroxyl group, thiol group or formyl group; and in the case where said bivalent group is not formed, at least one of $R^1$ to $R^{11}$ has the group represented by the general formula [2], the group represented by the general formula [3], amino group, hydroxyl group, thiol group or formyl group]; (2) a labeled compound obtained by subjecting the above compound to direct or indirect binding to a substance to be labeled, and (3) a method for labeling a substance to be labeled, comprising subjecting the above compound to direct or indirect binding to the substance to be labeled.

28 Claims, No Drawings

PYRAZOLE-BASED CYANINE DYE

TECHNICAL FIELD

The present invention relates to a novel pyrazole-based cyanine dye.

BACKGROUND ART

Recently, in a field of biochemical test or genetic test, high detection sensitivity for a measurement object has been required, and positioning of a fluorescent dye as a labeling agent (a labeling substance) has become an important factor.

As the fluorescent dye, there have been used, for example, a cyanine dye derivative, a coumarin dye derivative, a fluorescein dye derivative, a rhodamine dye derivative and the like, depending on various objectives, and among these, the cyanine dye derivative has been widely used as a dye having fluorescence characteristics in a near-infrared region of equal to or higher than 600 nm.

As the cyanine dye derivative, for example, Cy3, Cy5 [manufactured by GE Healthcare Bioscience Co., Ltd. (former name: Amasham Bioscience Co., Ltd.)] or the like are known as a leading fluorescent reagent, and it is a present situation that also as a photometric specification of a detection apparatus, fluorescence characteristics of Cy5 is used as a basis.

Under these circumstances, development of the cyanine dye derivative has been continued, using two wavelengths of Cy3 and Cy5 as bases of excitation wavelength. Cy3 and Cy5 have a structure (an indolenine-based cyanine dye) where two indolenine skeletons are bound to a polymethine chain, and by using this structure as a basic structure, various cyanine dye derivatives have been developed aiming at, for example, improvement of water-solubility, higher sensitivity by avoiding an aggregation state or the like (see Patent Document 1, Patent Document 2, Patent Document 3 or the like).

In addition, as other cyanine dye derivatives, there have been developed those having a structure where an azaindolenine skeleton and a pyrazole skeleton are bound to a polymethine chain (see Patent Document 4, Patent Document 5 or the like).

Still more, there have been developed those having a structure where two indolenine skeletons bound to, for example, a polymethine chain or the like are further cross-linked with a spacer or the like (see Patent Document 6, Patent Document 7, Patent Document 8 or the like).

On the other hand, a laser light source used in an optical system has been made to have increasingly shorter wavelength, and higher output, in order to attain larger capacity of a magnetic optical disk. In addition, also a semiconductor laser or the like, having very small and stable temperature drift width, has become available.

Under these circumstances, there has been desired development of a novel cyanine dye derivative having fluorescent characteristics with higher sensitivity than a conventional dye, in an energetically more efficient short wavelength region than conventional optical characteristics.

Patent Document 1: U.S. Pat. No. 5,268,486
Patent Document 2: U.S. Pat. No. 5,486,616
Patent Document 3: U.S. Pat. No. 5,569,766
Patent Document 4: JP-A-2003-034696
Patent Document 5: JP-A-2003-034697
Patent Document 6: U.S. Pat. No. 5,571,388
Patent Document 7: U.S. Pat. No. 5,800,995
Patent Document 8: WO01/02374

DISCLOSURE OF INVENTION

Problem to be Solved by the Invention

The present invention has been made under these circumstances, and it is a subject of the present invention, to provide a novel cyanine dye derivative with a pyrazole skeleton and an indole skeleton, having high sensitivity performance in a shorter wavelength region as compared with a conventional optical system, and showing high water solubility.

Means for Solving the Problem

The present invention includes the following aspects (1) to (3):
(1) A compound represented by the following general formula [50], and a salt thereof:

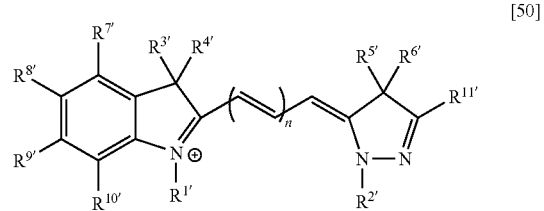

[50]

[wherein $R^{1'}$ to $R^{6'}$ each independently represent a substituted or unsubstituted alkyl group which may have an amide bond; $R^{7'}$ to $R^{10'}$ each independently represent alkyl group, alkenyl group, alkynyl group, aryl group, alkoxy group, aryloxy group, alkylthio group, arylthio group, alkylsulfonyl group, arylsulfonyl group, carbamoyl group, sulfamoyl group, ureido group or amino group, those groups being able to have substituents; a group represented by the general formula [2]:

$$-COOR^{12} \qquad [2]$$

(wherein $R^{12}$ represents hydrogen atom, $C_1$ to $C_{10}$ alkyl group, alkali metal atom, organic ammonium ion, ammonium ion or anion); a group represented by the general formula [3]:

$$-SO_3R^{13} \qquad [3]$$

(wherein $R^{13}$ represents hydrogen atom, alkali metal atom, organic ammonium ion, ammonium ion or anion), halogen atom, aromatic heterocyclic thio group, hydrogen atom, hydroxyl group, cyano group, formyl group, thiol group or nitro group; $R^{11'}$ represents hydrogen atom, or alkyl group, alkenyl group, alkynyl group or aryl group, those groups being able to have substituents; and n represents an integer of from 0 to 3, provided that any of $R^{1'}$ and $R^{2'}$, $R^{4'}$ and $R^{5'}$, $R^{1'}$ and $R^{6'}$, and $R^{2'}$ and $R^{4'}$ may form a bivalent group with a group selected from —O— group, —S— group, —COO— group and the groups represented by the general formulae [52] to [54]:

[52]

[53]
[54]

(wherein $R^{50}$ represents hydrogen atom, or alkyl group, alkenyl group or aryl group, those groups being able to have substituents), and substituted or unsubstituted alkylene group; and in the case where the bivalent group is formed, at least one of $R^{1'}$ to $R^{11'}$, along with the bivalent group formed by any of $R^{1'}$ and $R^{2'}$, $R^{4'}$ and $R^{5'}$, $R^{1'}$ and $R^{6'}$, and $R^{2'}$ and $R^{4'}$, has the group represented by the general formula [2], the group represented by the general formula [3], amino group, hydroxyl group, thiol group or formyl group; and in the case where the bivalent group is not formed, at least one of $R^{1'}$ to $R^{11'}$ has the group represented by the general formula [2], the group represented by the general formula [3], amino group, hydroxyl group, thiol group or formyl group], (2) a labeled compound obtained by subjecting the above compound (1) and a substance to be labeled to direct or indirect binding, and (3) a labeling method for a substance to be labeled, comprising subjecting the above compound [1] to direct or indirect binding to the substance to be labeled.

Effects of the Invention

Because a pyrazole-based cyanine dye of the present invention has a structure where a pyrazole skeleton and an indole skeleton are bound to a polymethine chain and exerts fluorescence characteristics in sorter wavelength region as compared with a conventional light source, it becomes possible to use a light source of a short wavelength region with high energy efficiency. In addition, in the case where a measurement object is detected by using this as a labeling agent (a labeling substance), it becomes possible to detect the measurement object in high detection sensitivity without having problems, for example, low water-solubility, reduced detection sensitivity by optical quenching caused by aggregation of dyes themselves and the like, which a conventional cyanine dye derivative had.

BEST MODE FOR CARRYING OUT THE INVENTION

Among compounds represented by the general formula [50], a compound, wherein any of $R^{1'}$ and $R^{2'}$, $R^{4'}$ and $R^{5'}$, $R^{1'}$ and $R^{6'}$ and $R^{2'}$ and $R^{4'}$ do not form a bivalent group with a group selected from —O— group, —S— group, —COO— group and the groups represented by the general formulae [52] to [54], and substituted or unsubstituted alkylene group includes, for example, one represented by the following general formula [1]:

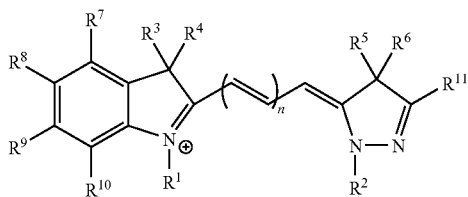

[1]

[wherein $R^1$ to $R^6$ each independently represent substituted or unsubstituted alkyl group which may have an amide bond; $R^7$ to $R^{10}$ each independently represent alkyl group, alkenyl group, alkynyl group, aryl group, alkoxy group, aryloxy group, alkylthio group, arylthio group, alkylsulfonyl group, arylsulfonyl group, carbamoyl group, sulfamoyl group, ureido group or amino group, those groups being able to have substituents; the group represented by the general formula [2]:

—COOR$^{12}$ [2]

(wherein $R^{12}$ represents hydrogen atom, $C_1$ to $C_{10}$ alkyl group, alkali metal atom, organic ammonium ion, ammonium ion or anion); the group represented by the general formula [3]:

—SO$_3$R$^{13}$ [3]

(where $R^{13}$ represents hydrogen atom, alkali metal atom, organic ammonium ion, ammonium ion or anion), halogen atom, aromatic heterocyclic thio group, hydrogen atom, hydroxyl group, cyano group, formyl group, thiol group or nitro group; $R^{11}$ represents hydrogen atom, or alkyl group, alkenyl group, alkynyl group or aryl group, those groups being able to have substituents; and n represents an integer of from 0 to 3, provided that at least one of $R^1$ to $R^{11}$ has the group represented by the general formula [2], the group represented by the general formula [3], amino group, hydroxyl group, thiol group or formyl group].

Among compounds represented by the general formula [50], a compound, where any of $R^{1'}$ and $R^{2'}$, $R^{4'}$ and $R^{5'}$, $R^{1'}$ and $R^{6'}$, and $R^{2'}$ and $R^{4'}$ form a bivalent group with a group selected from —O— group, —S— group, —COO— group and the groups represented by the general formulae [52] to [54], and substituted or unsubstituted alkylene group includes, for example, one represented by the following general formula [51]:

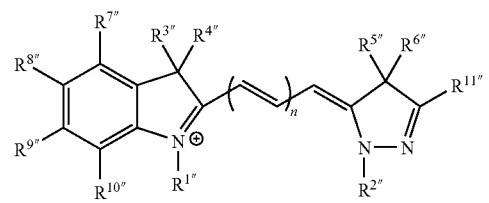

[51]

[wherein $R^{1''}$ to $R^{6''}$ each independently represent a substituted or unsubstituted alkyl group which may have an amide bond; $R^{7''}$ to $R^{10''}$ each independently represent alkyl group, alkenyl group, alkynyl group, aryl group, alkoxy group, aryloxy group, alkylthio group, arylthio group, alkylsulfonyl group, arylsulfonyl group, carbamoyl group, sulfamoyl group, ureido group or amino group, those groups being able to have substituents; the group represented by the general formula [2]:

—COOR$^{12}$ [2]

(wherein $R^{12}$ represents hydrogen atom, $C_1$ to $C_{10}$ alkyl group, alkali metal atom, organic ammonium ion, ammonium ion or anion); the group represented by the general formula [3]:

—SO$_3$R$^{13}$ [3]

(wherein $R^{13}$ represents hydrogen atom, alkali metal atom, organic ammonium ion, ammonium ion or anion), halogen atom, aromatic heterocyclic thio group, hydrogen atom, hydroxyl group, cyano group, formyl group, thiol group or nitro group; $R^{11''}$ represents hydrogen atom, or alkyl group, alkenyl group, alkynyl group or aryl group, those groups being able to have substituents; and n represents an integer of from 0 to 3, provided that any of $R^{1''}$ and $R^{2''}$, $R^{4''}$ and $R^{5''}$, $R^{1''}$ and $R^{6''}$, and $R^{2''}$ and $R^{4''}$ form a bivalent group with a group selected from —O— group, —S— group, —COO— group and the groups represented by the general formulae [52] to [54]:

[52]

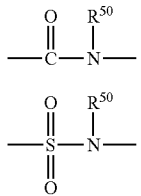

(wherein $R^{50}$ represents hydrogen atom, or alkyl group, alkenyl group or aryl group, those groups being able to have substituents), and substituted or unsubstituted alkylene group: In addition, at least one of $R^{1''}$ to $R^{11''}$, along with the bivalent group formed by any of $R^{1''}$ and $R^{2''}$, $R^{4''}$ and $R^{5''}$, $R^{1''}$ and $R^{6''}$, and $R^{2''}$ and $R^{4''}$, has the group represented by the general formula [2], the group represented by the general formula [3], amino group, hydroxyl group, thiol group or formyl group].

Explanation will be given below in detail on compounds represented by the general formula [1] and [5], which are more specific compounds of compounds represented by the general formula [50].

Accordingly, definitions and the like of $R^{1'}$ to $R^{11'}$ in the general formula [50] are substantially the same as definitions and the like of $R^1$ to $R^{11}$ in the following general formula [1], and $R^{1''}$ to $R^{11''}$ in compounds represented by the general formula [51].

1. The Compound [1] of the Present Invention
1-1. The Compound [1] of the Present Invention Among compounds represented by the general formula [50], a compound, where any of $R^{1'}$ and $R^{2'}$, $R^{4'}$ and $R^{5'}$, $R^{1'}$ and $R^{6'}$, and $R^{2'}$ and $R^{4'}$ do not form a bivalent group with a group selected from —O— group, —S— group, —COO— group and the groups represented by the general formulae [52] to [54], and substituted or unsubstituted alkylene group includes, for example, one represented by the following general formula [1]:

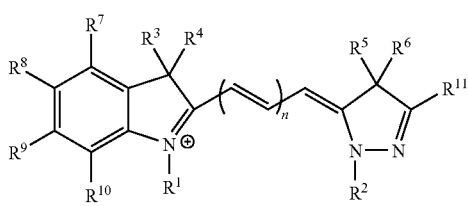

[wherein $R^1$ to $R^6$ each independently represent substituted or unsubstituted alkyl group which may have an amide bond; $R^7$ to $R^{10}$ each independently represent alkyl group, alkenyl group, alkynyl group, aryl group, alkoxy group, aryloxy group, alkylthio group, arylthio group, alkylsulfonyl group, arylsulfonyl group, carbamoyl group, sulfamoyl group, ureido group or amino group, those groups being able to have substituents; the group represented by the general formula [2]:

   —COOR$^{12}$   [2]

(wherein $R^{12}$ represents hydrogen atom, $C_1$ to $C_{10}$ alkyl group, alkali metal atom, organic ammonium ion, ammonium ion or anion); the group represented by the general formula [3]:

   —SO$_3$R$^{13}$   [3]

(wherein $R^{13}$ represents hydrogen atom, alkali metal atom, organic ammonium ion, ammonium ion or anion), halogen atom, aromatic heterocyclic thio group, hydrogen atom, hydroxyl group, cyano group, formyl group, thiol group or nitro group; $R^{11}$ represents hydrogen atom, or alkyl group, alkenyl group, alkynyl group or aryl group, those groups being able to have substituents; and n represents an integer of from 0 to 3, provided that at least one of $R^1$ to $R^{11}$ has the group represented by the general formula [2], the group represented by the general formula [3], amino group, hydroxyl group, thiol group or formyl group].

In the general formula [1], the substituted or unsubstituted alkyl group, which may have the amide bond, represented by $R^1$ to $R^6$, includes one having usually from 1 to 10, preferably from 1 to 3, and more preferably one amide bond in the alkyl chain of the substituted or unsubstituted alkyl group.

The alkyl group of the substituted or unsubstituted alkyl group, which may have the amide bond, represented by $R^1$ to $R^6$, may be any of straight-chained, branched and cyclic one, and includes one having usually C1 to C10, preferably C1 to C6, and specifically, for example methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like: among these, for example, a straight-chained alkyl group such as methyl group, ethyl group, n-propyl group, n-pentyl group is preferable.

The substituent of the substituted or unsubstituted alkyl group, which may have the amide bond, represented by $R^1$ to $R^6$, includes one where a part of hydrogen atoms in the alkyl group, which may have the amide bond, is substituted with a substituent, and the said substituent includes, for example, the group represented by the general formula [2], the group represented by the general formula [3] or the like.

In the general formula [2] and [3], the alkali metal atom represented by $R^{12}$ and $R^{13}$, includes, for example, lithium atom, sodium atom, potassium atom, rubidium atom or the like, and among these sodium atom or potassium atom is preferable, and in particular, sodium atom is more preferable.

The organic ammonium ion represented by $R^{12}$ and $R^{13}$ includes, for example, a trialylammonium ion or the like. The said trialylammonium ion may be any of straight-chained, branched and cyclic one, and includes one having usually $C_1$ to $C_{10}$, preferably $C_1$ to $C_6$, and specifically, for example, trimethylammonium ion, triethylammonium ion, tri-n-propylammonium ion, triisopropylammoniumion, tributylammonium ion, tripentylammonium ion, trihexylammonium ion, triheptylammonium ion, trioctylammonium ion, trinonylammonium ion, tridecylammonium ion, tricyclopropylammonium ion, tricyclobutylammonium ion, tricyclopentylammonium ion, tricyclohexylammonium ion, tricycloheptylammonium ion, tricyclooctylammonium ion, tricyclononylammonium ion, tricyclodecylammonium ion or the like, and among these, trimethylammonium ion or triethylammonium ion is preferable, and in particular, triethylammonium ion is preferable.

In the general formula [2], the $C_1$ to $C_{10}$ alkyl group represented by $R^{12}$ may be any of straight-chained, branched and cyclic one, and includes one having usually $C_1$ to $C_{10}$, preferably $C_1$ to $C_6$, more preferably $C_1$ to $C_3$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, isononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

A preferable specific example of the group represented by the general formula [2], includes, for example, a carboxyl group (—COOH), an anion thereof [carboxylate (—COO⁻)], alkali metal salt thereof (for example, lithium salt, sodium salt, potassium salt, rubidium salt or the like), ammonium salt thereof, organic ammonium salt thereof (for example, trimethylammonium salt, triethylammonium salt, tripropylammonium salt or the like) or the like.

A preferable specific example of the group represented by the general formula [3], includes, for example, sulfo group (—SO$_3$H), anion thereof [a sulfonate (—SO$_3^-$)], alkali metal salt thereof (for example, lithium salt, sodium salt, potassium salt, rubidium salt or the like), ammonium salt thereof, organic ammonium salt thereof (for example, trimethylammonium salt, triethylammonium salt, tripropylammonium salt or the like) or the like.

As for the substituent of the substituted alkyl group, which may have the amide bond, represented by $R^1$ to $R^6$ (that is the group represented by the general formula [2] or the group represented by the general formula [3]), it is preferably one substituted at a terminal hydrogen atom of the alkyl group.

A preferable specific example of $R^1$ and $R^2$, includes, a $C_1$ to $C_5$ alkyl group having, as a substituent, a group represented by the general formula [2], such as carboxyethyl group, carboxypropyl group, carboxybutyl group, carboxypentyl group, anion thereof (carboxylate), alkali metal salt group thereof (for example, sodium salt, potassium salt, or the like), organic ammonium salt group thereof (for example, trimethylammonium salt, triethylammonium salt, or the like) and ammonium salt; a $C_1$ to $C_5$ alkyl group having, as a substituent, a group represented by the general formula [3], such as sulfoethyl group, sulfopropyl group, sulfobutyl group, sulfopentyl group, anion thereof (sulfonate), alkali metal salt group thereof (for example, sodium salt, potassium salt, or the like) and organic ammonium salt group thereof (for example, trimethylammonium salt, triethylammonium salt or the like), ammonium salt thereof; or the like.

In addition, a preferable combination of $R^3$ and $R^4$, and a preferable combination of $R^5$ and $R^6$, includes preferably one wherein either of them (that is, either of $R^3$ and $R^4$, and either of $R^5$ and $R^6$) is a $C_1$ to $C_6$ alkyl group (for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group or the like), and the other is a $C_1$ to $C_5$ alkyl group having, as a substituent, a group represented by the general formula [2], including for example, carboxyethyl group, carboxypropyl group, carboxybutyl group, carboxypentyl group, anion thereof (carboxylate), alkali metal salt group thereof (for example, sodium salt, potassium salt, or the like), ammonium salt group thereof or organic ammonium salt group thereof (for example, trimethylammonium salt, triethylammonium salt, or the like); a $C_1$ to $C_5$ alkyl group having, as a substituent, a group represented by the general formula [3], including for example, sulfoethyl group, sulfopropyl group, sulfobutyl group, sulfopentyl group, anion thereof (sulfonate), alkali metal salt group thereof (for example, sodium salt, potassium salt, or the like), ammonium salt, organic ammonium salt group thereof (for example, trimethylammonium salt, triethylammonium salt or the like).

In the general formula [1], the alkyl group of the substituted or unsubstituted alkyl group represented by $R^7$ to $R^{10}$ may be any of straight-chained, branched and cyclic one and includes one having usually $C_1$ to $C_6$, preferably $C_1$ to $C_3$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, cyclopropyl group, cyclobutyl group, cyclopentyl group, cyclohexyl group or the like.

The alkenyl group of the substituted or unsubstituted alkenyl group represented by $R^7$ to $R^{10}$, may be any of straight-chained, branched and cyclic one, and includes one having usually $C_2$ to $C_6$, preferably $C_2$ to $C_4$, and specifically, for example, vinyl group, allyl group, 1-propenyl group, isopropenyl group, 3-butenyl group, 2-butenyl group, 1-butenyl group, 1,3-butadienyl group, 4-pentenyl group, 3-pentenyl group, 2-pentenyl group, 1-pentenyl group, 1,3-pentadienyl group, 2,4-pentadienyl group, 1,1-dimethyl-2-propenyl group, 1-ethyl-2-propenyl group, 1,2-dimethyl-1-propenyl group, 1-methyl-1-butenyl group, 5-hexenyl group, 4-hexenyl group, 3-hexenyl group, 2-hexenyl group, 1-hexenyl group, 1-cyclopropenyl group, 2-cyclopentenyl group, 2,4-cyclopentadienyl group, 1-cyclohexenyl group, 2-cyclohexenyl group, 3-cyclohexenyl group or the like.

The alkynyl group of the substituted or unsubstituted alkynyl group represented by $R^7$ to $R^{10}$, includes one having usually $C_2$ to $C_6$, preferably $C_2$ to $C_4$, and specifically, for example, ethynyl group, 2-propynyl group, 3-butynyl group, 1-methyl-2-propynyl group, 4-pentynyl group, 2-methyl-4-pentynyl group, 5-hexynyl group or the like.

The aryl group of the substituted or unsubstituted aryl group represented by $R^7$ to $R^{10}$, includes one having usually $C_6$ to $C_{10}$, and specifically, for example, phenyl group, naphthyl group or the like.

The alkoxy group of the substituted or unsubstituted alkoxy group represented by $R^7$ to $R^{10}$, may be any of straight-chained, branched and cyclic one, and includes one having usually $C_1$ to $C_6$, preferably $C_1$ to $C_3$, and specifically, for example, methoxy group, ethoxy group, n-propoxy group, isopropoxy group, n-butoxy group, isobutoxy group, sec-butoxy group, tert-butoxy group, n-pentyloxy group, isopentyloxy group, sec-pentyloxy group, tert-pentyloxy group, neopentyloxy group, n-hexyloxy group, isohexyloxy group, sec-hexyloxy group, tert-hexyloxy group, neohexyloxy group, cyclopropoxy group, cyclopentyloxy group, cyclohexyloxy group or the like.

The aryloxy group of the substituted or unsubstituted aryloxy group represented by $R^7$ to $R^{10}$, includes one having usually $C_6$ to $C_{10}$, and specifically, for example, phenyloxy group, naphthoxy group the like.

The alkylthio group of the substituted or unsubstituted alkylthio group represented by $R^7$ to $R^{10}$, includes one where an oxygen atom of the alkoxy group is substituted with a sulfur atom, and may be any of straight-chained, branched and cyclic one, and includes one having usually $C_1$ to $C_6$, preferably $C_1$ to $C_3$, and specifically, for example, methylthio group, ethylthio group, n-propylthio group, isopropylthio group, n-butylthio group, isobutylthio group, sec-butylthio group, tert-butylthio group, n-pentylthio group, isopentylthio group, sec-pentylthio group, tert-pentylthio group, neopentylthio group, n-hexylthio group, isohexylthio group, sec-hexylthio group, tert-hexylthio group, neohexylthio group, cyclopropylthio group, cyclobutylthio group, cyclopentylthio group, cyclohexylthio group or the like.

The arylthio group of the substituted or unsubstituted arylthio group represented by $R^7$ to $R^{10}$, includes one where an oxygen atom of the aryloxy group is substituted with a sulfur atom, and includes one having usually $C_6$ to $C_{10}$, and specifically, for example, phenylthio group, naphthylthio group or the like.

The alkylsulfonyl group of the substituted or unsubstituted alkylsulfonyl group represented by $R^7$ to $R^{10}$, includes one where an —OH group of a sulfo group (—$SO_2OH$) is substituted with an alkyl group, and may be any of straight-chained, branched and cyclic one, and includes one having usually $C_1$ to $C_6$, and specifically, for example, methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, sec-pentylsulfonyl group, tert-pentylsulfonyl group, neopentylsulfonyl group, n-hexylsulfonyl group, isohexylsulfonyl group, sec-hexylsulfonyl group, tert-hexylsulfonyl group, neohexylsulfonyl group, cyclopropylsulfonyl group, cyclobutylsulfonyl group, cyclopentylsulfonyl group, cyclohexylsulfonyl group or the like.

The arylsulfonyl group of the substituted or unsubstituted arylsulfonyl group represented by $R^7$ to $R^{10}$, includes one where an —OH group of a sulfo group (—$SO_2OH$) is substituted with an aryl group, and may be any of straight-chained, branched and cyclic one, and includes one having usually $C_6$ to $C_{10}$, and specifically, for example, phenylsulfonyl group, naphthylsulfonyl group or the like.

The halogen atom represented by $R^7$ to $R^{10}$, includes, for example, fluorine atom, chlorine atom, bromine atom, iodine atom or the like.

The aromatic heterocyclic thio group represented by $R^7$ to $R^{10}$, includes one where a hydrogen atom of the thiol group (—SH) is substituted with the aromatic heterocyclic group. The aromatic heterocyclic group includes, for example, a five member ring or a six member ring, and includes preferably one containing, as the hetero atom, for example, 1 to 3 nitrogen atoms, oxygen atoms, sulfur atoms or the like, and specifically, for example, furyl group, pyrrolyl group, indolyl group, purinyl group, quinolyl group, pyridyl group, pyrazyl group, pyrimidyl group, oxazolyl group, imidazolyl group, thiazolyl group, pyranyl group or the like.

The substituted carbamoyl group represented by $R^7$ to $R^{10}$, includes, for example, one where 1 to 2 hydrogen atoms of the carbamoyl (—$CONH_2$) group is substituted with a $C_1$ to $C_6$ alkyl group or a $C_6$ to $C_{10}$ aryl group, and specifically, for example, N-alkylcarbamoyl group such as N-methylcarbamoyl group, N-ethylcarbamoyl group, N-n-propylcarbamoyl group, N-isopropylcarbamoyl group, N-n-butylcarbamoyl group, N-tert-butylcarbamoyl group, N-n-hexylcarbamoyl group, N-cyclohexylcarbamoyl group, N-methylethylcarbamoyl group, N-dicyclohexylcarbamoyl group; for example, N-arylcarbamoyl group such as N-phenylcarbamoyl group, N-diphenylcarbamoyl group; or the like.

The substituted sulfamoyl group represented by $R^7$ to $R^{10}$, includes, for example, one where 1 to 2 hydrogen atoms of the sulfamoyl (—$SO_2NH_2$) group is substituted with a $C_1$ to $C_6$ alkyl group or a $C_6$ to $C_{10}$ aryl group, and specifically, for example, N-alkylsulfamoyl group such as N-methylsulfamoyl group, N-ethylsulfamoyl group, N-n-propylsulfamoyl group, N-isopropylsulfamoyl group, N-n-butylsulfamoyl group, N-tert-butylsulfamoyl group, N-n-hexylsulfamoyl group, N-cyclohexylsulfamoyl group, N-methylethylsulfamoyl group, N-dicyclohexylsulfamoyl group; N-arylsulfamoyl group such as N-phenylsulfamoyl group, N-diphenylsulfamoyl group; or the like.

The substituted ureido group represented by $R^7$ to $R^{10}$, includes one where 1 to 3 hydrogen atoms of the ureido group (—$NHCONH_2$) are substituted and, for example, includes groups represented by the following general formulae [4] to [7]:

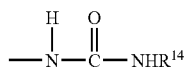

[4]

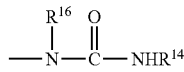

[5]

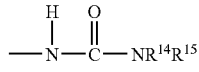

[6]

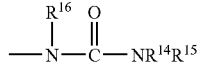

[7]

(wherein $R^{14}$ to $R^{16}$ each independently represent halogen atom, alkyl group, sulfoamide group, carboamide group, sulfo group, carboxyl group, phospho group, hydroxyl group or amino group).

In the general formula [4] to [7], the halogen group represented by $R^{14}$ to $R^{16}$, includes, for example, fluorine atom, chlorine atom, bromine atom, iodine atom or the like.

The alkyl group represented by $R^{14}$ to $R^{16}$, may be any of straight-chained, branched and cyclic one, and includes one having usually $C_1$ to $C_{10}$, preferably $C_1$ to $C_6$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The sulfoamide group (—$NHSO_2R$) represented by $R^{14}$ to $R^{16}$, includes one where a hydrogen atom of the amino group is substituted with an alkylsulfonyl group (alkylsulfoamide group), or with an arylsulfonyl group (arylsulfoamide group).

The alkylsulfoamide group, may be any of straight-chained, branched and cyclic one, and includes one having usually $C_1$ to $C_{10}$, preferably $C_1$ to $C_6$, and specifically, for example, methylsulfoamide group, ethylsulfoamide group, n-propylsulfoamide group, isopropylsulfoamide group, n-butylsulfoamide group, isobutylsulfoamide group, sec-butylsulfoamide group, tert-butylsulfoamide group, n-pentylsulfoamide group, isopentylsulfoamide group, sec-pentylsulfoamide group, tert-pentylsulfoamide group, neopentylsulfoamide group, n-hexylsulfoamide group, isohexylsulfoamide group, sec-hexylsulfoamide group, tert-hexylsulfoamide group, neohexylsulfoamide group, cyclopropylsulfoamide group, cyclobutylsulfoamide group, cyclopentylsulfoamide group, cyclohexylsulfoamide group, n-heptylsulfoamide group, isoheptylsulfoamide group, sec-heptylsulfoamide group, tert-heptylsulfoamide group, neoheptylsulfoamide group, n-octylsulfoamide group, isooctylsulfoamide group, sec-octylsulfoamide group, tert-octylsulfoamide group, neooctylsulfoamide group, n-nonylsulfoamide group, isononylsulfoamide group, sec-nonylsulfoamide group, tert-nonylsulfoamide group, isononylsulfoamide group, n-decylsulfoamide group, isodecylsulfoamide group, sec-decylsulfoamide group, tert-decylsulfoamide group, neodecylsulfoamide group, cycloheptylsulfoamide group, cyclooctylsulfoamide group, cyclononylsulfoamide group, cyclodecylsulfoamide group or the like.

The arylsulfoamide group includes one having $C_6$ to $C_{10}$, and specifically, for example, phenylsulfoamide group, or naphthylsulfoamide group or the like.

The carboamide group (—NHCOR) represented by $R^{14}$ to $R^{16}$ includes one where a hydrogen atom of the amino group is substituted with an acyl group. The acyl group includes, for example, one derived from an aliphatic carboxylic acid, one derived from an aromatic carboxylic acid or the like.

The carboamide group derived from an aliphatic carboxylic acid, may be any of straight-chained, branched and cyclic one, and may still contain more a double bond in the chain, and includes one having usually $C_2$ to $C_{20}$, preferably $C_2$ to $C_{15}$, more preferably $C_2$ to $C_{10}$, still more preferably $C_2$ to $C_6$, and specifically, for example, acetylamide group, propionylamide group, butyrylamide group, isobutyrylamide group, valerylamide group, isovalerylamide group, pivaloylamide group, hexanoylamide group, heptanoylamide group, octanoylamide group, decanoylamide group, lauroylamide group, myristoylamide group, palmitoylamide group, stearoylamide group, icosanoylamide group, acryloylamide group, methacryloylamide group, crotonoylamide group, oleoylamide group or the like.

The carboamide group derived from an aromatic carboxylic acid, includes one having usually $C_7$ to $C_{15}$, preferably $C_7$ to $C_{11}$, and specifically, for example, benzoylamide group, naphthoylamide group, anthoylamide group or the like.

The substituted amino group represented by $R^7$ to $R^{10}$ includes one where 1 to 2 hydrogen atoms of the amino group are substituted with substituents, and these substituents includes, for example, alkyl group, alkoxycarbonyl group, acyl group, sulfo group and the like.

The alkyl group included as a substituent of the substituted amino group, may be any of straight-chained, branched and cyclic one, and includes one having usually $C_1$ to $C_{10}$, preferably $C_1$ to $C_6$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The alkoxycaronyl group included as a substituent of the substituted amino group, may be any of straight-chained, branched and cyclic one, and includes one having usually $C_1$ to $C_{10}$, preferably $C_1$ to $C_6$, and specifically, for example, methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentyloxycarbonyl group, isopentyloxycarbonyl group, sec-pentyloxycarbonyl group, tert-pentyloxycarbonyl group, neopentyloxycarbonyl group, n-hexyloxycarbonyl group, isohexylcarbonyl group, sec-hexyloxycarbonyl group, tert-hexyloxycarbonyl group, neohexyloxycarbonyl group, n-heptyloxycarbonyl group, isoheptyloxycarbonyl group, sec-heptyloxycarbonyl group, tert-heptyloxycarbonyl group, neoheptyloxycarbonyl group, n-octyloxycarbonyl group, isooctyloxycarbonyl group, sec-octyloxycarbonyl group, tert-octyloxycarbonyl group, neooctyloxycarbonyl group, n-nonyloxycarbonyl group, isononyloxycarbonyl group, sec-nonyloxycarbonyl group, tert-nonyloxycarbonyl group, neononyloxycarbonyl group, n-decyloxycarbonyl group, isodecyloxycarbonyl group, sec-decyloxycarbonyl group, tert-decyloxycarbonyl group, neodecyloxycarbonyl group, cyclopropoxycarbonyl group, cyclobutoxycarbonyl group, cyclopentyloxycarbonyl group, cyclohexyloxycarbonyl group, cycloheptyloxycarbonyl group, cyclooctyloxycarbonyl group, cyclononyloxycarbonyl group, cyclodecyloxycarbonyl group or the like.

The acyl group included as a substituent of the substituted amino group, includes one derived from an aliphatic carboxylic acid, one derived from an aromatic carboxylic acid or the like.

The acyl group derived from the aliphatic carboxylic acid, may be any of straight-chained, branched and cyclic one, and may still contain more a double bond in the chain, and includes one having usually $C_2$ to $C_{20}$, preferably $C_2$ to $C_{15}$, more preferably $C_2$ to $C_{10}$, still more preferably $C_2$ to $C_6$, and specifically, for example, acetyl group, propionyl group, butyryl group, isobutyryl group, valeryl group, isovaleryl group, pivaloyl group, hexanoyl group, heptanoyl group, octanoyl group, decanoyl group, lauroyl group, myristoyl group, palmitoyl group, stearoyl group, icosanoyl group, acryloyl group, methacryloyl group, crotonoyl group, oleoyl group or the like.

The acyl group derived from the aromatic carboxylic acid, includes one having usually $C_7$ to $C_{15}$, preferably $C_7$ to $C_{11}$, and specifically, for example, benzoyl group, naphthoyl group, anthoyl group or the like.

In the general formula [1], the substituent of the substituted alkyl group, substituted alkenyl group, substituted alkynyl group, substituted aryl group, substituted alkoxy group, substituted aryloxy group, substituted alkylthio group, substituted arylthio group, substituted alkylsulfonyl group, or substituted arylsulfonyl group, represented by $R^7$ to $R^{10}$, includes, for example, halogen atom, sulfonamide group, carboamide group, sulfo group, carboxyl group, phospho group (phosphate group), hydroxyl group, amino group or the like. A specific example of the halogen atom, sulfonamide group and carboamide group, included as the substituent, includes a similar one as an exemplification of the halogen atom, sulfonamide group and carboamide group, represented by $R^{14}$ to $R^{16}$ in the general formulae [4] to [7].

A preferable example of $R^7$ to $R^{10}$ includes one where three of $R^7$ to $R^{10}$ are hydrogen atoms, and one of the remaining is a group derived from a sulfonic acid represented by the general formula [3], and in the group derived from a sulfonic acid, for example, sulfo group, anion thereof (sulfonate), alkali metal salt or organic ammonium salt thereof, or the like is preferable, and among them, for example, sulfo group, sulfonate, alkali metal salt thereof (for example, sodium salt or the like) or the like is more preferable, and in particular, one where $R^8$ is the group represented by the general formula [3] is preferable.

In the general formula [1], the alkyl group of the substituted or unsubstituted alkyl group represented by $R^{11}$ may be any of straight-chained, branched and cyclic one, and includes one having usually $C_1$ to $C_{10}$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The alkenyl group of the substituted or unsubstituted alkenyl group represented by $R^{11}$, may be any of straight-chained, branched and cyclic one, and includes one having usually $C_2$ to $C_6$, preferably $C_2$ to $C_4$, and specifically, for example, vinyl group, allyl group, 1-propenyl group, isopropenyl group, 3-butenyl group, 2-butenyl group, 1-butenyl group, 1,3-butadienyl group, 4-pentenyl group, 3-pentenyl group, 2-pentenyl group, 1-pentenyl group, 1,3-pentadienyl group, 2,4-pentadienyl group, 1,1-dimethyl-2-propenyl group, 1-ethyl-2-propenyl group, 1,2-dimethyl-1-propenyl group, 1-methyl-1-butenyl group, 5-hexenyl group, 4-hexenyl group, 3-hexenyl group, 2-hexenyl group, 1-hexenyl group, 1-cyclopropenyl group, 2-cyclopentenyl group, 2,4-cyclopentadienyl group, 1-cyclohexenyl group, 2-cyclohexenyl group, 3-cyclohexenyl group or the like.

The alkynyl group of the substituted or unsubstituted alkynyl group represented by $R^{11}$, includes one having usually $C_2$ to $C_6$, preferably $C_2$ to $C_4$, and specifically, for example, ethynyl group, 2-propynyl group, 3-butynyl group, 1-methyl-2-propynyl group, 4-pentynyl group, 2-methyl-4-pentynyl group, 5-hexynyl group or the like.

The aryl group of the substituted or unsubstituted aryl group represented by $R^{11}$, includes usually one having $C_6$ to $C_{10}$, and specifically, for example, phenyl group, naphthyl group or the like.

The substituent of the substituted alkyl group, substituted alkenyl group, substituted alkynyl group, or substituted aryl group, represented by $R^{11}$, includes, for example, halogen atom, sulfoamide group, carboamide group, sulfo group, carboxyl group, phospho group, hydroxyl group or amino group or the like, and a specific example of these halogen atom, sulfoamide group and carboamide group, includes a similar one as an exemplification of the halogen atom, sulfoamide group and carboamide group, represented by $R^{14}$ to $R^{16}$ in the general formulae [4] to [7].

In $R^{11}$, unsubstituted alkyl groups are preferable, and among them, methyl group, ethyl group, n-propyl group, isopropyl group, n-butyl group, n-pentyl group, n-hexyl group and the like are more preferable.

In the general formula [1], n is an integer of usually from 0 to 3, and preferably 1 or 2.

Among the group represented by the general formula [2], the group represented by the general formula [3], amino group, hydroxyl group, thiol group or formyl group, contained at least one in $R^1$ to $R^{11}$ in the general formula [1], the group represented by the general formula [2], or the group represented by the general formula [3] is preferable.

The group represented by the general formula [3] (for example a sulfo group or the like) contained in a compound of the present invention, is preferably introduced much more to enhance water-solubility, suppress fluorescence quenching caused by aggregation between the dye molecules, and enhance fluorescence intensity, and usually 1 to 4, preferable 2 to 4 groups are contained in the compound of the present invention.

The group represented by the general formula [2] (for example a carboxyl group or the like) contained in a compound of the present invention, is preferably contained usually 1 to 3, preferable 1 to 2 in the compound of the present invention, so as to easily introduce a group bindable to a substance to be labeled (for example, a reaction activation group such as a succinimide group, a norbornene group).

The group represented by the general formula [2], the group represented by the general formula [3], amino group, hydroxyl group, thiol group or formyl group, contained, at least in $R^1$ to $R^{11}$ (hereafter referred to as "a reactive group of the present invention") may be any one where the reactive group itself of the present invention is present as $R^1$ to $R^{11}$ (that is, one where the reactive group is bound directly to a pyrazole skeleton or an indole skeleton), or one contained in $R^1$ to $R^{11}$ as a substituent, however, in the case where the reactive group is contained in $R^{11}$, it is preferable to be contained as a substituent.

The compound represented by the general formula [1] includes, for example, the compound represented by the general formula [1-1]:

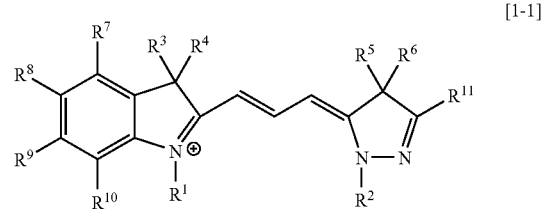

[1-1]

(wherein $R^1$ to $R^{11}$ are the same as above), (it corresponds to one where n=1 in the general formula [1]); the compound represented by the general formula [1-2]:

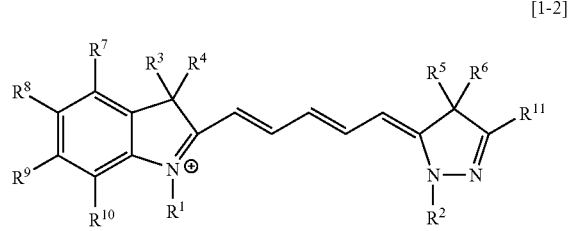

[1-2]

(wherein $R^1$ to $R^{11}$ are the same as above), (it corresponds to one where n=2 in the general formula [1]); the compound represented by the general formula [1-3]:

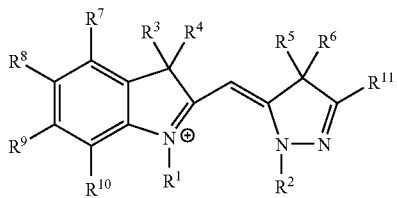

(wherein $R^1$ to $R^{11}$ are the same as above), (it corresponds to one where n=0 in the general formula [1]); and the compound represented by the general formula [1-4]:

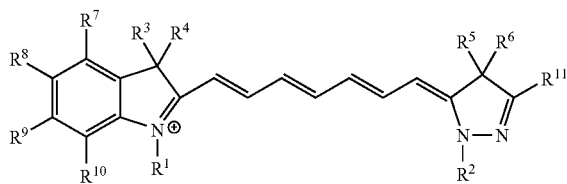

(wherein $R^1$ to $R^{11}$ are the same as above), (it corresponds to one where n=3 in the general formula [1]), and among these, one represented by the general formula [1-1] or [1-2] is preferable.

In addition, in the compound [1] of the present invention, for example, one represented by the following general formula [1'] is preferable:

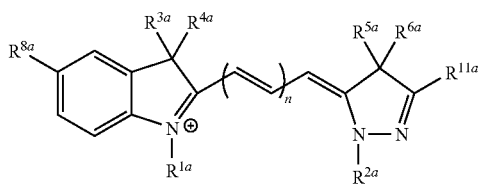

(wherein $R^{1a}$ to $R^{6a}$ each independently represent the alkyl group, which may have as a substituent the group represented by the general formula [2] or [3]; $R^{8a}$ represents the group represented by the general formula [3]; $R^{11a}$ represents an alkyl group; and n is the same as above).

In the general formula [1'], the alkyl group of the alkyl group, which may have as a substituent the group represented by the general formula [2] or [3] represented by $R^{1a}$ to $R^{6a}$, includes a similar one to an exemplification of the alkyl group of the substituted or unsubstituted alkyl group, which may have the amide bond, represented by $R^1$ to $R^6$ in the general formula [1].

$R^{3a}$ and $R^{4a}$ each independently include an alkyl group, which may have as a substituent the group represented by the general formula [2] or [3], and among them, it is preferable that one of them is an alkyl group having as a substituent the group represented by the general formula [2] or [3], and the other is an alkyl group.

$R^{5a}$ and $R^{6a}$ each independently include an alkyl group, which may have as a substituent the group represented by the general formula [2] or [3], and among them, it is preferable that one of them is an alkyl group having as a substituent the group represented by the general formula [2] or [3], and the other is an alkyl group.

The alkyl group represented by $R^{11a}$ includes a similar one to an exemplification of the alkyl group represented by $R^{11}$ in the above general formula [1].

A preferable specific example of the compound represented by the general formula [1-1], includes for example, one shown in the following Table 1 or the like.

TABLE 1

| | $R^1$ | $R^2$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|
| 1-1-1 | —$(CH_2)_5COOH$ | —$(CH_2)_3SO_3^-$ | —$CH_3$ | —$(CH_2)_3SO_3Na$ | —$CH_3$ | —$(CH_2)_2COOH$ | H | —$SO_3Na$ | H | H | —$CH_3$ |
| 1-1-2 | —$(CH_2)_5COO^-$ | —$(CH_2)_3SO_3H$ | —$CH_3$ | —$(CH_2)_3SO_3Na$ | —$CH_3$ | —$(CH_2)_2COOC_2H_5$ | H | —$SO_3Na$ | H | H | —$CH_3$ |
| 1-1-3 | —$(CH_2)_5COO^-$ | —$(CH_2)_3SO_3H$ | —$CH_3$ | —$(CH_2)_3SO_3Na$ | —$CH_3$ | —$(CH_2)_3SO_3Na$ | H | —$SO_3Na$ | H | H | —$CH_3$ |
| 1-1-4 | —$(CH_2)_2COO^-$ | —$(CH_2)_2COOH$ | —$CH_3$ | —$CH_3$ | —$CH_3$ | —$(CH_2)_3SO_3Na$ | H | —$SO_3Na$ | H | H | —$CH_3$ |
| 1-1-5 | —$(CH_2)_2COO^-$ | —$(CH_2)_3SO_3H$ | —$CH_3$ | —$CH_3$ | —$CH_3$ | —$(CH_2)_2COOH$ | H | —$SO_3Na$ | H | H | —$CH_3$ |
| 1-1-6 | —$(CH_2)_5COOH$ | —$(CH_2)_3SO_3H$ | —$CH_3$ | —$CH_3$ | —$CH_3$ | —$CH_3$ | H | —$SO_3Na$ | H | H | —$CH_3$ |
| 1-1-7 | —$CH_2CH_3$ | —$(CH_2)_3SO_3H$ | —$CH_3$ | —$CH_3$ | —$CH_3$ | —$(CH_2)_2COOH$ | H | —$SO_3Na$ | H | H | —$CH_3$ |

A preferable specific example of the compound represented by the general formula [1-2], includes for example, one shown in the following Table 2 or the like.

TABLE 2

| | $R^1$ | $R^2$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|
| 1-2-1 | —$(CH_2)_5COOH$ | —$(CH_2)_3SO_3^-$ | —$CH_3$ | —$(CH_2)_3SO_3Na$ | —$CH_3$ | —$(CH_2)_2COOH$ | H | —$SO_3Na$ | H | H | —$CH_3$ |
| 1-2-2 | —$(CH_2)_5COO^-$ | —$(CH_2)_3SO_3H$ | —$CH_3$ | —$(CH_2)_3SO_3Na$ | —$CH_3$ | —$(CH_2)_2COOC_2H_5$ | H | —$SO_3Na$ | H | H | —$CH_3$ |
| 1-2-3 | —$(CH_2)_5COOH$ | —$(CH_2)_3SO_3^-$ | —$CH_3$ | —$(CH_2)_3SO_3Na$ | —$CH_3$ | —$(CH_2)_3SO_3Na$ | H | —$SO_3Na$ | H | H | —$CH_3$ |
| 1-2-4 | —$(CH_2)_2COOH$ | —$(CH_2)_2COO^-$ | —$CH_3$ | —$CH_3$ | —$CH_3$ | —$(CH_2)_3SO_3Na$ | H | —$SO_3Na$ | H | H | —$CH_3$ |
| 1-2-5 | —$(CH_2)_2COO^-$ | —$(CH_2)_3SO_3H$ | —$CH_3$ | —$CH_3$ | —$CH_3$ | —$(CH_2)_2COOH$ | H | —$SO_3Na$ | H | H | —$CH_3$ |
| 1-2-6 | —$(CH_2)_5COOH$ | —$(CH_2)_3SO_3H$ | —$CH_3$ | —$CH_3$ | —$CH_3$ | —$CH_3$ | H | —$SO_3Na$ | H | H | —$CH_3$ |
| 1-2-7 | —$CH_2CH_3$ | —$(CH_2)_3SO_3H$ | —$CH_3$ | —$CH_3$ | —$CH_3$ | —$(CH_2)_2COOH$ | H | —$SO_3Na$ | H | H | —$CH_3$ |

A preferable specific example of the compound represented by the general formula [1-3], includes for example, one shown in the following Table 3 or the like.

TABLE 3

| | $R^1$ | $R^2$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|
| 1-3-1 | —(CH$_2$)$_5$COOH | —(CH$_2$)$_3$SO$_3^-$ | —CH$_3$ | —(CH$_2$)$_3$SO$_3$Na | —CH$_3$ | —(CH$_2$)$_2$COOH | H | —SO$_3$Na | H | H | —CH$_3$ |
| 1-3-2 | —(CH$_2$)$_5$COO$^-$ | —(CH$_2$)$_3$SO$_3$H | —CH$_3$ | —(CH$_2$)$_3$SO$_3$Na | —CH$_3$ | —(CH$_2$)$_2$COOC$_2$H$_5$ | H | —SO$_3$Na | H | H | —CH$_3$ |
| 1-3-3 | —(CH$_2$)$_5$COO$^-$ | —(CH$_2$)$_3$SO$_3$H | —CH$_3$ | —(CH$_2$)$_3$SO$_3$Na | —CH$_3$ | —(CH$_2$)$_3$SO$_3$Na | H | —SO$_3$Na | H | H | —CH$_3$ |
| 1-3-4 | —(CH$_2$)$_2$COO$^-$ | —(CH$_2$)$_2$COOH | —CH$_3$ | —CH$_3$ | —CH$_3$ | —(CH$_2$)$_3$SO$_3$Na | H | —SO$_3$Na | H | H | —CH$_3$ |
| 1-3-5 | —(CH$_2$)$_2$COO$^-$ | —(CH$_2$)$_3$SO$_3$H | —CH$_3$ | —CH$_3$ | —CH$_3$ | —(CH$_2$)$_2$COOH | H | —SO$_3$Na | H | H | —CH$_3$ |
| 1-3-6 | —(CH$_2$)$_5$COOH | —(CH$_2$)$_3$SO$_3$H | —CH$_3$ | —CH$_3$ | —CH$_3$ | —CH$_3$ | H | —SO$_3$Na | H | H | —CH$_3$ |
| 1-3-7 | —CH$_2$CH$_3$ | —(CH$_2$)$_3$SO$_3$H | —CH$_3$ | —CH$_3$ | —CH$_3$ | —(CH$_2$)$_2$COOH | H | —SO$_3$Na | H | H | —CH$_3$ |

A preferable specific example of the compound represented by the general formula [1-4], includes for example, one shown in the following Table 4 or the like.

TABLE 4

| | $R^1$ | $R^2$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|
| 1-4-1 | —(CH$_2$)$_5$COOH | —(CH$_2$)$_3$SO$_3^-$ | —CH$_3$ | —(CH$_2$)$_3$SO$_3$Na | —CH$_3$ | —(CH$_2$)$_2$COOH | H | —SO$_3$Na | H | H | —CH$_3$ |
| 1-4-2 | —(CH$_2$)$_5$COO$^-$ | —(CH$_2$)$_3$SO$_3$H | —CH$_3$ | —(CH$_2$)$_3$SO$_3$Na | —CH$_3$ | —(CH$_2$)$_2$COOC$_2$H$_5$ | H | —SO$_3$Na | H | H | —CH$_3$ |
| 1-4-3 | —(CH$_2$)$_5$COO$^-$ | —(CH$_2$)$_3$SO$_3$H | —CH$_3$ | —(CH$_2$)$_3$SO$_3$Na | —CH$_3$ | —(CH$_2$)$_3$SO$_3$Na | H | —SO$_3$Na | H | H | —CH$_3$ |
| 1-4-4 | —(CH$_2$)$_2$COO$^-$ | —(CH$_2$)$_2$COOH | —CH$_3$ | —CH$_3$ | —CH$_3$ | —(CH$_2$)$_3$SO$_3$Na | H | —SO$_3$Na | H | H | —CH$_3$ |
| 1-4-5 | —(CH$_2$)$_2$COO$^-$ | —(CH$_2$)$_3$SO$_3$H | —CH$_3$ | —CH$_3$ | —CH$_3$ | —(CH$_2$)$_2$COOH | H | —SO$_3$Na | H | H | —CH$_3$ |
| 1-4-6 | —(CH$_2$)$_5$COOH | —(CH$_2$)$_3$SO$_3$H | —CH$_3$ | —CH$_3$ | —CH$_3$ | —CH$_3$ | H | —SO$_3$Na | H | H | —CH$_3$ |
| 1-4-7 | —CH$_2$CH$_3$ | —(CH$_2$)$_3$SO$_3$H | —CH$_3$ | —CH$_3$ | —CH$_3$ | —(CH$_2$)$_2$COOH | H | —SO$_3$Na | H | H | —CH$_3$ |

In addition, in the case where, a reactive group of the present invention, contained in a compound of the present invention, is subjected to binding, for example, to a substance to be labeled or the like, there may be introduced further to the reactive group, such a group (hereafter may be abbreviated as "a reaction activation group of the present invention") that enhances (in other words activates) binding ability to a functional group to be contained in the substance to be labeled (for example, amino group, carboxyl group, thiol group, hydroxyl group, formyl group or the like) (hereafter may be abbreviated as "a functional group of the substance to be labeled").

It should be noted that such a reaction activation group of the present invention, that is, one where a group, which enhances binding ability to a functional group of a substance to be labeled, is introduced to a reactive group of the present invention, is also included in "the reactive group of the present invention".

As such a reaction activation group, it is not especially limited as long as it is one capable of binding to a functional group of a substance to be labeled, and, all those usually used in this field are included.

As the reaction activation group of the present invention, it is not especially limited, as long as it is one capable of binding to a functional group of a substance to be labeled, and all those usually used in this field are included, such as one activating reactivity with an amino group (hereafter referred to as "a reaction activation group to an amino group"), one activating reactivity with a thiol group (hereafter referred to as "a reaction activation group to a thiol group"), one activating reactivity with a hydroxyl group (hereafter referred to as "a reaction activation group to a hydroxyl group"), one activating reactivity with a formyl group (hereafter referred to as "a reaction activation group to a formyl group") or the like.

A preferable specific example of the reaction activation group to an amino group, includes, for example, succinimide group, sulfosuccinimide group, norbornene group, 4-nitrophenoxy group, a group derived from carboxylic anhydride (for example, acetoxycarbonylmethyl group, propionyloxycarbonylethyl group, benzoyloxybenzyl group, or the like), $C_1$ to $C_3$ halosulfonylalkyl group (for example, fluorosulfonylmethyl group, fluorosulfonylethyl group, fluorosulfonylpropyl group, chlorosulfonylmethyl group, chlorosulfonylethyl group, chlorosulfonylpropyl group, bromosulfonylmethyl group, bromosulfonylethyl group, bromosulfonylpropyl group, iodosulfonylmethyl group, iodosulfonylethyl group, iodosulfonylpropyl group, or the like), halosulfonylaryl group (for example, fluorosulfonylphenyl group, chlorosulfonylphenyl group, bromosulfonylphenyl group, iodosulfonylphenyl group, or the like), $C_1$ to $C_3$ halocarbonylalkyl group (for example, fluorocarbonylmethyl group, fluorocarbonylethyl group, fluorocarbonylpropyl group, chlorocarbonylmethyl group, chlorocarbonylethyl group, chlorocarbonylpropyl group, bromocarbonylmethyl group, bromocarbonylethyl group, bromocarbonylpropyl group, iodocarbonylmethyl group, iodocarbonylethyl group, iodocarbonylpropyl group, or the like), halocarbonylaryl group (for example, fluorocarbonylphenyl group, chlorocarbonylphenyl group, bromocarbonylphenyl group, iodocarbonylphenyl group, or the like), phosphoamidite group, isothiocyanate group, isocyanate group, monohalogen (for example, F, Cl, Br, I, or the like), substituted triazino group, dihalogen (for example, F, Cl, Br, I, or the like) substituted triazino group, monohalogen (for example, F, Cl, Br, I, or the like) substituted pyrimidino group, dihalogen (for example, F, Cl, Br, I, or the like) substituted pyrimidino group, monohalogen (for example, F, Cl, Br, I, or the like) substituted pyridino group, dihalogen (for example, F, Cl, Br, I, or the like) substituted pyridino group, phosphoryl halide (for example, F, Cl, Br, I, or the like) or the like.

A preferable specific example of the reaction activation group to a thiol group, includes, for example, a group derived from a carboxylic anhydride (for example, acetoxycarbonylmethyl group, propionyloxycarbonylethyl group, benzoyloxybenzyl group, or the like), maleimide group, sulfomaleimide group, sulfonylhalide group (for example, F, Cl, Br, I, or the like), α-halogeno (for example, F, Cl, Br, I, or the like) acetamide group, $C_1$ to $C_3$ halocarbonylalkyl group (for example, fluorocarbonylmethyl group, fluorocarbonylethyl group, fluorocarbonylpropyl group, chlorocarbonylmethyl group, chlorocarbonylethyl group, chlorocarbonylpropyl group, bromocarbonylmethyl group, bromocarbonylethyl group, bromocarbonylpropyl group, iodocarbonylmethyl group, iodocarbonylethyl group, iodocarbonylpropyl group, or the like), halocarbonylaryl group (for example, fluorocarbonylphenyl group, chlorocarbonylphenyl group, bromocarbonylphenyl group, iodocarbonylphenyl group, or the like), isothiocyanate group, isocyanate group, 2-pyridyldithio group or the like.

A preferable specific example of the reaction activation group to a hydroxyl group, includes, for example, a group derived from a carboxylic anhydride (for example, acetoxycarbonylmethyl group, propionyloxycarbonylethyl group, benzoyloxybenzyl group, or the like), $C_1$ to $C_3$ halosulfonylalkyl group (for example, fluorosulfonylmethyl group, fluorosulfonylethyl group, fluorosulfonylpropyl group, chlorosulfonylmethyl group, chlorosulfonylethyl group, chlorosulfonylpropyl group, bromosulfonylmethyl group, bromosulfonylethyl group, bromosulfonylpropyl group, iodosulfonylmethyl group, iodosulfonylethyl group, iodosulfonylpropyl group or the like), halosulfonylaryl group (for example, fluorosulfonylphenyl group, chlorosulfonylphenyl group, bromosulfonylphenyl group, iodosulfonylphenyl group or the like), phosphoamidite group, $C_1$ to $C_3$ halocarbonylalkyl group (for example, fluorocarbonylmethyl group, fluorocarbonylethyl group, fluorocarbonylpropyl group, chlorocarbonylmethyl group, chlorocarbonylethyl group, chlorocarbonylpropyl group, bromocarbonylmethyl group, bromocarbonylethyl group, bromocarbonylpropyl group, iodocarbonylmethyl group, iodocarbonylethyl group, iodocarbonylpropyl group or the like), halocarbonylaryl group (for example, fluorocarbonylphenyl group, chlorocarbonylphenyl group, bromocarbonylphenyl group, iodocarbonylphenyl group or the like), isothiocyanate group, isocyanate group, phosphoryl halide (for example, F, Cl, Br, I, or the like) group or the like.

A preferable specific example of the reaction activation group to a formyl group, includes, for example, hydrazide group or the like.

In addition, it is also possible to label a substance to be labeled, after introducing the above reaction activation group to a functional group of a substance to be labeled, by subjecting it to a reaction with the reactive group of the present invention, and a reaction activation group of a functional group of a substance to be labeled in this case, includes also similar one to the above reaction activation group of the present invention.

In the reaction activation group of the present invention, for example, a succinimide (Su) group, a maleimide (Ma) group or the like is preferable.

A preferable specific example of a group where the reaction activation group is introduced to the reactive group of the present invention, includes, for example, —COOSu group, —CONH(CH$_2$)$_4$Ma group or the like. Such a compound containing the reaction activation group of the present invention is also included in the compound of the present invention represented by the general formula [1].

A specific example of a compound of the present invention containing such a reaction activation group of the present invention includes all of the compounds where the above reaction activation group of the present invention is further introduced to the reactive group of the present invention in the compound of the present invention, for example, one where the above reaction activation group is contained in $R^1$, $R^2$ and $R^6$ in the general formulae [1-1] to [1-4].

An example of the compound of the present invention introduced with such a reaction activation group of the present invention is shown below.

A preferable specific example of the compound represented by the general formula [1-1], containing the reaction activation group of the present invention includes, for example, one shown in the following Table 5.

TABLE 5

| | $R^1$ | $R^2$ | $R^3$ | $R^4$ | $R^5$ |
|---|---|---|---|---|---|
| 1-1-3(1) | —(CH$_2$)$_5$COOSu | —(CH$_2$)$_3$SO$_3^-$ | —CH$_3$ | —(CH$_2$)$_3$SO$_3$Na | —CH$_3$ |
| 1-1-3(2) | —(CH$_2$)$_5$CONH(CH$_2$)$_4$Ma | —(CH$_2$)$_3$SO$_3^-$ | —CH$_3$ | —(CH$_2$)$_3$SO$_3$Na | —CH$_3$ |

| | $R^6$ | $R^7$ | $R^8$ | $R^9$ | $R^{10}$ | $R^{11}$ |
|---|---|---|---|---|---|---|
| 1-1-3(1) | —(CH$_2$)$_3$SO$_3$Na | —H | —SO$_3$Na | —H | —H | —CH$_3$ |
| 1-1-3(2) | —(CH$_2$)$_3$SO$_3$Na | —H | —SO$_3$Na | —H | —H | —CH$_3$ |

A preferable specific example of the compound represented by the general formula [1-2], containing the reaction activation group of the present invention includes for example, one shown in the following Table 6.

TABLE 6

| | $R^1$ | $R^2$ | $R^3$ | $R^4$ | $R^5$ |
|---|---|---|---|---|---|
| 1-2-1(1) | —(CH$_2$)$_5$COOSu | —(CH$_2$)$_3$SO$_3^-$ | —CH$_3$ | —(CH$_2$)$_3$SO$_3$Na | —CH$_3$ |
| 1-2-3(1) | —(CH$_2$)$_5$COOSu | —(CH$_2$)$_3$SO$_3^-$ | —CH$_3$ | —(CH$_2$)$_3$SO$_3$Na | —CH$_3$ |
| 1-2-3(2) | —(CH$_2$)$_5$CONH(CH$_2$)$_4$Ma | —(CH$_2$)$_3$SO$_3^-$ | —CH$_3$ | —(CH$_2$)$_3$SO$_3$Na | —CH$_3$ |
| 1-2-4(1) | —(CH$_2$)$_2$COOSu | —(CH$_2$)$_2$COOSu | —CH$_3$ | —CH$_3$ | —CH$_3$ |

| | $R^6$ | $R^7$ | $R^8$ | $R^9$ | $R^{10}$ | $R^{11}$ |
|---|---|---|---|---|---|---|
| 1-2-1(1) | —(CH$_2$)$_2$COOSu | —H | —SO$_3$Na | —H | —H | —CH$_3$ |
| 1-2-3(1) | —(CH$_2$)$_3$SO$_3$Na | —H | —SO$_3$Na | —H | —H | —CH$_3$ |
| 1-2-3(2) | —(CH$_2$)$_3$SO$_3$Na | —H | —SO$_3$Na | —H | —H | —CH$_3$ |
| 1-2-4(1) | —(CH$_2$)$_3$SO$_3$Na | —H | —SO$_3$Na | —H | —H | —CH$_3$ |

A preferable specific example of the compound represented by the general formula [1-3], containing the reaction activation group of the present invention includes for example, one shown in the following Table 7 or the like.

TABLE 7

| | R¹ | R² | R³ | R⁴ | R⁵ |
|---|---|---|---|---|---|
| 1-3-3(1) | —(CH₂)₅CONH(CH₂)₄Ma | —(CH₂)₃SO₃⁻ | —CH₃ | —(CH₂)₃SO₃Na | —CH₃ |
| 1-3-3(2) | —(CH₂)₅COOSu | —(CH₂)₃SO₃⁻ | —CH₃ | —(CH₂)₃SO₃Na | —CH₃ |

| | R⁶ | R⁷ | R⁸ | R⁹ | R¹⁰ | R¹¹ |
|---|---|---|---|---|---|---|
| 1-3-3(1) | —(CH₂)₃SO₃Na | —H | —SO₃Na | —H | —H | —CH₃ |
| 1-3-3(2) | —(CH₂)₃SO₃Na | —H | —SO₃Na | —H | —H | —CH₃ |

A preferable specific example of the compound represented by the general formula [1-4], containing the reaction activation group of the present invention includes for example, one shown in the following Table 8 or the like.

TABLE 8

| | R¹ | R² | R³ | R⁴ | R⁵ |
|---|---|---|---|---|---|
| 1-4-3(1) | —(CH₂)₅COOSu | —(CH₂)₃SO₃H | —CH₃ | —(CH₂)₃SO₃Na | —CH₃ |
| 1-4-3(2) | —(CH₂)₅CONH(CH₂)₄Ma | —(CH₂)₃SO₃⁻ | —CH₃ | —(CH₂)₃SO₃Na | —CH₃ |

| | R⁶ | R⁷ | R⁸ | R⁹ | R¹⁰ | R¹¹ |
|---|---|---|---|---|---|---|
| 1-4-3(1) | —(CH₂)₃SO₃Na | —H | —SO₃Na | —H | —H | —CH₃ |
| 1-4-3(2) | —(CH₂)₃SO₃Na | —H | —SO₃Na | —H | —H | —CH₃ |

A compound wherein is the reaction activation group of the present invention introduced to the reactive group of the present invention in this way is also included in the compound of the present invention.

1-2. A Synthesis Method for the Compound [1] of the Present Invention 1-2-1. Synthesis of an Indolenine Compound—Pyrazole Compound Complex (it Corresponds to the Compound Represented by the General Formula [1])

The compound represented by the general formula [1] can be synthesized, for example, by the following method.

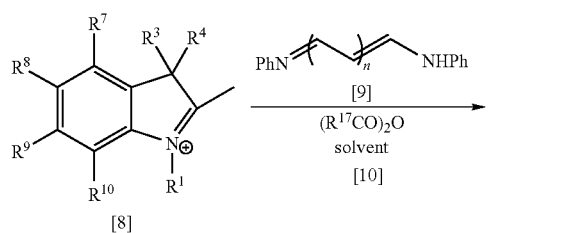

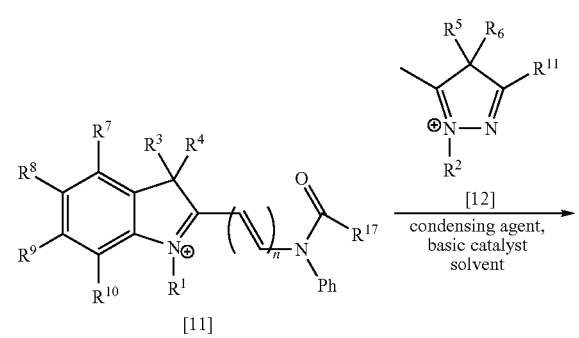

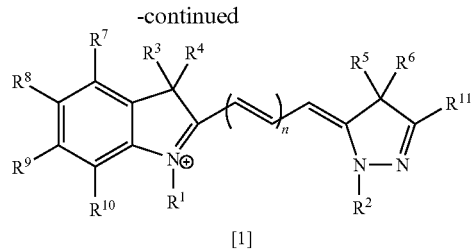

(wherein $R^{17}$ represents alkyl group or aryl group; and $R^1$ to $R^{11}$ and n are the same as above).

In the general formulae [10] and [11], the alkyl group represented by $R^{17}$ may be any of straight-chained, branched and cyclic one, and includes one having usually $C_1$ to $C_{10}$, preferably $C_1$ to $C_3$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The aryl group represented by $R^{17}$, includes one having usually $C_6$ to $C_{10}$, and specifically, for example, phenyl group or naphthyl group the like.

That is, first of all, the indolenine compound represented by the general formula [8] (an indolenine skeleton part), the compound represented by the general formula [9] [from 1 to 2 times mole relative to the compound represented by the general formula [8]] and the acid anhydride represented by the general formula [10] [from 1 to 20 times mole relative to the compound represented by the general formula [8]] (for example, acetic anhydride, propionic anhydride, butyric anhydride, benzoic anhydride or the like) are dissolved, if necessary, in a solvent (carboxylic acids such as acetic acid, propionic acid and butyric acid; nitrites such as acetonitrile, propionitrile and n-butyronitrile; or the like), and are subjected to a reaction at 0 to 150° C. (preferably at 40 to 120° C.) for 0.1 to 24 hours (preferably for 0.5 to 12 hours, and more preferably for 1 to 8 hours) to obtain the compound represented by the general formula [11].

Then, the compound represented by the general formula [11] and the compound represented by the general formula [12] (a pyrazole skeleton part) [from 0.5 to 10 times mole, preferably from 1 to 5 times mole relative to the compound represented by the general formula [11]] are subjected to a reaction at 0 to 150° C. (preferably at 40 to 120° C.) for 0.1 to 24 hours (preferably for 0.5 to 12 hours, and more preferably for 1 to 8 hours), in the presence of a basic catalyst (organic amines such as pyridine, triethylamine, N,N-dimethylaniline, piperidine, pyridine, 4-dimethylaminopyridine, 1,5-diazabicyclo [4.3.0] nona-5-ene, 1,8-diazabicyclo [5.4.0] undec-7-ene and tri-n-butylamine; metal hydrides such as sodium hydride; basic alkali metal compounds such as n-butyllithium; or the like), by using dehydrating condensing agent (inorganic dehydrating agents such as concentrated sulfuric acid, diphosphorus pentaoxide and anhydrous zinc chloride; carbodiimides such as dicyclohexylcarbodiimide, diisopropylcarbodiimide and 1-ethyl-3-(3-dimethylaminopropyl)carbodiimide hydrochloride; acetic anhydride, polyphosphoric acid, carbonyldiimidazole, p-toluenesulfonylchloride; or the like), and, if necessary, in a solvent (amides such as N,N-dimethylformamide(DMF), N,N-dimethylacetamide (DMA), acetamide and N-methylpyrrolidone; nitriles such as acetonitrile, propionitrile and n-butyronitrile; alcohols such as methanol, ethanol, propanol, isopropanol, butanol, ethylene glycol and 1,4-butanediol; ethers such as tetrahydrofuran, dioxane, anisole and ethylene glycol monoethyl ether; sulfoxides such as dimethylsulfoxide and the like) to obtain the object compound represented by the general formula [1].

1-2-2. Synthesis of a Compound of the Present Invention Containing the Reaction Activation Group of the Present Invention (a Group Activating the Reactive Group of the Present Invention)

Explanation will be given on a method for introducing the reaction activation group of the present invention to the reactive group of the present invention, with reference to an example of the case using the compound represented by the general formula [22] (that is, it corresponds to a compound where $R^1$ in the general formula [1] is an alkyl group having as a substituent the group represented by the general formula [2]).

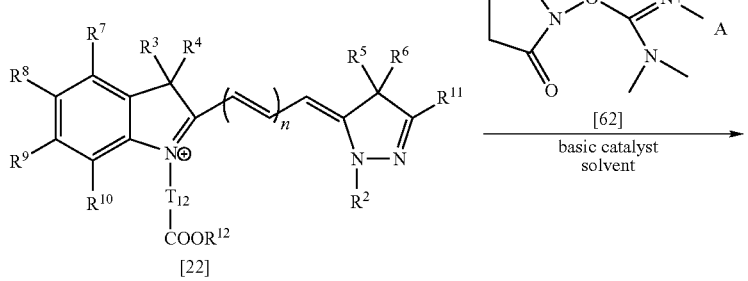

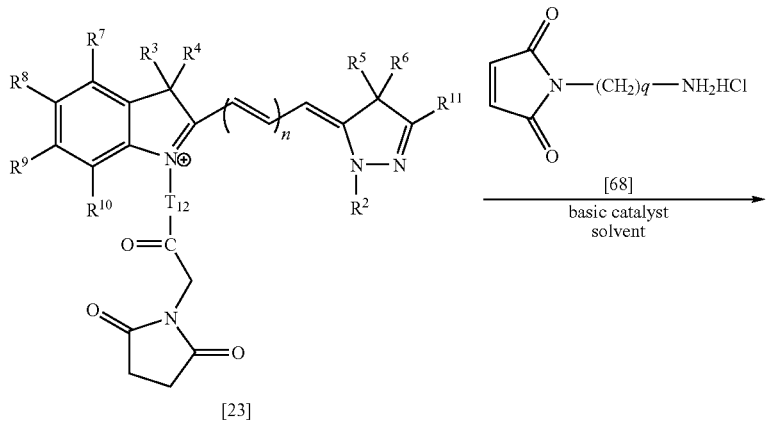

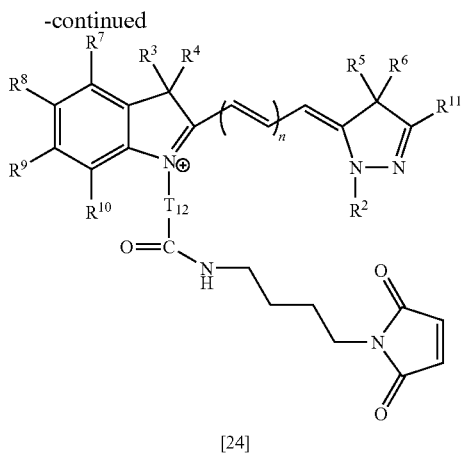

[24]

(wherein $T_{12}$ represents an alkylene group; A represents tetrafluoroborate or hexafluorophosphate; q represents an integer of from 2 to 10; and $R^3$ to $R^{11}$, $R^{12}$, A and n are the same as above).

It should be noted that the compound represented by the general formula [22] corresponds to a compound, among the compounds represented by the general formula [1], where $R^1$ is an alkyl group having as a substituent the group represented by the general formula [2], (that is, it corresponds to a -$T_{12}$-$COOR^{12}$ group).

In the general formulae [22] to [24], as the alkylene group represented by $T_{12}$ may be any of straight-chained and branched one, preferably a straight-chained one, and includes one having usually $C_1$ to $C_6$, preferably $C_1$ to $C_4$, and specifically, straight-chained alkylene group such as methylene group, ethylene group, trimethylene group, tetramethylene group, tetramethylene group and hexamethylene group; branched alkylene group such as ethylidene group, propylene group, isopropylidene group, ethylethylene group, 1,2-dimethylethylene group, 1,2-diethylethylene group, 1,2-di-n-propylethylene group and 1,2-di-n-butylethylene group; or the like: among these, a straight-chained alkylene group is preferable, and in particular, ethylene group or pentamethylene group or the like is more preferable.

That is, the compound represented by the general formula [22] (a compound having the reactive group of the present invention) is subjected to a reaction at 0 to 40° C. for 0.1 to 12 hours, in the presence of a succinimidation reagent such as the compound represented by the general formula [62] (from 1 to 10 times mole relative to the compound represented by the general formula [22]), and a basic catalyst (organic amines such as N-ethyldiisopropylamine, pyridine, triethylamine, N,N-dimethylaniline, piperidine, 4-dimethylaminopyridine, 1,5-diazabicyclo [4.3.0] nona-5-ene, 1,8-diazabicyclo [5.4.0] undec-7-ene and tri-n-butylamine) in a suitable solvent (amides such as DMF, DMA, acetamide and N-methylpyrrolidone) to obtain the compound represented by the general formula [23] (a compound having a succinimide group as the reaction activation group of the present invention).

The compound represented by the general formula [23] is subjected to a reaction with a maleimidation reagent such as the compound represented by the general formula [68] (from 1 to 10 times mole relative to the compound represented by the general formula [23]), at 0 to 40° C. for 0.1 to 12 hours, in the presence of a basic catalyst (organic amines such as triethylamine, N-ethyldiisopropylamine, pyridine, N,N-dimethylaniline, piperidine, 4-dimethylaminopyridine, 1,5-diazabicyclo [4.3.0] nona-5-ene, 1,8-diazabicyclo [5.4.0] undec-7-ene and tri-n-butylamine), in a suitable solvent (amides such as DMF, DMA, acetamide and N-methylpyrrolidone) to obtain the compound represented by the general formula [24] (a compound having a maleimide group as the reaction activation group of the present invention).

The succinimidation reagent relevant to the present invention, without limiting to the compound represented by the general formula [62], includes all of those usually used in this field, however, specifically, for example, di(N-succinimidyl) carbonate (DSC), 2-succinimide-1,1,3,3-tetramethyluronium tetrafluoroborate (TSTU), 2-(5-norbornene-2,3-dicarboxylmide)-1,1,3,3-tetramet hyluronium tetrafluoroborate (TNTU) or the like.

A method for introducing the reaction activate group of the present invention other than the reaction activate group as above, may use corresponding raw materials, and subject them to synthesis as appropriate in accordance with the above method to obtain an objective compound.

1-2-3. Synthesis of an Indolenine Compound

Explanation will be given below on a synthesis method for the compound represented by the general formula [8] (an indolenine skeleton part).

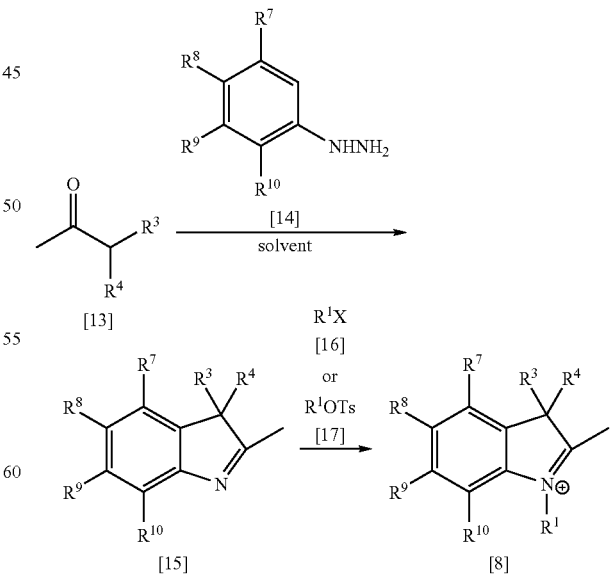

(wherein X represents a halogen atom; and $R^1$, $R^3$, $R^4$ and $R^7$ to $R^{10}$ are the same as above).

In the general formula [16], the halogen atom represented by X, includes, for example, fluorine atom, chlorine atom, bromine atom, iodine atom or the like.

That is, the ketone compound represented by the general formula [13] and the compound represented by the general formula [14] are subjected to a reaction at 40 to 250° C. for 0.1 to 24 hours, in a suitable solvent (carboxylic acids such as acetic acid and propionic acid; alcohols such as ethylene glycol and 1,4-butanediol; or the like) to obtain the compound represented by the general formula [21] (see for example, Journal of Organic Chemistry, 42 (14), 2474-80, 1977 or the like).

Then, the compound represented by the general formula [15] and the halide represented by the general formula [16] or the tosylate compound represented by the general formula [17] are dissolved in a suitable solvent (halogenated aromatic hydrocarbons such as chlorobenzene and 1,2-dichlorobenzene; halogenated hydrocarbons such as 1,2-dichloroethane; aromatic hydrocarbons such as toluene, xylene and benzene; amides such as DMA, DMF, acetamide and N-methylpyrrolidone; or the like), and are subjected to a reaction at 40 to 200° C. for 1 to 24 hours to obtain the compound represented by the general formula [8] (see for example, J. Chem. Soc., Perkin Trans. 1. 947-952, 1984 or the like).

The ketone compound represented by the general formula [13], may use a commercial product (for example, 3-methyl-2-butanone, 3-methyl-2-pentanone, 3-methyl-2-hexanone, 1-cyclopropylethanone, 1-cyclobutylethanone or the like), or one synthesized as appropriate by a usual method: Specifically, there is included, for example, a method where ethyl 2-methylacetoacetate and a compound having a leaving group (for example, halogen atom, tosylate group, or the like) are subjected to a reaction at −80 to 100° C. for 0.1 to 24 hours, in the presence of a basic catalyst (metal hydrides such as sodium hydride and potassium hydride; alkali metal carbonates such as lithium carbonate, sodium carbonate and potassium carbonate; alkali metal alkoxides such as sodium methoxide, sodium ethoxide and potassium tert-butoxide; basic alkali metal compounds such as n-butyllithium; alkali metal amides such as lithium diisopropylamide; or the like), in a suitable solvent (amides such as DMF, DMA, acetamide and N-methylpyrrolidone; alcohols such as methanol, ethanol, propanol, isopropanol, butanol and ethylene glycol; ethers such as tetrahydrofuran, dioxane and ethylene glycol monoethyl ether; sulfoxides such as dimethylsulfoxide; or the like), and then the resulting solution is subjected to a decarbonation by using an acid catalyst (refer to, for example, Modern Synthetic Reactions, California, $2^{nd}$ ed., p. 492, 510 and 756 (1972) or the like); or the like.

The compound represented by the general formula [14] may use a commercial product, or one synthesized as appropriate by a usual method.

1-2-4. Synthesis of a Pyrazole Compound

Explanation will be given below on a synthesis method for the compound represented by the general formula [12] (a pyrazole skeleton part).

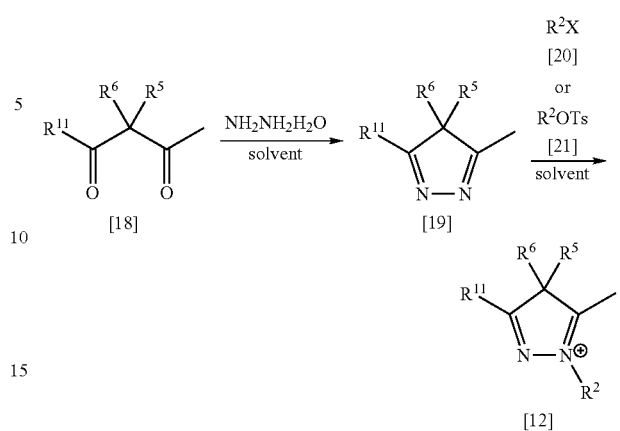

(wherein $R^2$, $R^5$ to $R^6$, $R^{11}$ and X are the same as above).

That is, the diketone compound represented by the general formula [18] and hydrazine are subjected to a dehydration reaction at 60 to 100° C. for 1 to 4 hours in a suitable solvent (alcohols such as methanol, ethanol, propanol, isopropanol, butanol and ethylene glycol; or the like), to obtain a 4H-pyrazole compound represented by the general formula [26] (see for example, Adv. Heterocycle Chem., Vol. 34, 53-78, 1983 or the like).

Then, the 4H-pyrazole compound represented by the general formula [19] is subjected to an N-alkylation reaction with a halide compound represented by the general formula [20] or a tosylate compound represented by the general formula [21], at 80 to 140° C. for 1 to 12 hours in a suitable solvent (halogenated aromatic hydrocarbons such as chlorobenzene and 1,2-dichlorobenzene; halogenated hydrocarbons such as 1,2-dichloroethane; aromatic hydrocarbons such as toluene, xylene and benzene; amides such as DMF, DMA, acetamide and N-methylpyrrolidone; or the like), to obtain a compound represented by the general formula [12] (see for example, J. Chem. Soc., Perkin Trans. 1. 947-952, 1984 or the like).

The diketone compound represented by the general formula [18] may use a commercial product (for example, 3,3-dimethyl-2,4-pentanedione or the like), or one synthesized as appropriate by a usual method: Specifically, includes, for example, a method where 3-methyl-2,4-pentanedione or 4-acetyl-5-oxohexanoic acid ethyl ester, and a compound having a leaving group (for example, halogen atom, tosylate group, or the like) are subjected to a reaction at −80 to 100° C. for 0.1 to 24 hours, in the presence of a basic catalyst (metal hydrides such as sodium hydride and potassium hydride; alkali metal carbonates such as lithium carbonate, sodium carbonate and carbonate potassium; alkali metal alkoxides such as sodium methoxide, sodium ethoxide and potassium tert-butoxide; basic alkali metal compounds such as n-butyl lithium; alkali metal amides such as lithium diisopropylamide; or the like), in a suitable solvent (amides such as DMF, DMA, acetamide and N-methylpyrrolidone; alcohols such as methanol, ethanol, propanol, isopropanol, butanol and ethylene glycol; ethers such as tetrahydrofuran, dioxane and ethylene glycol monoethyl ether; sulfoxides such as dimethylsulfoxide; or the like) (for example, Modern Synthetic Reactions, California, $2^{nd}$ ed., pages 492, 510 and 756 (1972) or the like); or the like.

1-3. Property of the Compound [1] of the Present Invention

The compound [1] of the present invention obtained in this way is expected to be used as a fluorescent labeling substance of, for example, a nucleic acid extraction method, an immunoassay method or the like.

2. A Labeled Compound and a Labeling Method of the Present Invention

2-1. A Labeled Compound of the Present Invention (a Compound Labeled with the Compound [1] of the Present Invention)

A labeled compound of the present invention, includes, one where the compound of the present invention (labeling substance) and the substance to be labeled are bound directly or indirectly, and specifically includes one where the group represented by the general formula [2] (for example, a carboxyl group or the like), the group represented by the general formula [3] (for example, a sulfo group or the like), amino group, hydroxyl group, thiol group, or formyl group, is bound directly or indirectly to a substance to be labeled.

The group represented by the general formula [2] (for example, a carboxyl group or the like), the group represented by the general formula [3] (for example, a sulfo group or the like), amino group, hydroxyl group, thiol group or formyl group (hereafter may be abbreviated as "a reactive group of the present invention"), in the compound of the present invention to be bound to a substance to be labeled are preferably those contained in usually $R^1$ to $R^{11}$, preferably in $R^1$ to $R^6$, more preferably in $R^1$ or $R^6$ in the general formula [1].

A substance to be labeled, which is labeled with a compound of the present invention, includes, for example, all of those usually used as a substance to be labeled in this field, and specifically, for example, biotin, avidin, streptavidin, antibody or degradation products thereof (for example, Fab, Fab', F(ab')$_2$, and the like), amino acid, protein, peptide, enzyme substrate, hormone, lymphokine, metabolite, receptor, ligand, agonist, antagonist, antigen, hapten, dendrimer, lectin, toxin, carbohydrate, saccharides such as fructose and polysaccharides; nucleoside (for example, ribonucleoside, deoxyribonucleoside, or the like), nucleotide (for example, ribonucleotide, deoxyribonucleotide, or the like), nucleic acid (oligonucleotide, polynucleotide) [for example, deoxyribonucleic acid(DNA), ribonucleic acid(RNA), or the like], nucleic acid derivatives (for example, DNA fragment, RNA fragment, or the like), natural drugs, virus, virus components, yeast components, hemocyte, hemocyte components, biological cells, non-cellular hemocyte components, bacteria, bacteria components, natural and synthetic lipid cysts, synthetic and natural drugs, poisons, environmental pollutants, polymers, polymer particles, glass particles, glass surface materials, plastic particles, plastic surface materials, polymer films, conductors and semiconductors or the like, and among these, for example, nucleotide, antibody or degradation products thereof or the like is preferable.

Nucleoside is composed of a purine base or a pyrimidine base, and pentose as a saccharide moiety, and specifically includes, ribonucleoside where, for example, the saccharide moiety is D-ribose; deoxyribonucleoside where, for example, the saccharide moiety is D-2-deoxyribose, or the like.

Nucleotide is composed of a purine base or a pyrimidine base, and pentose as a saccharide moiety, and phosphoric acid, and specifically includes, ribonucleotide where, for example, the saccharide moiety is D-ribose; deoxyribonucleotide where, for example, the saccharide moiety is D-2-deoxyribose, or the like.

In addition, the nucleoside and nucleotide includes also, for example, like nucleoside antibiotics, one where a salt moiety as a fundamental part thereof is not a purine structure or a pyrimidine structure, one where these structures are modified, one where the saccharide moiety is not D-ribose or deoxy-D-ribose, one where they are modified, one where a phosphoric acid moiety ($-OPO_3^-$) is substituted with other element [for example, a sulfur atom ($-OPO_2S^-$) or the like), one where the phosphoric acid moiety is modified; or the like.

Nucleic acid has the nucleotide as a fundamental unit, and is a chain-like oligo- or polynucleotide, where this phosphoric acid is bound by a diester bond between 3' and 5' site carbons of saccharide in each of nucleotides, and specifically includes, ribonucleic acid (RNA) where, for example, the saccharide moiety is ribose; deoxyribonucleic acid (DNA) where, for example, the saccharide moiety is D-2-deoxyribose, or the like.

These nucleotide, nucleic acid and derivative nucleic acid may be those composed of nucleic acid chains of any of a single strand, a double strand and more than two strands. In addition, they may be modified as appropriate with a suitable one, as long as it is within a range where an object of the present invention can be attained.

"A compound of the present invention and a substance to be labeled are directly bound" means that, for example, the compound of the present invention (namely, a reactive group of the present invention) binds to a functional group in the substance to be labeled (for example, amino group, carboxyl group, thiol group, hydroxyl group, formyl group or the like) by, for example, an ionic bond, a covalent bond or the like. In addition, "a compound of the present invention and a substance to be labeled are indirectly bound" means that, for example, a reactive group of the present invention binds to the functional group in the substance to be labeled, via a linker or the like (for example, an ionic bond, a covalent bond or the like). The linker used in the indirect binding includes all of those usually used in this field.

2-2. A Labeling Method of the Present Invention

As for a method for labeling a substance to be labeled by using the compound [1] of the present invention, the labeling may be carried out by selecting, as appropriate, a known method itself, and the labeling may be easily carried out, for example, by subjecting the reactive group of the present invention (that is, the group represented by the general formula [2] (for example, a carboxyl group or the like), the group represented by the general formula [3] (for example, a sulfo group or the like), amino group, hydroxyl group, thiol group, or formyl group), contained in at least one of $R^1$ to $R^{11}$ in the general formula [1]], and a functional group of the substance to be labeled (for example, amino group, carboxyl group, thiol group, hydroxyl group, formyl group or the like), (hereinafter "a functional group of the substance to be labeled"), to direct binding by, for example, an ionic bond, a covalent bond or the like; or binding via a linker introduced to a part of the substance to be labeled.

In addition, as for a method for labeling nucleotide (a substance to be labeled), labeling can be carried out easily by a method for using an enzyme, other than a method for labeling by using the above chemical reaction, and the enzyme used here includes all of those usually used in this field.

The reactive group of the present invention may be introduced further with a group which enhances reactivity with a functional group of a substance to be labeled (hereinafter may be abbreviated as "a reaction activation group").

It should be noted that, such a reaction activation group also is included in a reactive group of the present invention, and a compound containing such a reaction activation group is also included in a compound of the present invention.

A specific example of a method for labeling a substance to be labeled by using a compound of the present invention, includes, for example, (1) a labeling method by further introducing a reaction activation group of the present invention to a reactive group of the present invention, and then binding thereto a functional group of a substance to be labeled (hereinafter may be abbreviated as simply "a functional group"), (2) a labeling method by introducing a reaction activation group of the present invention to a functional group of a substance to be labeled, and then binding thereto a reactive group of the present invention, (3) a labeling method by binding a multivalent reactive linker reagent, usually used in this field, to a reactive group of the present invention and a functional group of a substance to be labeled, and (4) a labeling method by introducing the same or different reaction activation group to a reactive group of the present invention and a functional group of a substance to be labeled, and then binding thereto a linker usually used in this field, or the like.

As the reaction activation group of the present invention, it is not especially limited as long as it is one capable of binding to a functional group of a substance to be labeled, and all those usually used in this field are included, for example, one activating reactivity with an amino group (hereinafter referred to as "a reaction activation group to an amino group"), one activating reactivity with a thiol group (hereinafter referred to as "a reaction activation group to a thiol group"), one activating reactivity with a hydroxyl group (hereinafter referred to as "a reaction activation group to a hydroxyl group"), one activating reactivity with a formyl group (hereinafter referred to as "a reaction activation group to a formyl group") or the like.

In addition, it is also possible to label a substance to be labeled, after introducing the above reaction activation group to a functional group of a substance to be labeled, by subjecting it to a reaction with the reactive group of the present invention, and also a reaction activation group of a functional group of a substance to be labeled in this case, includes similar one to the above reaction activation group of the present invention.

In the reaction activation group of the present invention, for example, a succinimide (Su) group, a maleimide (Ma) group or the like is preferable.

A preferable specific example of a group where the reaction activation group is introduced to the reactive group of the present invention, includes, for example, —COOSu group, —CONH(CH$_2$)$_4$Ma group or the like. Such a compound containing the reaction activation group of the present invention is also included in the compound of the present invention represented by the general formula [1].

In the case where the reactive group of the present invention is the group represented by the general formula [2] (hereinafter abbreviated as "a carboxyl group of the present invention"), and a substance to be labeled is bound thereto, it is preferable that it is bound to amino group, thiol group or hydroxyl group, which is a functional group of a substance to be labeled, or of a linker introduced thereto (hereafter abbreviated simply as "a substance to be labeled"), and a method therefor, includes (i) a method for subjecting to a reaction by using, for example, a condensing reagent such as N-hyroxysuccinimide and carbodiimide, (ii) a method for forming a carboxylchloride by subjecting thionyl chloride to action to a carboxyl group of the present invention, and then subjecting it to a reaction with an amino group of a substance to be labeled, (iii) a method for subjecting to a reaction by the addition of hydrochloric acid and methanol to a carboxyl group of the present invention, and then subjecting to a reaction by the addition of hydrazine to form hydrazide, and subjecting to activation by the further addition of sodium nitrite and hydrochloric acid thereto to make acylazide, and then subjecting it to a reaction with amino group, thiol group or hydroxyl group of a substance to be labeled, (iv) a method for forming an anhydride from a carboxyl group of the present invention, and then subjecting it to a reaction (dehydrating condensation) with an amino group of a substance to be labeled; or the like.

In addition, in the case where a reactive group of the present invention is the group represented by the general formula [3] (hereafter abbreviated as "a sulfo group of the present invention"), and this is bound to a substance to be labeled, it is preferable to bind to amino group, imidazole group, thiol group or phenol group of the substance to be labeled, and there is included, as a method therefore includes, for example, (i) a method for subjecting chlorosulfonic acid to a reaction with the sulfo group of the present invention to form sulfochloride, and then subjecting it to a reaction with amino group, imidazole group, thiol group or phenol group of a substance to be labeled.

In the case where the reactive group of the present invention is an amino group (hereafter abbreviated as "an amino group of the present invention"), and this is bound to a substance to be labeled, it is preferable to bind to carboxyl group, amino group, phenol group or thiol group, which is a functional group of a substance to be labeled or a linker thereof, and there is included, as a method therefore includes, for example, (i) a method for subjecting the amino group of the present invention to binding to the amino group of a substance to be labeled or a linker thereof, by using a condensing reagent such as N-hydroxysuccinimide and carboxydiimide, (ii) a method for making phosgene to act to the amino group of the present invention to convert to an isocyanate, and then subjecting it to binding to the amino group of the substance to be labeled or the linker thereof, (iii) a method for subjecting glutaraldehyde to a reaction to the amino group of the present invention, and then subjecting it to a reaction with amino group, or phenol group of the substance to be labeled or the linker thereof, (iv) in the case where the substance to be labeled or the linker thereof is one derived from saccharide or saccharide protein, a method for subjecting it to a reaction with periodic acid in advance, and then subjecting it to a reaction with the amino group of the present invention, and further subjecting it to reduction by using sodium borohydride or the like and (v) a method for subjecting the amino group of the present invention to maleimidation or pyridyldithiosulfidation with a bivalent spacer having a maleimide group (for example, m-maleimidebenzoyl N-hydroxysuccinimde ester), or a bivalent spacer having a pyridyldithiosulfide group (for example, 4-succinimidyloxy-carbonyl-α-(2-pyridyldithio) toluene or the like), and then subjecting it to a reaction with the thiol group of the substance to be labeled or the linker thereof.

In the case where the reactive group of the present invention is a hydroxyl group (hereinafter abbreviated as "a hydroxyl group of the present invention"), and a substance to be labeled is subjected to a reaction therewith, it is preferable to be subjected to binding to amino group, thiol group or hydroxyl group, which is a functional group of a substance to be labeled or a linker thereof, and a method therefore includes, for example, (i) a method for forming a triazinyl derivative by subjecting a cyanuric chloride group to action to the hydroxyl group of the present invention, and subjecting it to a reaction with the amino group of the substance to be labeled or a linker thereof, (ii) a method for subjecting the hydroxyl group of the present invention to acetylation, then bromination, bromine-iodine exchange by using sodium iodide, and then subjecting it to a reaction with the amino group, thiol group or hydroxyl group of the substance to be labeled or a linker thereof, (iii) a method for subjecting cyanogen bromide to action to the hydroxyl group of the present invention for activation thereof, and then subjecting it to a reaction with the amino group of the substance to be labeled or a linker thereof.

In the case where the reactive group of the present invention is a thiol group (hereinafter abbreviated as "a thiol group of the present invention"), and a substance to be labeled is subjected to a reaction therewith, it is preferable to be subjected to binding to amino group, thiol group or hydroxyl group, which is a functional group of a substance to be labeled or a linker thereof, and a method therefore includes, for example, (i) a method for subjecting the amino group of the substance to be labeled or a linker thereof to maleimidation or pyridyldithiosulfidation with a bivalent spacer having a maleimide group (for example, m-maleimidebenzoyl N-hydroxysuccinmide ester) or a bivalent spacer having a pyridyldithiosulfide group (for example, 4-succinimidyloxycarbonyl-α-(2-pyridyldithio) toluene or the like), and then subjecting the thiol group of the present invention to a reaction therewith, and (ii) a method for subjecting the thiol group of the present invention to a reaction with the thiol group of the substance to be labeled or a linker thereof, by using a bivalent spacer such as bismaleimidehexane and 1,4-di-[3'-2'-pyridyldithio(propionamide)]butane.

In the case where the reactive group of the present invention is a formyl group (hereafter abbreviated as "a formyl group of the present invention"), and a substance to be labeled is subjected to a reaction therewith, it is preferable to be subjected to binding to amino group or the like, which is a functional group of a substance to be labeled or a linker thereof, and there is included, as a method therefore includes, for example, (i) a method for subjecting the amino group of a substance to be labeled or a linker thereof to a direct reaction with the formyl group of the present invention, and then subjecting it to reduction by using sodium borohydride or the like.

A polyvalent reactive linker reagent includes all of those usually used in this field, however, specifically, for example, a bivalent reagent in the case where one of the reactive group of the present invention and a functional group of a substance to be labeled is an amino group, and the other is a thiol group (hereafter abbreviated as "a bivalent reagent of amino group and thiol group"); a bivalent reagent in the case where one of the reactive group and the functional group is an amino group, and the other is the group represented by the general formula [2] (carboxyl group or the like)(hereafter abbreviated as "a bivalent reagent of amino group and carboxyl group"); a bivalent reagent in the case where one of the reactive group and the functional group is an thiol group, and the other is a hydroxyl group (hereafter abbreviated as "a bivalent reagent of thiol group and hydroxyl group"); a bivalent reagent in the case where both of the reactive group and the functional group are amino groups (hereafter abbreviated as "a bivalent reagent of amino group and amino group"); a bivalent reagent in the case where both of the reactive group and the functional group are thiol groups (hereafter abbreviated as "a bivalent reagent of thiol group and thiol group"); or the like.

A specific example of the bivalent reagent of amino group and thiol group, includes, for example, N-α-maleimideacetoxy)succinimide, N-[γ-maleimidebutyryloxy]succinimide, N-(6-maleimidecaproyloxy)succinimide, N-(8-maleimidecapryloxy)succinimide, N-(11-maleimideundecanoyloxy) succinimide, m-maleimidebenzoyl-N-hydroxysuccinimide, succinimidyl 4-[p-maleimidephenyl]butyrate, succinimidyl 4-[N-maleimidemethyl]cyclohexane-1-carboxylate, succinimidyl 6-[β-maleimidepropionamide]hexanoate, N-succinimidyl 3-(2-pyridyldithio)propionate or the like.

A specific example of the bivalent reagent of amino group and carboxyl group, includes, for example, 3-[(2-aminoethyl) dithio]propionic acid hydrochloride, 1-ethyl-3-[3-dimethylaminopropyl]carbodiimide hydrochloride or the like.

A specific example of the bivalent reagent of thiol group and hydroxyl group, includes, for example, N-[p-maleimidephenyl] isocyanate or the like.

A specific example of the bivalent reagent of amino group and amino group, includes, for example, methyl N-succinimidyl adipate, disuccinimidyl glutarate, disuccinimidyl suberate, ethylene glycol bis[succinimidyl succinate], dithiobis [succinimidyl propionate], disuccinimidyl tartrate, bis[2-(succinimideoxycarbonyloxy)ethyl]sulfone, 1,5-difluoro-2,4-dinitrobenzene or the like.

A specific example of the bivalent reagent of thiol group and thiol group, includes, for example, bis-maleimideethane, 1,4-bis-maleimidebutane, bis-maleimidehexane, 1,4-bis-maleimidyl-2,3-dihydroxybutane, dithio-bis-maleimideethane, 1,6-hexane-bis-vinylsulfone, 1,8-bis-maleimide diethylene glycol, 1,11-bis-maleimidetriethylene glycol, 1,4-di-[3'-(2'-pyridyldithio)-propionamide]butane or the like.

2-3. Preparation of Labeled Nucleotide by Using a Compound of the Present Invention As a specific example of a method for labeling a substance to be labeled by using the compound [1] of the present invention, explanation will be given with reference to an example of the case of labeling nucleotide (a substance to be labeled).

That is, in the case of labeling nucleotide having an amino group on a base thereof (for example, cytidine, adenine, guanine or the like), the reactive group in the compound of the present invention may be directly bound, or the activated group of a reactive group of the compound of the present invention (reaction activation group) may be directly bound, and among them, it is preferable to be subjected to binding to an activated ester group or a carboxyl group, and particularly preferable to be subjected to binding to the activated ester group.

In addition, in the case where the compound of the present invention is subjected to indirect binding to nucleotide, first, on a base or a hydroxyl group of the nucleotide, a derivative introduced with a linker having a functional group such as amino group, carboxyl group and thiol group (hereafter abbreviated as "a nucleotide derivative") is synthesized, and then, in the case of subjecting, for example, to binding to the amino group in the nucleotide derivative, it may be subjected to binding to the activated ester group or carboxyl group in the compound of the present invention; in the case of subjecting to binding, for example, to the carboxyl group in the nucleotide derivative, it may be subjected to binding to the amino group in the compound of the present invention; and in the case of subjecting to binding, for example, to the thiol group in the nucleotide derivative, it may be subjected to binding to the maleimide group (reaction activation group) in the compound of the present invention. The linker to be used may be any one usually used in this field, and an ester bond, an ether bond and/or an amide bond may be contained in the linker.

Explanation will be given on a labeling method by using the compound [1] of the present invention, with reference to an example of one, among compounds of the present invention, where a carboxyalkyl group contained in $R^1$ (that is, it corresponds to the case where $R^1$ is an alkyl group having as a substituent the group represented by the general formula [2]) is indirectly bound to a nucleotide residue, via a linker or the like.

In the above case, as a linker, there can be used all of those that are used in this field, and specifically, there is included a linker with a structure represented by the following general formula (A):

-E-X-T10-Y—NH— (A)

(wherein E represents —CH═CH— or —C≡C—; X and Y each independently represent alkylene group; and T10 represents —O— or —NH—CO—).

In the general formula (A), the alkylene group represented by X may be any of straight-chained, branched and cyclic one, and preferably straight-chained one, and includes one having usually $C_1$ to $C_{10}$, preferably $C_1$ to $C_6$, more preferably $C_1$ to $C_3$, and specifically, straight-chained alkylene group such as methylene group, ethylene group, trimethylene group, tetramethylene group, pentamethylene group, hexamethylene group, heptamethylene group, octamethylene group, nonamethylene group and decamethylene group; branched alkylene group such as ethylidene group, propylene group, isopropylidene group, 1-methyltrimethylene group, 2-methyltrimethylene group, 1,1-dimethylethylene group, 1,2-dimethylethylene group, ethylethylene group, 1-methyltetramethylene group, 1,1-dimethyltrimethylene group, 2,2-dimethyltrimethylene group, 2-ethyltrimethylene group, 1-methylpentamethylene group, 1-methylhexamethylene group, 1-methylheptamethylene group, 1,4-diethyltetramethylene group, 2,4-dimethylheptamethylene group, 1-methyloctamethylene group and 1-methylnonamethylene group; cyclic alkylene group such as cyclopropylene group, 1,3-cyclobutylene group, 1,3-cyclopentylene group, 1,4-cyclohexylene group, 1,5-cycloheptylene group, 1,5-cyclooctylene group, 1,5-cyclononylene group and 1,6-cyclodecalene group; or the like.

The alkylene group represented by Y may be any of straight-chained, branched and cyclic one, and preferably straight-chained one, and includes one having usually $C_1$ to $C_{10}$, preferably $C_2$ to $C_8$, more preferably $C_2$ to $C_6$, and specifically, for example, straight-chained alkylene group such as methylene group, ethylene group, trimethylene group, tetramethylene group, pentamethylene group, hexamethylene group, heptamethylene group, octamethylene group, nonamethylene group and decamethylene group; branched alkylene group such as ethylidene group, propylene group, isopropylidene group, 1-methyltrimethylene group, 2-methyltrimethylene group, 1,1-dimethylethylene group, 1,2-dimethylethylene group, ethylethylene group, 1-methyltetramethylene group, 1,1-dimethyltrimethylene group, 2,2-dimethyltrimethylene group, 2-ethyltrimethylene group, 1-methylpentamethylene group, 1-methylhexamethylene group, 1-methylheptamethylene group, 1,4-diethyltetramethylene group, 2,4-dimethylheptamethylene group, 1-methyloctamethylene group and 1-methylnonamethylene group; cyclic alkylene group such as cyclopropylene group, 1,3-cyclobutylene group, 1,3-cyclopentylene group, 1,4-cyclohexylene group, 1,5-cycloheptylene group, 1,5-cyclooctylene group, 1,5-cyclononylene group and 1,6-cyclodecalene group; or the like.

The labeled nucleotide relevant to the present invention, includes a nucleotide residue labeled with the compound [1] of the present invention, directly or indirectly via linker or the like, and specifically, for example, a nucleotide residue represented by the following general formula [22]:

Q1-V1-W1 [22]

[wherein Q1 represents a nucleotide residue; V1 represents a linker; and W1 represents the following general formula [1']:]

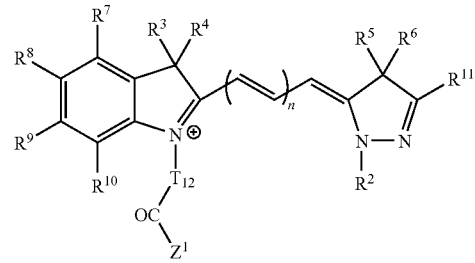

(wherein $Z^1$ represents a linking moiety for binding to V1; and $R^2$ to $R^{11}$, $T_{12}$ and n are the same as above).

It should be noted that the compound represented by the general formula [1'] corresponds to a compound derivative in the case where, among compounds represented by the general formula [1], $R^1$ is an alkyl group having as a substituent the group represented by the general formula [2] (that is, it corresponds to a -$T_{12}$-COOR$^{12}$ group).

The nucleotide residue represented by Q1 in the general formula [22], includes, for example, ribonucleotide residue, 2'-deoxyribonucleotide residue, 3'-deoxyribonucleotide residue, 5'-deoxyribonucleotide residue, 2',3'-dideoxyribonucleotide residue or the like.

Specifically, such a nucleotide residue includes, for example, purinenucleotide residue represented by the general formula (I), (ii), (v), (vi), (vii), (viii), (xii) and (viii), or pyrimidine nucleotide residue represented by the general formula (iii), (iv), (x) and (xi).

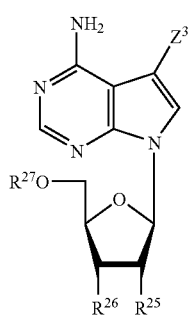

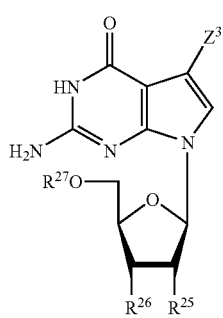

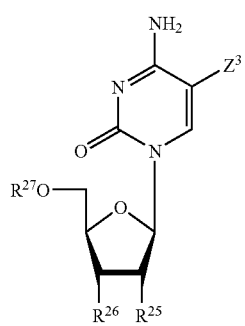
(iii)
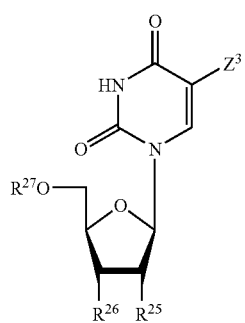
(iv)
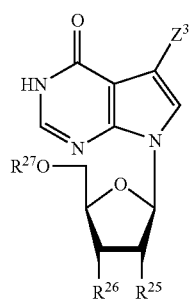
(v)
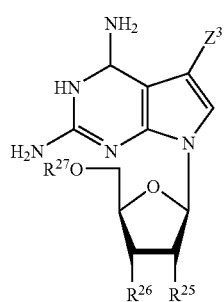
(vi)
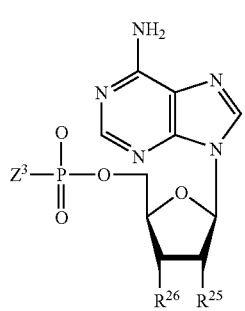
(vii)
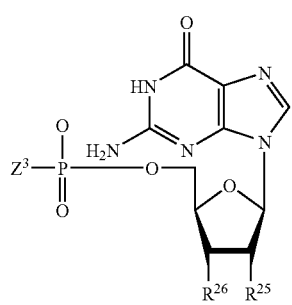
(viii)
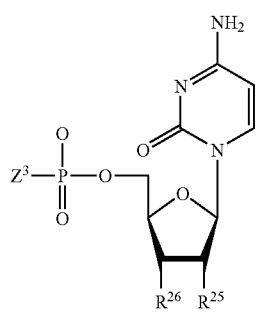
(ix)
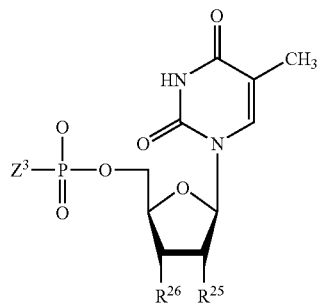
(x)
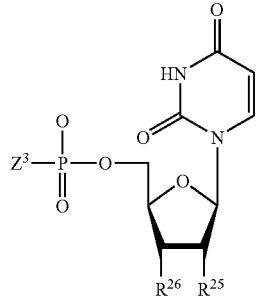
(xi)
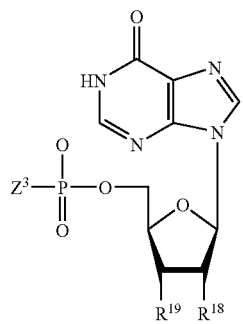
(xii)

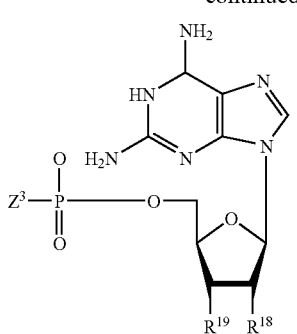

(xiii)

In the above general formula, $Z^3$ represents a linker for binding to V1; $R^2$ and $R^{26}$ each independently represent H, OH or O—; $R^{27}$ represents —$PO_2H$—, $PO_3H_2$—, —$P_2O_6H_3$, —$P_3O_9H_4$, or a salt thereof. It should be noted that a specific example of the salt includes, an alkali metal salt such as sodium salt, potassium salt and lithium salt; an alkaline earth salt such as barium salt; ammonium salt; an organic amine salt such as triethylammonium salt and pyridine salt.

The linker represented by V1 in the general formula [22] is a linker for bonding the nucleotide residue represented by Q1 and the compound derivative (fluorescent labeling) of the present invention represented by W1 [the general formula [1']].

That is, as for a pyrimidine nucleotide residue, among nucleotide residues represented by the above Q1, one terminal of the linker is bound to 5 position of a pyrimidine ring thereof [in the case of the general formulae (iii) and (iv)], or to a phosphorus atom in a phosphate residue thereof [in the case of the general formulae (x) and (xi)]; and as for a purine nucleotide residue, it is bound to 7 position of a 7-deaza (7-deaza) purine ring thereof [in the case of the general formulae (i), (ii), (v), and (vi)], or to a phosphorous atom of the phosphate residue of a purine ring thereof (or a 7-deazapurine ring) [in the case of the general formulae (vii), (viii), (ix), (xii) and (xiii)].

Still more, the other terminal of the linker is bound to a carbonyl group [a carbonyl group binding to $T_{12}$ in the general formula [1']] of the compound derivative (labeling substance) of the present invention, represented by W1 [the general formula [1']].

As such a linker, there can be used all of those that are capable of bonding a carbonyl group [a carbonyl group binding to $T_{12}$ in the general formula [1']] of the compound derivative (labeling substance) of the present invention represented by W1 [the general formula [1']], and the nucleotide residue represented by Q1, and specifically includes a linker with a structure represented by the following general formula (A):

-E-X-T10-Y—NH— (A)

(wherein E, X, T10 and Y are the same as above, and specific examples and preferable examples thereof and the like are also as described above).

Therefore, as the nucleotide residue represented by the general formula [22], one each represented by the following general formula [22'] is preferable, and one represented by the following general formula [22''] is more preferable:

Q1-E-X1-T11-Y1-NH—W1 [22']

(wherein E1 represents —CH=CH— or —C≡C—; X1 and Y1 each independently represent alkylene group; T11 represents —O— or —NH—CO—; and in addition, Q1 and W1 are the same as above).

It should be noted that, in the above description, the alkylene group represented by X1 is the same as the alkylene group represented by the above X, and specific examples and preferable examples thereof and the like are also similar. In addition, the alkylene group represented by Y1 is the same as the alkylene group represented by the above Y, and specific examples and preferable examples thereof and the like are also similar.

Q1-E-($CH_2$)$_r$-T11-($CH_2$)$_s$—NH—W1 [22'']

(wherein r represents an integer of from 1 to 10, preferably from 1 to 6, more preferably from 1 to 4; s represents an integer of from 1 to 10, preferably from 2 to 8, more preferably from 2 to 4; and in addition, Q1, W1, E1 and T11 are the same as above).

In addition, $R^1$ to $R^{11}$ are the same as above, and specific examples and preferable examples thereof and the like are also as described above.

Such a compound derivative (labeling substance) of the present invention represented by W1 [the general formula [1']] is one derived from the compound [1] of the present invention as described above, and specific examples and preferable examples thereof and the like are also similar to the compound [1] of the present invention as described above.

As a method for labeling the above described nucleotide with the compound [1] (labeling substance) relevant to the present invention, includes a direct labeling method or an indirect labeling method, known itself, [for example, a method described in WO96/17628 pamphlet (JP-A-2002-12782), U.S. Pat. No. 6,974,873, JP-A-2002-193991, WO99/12544 pamphlet, JP-A-11-80189 or the like]

In addition, in labeling the nucleotide with the compound [1] (labeling substance) relevant to the present invention, it is simpler and more convenient to use a commercially available standard labeling kit relative to the labeling method as described above, except for using the compound [1] relevant to the present invention.

It should be noted that in utilizing these methods in the present invention, it is required a labeled nucleotide bound to the compound [1] (labeling substance) relevant to the present invention, and, the labeled nucleotide can be prepared by a known method itself (for example, the above labeling method or the like).

Specifically, it can be prepared in accordance with a method described in, for example, JP-A-2002-193991 (paragraphs from to [0121]), and also can be prepared as follows:

That is, it can be obtained easily, for example, by subjecting a nucleotide derivative represented by the following general formula (a) to a reaction with the compound [1] represented by the following general formula (b) (labeling substance) [a succinimidyl ester substance] relevant to the present invention Q-E-X-T10-Y1-$NH_2$ (a)

(wherein Q represents Q1; and Q1, E, X, T10 and Y are the same a above).

W—OSu (b)

(wherein W represents W1; Su represents a succinimide group; and W1 is the same a above).

In addition, in the case where T10 of the linker part represented by the general formula (a), as described above, is —NH—CO—, it can be prepared, for example, as follows:

That is, for example, first a part of a linker (a partial linker A) represented by the following general formula (c) is introduced, and subjected further to a reaction with the succinimidyl ester substance of the remaining linker part (a partial linker B) to prepare a nucleotide derivative represented by the following general formula (d), which is introduced with the linker. Still more, it can be obtained easily by subjecting the nucleotide derivative represented by the following general formula (d) to a reaction with the compound [1] (labeling substance) [the succinimidyl ester substance] of the present invention represented by the following general formula (b).

-E-X—NH$_2$ (c)

(wherein E and X are the same as above).

Q-E-X—NH—CO—Y1-NH$_2$ (d)

(wherein Q, E, X and Y are the same as above).

W—OSu (b)

(wherein W and Su are the same as above).

More specifically, among the labeled mononucleotides bound to the compound [1] (labeling substance) of the present invention as above, a fluorescent labeling, 2'-deoxycytidine-5'-triphophate derivative and a fluorescent labeling, 2'-deoxyuridine-5'-triphosphate derivative can be synthesized, for example, according to the following synthesis route.

It should be noted that abbreviated formal names used in the following synthesis route are as follows;
MeOTfa: methyl trifluoroacetate
-Tfa: trifluoroacetyl group
Bu$_3$SnH: tri(n-butyl)tin hydride
AIBN: azobisisobutyronitrile
Et$_3$N: triethylamine
HO-Su: N-hydroxysuccinimide
DMF: N,N-dimethylformamide
TMS-Acetamide: N,O-bis(trimethylsilyl)acetamide
PdCl$_2$(CH$_3$CN)$_2$: bis(acetonitrile)dichloropalladium(II)
tris(TBAPP): tris(tri-n-butylammonium) pyrophosphate
(EtO)$_3$PO: triethyl phosphate
TFP: tri-2-furylphosphine
Pd$_2$(dba)$_3$: tris(dibenzylideneacetone)dipalladium(0)

(1) Synthesis of the Partial Linker (A)

It should be noted that this compound is a compound corresponding to -E-X—NH— in the case where T10 is —NH—CO—, in the linker (-E-X-T10-Y—NH—) represented by the above general formula (A), and a compound where E is —CH=CH— and X is a methylene group.

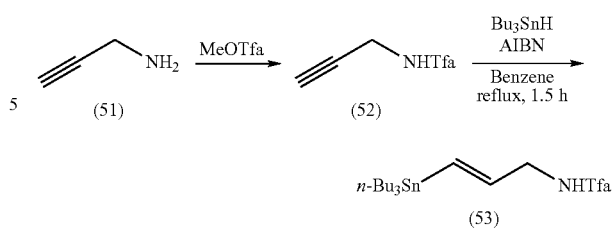

(2) Synthesis of the Partial Linker (B)

It should be noted that this compound is a compound corresponding to —CO—Y—NH— in the case where T10 is —NH—CO—, in the linker (-E-X-T10-Y—NH—) represented by the above general formula (A), and a compound where Y is a pentamethylene group.

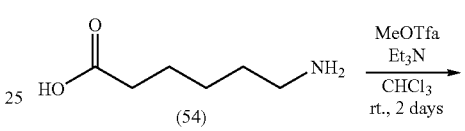

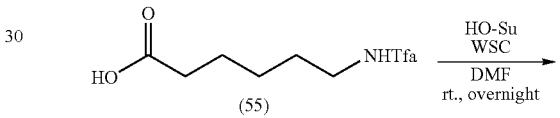

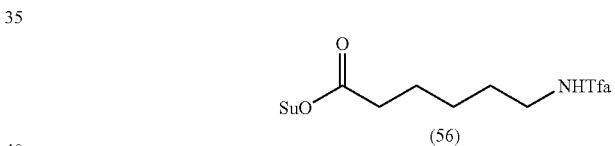

(3) Synthesis of a 2'-deoxycytidine-5'-triphosphate Derivative [a Compound of the General Formula (d)]

It should be noted that this compound is a compound corresponding to Q1-E1-X1-T11-Y1-NH— of the general formula [22'] (Q1-E1-X1-T11-Y1-NH—W1), and a compound where Q1 is 2'-deoxycytidine, E1 is —CH=CH—, X1 is a methylene group, T11 is —NH—CO—, and Y1 is a pentamethylene group.

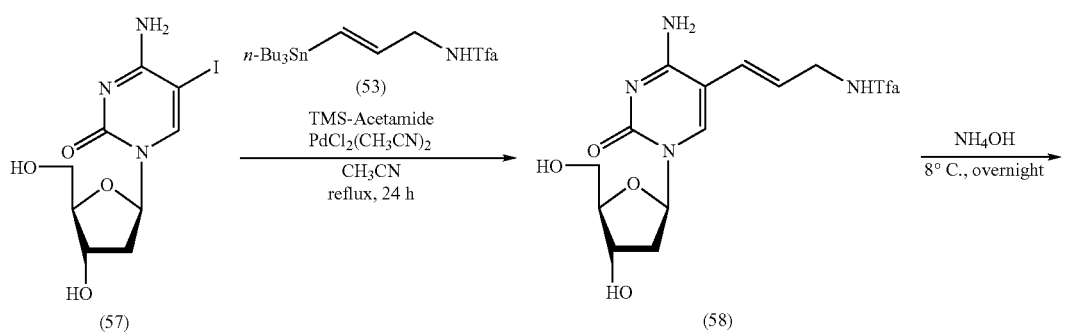

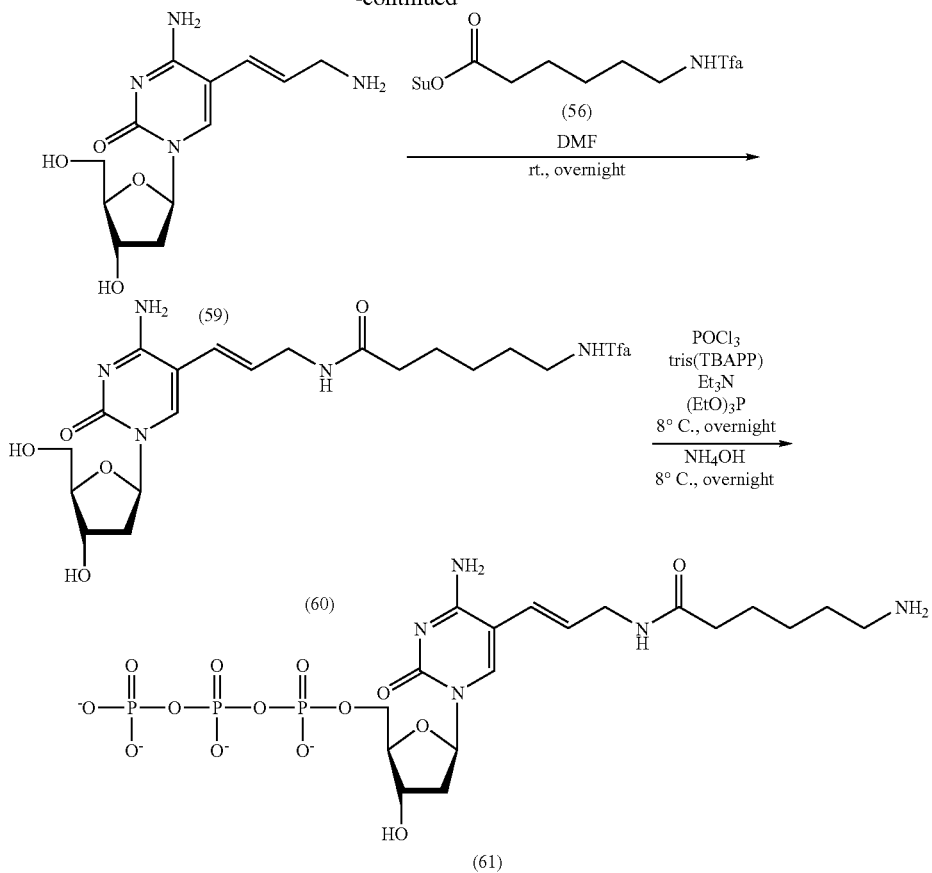

(4) Synthesis of a Fluorescent Labeling, a 2'-deoxycytidine-5'-triphosphate Derivative (Mononucleotide Labeled with the Compound [1] (a Labeling Substance) of the Present Invention)

It should be noted that this compound is a compound, in the general formula [22'] (Q1-X1-T11-Y1-NH—W1), where Q1 is 2'-deoxycytidine, E1 is —CH═CH—, X1 is a methylene group, T11 is —NH—CO—, Y1 is a pentamethylene group and W1 is the following compound (14) or (25):

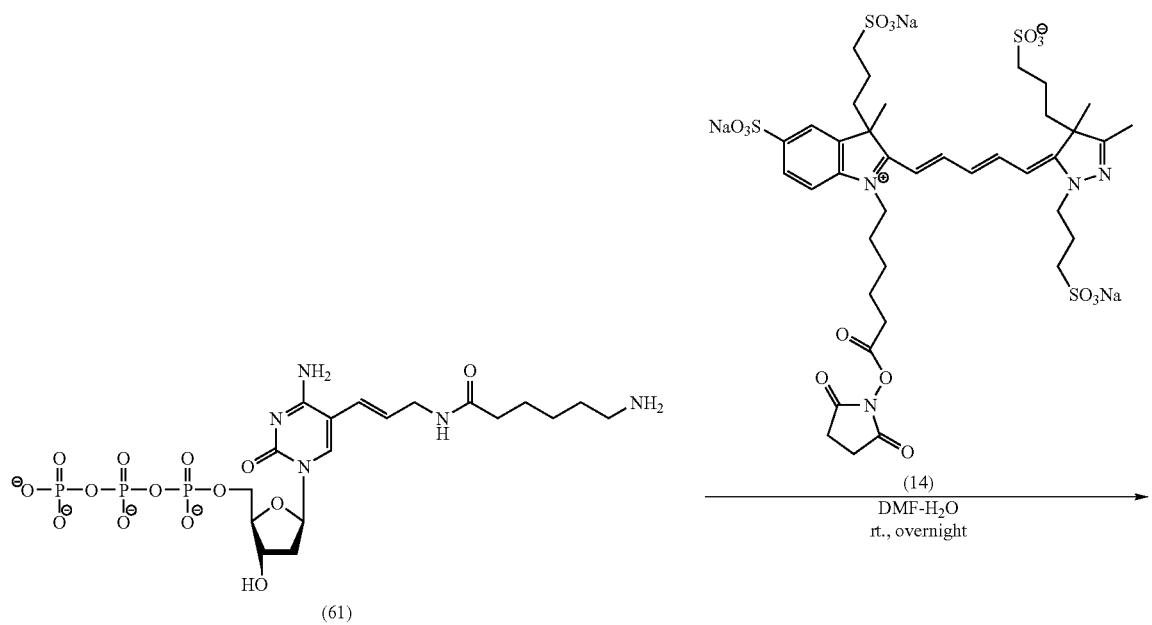

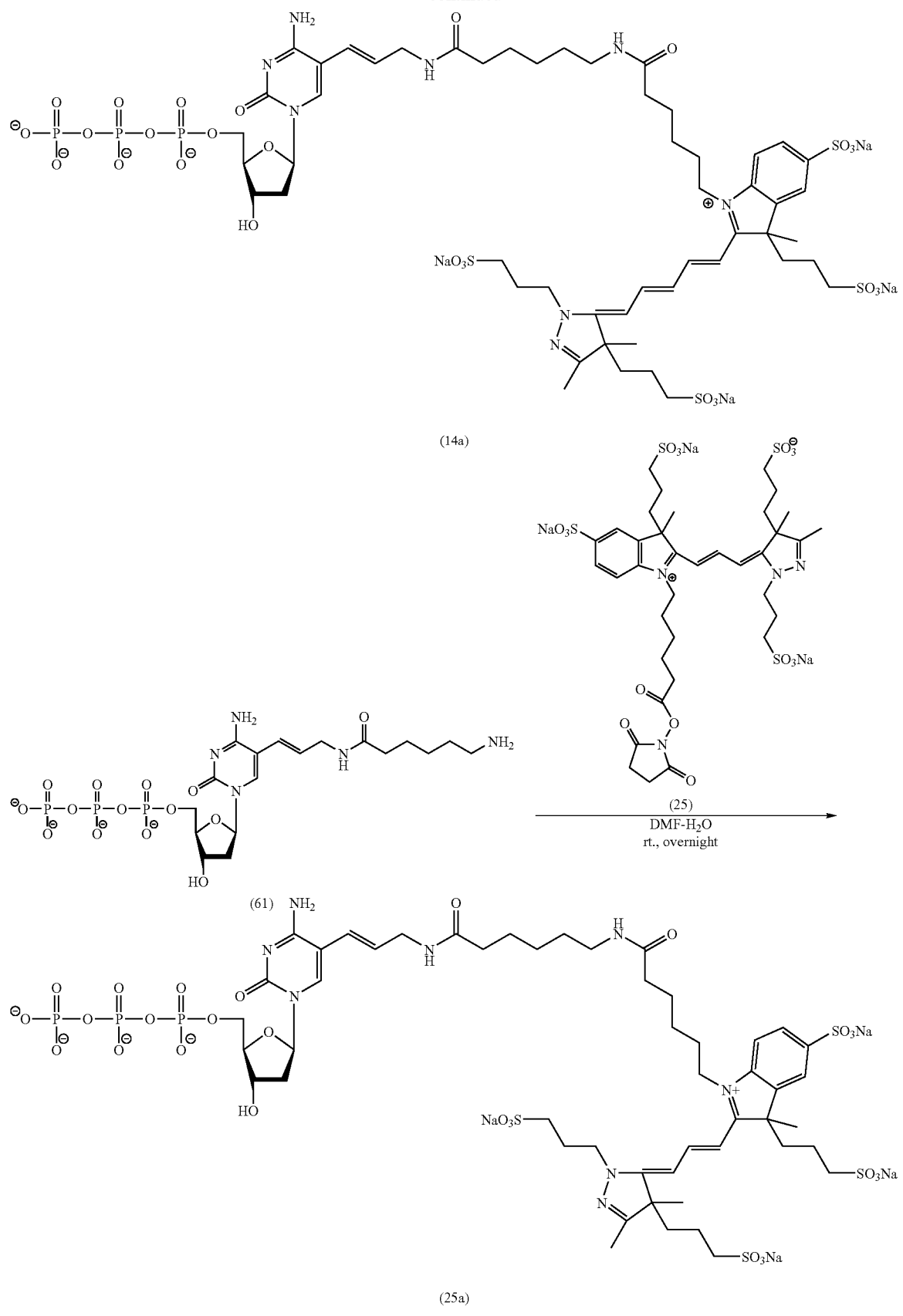

It should be noted that similarly in a labeled nucleotide other than the above also, it can be synthesized as appropriate in accordance with the above, by using corresponding raw materials.

Because a pyrazole-based cyanine dye of the present invention has a structure where a pyrazole skeleton and an indole skeleton are bound to a polymethine chain, and exerts fluorescence characteristics in sorter wavelength region as compared with a conventional light source, it becomes possible to use a light source of a short wavelength region with high energy efficiency. In addition, in the case where a measurement object is detected by using this as a labeling agent (a labeling substance), it becomes possible to detect the measurement object in high detection sensitivity, without having problems such as low water-solubility and reduced detection sensitivity by optical quenching caused by aggregation of dyes themselves and the like, which a conventional cyanine dye derivative had.

3-1. The Compound [51] of the Present Invention

Among compounds represented by the general formula [50], a compound, where any of $R^{1'}$ and $R^{2'}$, $R^{4'}$ and $R^{5'}$, $R^{1'}$ and $R^{6'}$, and $R^{2'}$ and $R^{4'}$ form a bivalent group with a group selected from —O— group, —S— group, —COO— group and groups represented by the general formulae [52] to [54], and substituted or unsubstituted alkylene group includes, for example, one represented by the following general formula [51]:

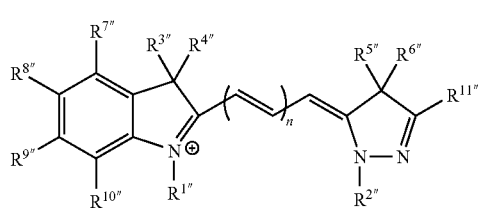

[51]

[wherein $R^{1''}$ to $R^{6''}$ each independently represent a substituted or unsubstituted alkyl group which may have an amide bond; $R^{7''}$ to $R^{10''}$ each independently represent alkyl group, alkenyl group, alkynyl group, aryl group, alkoxy group, aryloxy group, alkylthio group, arylthio group, alkylsulfonyl group, arylsulfonyl group, carbamoyl group, sulfamoyl group, ureido group or amino group, those groups being able to have substituents; the group represented by the general formula [2]:

—COOR$^{12}$ [2]

(wherein $R^{12}$ represents hydrogen atom, $C_1$ to $C_{10}$ alkyl group, alkali metal atom, organic ammonium ion, ammonium ion or anion); the group represented by the general formula [3]:

—SO$_3$R$^{13}$ [3]

(wherein $R^{13}$ represents hydrogen atom, alkali metal atom, organic ammonium ion, ammonium ion or anion), halogen atom, aromatic heterocyclic thio group, hydrogen atom, hydroxyl group, cyano group, formyl group, thiol group or nitro group; $R^{11''}$ represents hydrogen atom, or alkyl group, alkenyl group, alkynyl group or aryl group, those groups being able to have substituents; and n represents an integer of from 0 to 3, provided that any of $R^{1''}$ and $R^{2''}$, $R^{4''}$ and $R^{5''}$, $R^{1''}$ and $R^{6''}$, and $R^{2''}$ and $R^{4''}$ form a bivalent group with a group selected from —O— group, —S— group, —COO— group, and the groups represented by the general formulae [52] to [54]:

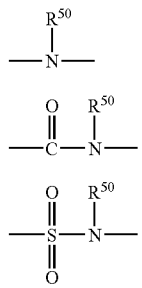

(wherein $R^{50}$ represents hydrogen atom, or alkyl group, alkenyl group or aryl group, those groups being able to have substituents), and substituted or unsubstituted alkylene group: In addition, at least one of $R^{1''}$ to $R^{11''}$, along with the bivalent group formed by any of $R^{1''}$ and $R^{2''}$, $R^{4''}$ and $R^{5''}$, $R^{1''}$ and $R^{6''}$, and $R^{2''}$ and $R^{4''}$, has the group represented by the general formula [2], the group represented by the general formula [3], amino group, hydroxyl group, thiol group or formyl group].

In the general formula [51], any of $R^{1''}$ and $R^{2''}$, $R^{4''}$ and $R^{5''}$, $R^{1''}$ and $R^{6''}$, and $R^{2''}$ and $R^{4''}$ form a bivalent group with a group selected from —O— group, —S— group, —COO— group, and the groups represented by the general formulae [52] to [54]:

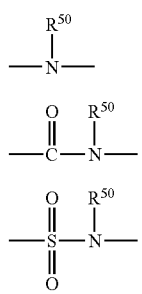

(wherein $R^{50}$ represents hydrogen atom, or alkyl group, alkenyl group or aryl group, those groups being able to have substituents), and substituted or unsubstituted alkylene group, and such a compound represented by the general formula [51], includes, for example, compounds represented by the general formulae [55] to [58]:

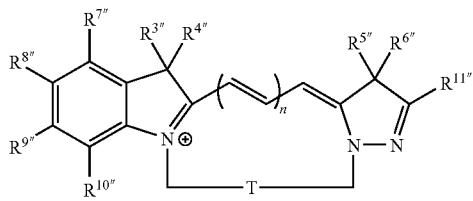

[55]

(wherein T forms a bivalent group with a group selected from —O— group, —S— group, —COO— group and the groups represented by the general formulae [4] to [6], and substituted or unsubstituted alkylene group; and $R^{3'}$ to $R^{11''}$ and n are the same as above, provided that at least one of $R^{3'}$ to $R^{11''}$ along with the bivalent group, represented by T has the group represented by the general formula [2], the group represented by the general formula [3], amino group, hydroxyl group, thiol group or formyl group).

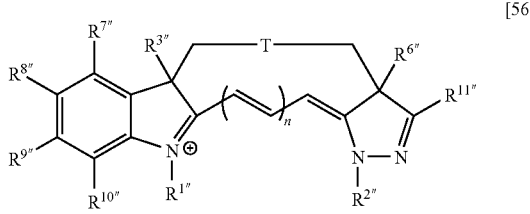

[56]

(wherein $R^{1''}$ to $R^{3''}$, $R^{6''}$ to $R^{11''}$, T and n are the same as above, provided that at least one of $R^{1''}$ to $R^{3''}$, $R^{6''}$ to $R^{11''}$, along with the bivalent group, represented by T, has the group represented by the general formula [2], the group represented by the general formula [3], amino group, hydroxyl group, thiol group or formyl group).

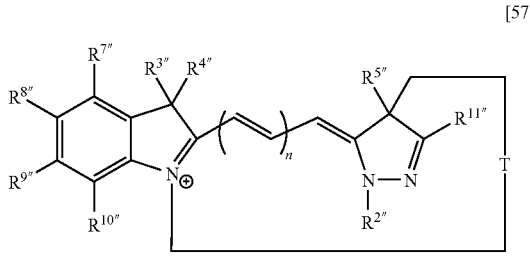

[57]

(wherein $R^{2''}$ to $R^{5''}$, $R^{7''}$ to $R^{11''}$, T and n are the same as above, provided that at least one of $R^{2''}$ to $R^{5''}$, $R^{7''}$ to $R^{11''}$, along the bivalent group represented by T, has the group represented by the general formula [2], the group represented by the general formula [3], amino group, hydroxyl group, thiol group or formyl group).

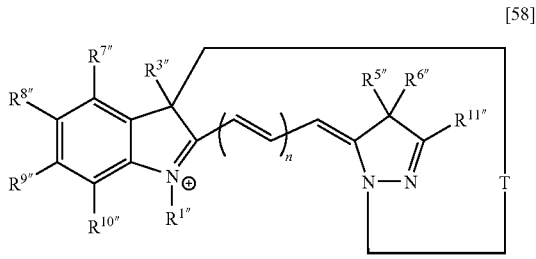

[58]

(wherein $R^{1''}$, $R^{3''}$, $R^{5''}$ to $R^{11''}$, T and n are the same as above, provided that at least one of $R^{1''}$, $R^{3''}$, $R^{5''}$ to $R^{11''}$, along with the bivalent group represented by T has the group represented by the general formula [2], the group represented by the general formula [3], amino group, hydroxyl group, thiol group or formyl group).

Among these compounds, for example, the compound represented by the general formula [55], the compound represented by the general formula [57] or the like is preferable.

In the general formulae [51] and [55] to [58], n represents an integer of usually from 0 to 3, preferably 1 or 2 and more preferably 2.

The alkyl group of the substituted or unsubstituted alkyl group, which may have the amide bond, represented by $R^{1''}$ to $R^{6''}$, in the general formulae [51] and [55] to [58], may be any of straight-chained, branched and cyclic one, and includes one having usually $C_1$ to $C_{10}$, preferably $C_1$ to $C_5$, and specifically, for example methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like: among these, for example, a straight-chained one is preferable, in particular, for example, methyl group, ethyl group, n-propyl group, n-butyl group, n-pentyl group or the like is preferable.

The substituted or unsubstituted alkyl group, which may have the amide bond, represented by $R^{1''}$ to $R^{6''}$, may includes a substituted or unsubstituted alkyl group not having an amide bond, or one having amide bonds in an amount of usually from 1 to 10, preferably from 1 to 3, and more preferably 1, in an alkyl chain of the substituted or unsubstituted alkyl group.

A preferable specific example of the unsubstituted alkyl group which may have an amide bond, includes, for example, a group represented by the following general formula [59]:

(wherein $R^{21}$ represents a hydrogen atom or an alkyl group; $T_1$ and m pieces of $T_2$s represent alkylene groups; and m represents an integer of from 0 to 10).

The alkyl group represented by $R^{21}$, in the general formula [51], may be any of straight-chained, branched and cyclic one, and includes one having usually $C_1$ to $C_{10}$, preferably $C_1$ to $C_6$, and specifically, for example methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The alkylene groups represented by $T_1$ and m pieces of $T_2$s, may be any of straight-chained, branched and cyclic one, and includes one having usually $C_2$ to $C_{10}$, preferably $C_2$ to $C_8$, and specifically, straight-chained alkylene group such as methylene group, ethylene group, trimethylene group, tetramethylene group, pentamethylene group, hexamethylene group, heptamethylene group, octamethylene group, nonamethylene group and decamethylene group; branched alkylene group such as ethylidene group, propylene group, isopropylidene group, 1-methyltrimethylene group, 2-methyltrimethylene group, 1,1-dimethylethylene group, 1,2-dimethylethylene group, ethylethylene group, 1-methyltetramethylene group, 1,1-dimethyltrimethylene group, 2,2-dimethyltrimethylene group, 2-ethyltrimethylene group, 1-methylpentamethylene group, 2-methylpentamethylene group, 1,3-dimethyltetramethylene group, 3-ethyltetramethylene group, 1-methylhexamethylene group, 1-methylheptamethylene group, 1,4-diethyltetramethylene group, 2,4-dimethylheptamethylene group, 1-methyloctamethylene group and 1-methylnonamethylene group; cyclic alkylene group such as cyclopropylene group, 1,3-cyclobutylene group, 1,3-cyclopentylene group, 1,4-cyclohexylene group, 1,5-cycloheptylene group, 1,5-cyclooctylene group, 1,5-cyclononylene group and 1,6-cyclodecalene group; or the like.

"m" represents an integer of usually from 0 to 10, preferably an integer of from 0 to 3, more preferably 0 or 1.

In the general formulae [51] and [55] to [58], the substituent of the substituted alkyl group, which may have the amide bond, represented by $R^{1'''}$ to $R^{6'''}$, includes one where a part of hydrogen atoms in the alkyl group which may have the amide bond, is substituted with a substituent, and the substituent, includes, for example, the group represented by the general formula [2], the group represented by the general formula [3], hydroxyl group, cyano group, formyl group, thiol group or the like, and among these, the group represented by the general formula [2], or the group represented by the general formula [3], is preferable.

The substituted alkyl group which has the amide bond, represented by $R^{1'''}$ to $R^{6'''}$, includes preferably one where a part of hydrogen atoms, in an unsubstituted alkyl group having an amide bond, represented by the above general formula [59], is substituted with the group represented by the above general formula [2], or the group represented by the general formula [3].

In the general formula [2] and [3], the alkali metal atom represented by $R^{12}$ and $R^{13}$, includes, for example, lithium atom, sodium atom, potassium atom, rubidium atom or the like, and among these, sodium atom or potassium atom is preferable, and in particular, sodium atom is more preferable.

The organic ammonium ion represented by $R^{12}$ and $R^{13}$, includes for example, a trialylammonium ion or the like. The trialylammonium ion may be any of straight-chained, branched and cyclic one, and includes one having usually $C_1$ to $C_{10}$, preferably $C_1$ to $C_6$, and specifically, for example, trimethylammonium ion, triethylammonium ion, tri-n-propylammonium ion, triisopropylammonium ion, tributylammonium ion, tripentylammonium ion, trihexylammonium ion, triheptylammonium ion, trioctylammonium ion, trinonylammonium ion, tridecylammonium ion, tricyclopropylammonium ion, tricyclobutylammonium ion, tricyclopentylammonium ion, tricyclohexylammonium ion, tricycloheptylammonium ion, tricyclooctylammonium ion, tricyclononylammonium ion, tricyclodecylammonium ion or the like, and among these, trimethylammonium ion or triethylammonium ion is preferable, and in particular, triethylammonium ion is more preferable.

In the general formula [2], the $C_1$ to $C_{10}$ alkyl group represented by $R^{12}$, may be any of straight-chained, branched and cyclic one, and includes one having usually $C_1$ to $C_{10}$, preferably $C_1$ to $C_6$, more preferably $C_1$ to $C_3$, and specifically, for example methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

A preferable specific example of the group represented by the general formula [2], includes, for example, a carboxyl group (—COOH), an anion thereof [a carboxylate (—COO⁻)], an alkali metal salt thereof (for example, lithium salt, sodium salt, potassium salt, rubidium salt or the like), an ammonium salt thereof, an organic ammonium salt thereof (for example, trimethylammonium salt, triethylammonium salt, tripropylammonium salt,) or the like, and among these, for example, the carboxyl group, the carboxylate group and the sodium salt thereof or the like are preferable. Hereinafter they may be abbreviated as "a carboxyl group or the like" as a general name.

A preferable specific example of the group represented by the general formula [3], includes, for example, a sulfo group (—SO₃H), an anion thereof [a sulfonate (—SO₃⁻)], an alkali metal salt thereof (for example, lithium salt, sodium salt, potassium salt, rubidium salt or the like), an ammonium salt thereof, an organic ammonium salt thereof (for example, trimethylammonium salt, triethylammonium salt, tripropylammonium salt,) or the like, and among these, the sulfo group, the sulfonate group and the sodium salt thereof or the like are preferable. Hereinafter they may be abbreviated "a sulfo group or the like" as a general name.

It should be noted that the substituent of the substituted alkyl group, which may have the amide bond, represented by $R^{1'''}$ to $R^{6'''}$ in the general formulae [51] and [55] to [58], (that is the group represented by the general formula [2], the group represented by the general formula [3], hydroxyl group, cyano group, formyl group, or thiol group), is preferably substituted with a terminal hydrogen atom of the alkyl group.

A preferable specific example of $R^{1'''}$ and $R^{2'''}$ in the general formulae [51] and [56] to [58], includes, for example, one where a terminal hydrogen atom of a $C_1$ to $C_6$ straight-chained alkyl group such as for example, methyl group, ethyl group, n-propyl group, n-butyl group, n-pentyl group and n-hexyl group, is substituted with the above substituent (that is the group represented by the general formula [2], the group represented by the general formula [3], hydroxyl group, cyano group, formyl group, or thiol group), and among these, one substituted with the group represented by the general formula [2], or the group represented by the general formula [3] is preferable.

In addition, As for a preferable combination of $R^{3'''}$ and $R^{4'''}$, and/or a preferable combination of $R^{5'''}$ and $R^{6'''}$, in the general formulae [51], [55], [57] and [58], it is preferable that either of them (that is, either of $R^{3'''}$ and $R^{4'''}$, and either of $R^{5'''}$ and $R^{6'}$) is a $C_1$ to $C_6$ alkyl group (for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, or the like), and the other is a $C_1$ to $C_6$ alkyl group having as a substituent the group represented by the general formula [2], the group represented by the general formula [3], hydroxyl group, cyano group, formyl group, or thiol group, (among these, one having as a substituent the group represented by the general formula [2], or the group represented by the general formula [3], is preferable).

Still more, in the case where either of $R^{3'''}$ and $R^{4'''}$, or $R^{5'''}$ and $R^{6'''}$ in the general formulae [51], [56] to [58] forms a bivalent group represented by T, it is preferable that the other (that is $R^{3'''}$ and $R^{6'''}$ in the general formula [56], $R^5$ in the general formula [57], $R^{3'''}$ in the general formula [58]) is a $C_1$ to $C_6$ alkyl group (for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group or the like).

The alkyl group of the substituted or unsubstituted alkyl group represented by $R^{7'''}$ to $R^{10'''}$ in the general formulae [51], [55] to [58], may be any of straight-chained, branched and cyclic one, and includes one having usually $C_1$ to $C_6$, preferably $C_1$ to $C_3$, and specifically, for example methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, cyclopropyl group, cyclobutyl group, cyclopentyl group, cyclohexyl group or the like.

The alkenyl group of the substituted or unsubstituted alkenyl group represented by $R^{7'''}$ to $R^{10'''}$, may be any of straight-chained, branched and cyclic one, and includes one having usually $C_2$ to $C_6$, preferably $C_2$ to $C_4$, and specifically, for example, vinyl group, allyl group, 1-propenyl group, isopropenyl group, 3-butenyl group, 2-butenyl group, 1-butenyl group, 1,3-butadienyl group, 4-pentenyl group, 3-pentenyl group, 2-pentenyl group, 1-pentenyl group, 1,3-pentadienyl group, 2,4-pentadienyl group, 1,1-dimethyl-2-propenyl group, 1-ethyl-2-propenyl group, 1,2-dimethyl-1-propenyl group, 1-methyl-1-butenyl group, 5-hexenyl group, 4-hexenyl group, 3-hexenyl group, 2-hexenyl group, 1-hexenyl group, 1-cyclopropenyl group, 2-cyclopentenyl group, 2,4-cyclopentadienyl group, 1-cyclohexenyl group, 2-cyclohexenyl group, 3-cyclohexenyl group or the like.

The alkynyl group of the substituted or unsubstituted alkynyl group represented by $R^{7'''}$ to $R^{10'''}$, includes one having usually $C_2$ to $C_6$, preferably $C_2$ to $C_4$, and specifically, for example, ethynyl group, 2-propynyl group, 3-butynyl group, 1-methyl-2-propynyl group, 4-pentynyl group, 2-methyl-4-pentynyl group, 5-hexynyl group or the like.

The aryl group of the substituted or unsubstituted aryl group represented by $R^{7'''}$ to $R^{10'''}$, includes one having usually $C_6$ to $C_{10}$, and specifically, for example, phenyl group, naphthyl group or the like.

The alkoxy group of the substituted or unsubstituted alkoxy group represented by $R^{7'''}$ to $R^{10'''}$ may be any of straight-chained, branched and cyclic one, and includes one having usually $C_1$ to $C_6$, preferably $C_1$ to $C_3$, and specifically, for example, methoxy group, ethoxy group, n-propoxy group, isopropoxy group, n-butoxy group, isobutoxy group, sec-butoxy group, tert-butoxy group, n-pentyloxy group, isopentyloxy group, sec-pentyloxy group, tert-pentyloxy group, neopentyloxy group, n-hexyloxy group, isohexyloxy group, sec-hexyloxy group, tert-hexyloxy group, neohexyloxy group, cyclopropoxy group, cyclopentyloxy group, cyclohexyloxy group or the like.

The aryloxy group of the substituted or unsubstituted aryloxy group represented by $R^{7'''}$ to $R^{10'''}$, includes one having usually $C_6$ to $C_{10}$, and specifically, for example, phenyloxy group, naphthyloxy group or the like.

The alkylthio group of the substituted or unsubstituted alkylthio group represented by $R^{7'''}$ to $R^{10'''}$, includes one where the oxygen atom of the alkoxy group is substituted with a sulfur atom, and may be any of straight-chained, branched and cyclic one may be adopted, and includes one having usually $C_1$ to $C_6$, preferably $C_1$ to $C_3$, and specifically, for example, methylthio group, ethylthio group, n-propylthio group, isopropylthio group, n-butylthio group, isobutylthio group, sec-butylthio group, tert-butylthio group, n-pentylthio group, isopentylthio group, sec-pentylthio group, tert-pentylthio group, neopentylthio group, n-hexylthio group, isohexylthio group, sec-hexylthio group, tert-hexylthio group, neohexylthio group, cyclopropylthio group, cyclobutylthio group, cyclopentylthio group, cyclohexylthio group or the like.

The arylthio group of the substituted or unsubstituted arylthio group represented by $R^{7'''}$ to $R^{10'''}$, includes one where the oxygen atom of the aryloxy group is substituted with a sulfur atom, and includes one having usually $C_6$ to $C_{10}$, and specifically, for example, phenylthio group, naphthylthio group or the like.

The alkylsulfonyl group of the substituted or unsubstituted alkylsulfonyl group represented by $R^{7'''}$ to $R^{10'''}$, includes one where the OH group of a sulfo group (—SO$_2$OH) is substituted with an alkyl group, and may be any of straight-chained, branched and cyclic one, and there is included one with usually $C_1$ to $C_6$, and specifically, for example, methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, sec-pentylsulfonyl group, tert-pentylsulfonyl group, neopentylsulfonyl group, n-hexylsulfonyl group, isohexylsulfonyl group, sec-hexylsulfonyl group, tert-hexylsulfonyl group, neohexylsulfonyl group, cyclopropylsulfonyl group, cyclobutylsulfonyl group, cyclopentylsulfonyl group, cyclohexylsulfonyl group or the like.

The arylsulfonyl group of the substituted or unsubstituted arylsulfonyl group represented by $R^{7'''}$ to $R^{10'''}$, includes one where the —OH group of a sulfo group (—SO$_2$OH) is substituted with an aryl group, and any of straight-chained, branched and cyclic one may be adopted, and includes one having usually $C_6$ to $C_{10}$, and specifically, for example, phenylsulfonyl group, naphthylsulfonyl group or the like.

The substituted carbamoyl group represented by $R^{7'''}$ to $R^{10'''}$, includes, for example, one where 1 to 2 hydrogen atoms of the carbamoyl group (—CONH$_2$) is substituted with a $C_1$ to $C_6$ alkyl group or a $C_6$ to $C_{10}$ aryl group, and specifically, for example, N-alkylcarbamoyl group such as N-methylcarbamoyl group, N-ethylcarbamoyl group, N-n-propylcarbamoyl group, N-isopropylcarbamoyl group, N-n-butylcarbamoyl group, N-tert-butylcarbamoyl group, N-n-hexylcarbamoyl group, N-cyclohexylcarbamoyl group, N-methylethylcarbamoyl group and N-dicyclohexylcarbamoyl group; N-arylcarbamoyl group such as N-phenylcarbamoyl group and N-diphenylcarbamoyl group; or the like.

The substituted sulfamoyl group represented by $R^{7'''}$ to $R^{10'''}$, includes, for example, one where 1 to 2 hydrogen atoms of the sulfamoyl (—SO$_2$NH$_2$) group is substituted with a $C_1$ to $C_6$ alkyl group or a $C_6$ to $C_{10}$ aryl group, and specifically, for example, N-alkylsulfamoyl group such as N-methylsulfamoyl group, N-ethylsulfamoyl group, N-n-propylsulfamoyl group, N-isopropylsulfamoyl group, N-n-butylsulfamoyl group, N-tert-butylsulfamoyl group, N-n-hexylsulfamoyl group, N-cyclohexylsulfamoyl group, N-methylethylsulfamoyl group and N-dicyclohexylsulfamoyl group; N-arylsulfamoyl group such as N-phenylsulfamoyl group and N-diphenylsulfamoyl group; or the like.

The substituted ureido group represented by $R^{7'''}$ to $R^{10'''}$, includes one where 1 to 3 hydrogen atoms of the ureido group (—NHCONH$_2$) is substituted, for example, groups represented by the following general formulae [4] to [7]:

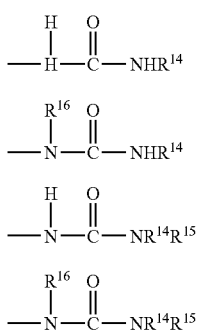

(wherein $R^{14}$ to $R^{16}$ each independently represent halogen atom, alkyl group, sulfoamide atom, carboamide group, sulfo group, carboxyl group, phospho group, hydroxyl group, or amino group).

In the general formulae [4] to [7], the halogen atom represented by $R^{14}$ to $R^{16}$, includes, for example, fluorine atom, chlorine atom, bromine atom, iodine atom or the like.

The alkyl group represented by $R^{14}$ to $R^{16}$ may be any of straight-chained, branched and cyclic one, and included one having usually $C_1$ to $C_{10}$, preferably $C_1$ to $C_6$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The sulfoamide group (—NHSO$_2$R) represented by $R^{14}$ to $R^{16}$, includes one where the hydrogen atom of the amino group is substituted with an alkylsulfonyl group (alkylsulfoamide group), or with an arylsulfonyl group (arylsulfoamide group).

The alkylsulfoamide group may be any of straight-chained, branched and cyclic one, and includes one having usually $C_1$ to $C_{10}$, preferably $C_1$ to $C_6$, and specifically, for example, methylsulfoamide group, ethylsulfoamide group, n-propylsulfoamide group, isopropylsulfoamide group, n-butylsulfoamide group, isobutylsulfoamide group, sec-butylsulfoamide group, tert-butylsulfoamide group, n-pentylsulfoamide group, isopentylsulfoamide group, sec-pentylsulfoamide group, tert-pentylsulfoamide group, neopentylsulfoamide group, n-hexylsulfoamide group, isohexylsulfoamide group, sec-hexylsulfoamide group, tert-hexylsulfoamide group, neohexylsulfoamide group, cyclopropylsulfoamide group, cyclobutylsulfoamide group, cyclopentylsulfoamide group, cyclohexylsulfoamide group, n-heptylsulfoamide group, isoheptylsulfoamide group, sec-heptylsulfoamide group, tert-heptylsulfoamide group, neoheptylsulfoamide group, n-octylsulfoamide group, isooctylsulfoamide group, sec-octylsulfoamide group, tert-octylsulfoamide group, neooctylsulfoamide group, n-nonylsulfoamide group, isononylsulfoamide group, sec-nonylsulfoamide group, tert-nonylsulfoamide group, isononylsulfoamide group, n-decylsulfoamide group, isodecylsulfoamide group, sec-decylsulfoamide group, tert-decylsulfoamide group, neodecylsulfoamide group, cycloheptylsulfoamide group, cyclooctylsulfoamide group, cyclononylsulfoamide group, cyclodecylsulfoamide group or the like.

The arylsulfoamide group includes one having usually $C_6$ to $C_{10}$, and specifically, for example, phenylsulfoamide group, or naphthylsulfoamide group or the like.

The carboamide group (—NHCOR) represented by $R^{14}$ to $R^{16}$, includes one where the hydrogen atom of the amino group is substituted with an acyl group. The acyl group includes, for example, one derived from an aliphatic carboxylic acid, one derived from an aromatic carboxylic acid or the like.

The carboamide group derived from an aliphatic carboxylic acid, may be any of straight-chained, branched and cyclic one, and may still contain more a double bond in the chain, and includes one having usually $C_2$ to $C_{20}$, preferably $C_2$ to $C_{15}$, more preferably $C_2$ to $C_{10}$, still more preferably $C_2$ to $C_6$, and specifically, for example, acetylamide group, propionylamide group, butyrylamide group, isobutyrylamide group, valerylamide group, isovalerylamide group, pivaloylamide group, hexanoylamide group, heptanoylamide group, octanoylamide group, decanoylamide group, lauroylamide group, myristoylamide group, palmitoylamide group, stearoylamide group, icosanoylamide group, acryloylamide group, methacryloylamide group, crotonoylamide group, oleoylamide group or the like.

The carboamide group derived from an aromatic carboxylic acid, includes one having usually $C_7$ to $C_{15}$, preferably $C_7$ to $Cl_1$, and specifically, for example, benzoylamide group, naphthoylamide group, anthoylamide group or the like.

The substituted amino group represented by $R^{7''}$ to $R^{10''}$, includes one where 1 to 2 hydrogen atoms of the amino group are substituted with substituents, and these substituents includes for example, alkyl group, alkoxycarbonyl group, carbonyl group, acyl group, sulfo group and the like.

The alkyl group included as a substituent of the substituted amino group may be any of straight-chained, branched and cyclic one, and includes one having usually $C_1$ to $C_{10}$, preferably $C_1$ to $C_6$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The alkoxycaronyl group included as a substituent of the substituted amino group, may be any of straight-chained, branched and cyclic one, and includes one having usually $C_1$ to $C_{10}$, preferably $C_1$ to $C_6$, and specifically, for example, methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentyloxycarbonyl group, isopentyloxycarbonyl group, sec-pentyloxycarbonyl group, tert-pentyloxycarbonyl group, neopentyloxycarbonyl group, n-hexyloxycarbonyl group, isohexyloxycarbonyl group, sec-hexyloxycarbonyl group, tert-hexyloxycarbonyl group, neohexyloxycarbonyl group, n-heptyloxycarbonyl group, isoheptyloxycarbonyl group, sec-heptyloxycarbonyl group, tert-heptyloxycarbonyl group, neoheptyloxycarbonyl group, n-octyloxycarbonyl group, isooctyloxycarbonyl group, sec-octyloxycarbonyl group, tert-octyloxycarbonyl group, neooctyloxycarbonyl group, n-nonyloxycarbonyl group, isononyloxycarbonyl group, sec-nonyloxycarbonyl group, tert-nonyloxycarbonyl group, neononyloxycarbonyl group, n-decyloxycarbonyl group, isodecyloxycarbonyl group, sec-decyloxycarbonyl group, tert-decyloxycarbonyl group, neo-decyloxycarbonyl group, cyclopropoxycarbonyl group, cyclobutoxycarbonyl group, cyclopentyloxycarbonyl group, cyclohexyloxycarbonyl group, cycloheptyloxycarbonyl group, cyclooctyloxycarbonyl group, cyclononyloxycarbonyl group, cyclodecyloxycarbonyl group or the like.

The acyl group included as a substituent of the substituted amino group, includes one derived from an aliphatic carboxylic acid, one derived from an aromatic carboxylic acid or the like.

The acyl group derived from an aliphatic carboxylic acid may be any of straight-chained, branched and cyclic one, and may still contain more a double bond in the chain, and includes one having usually $C_2$ to $C_{20}$, preferably $C_2$ to $C_{15}$, more preferably $C_2$ to $C_{10}$, still more preferably $C_2$ to $C_6$, and specifically, for example, acetyl group, propionyl group, butyryl group, isobutyryl group, valeryl group, isovaleryl group, pivaloyl group, hexanoyl group, heptanoyl group, octanoyl group, decanoyl group, lauroyl group, myristoyl group, palmitoyl group, stearoyl group, icosanoyl group, acryloyl group, methacryloyl group, crotonoyl group, oleoyl group or the like.

The acyl group derived from an aromatic carboxylic acid, includes one having usually $C_7$ to $C_{15}$, preferably $C_7$ to $C_{11}$, and specifically, for example, benzoyl group, naphthoyl group, anthoyl group or the like The halogen atom represented by $R^{7'''}$ to $R^{10'''}$ includes, for example, fluorine atom, chlorine atom, bromine atom, iodine atom or the like.

The aromatic heterocyclic thio group represented by $R^{7'''}$ to $R^{10'''}$, includes one where the hydrogen atom of the thiol group (—SH) is substituted with an aromatic heterocyclic group. The aromatic heterocyclic group includes, for example, a five member ring or a six member ring, and preferably one containing, as the hetero atom, for example, 1 to 3 nitrogen atoms, oxygen atoms, sulfur atoms or the like, and specifically, for example, furyl group, pyrrolyl group, indolyl group, purinyl group, quinolyl group, pyridyl group, pyrazyl group, pyrimidyl group, oxazolyl group, imidazolyl group, thiazolyl group, pyranyl group or the like.

In the general formulae [51] and [55] to [58], a substituent of the substituted alkyl group, substituted alkenyl group, substituted alkynyl group, substituted aryl group, substituted alkoxy group, substituted aryloxy group, substituted alkylthio group, substituted arylthio group, substituted alkylsulfonyl group, or substituted arylsulfonyl group, represented by $R^{7'''}$ to $R^{10'''}$, includes, for example, halogen atom, sulfoamide group, carboamide group, phospho group (phosphate group), the group represented by the above general formula [2], the group represented by the general formula [3], amino group, hydroxyl group, thiol group, formyl group, or the like.

A specific example of the halogen atom, sulfoamide group, and carboamide group, included as a substituent, includes, for example, a similar one as exemplification of the halogen atom, sulfoamide group and carboamide group, represented by $R^{14}$ to $R^{16}$ in the general formulae [4] to [7].

A preferable example of $R^{7'''}$ to $R^{10'''}$ in the general formulae [51] and [55] to [58], includes one where three of $R^{7'''}$ to $R^{10'''}$ are hydrogen atoms, and the remaining one is a group derived from a sulfonic acid represented by the general formula [3], and among the groups derived from the sulfonic acid, for example, sulfo group, anion thereof (sulfonate), alkali metal salt thereof or organic ammonium salt thereof, or the like is preferable, and among them, for example, sulfo group, sulfonate, alkali metal salt thereof (for example, sodium salt or the like) or the like is more preferable, and in particular, one where $R^{8'''}$ is the group represented by the general formula [3] is preferable.

In the general formulae [51] and [55] to [58], the alkyl group of the substituted or unsubstituted alkyl group, represented by $R^{11'''}$, may be any of straight-chained, branched and cyclic one, and includes one having usually $C_1$ to $C_{10}$, [preferably $C_1$ to $C_{10}$,] and specifically, for example methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The alkenyl group of the substituted or unsubstituted alkenyl group represented by $R^{11'''}$ may be any of straight-chained, branched and cyclic one may be adopted, and includes one having usually $C_2$ to $C_6$, preferably $C_2$ to $C_4$, and specifically, for example, vinyl group, allyl group, 1-propenyl group, isopropenyl group, 3-butenyl group, 2-butenyl group, 1-butenyl group, 1,3-butadienyl group, 4-pentenyl group, 3-pentenyl group, 2-pentenyl group, 1-pentenyl group, 1,3-pentadienyl group, 2,4-pentadienyl group, 1,1-dimethyl-2-propenyl group, 1-ethyl-2-propenyl group, 1,2-dimethyl-1-propenyl group, 1-methyl-1-butenyl group, 5-hexenyl group, 4-hexenyl group, 3-hexenyl group, 2-hexenyl group, 1-hexenyl group, 1-cyclopropenyl group, 2-cyclopentenyl group, 2,4-cyclopentadienyl group, 1-cyclohexenyl group, 2-cyclohexenyl group, 3-cyclohexenyl group or the like.

The alkynyl group of the substituted or unsubstituted alkynyl group, represented by $R^{11'''}$, includes one having usually $C_2$ to $C_6$, preferably $C_2$ to $C_4$, and specifically, for example, ethynyl group, 2-propynyl group, 3-butynyl group, 1-methyl-2-propynyl group, 4-pentynyl group, 2-methyl-4-pentynyl group, 5-hexynyl group or the like.

The aryl group of the substituted or unsubstituted aryl group, represented by $R^{11'''}$, includes specifically, for example, phenyl group, naphthyl group or the like.

A substituent of the substituted alkyl group, substituted alkenyl group, substituted alkynyl group, or substituted aryl group, represented by $R^{11'''}$, includes, for example, halogen atom, sulfoamide group and carboamide group, sulfo group, carboxyl group, phospho group, hydroxyl group, amino group, or the like, and a specific example of the halogen atom, sulfoamide group and carboamide group includes similar one as an exemplification of the halogen atom, sulfoamide group and carboamide group represented by $R^{14}$ to $R^{16}$ in the general formulae [14] to [17].

Among $R^{11'''}$, an unsubstituted alkyl group is preferable, and in particular, for example, methyl group, ethyl group, n-propyl group, isopropyl group, n-butyl group, n-pentyl group, n-hexyl group or the like is more preferable.

In the general formula [51], a bivalent group formed by any of $R^{1'''}$ and $R^{2'''}$, $R^{4'''}$ and $R^{5'''}$, $R^{1'''}$ and $R^{6'''}$, and $R^{2'''}$ and $R^{4'''}$ that is, a bivalent group formed by a group selected from —O— group, —S— group, —COO— group, and the groups represented by the general formulae [52] to [54]:

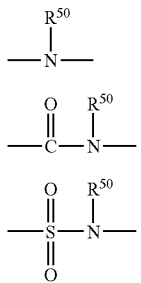

(wherein $R^{50}$ represents hydrogen atom, or alkyl group, alkenyl group or aryl group, those groups being able to have substituents), and substituted or unsubstituted alkylene group, and in detail, a bivalent group represented by T in the general formulae [55] to [58], includes, for example, a group represented by the general formula [60]:

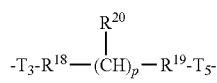

[wherein $R^{18}$ and $R^{19}$ each independently represent —O— group, —S— group, —COO— group, or the groups represented by the general formulae [52] to [54]; and $R^{20}$ represents groups represented by the following general formulae [70] to [72]:

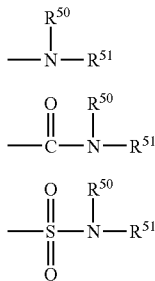

(wherein $R^{51}$ represents hydrogen atom, or alkyl group, alkenyl group or aryl group, those groups being able to have substituents; $R^{50}$ is the same as above), hydrogen atom, the group represented by the general formula [2], the group represented by the general formula [3], amino group, hydroxyl group, thiol group or formyl group; $T_3$ and $T_5$ each independently represent alkylene group; and p represents an integer of from 1 to 20].

In the general formulae [52] to [54] and [70] to [72], the alkyl group of the substituted or unsubstituted alkyl group, represented by $R^{51}$, may be any of straight-chained, branched and cyclic one, and includes one having usually $C_1$ to $C_{10}$, preferably $C_1$ to $C_6$, and specifically, for example methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The substituted or unsubstituted alkenyl group represented by $R^{51}$, may be any of straight-chained, branched and cyclic one, and includes one having usually $C_2$ to $C_6$, preferably $C_2$ to $C_6$, and specifically, for example, vinyl group, allyl group, 1-propenyl group, isopropenyl group, 3-butenyl group, 2-butenyl group, 1-butenyl group, 1,3-butadienyl group, 4-pentenyl group, 3-pentenyl group, 2-pentenyl group, 1-pentenyl group, 1,3-pentadienyl group, 2,4-pentadienyl group, 1,1-dimethyl-2-propenyl group, 1-ethyl-2-propenyl group, 1,2-dimethyl-1-propenyl group, 1-methyl-1-butenyl group, 5-hexenyl group, 4-hexenyl group, 3-hexenyl group, 2-hexenyl group, 1-hexenyl group, 1-cyclopropenyl group, 2-cyclopentenyl group, 2,4-cyclopentadienyl group, 1-cyclohexenyl group, 2-cyclohexenyl group, 3-cyclohexenyl group, cycloheptenyl group, cyclooctenyl group, cyclononenyl group, cyclodecenyl group or the like.

The substituted or unsubstituted aryl group represented by $R^{51}$, includes one having usually $C_6$ to $C_{10}$, and specifically, for example, phenyl group, naphthyl group or the like.

A substituent of the substituted alkyl group, substituted alkenyl group or substituted aryl group, represented by $R^{51}$, includes, for example, $C_1$ to $C_{10}$ alkyl group, halogen atom, sulfoamide group, carboamide group, phospho group (phosphate group), the group represented by the above general formula [2], the group represented by the above general formula [3], amino group, hydroxyl group, thiol group, formyl group or the like.

The $C_1$ to $C_{10}$ alkyl group included as a substituent, may be any of straight-chained, branched and cyclic one, and includes one having usually $C_1$ to $C_{10}$, preferably $C_1$ to $C_6$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

A specific example of the halogen atom, sulfoamide group and carboamide group, included as a substituent, includes a similar one to an exemplification of the halogen atom, sulfoamide group and carboamide group represented by $R^{14}$ to $R^{16}$ in the general formulae [4] to [7].

In the general formula [60], as the alkylene group represented by $T_3$ and $T_4$ may be any of straight-chained and cyclic one, and includes one having usually $C_1$ to $C_6$, and specifically, straight-chained alkylene group such as methylene group, ethylene group, trimethylene group, tetramethylene group, pentamethylene group and hexamethylene group; branched alkylene group such as ethylidene group, propylene group, isopropylidene group, ethylethylene group, 1,2-dimethylethylene group, 1,2-diethylethylene group, 1,2-di-n-propylethylene group and 1,2-di-n-butylethylene group; or the like, and among these, a straight-chained alkylene group is preferable, and in particular, ethylene group, pentamethylene group or the like is more preferable.

"p" is an integer of usually from 1 to 20, preferably from 1 to 10, and more preferably from 1 to 6.

It is a preferable one where at least one of p pieces of $R^{20}$s is the group represented by the general formulae [70] to [72], the general formula [2], the group represented by the general formula [3], amino group, hydroxyl group, thiol group or formyl group, and in particular, one where the group represented by the general formula [2], or the group represented by the general formula [71] is more preferable.

Among the groups represented by the general formula [71], a group represented by the following general formula [73] is particularly preferable:

—CONH-T$_4$-COOR$^{12}$     [73]

(wherein T$_4$ represents an alkylene group; and R$^{12}$ is the same as above).

In the general formula [73], the alkylene group represented by T$_4$ includes a similar one as the alkylene group represented by T$_3$ and T$_5$ in the general formula [60].

Among the group represented by the general formula [2], the group represented by the general formula [3], amino group, hydroxyl group, thiol group or formyl group, contained at least one in R$^{1'''}$ to R$^{11'''}$ in the general formulae [51] and [55] to [58], the group represented by the general formula [2] or the group represented by the general formula [3] is preferable.

The group represented by the general formula [3] (a sulfo group or the like), contained in a compound of the present invention, is preferably contained more, usually 1 to 4, preferable 2 to 4 in the compound of the present invention, so as to enhance water-solubility, suppress fluorescence quenching caused by aggregation of the dyes themselves, and enhance fluorescence intensity.

In addition, the group (a carboxyl group or the like) represented by the general formula [2], contained in the compound of the present invention, is contained in the compound of the present invention in an amount of usually 1 to 3, preferably 1 to 2, so as to make possible easy introduction of a group (for example, a reaction activation group such as a succinimide group, a norbornene group or the like) bindable to a substance to be labeled.

In the case where the group represented by the general formula [2], the group represented by the general formula [3], amino group, hydroxyl group, thiol group or formyl group (hereinafter may be abbreviated as "a reactive group of the present invention"), contained at least one in the bivalent bond formed by any of R$^{1'''}$ to R$^{11'''}$, or R$^{1'''}$ and R$^{2'''}$, R$^{4'''}$ and R$^{5'''}$, R$^{1'''}$ and R$^{6'''}$, and R$^{2'''}$ and R$^{4'''}$ (that is, the bivalent group represented by T in the general formulae [55] to [58]), is contained in R$^{1'''}$ to R$^{11}$, it may be either one where these reactive groups of the present invention are present as R$^{1'''}$ to R$^{11'''}$ (that is, one where the reactive group is directly bound to a pyrazole skeleton or an indole skeleton), or one where they are contained as substituents in R$^{1'''}$ to R$^{11'''}$, however, in the case where the reactive group is contained in R$^{11'''}$, it is preferable to be contained as a substituent.

In addition, in the case where the reactive group of the present invention is contained in the bivalent group formed by any of R$^{1'''}$ and R$^{2'''}$, R$^{4'''}$ and R$^{5'''}$, R$^{1'''}$ and R$^{6'''}$, and R$^{2'''}$ and R$^{4'''}$ (that is, the bivalent group represented by T in the general formulae [55] to [58]), it is preferable that it is contained, for example, in R$^{20}$ in the above general formula [60].

In the compounds represented by the above the general formulae [55] to [58], it is a preferable one where n is 1 or 2, and in particular it is a more preferable one where n is 2.

In addition, among the compound [51] of the present invention, it is a preferable one represented by the following general formula [51']:

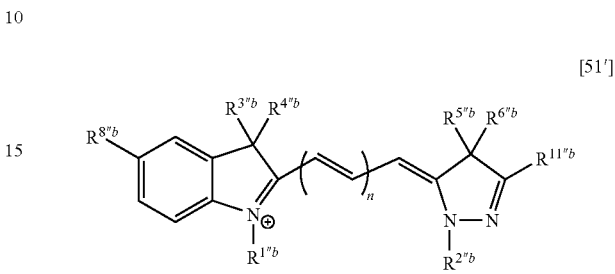

[51']

[wherein R$^{1''b}$ to R$^{6''b}$ each independently represent an alkyl group, which may have as a substituent the group represented by the general formula [2] or [3]; R$^{8''b}$ represents the group represented by the general formula [3]; R$^{11''b}$ represents an alkyl group; and n represents an integer of from 0 to 3, provided that any of R$^{1''b}$ and R$^{2''b}$, R$^{4''b}$ and R$^{5''b}$, R$^{1''b}$ and R$^{6''b}$, and R$^{2''b}$ and R$^{4''b}$ form a bivalent group with a group selected from —O— group, —S— group, —COO— group and the groups represented by the general formulae [52] to [54], and substituted or unsubstituted alkylene group: In addition, at least one of R$^{1''b}$ to R$^{1''b}$, along with the bivalent group formed by any of R$^{1''b}$ and R$^{2''b}$, R$^{4''b}$ and R$^{5''b}$, R$^{1''b}$ and R$^{6''b}$, and R$^{2''b}$ and R$^{4''b}$, has the group represented by the general formula [2], or the group represented by the general formula [3]].

In the general formula [51'], the alkyl group of the alkyl group which may have as a substituent the group represented by the general formula [2] or [3] represented by R$^{1''b}$ to R$^{6''b}$, includes a similar one as an exemplification of an alkyl group of the substituted or unsubstituted alkyl group, which may have the amide bond, represented by R$^{1'''}$ to R$^{6'''}$ in the above the general formula [51].

R$^{3a}$ and R$^{4a}$ each independently include an alkyl group, which may have as a substituent the group represented by the general formula [2] or [3], and in particular, it is preferable that one of them is an alkyl group having as a substituent the group represented by the general formula [2] or [3], and the other is an alkyl group.

R$^{5a}$ and R$^{6a}$ each independently include an alkyl group, which may have as a substituent the group represented by the general formula [2] or [3], and in particular, it is preferable that one of them is an alkyl group having as a substituent the group represented by the general formula [2] or [3], and the other is an alkyl group.

An alkyl group represented by R$^{11''b}$ includes a similar one as an exemplification of the alkyl group represented by R$^{11}$ in the above the general formula [51].

Preferable specific examples of the compounds represented by the general formula [55], includes for example, those represented by the following Tables 9 to 12. It should be noted that, in Tables 9 to 12, R$^{3'''}$, R$^{5'''}$ and R$^{11'''}$ represented by the general formula [55] are —CH$_3$ groups; R$^{7'''}$, R$^{9'''}$ and R$^{10'''}$ are hydrogen atoms; and R$^{8'''}$ is —SO$_3$Na group.

TABLE 9

| | n | R⁴" | R⁶" | T |
|---|---|---|---|---|
| 55-1 | 0-3 | —(CH$_2$)$_3$SO$_3$Na | —(CH$_2$)$_3$SO$_3$Na | —(CH$_2$)$_5$CONHC(COO$^-$)(CH$_2$)$_4$NHCO(CH$_2$)$_5$— |
| 55-2 | 0-3 | —(CH$_2$)$_3$SO$_3$Na | —(CH$_2$)$_4$SO$_3$Na | —(CH$_2$)$_5$CONHC(COO$^-$)(CH$_2$)$_4$NHCO(CH$_2$)$_5$— |
| 55-3 | 0-3 | —(CH$_2$)$_3$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 55-4 | 0-3 | —(CH$_2$)$_3$SO$_3$Na | —(CH$_2$)$_2$COOC$_2$H$_5$ | —(CH$_2$)$_5$CONHC(COO$^-$)(CH$_2$)$_4$NHCO(CH$_2$)$_5$— |
| 55-5 | 0-3 | —(CH$_2$)$_3$SO$_3$Na | —(CH$_2$)$_5$COOC$_2$H$_5$ | —(CH$_2$)$_5$CONHC(COO$^-$)(CH$_2$)$_4$NHCO(CH$_2$)$_5$— |
| 55-6 | 0-3 | —(CH$_2$)$_3$SO$_3$Na | —CH$_3$ | —(CH$_2$)$_5$CONHC(COO$^-$)(CH$_2$)$_4$NHCO(CH$_2$)$_5$— |
| 55-7 | 0-3 | —(CH$_2$)$_4$SO$_3$Na | —(CH$_2$)$_3$SO$_3$Na | —(CH$_2$)$_5$CONHC(COO$^-$)(CH$_2$)$_4$NHCO(CH$_2$)$_5$— |
| 55-8 | 0-3 | —(CH$_2$)$_4$SO$_3$Na | —(CH$_2$)$_4$SO$_3$Na | —(CH$_2$)$_5$CONHC(COO$^-$)(CH$_2$)$_4$NHCO(CH$_2$)$_5$— |
| 55-9 | 0-3 | —(CH$_2$)$_4$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 55-10 | 0-3 | —(CH$_2$)$_4$SO$_3$Na | —(CH$_2$)$_2$COOC$_2$H$_5$ | —(CH$_2$)$_5$CONHC(COO$^-$)(CH$_2$)$_4$NHCO(CH$_2$)$_5$— |
| 55-11 | 0-3 | —(CH$_2$)$_4$SO$_3$Na | —(CH$_2$)$_5$COOC$_2$H$_5$ | —(CH$_2$)$_5$CONHC(COO$^-$)(CH$_2$)$_4$NHCO(CH$_2$)$_5$— |
| 55-12 | 0-3 | —(CH$_2$)$_4$SO$_3$Na | —CH$_3$ | —(CH$_2$)$_5$CONHC(COO$^-$)(CH$_2$)$_4$NHCO(CH$_2$)$_5$— |
| 55-13 | 0-3 | —(CH$_2$)$_2$CH(CH$_3$)SO$_3$Na | —(CH$_2$)$_3$SO$_3$Na | —(CH$_2$)$_5$CONHC(COO$^-$)(CH$_2$)$_4$NHCO(CH$_2$)$_5$— |
| 55-14 | 0-3 | —(CH$_2$)$_2$CH(CH$_3$)SO$_3$Na | —(CH$_2$)$_4$SO$_3$Na | —(CH$_2$)$_5$CONHC(COO$^-$)(CH$_2$)$_4$NHCO(CH$_2$)$_5$— |
| 55-15 | 0-3 | —(CH$_2$)$_2$CH(CH$_3$)SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 55-16 | 0-3 | —(CH$_2$)$_2$CH(CH$_3$)SO$_3$Na | —(CH$_2$)$_2$COOC$_2$H$_5$ | —(CH$_2$)$_5$CONHC(COO$^-$)(CH$_2$)$_4$NHCO(CH$_2$)$_5$— |
| 55-17 | 0-3 | —(CH$_2$)$_2$CH(CH$_3$)SO$_3$Na | —(CH$_2$)$_5$COOC$_2$H$_5$ | —(CH$_2$)$_5$CONHC(COO$^-$)(CH$_2$)$_4$NHCO(CH$_2$)$_5$— |
| 55-18 | 0-3 | —(CH$_2$)$_2$CH(CH$_3$)SO$_3$Na | —CH$_3$ | —(CH$_2$)$_5$CONHC(COO$^-$)(CH$_2$)$_4$NHCO(CH$_2$)$_5$— |
| 55-19 | 0-3 | —(CH$_2$)$_2$COOC$_2$H$_5$ | —(CH$_2$)$_3$SO$_3$Na | —(CH$_2$)$_5$CONHC(COO$^-$)(CH$_2$)$_4$NHCO(CH$_2$)$_5$— |
| 55-20 | 0-3 | —(CH$_2$)$_2$COOC$_2$H$_5$ | —(CH$_2$)$_4$SO$_3$Na | —(CH$_2$)$_5$CONHC(COO$^-$)(CH$_2$)$_4$NHCO(CH$_2$)$_5$— |
| 55-21 | 0-3 | —(CH$_2$)$_2$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 55-22 | 0-3 | —(CH$_2$)$_2$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_5$— |
| 55-23 | 0-3 | —(CH$_2$)$_2$COOC$_2$H$_5$ | —(CH$_2$)$_5$COOC$_2$H$_5$ | —(CH$_2$)$_5$CONHC(COO$^-$)(CH$_2$)$_4$NHCO(CH$_2$)$_5$— |
| 55-24 | 0-3 | —(CH$_2$)$_2$COOC$_2$H$_5$ | —CH$_3$ | —(CH$_2$)$_5$CONHC(COO$^-$)(CH$_2$)$_4$NHCO(CH$_2$)$_5$— |
| 55-25 | 0-3 | —(CH$_2$)$_5$COOC$_2$H$_5$ | —(CH$_2$)$_3$SO$_3$Na | —(CH$_2$)$_5$CONHC(COO$^-$)(CH$_2$)$_4$NHCO(CH$_2$)$_5$— |
| 55-26 | 0-3 | —(CH$_2$)$_5$COOC$_2$H$_5$ | —(CH$_2$)$_4$SO$_3$Na | —(CH$_2$)$_5$CONHC(COO$^-$)(CH$_2$)$_4$NHCO(CH$_2$)$_5$— |
| 55-27 | 0-3 | —(CH$_2$)$_5$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 55-28 | 0-3 | —(CH$_2$)$_5$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_5$— |
| 55-29 | 0-3 | —(CH$_2$)$_5$COOC$_2$H$_5$ | —(CH$_2$)$_5$COOC$_2$H$_5$ | —(CH$_2$)$_5$CONHC(COO$^-$)(CH$_2$)$_4$NHCO(CH$_2$)$_5$— |
| 55-30 | 0-3 | —(CH$_2$)$_5$COOC$_2$H$_5$ | —CH$_3$ | —(CH$_2$)$_5$CONHC(COO$^-$)(CH$_2$)$_4$NHCO(CH$_2$)$_5$— |
| 55-31 | 0-3 | —CH$_3$ | —(CH$_2$)$_3$SO$_3$Na | —(CH$_2$)$_5$CONHC(COO$^-$)(CH$_2$)$_4$NHCO(CH$_2$)$_5$— |
| 55-32 | 0-3 | —CH$_3$ | —(CH$_2$)$_4$SO$_3$Na | —(CH$_2$)$_5$CONHC(COO$^-$)(CH$_2$)$_4$NHCO(CH$_2$)$_5$— |
| 55-33 | 0-3 | —CH$_3$ | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 55-34 | 0-3 | —CH$_3$ | —(CH$_2$)$_2$COOC$_2$H$_5$ | —(CH$_2$)$_5$CONHC(COO$^-$)(CH$_2$)$_4$NHCO(CH$_2$)$_5$— |
| 55-35 | 0-3 | —CH$_3$ | —(CH$_2$)$_5$COOC$_2$H$_5$ | —(CH$_2$)$_5$CONHC(COO$^-$)(CH$_2$)$_4$NHCO(CH$_2$)$_5$— |
| 55-36 | 0-3 | —CH$_3$ | —CH$_3$ | —(CH$_2$)$_5$CONHC(COO$^-$)(CH$_2$)$_4$NHCO(CH$_2$)$_5$— |
| 55-37 | 0-3 | —(CH$_2$)$_3$SO$_3$Na | —(CH$_2$)$_3$SO$_3$Na | —(CH$_2$)$_5$CONHC(COO$^-$)(CH$_2$)$_4$NHCO(CH$_2$)$_2$— |
| 55-38 | 0-3 | —(CH$_2$)$_3$SO$_3$Na | —(CH$_2$)$_4$SO$_3$Na | —(CH$_2$)$_5$CONHC(COO$^-$)(CH$_2$)$_4$NHCO(CH$_2$)$_2$— |
| 55-39 | 0-3 | —(CH$_2$)$_3$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 55-40 | 0-3 | —(CH$_2$)$_3$SO$_3$Na | —(CH$_2$)$_2$COOC$_2$H$_5$ | —(CH$_2$)$_5$CONHC(COO$^-$)(CH$_2$)$_4$NHCO(CH$_2$)$_2$— |

TABLE 10

| | n | R⁴" | R⁶" | T |
|---|---|---|---|---|
| 55-41 | 0-3 | —(CH$_2$)$_3$SO$_3$Na | —(CH$_2$)$_5$COOC$_2$H$_5$ | —(CH$_2$)$_5$CONHC(COO$^-$)(CH$_2$)$_4$NHCO(CH$_2$)$_2$— |
| 55-42 | 0-3 | —(CH$_2$)$_3$SO$_3$Na | —CH$_3$ | —(CH$_2$)$_5$CONHC(COO$^-$)(CH$_2$)$_4$NHCO(CH$_2$)$_2$— |
| 55-43 | 0-3 | —(CH$_2$)$_4$SO$_3$Na | —(CH$_2$)$_3$SO$_3$Na | —(CH$_2$)$_5$CONHC(COO$^-$)(CH$_2$)$_4$NHCO(CH$_2$)$_2$— |
| 55-44 | 0-3 | —(CH$_2$)$_4$SO$_3$Na | —(CH$_2$)$_4$SO$_3$Na | —(CH$_2$)$_5$CONHC(COO$^-$)(CH$_2$)$_4$NHCO(CH$_2$)$_2$— |
| 55-45 | 0-3 | —(CH$_2$)$_4$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 55-46 | 0-3 | —(CH$_2$)$_4$SO$_3$Na | —(CH$_2$)$_2$COOC$_2$H$_5$ | —(CH$_2$)$_5$CONHC(COO$^-$)(CH$_2$)$_4$NHCO(CH$_2$)$_2$— |
| 55-47 | 0-3 | —(CH$_2$)$_4$SO$_3$Na | —(CH$_2$)$_5$COOC$_2$H$_5$ | —(CH$_2$)$_5$CONHC(COO$^-$)(CH$_2$)$_4$NHCO(CH$_2$)$_2$— |
| 55-48 | 0-3 | —(CH$_2$)$_4$SO$_3$Na | —CH$_3$ | —(CH$_2$)$_5$CONHC(COO$^-$)(CH$_2$)$_4$NHCO(CH$_2$)$_2$— |
| 55-49 | 0-3 | —(CH$_2$)$_2$CH(CH$_3$)SO$_3$Na | —(CH$_2$)$_3$SO$_3$Na | —(CH$_2$)$_5$CONHC(COO$^-$)(CH$_2$)$_4$NHCO(CH$_2$)$_2$— |
| 55-50 | 0-3 | —(CH$_2$)$_2$CH(CH$_3$)SO$_3$Na | —(CH$_2$)$_4$SO$_3$Na | —(CH$_2$)$_5$CONHC(COO$^-$)(CH$_2$)$_4$NHCO(CH$_2$)$_2$— |
| 55-51 | 0-3 | —(CH$_2$)$_2$CH(CH$_3$)SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 55-52 | 0-3 | —(CH$_2$)$_2$CH(CH$_3$)SO$_3$Na | —(CH$_2$)$_2$COOC$_2$H$_5$ | —(CH$_2$)$_5$CONHC(COO$^-$)(CH$_2$)$_4$NHCO(CH$_2$)$_2$— |
| 55-53 | 0-3 | —(CH$_2$)$_2$CH(CH$_3$)SO$_3$Na | —(CH$_2$)$_5$COOC$_2$H$_5$ | —(CH$_2$)$_5$CONHC(COO$^-$)(CH$_2$)$_4$NHCO(CH$_2$)$_2$— |
| 55-54 | 0-3 | —(CH$_2$)$_2$CH(CH$_3$)SO$_3$Na | —CH$_3$ | —(CH$_2$)$_5$CONHC(COO$^-$)(CH$_2$)$_4$NHCO(CH$_2$)$_2$— |
| 55-55 | 0-3 | —(CH$_2$)$_2$COOC$_2$H$_5$ | —(CH$_2$)$_3$SO$_3$Na | —(CH$_2$)$_5$CONHC(COO$^-$)(CH$_2$)$_4$NHCO(CH$_2$)$_2$— |
| 55-56 | 0-3 | —(CH$_2$)$_2$COOC$_2$H$_5$ | —(CH$_2$)$_4$SO$_3$Na | —(CH$_2$)$_5$CONHC(COO$^-$)(CH$_2$)$_4$NHCO(CH$_2$)$_2$— |
| 55-57 | 0-3 | —(CH$_2$)$_2$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 55-58 | 0-3 | —(CH$_2$)$_2$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_2$— |
| 55-59 | 0-3 | —(CH$_2$)$_2$COOC$_2$H$_5$ | —(CH$_2$)$_5$COOC$_2$H$_5$ | —(CH$_2$)$_5$CONHC(COO$^-$)(CH$_2$)$_4$NHCO(CH$_2$)$_2$— |
| 55-60 | 0-3 | —(CH$_2$)$_2$COOC$_2$H$_5$ | —CH$_3$ | —(CH$_2$)$_5$CONHC(COO$^-$)(CH$_2$)$_4$NHCO(CH$_2$)$_2$— |
| 55-61 | 0-3 | —(CH$_2$)$_5$COOC$_2$H$_5$ | —(CH$_2$)$_3$SO$_3$Na | —(CH$_2$)$_5$CONHC(COO$^-$)(CH$_2$)$_4$NHCO(CH$_2$)$_2$— |
| 55-62 | 0-3 | —(CH$_2$)$_5$COOC$_2$H$_5$ | —(CH$_2$)$_4$SO$_3$Na | —(CH$_2$)$_5$CONHC(COO$^-$)(CH$_2$)$_4$NHCO(CH$_2$)$_2$— |
| 55-63 | 0-3 | —(CH$_2$)$_5$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 55-64 | 0-3 | —(CH$_2$)$_5$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_2$— |
| 55-65 | 0-3 | —(CH$_2$)$_5$COOC$_2$H$_5$ | —(CH$_2$)$_5$COOC$_2$H$_5$ | —(CH$_2$)$_5$CONHC(COO$^-$)(CH$_2$)$_4$NHCO(CH$_2$)$_2$— |
| 55-66 | 0-3 | —(CH$_2$)$_5$COOC$_2$H$_5$ | —CH$_3$ | —(CH$_2$)$_5$CONHC(COO$^-$)(CH$_2$)$_4$NHCO(CH$_2$)$_2$— |
| 55-67 | 0-3 | —CH$_3$ | —(CH$_2$)$_3$SO$_3$Na | —(CH$_2$)$_5$CONHC(COO$^-$)(CH$_2$)$_4$NHCO(CH$_2$)$_2$— |
| 55-68 | 0-3 | —CH$_3$ | —(CH$_2$)$_4$SO$_3$Na | —(CH$_2$)$_5$CONHC(COO$^-$)(CH$_2$)$_4$NHCO(CH$_2$)$_2$— |
| 55-69 | 0-3 | —CH$_3$ | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 55-70 | 0-3 | —CH$_3$ | —(CH$_2$)$_2$COOC$_2$H$_5$ | —(CH$_2$)$_5$CONHC(COO$^-$)(CH$_2$)$_4$NHCO(CH$_2$)$_2$— |

TABLE 10-continued

|  | n | R4" | R6" | T |
|---|---|---|---|---|
| 55-71 | 0-3 | —CH$_3$ | —(CH$_2$)$_5$COOC$_2$H$_5$ | —(CH$_2$)$_5$CONHC(COO$^-$)(CH$_2$)$_4$NHCO(CH$_2$)$_2$— |
| 55-72 | 0-3 | —CH$_3$ | —CH$_3$ | —(CH$_2$)$_5$CONHC(COO$^-$)(CH$_2$)$_4$NHCO(CH$_2$)$_2$— |
| 55-73 | 0-3 | —(CH$_2$)$_3$SO$_3$Na | —(CH$_2$)$_3$SO$_3$Na | —(CH$_2$)$_2$CONHC(COO$^-$)(CH$_2$)$_4$NHCO(CH$_2$)$_5$— |
| 55-74 | 0-3 | —(CH$_2$)$_3$SO$_3$Na | —(CH$_2$)$_4$SO$_3$Na | —(CH$_2$)$_2$CONHC(COO$^-$)(CH$_2$)$_4$NHCO(CH$_2$)$_5$— |
| 55-75 | 0-3 | —(CH$_2$)$_3$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 55-76 | 0-3 | —(CH$_2$)$_3$SO$_3$Na | —(CH$_2$)$_2$COOC$_2$H$_5$ | —(CH$_2$)$_2$CONHC(COO$^-$)(CH$_2$)$_4$NHCO(CH$_2$)$_5$— |
| 55-77 | 0-3 | —(CH$_2$)$_3$SO$_3$Na | —(CH$_2$)$_5$COOC$_2$H$_5$ | —(CH$_2$)$_2$CONHC(COO$^-$)(CH$_2$)$_4$NHCO(CH$_2$)$_5$— |
| 55-78 | 0-3 | —(CH$_2$)$_3$SO$_3$Na | —CH$_3$ | —(CH$_2$)$_2$CONHC(COO$^-$)(CH$_2$)$_4$NHCO(CH$_2$)$_5$— |
| 55-79 | 0-3 | —(CH$_2$)$_4$SO$_3$Na | —(CH$_2$)$_3$SO$_3$Na | —(CH$_2$)$_2$CONHC(COO$^-$)(CH$_2$)$_4$NHCO(CH$_2$)$_5$— |
| 55-80 | 0-3 | —(CH$_2$)$_4$SO$_3$Na | —(CH$_2$)$_4$SO$_3$Na | —(CH$_2$)$_2$CONHC(COO$^-$)(CH$_2$)$_4$NHCO(CH$_2$)$_5$— |

TABLE 11

|  | n | R4" | R6" | T |
|---|---|---|---|---|
| 55-81 | 0-3 | —(CH$_2$)$_4$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 55-82 | 0-3 | —(CH$_2$)$_4$SO$_3$Na | —(CH$_2$)$_2$COOC$_2$H$_5$ | —(CH$_2$)$_2$CONHC(COO$^-$)(CH$_2$)$_4$NHCO(CH$_2$)$_5$— |
| 55-83 | 0-3 | —(CH$_2$)$_4$SO$_3$Na | —(CH$_2$)$_5$COOC$_2$H$_5$ | —(CH$_2$)$_2$CONHC(COO$^-$)(CH$_2$)$_4$NHCO(CH$_2$)$_5$— |
| 55-84 | 0-3 | —(CH$_2$)$_4$SO$_3$Na | —CH$_3$ | —(CH$_2$)$_2$CONHC(COO$^-$)(CH$_2$)$_4$NHCO(CH$_2$)$_5$— |
| 55-85 | 0-3 | —(CH$_2$)$_2$CH(CH$_3$)SO$_3$Na | —(CH$_2$)$_3$SO$_3$Na | —(CH$_2$)$_2$CONHC(COO$^-$)(CH$_2$)$_4$NHCO(CH$_2$)$_5$— |
| 55-86 | 0-3 | —(CH$_2$)$_2$CH(CH$_3$)SO$_3$Na | —(CH$_2$)$_4$SO$_3$Na | —(CH$_2$)$_2$CONHC(COO$^-$)(CH$_2$)$_4$NHCO(CH$_2$)$_5$— |
| 55-87 | 0-3 | —(CH$_2$)$_2$CH(CH$_3$)SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 55-88 | 0-3 | —(CH$_2$)$_2$CH(CH$_3$)SO$_3$Na | —(CH$_2$)$_2$COOC$_2$H$_5$ | —(CH$_2$)$_2$CONHC(COO$^-$)(CH$_2$)$_4$NHCO(CH$_2$)$_5$— |
| 55-89 | 0-3 | —(CH$_2$)$_2$CH(CH$_3$)SO$_3$Na | —(CH$_2$)$_5$COOC$_2$H$_5$ | —(CH$_2$)$_2$CONHC(COO$^-$)(CH$_2$)$_4$NHCO(CH$_2$)$_5$— |
| 55-90 | 0-3 | —(CH$_2$)$_2$CH(CH$_3$)SO$_3$Na | —CH$_3$ | —(CH$_2$)$_2$CONHC(COO$^-$)(CH$_2$)$_4$NHCO(CH$_2$)$_5$— |
| 55-91 | 0-3 | —(CH$_2$)$_2$COOC$_2$H$_5$ | —(CH$_2$)$_3$SO$_3$Na | —(CH$_2$)$_2$CONHC(COO$^-$)(CH$_2$)$_4$NHCO(CH$_2$)$_5$— |
| 55-92 | 0-3 | —(CH$_2$)$_2$COOC$_2$H$_5$ | —(CH$_2$)$_4$SO$_3$Na | —(CH$_2$)$_2$CONHC(COO$^-$)(CH$_2$)$_4$NHCO(CH$_2$)$_5$— |
| 55-93 | 0-3 | —(CH$_2$)$_2$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 55-94 | 0-3 | —(CH$_2$)$_2$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_5$— |
| 55-95 | 0-3 | —(CH$_2$)$_2$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_5$— |
| 55-96 | 0-3 | —(CH$_2$)$_2$COOC$_2$H$_5$ | —CH$_3$ | —(CH$_2$)$_2$CONHC(COO$^-$)(CH$_2$)$_4$NHCO(CH$_2$)$_5$— |
| 55-97 | 0-3 | —(CH$_2$)$_5$COOC$_2$H$_5$ | —(CH$_2$)$_3$SO$_3$Na | —(CH$_2$)$_2$CONHC(COO$^-$)(CH$_2$)$_4$NHCO(CH$_2$)$_5$— |
| 55-98 | 0-3 | —(CH$_2$)$_5$COOC$_2$H$_5$ | —(CH$_2$)$_4$SO$_3$Na | —(CH$_2$)$_2$CONHC(COO$^-$)(CH$_2$)$_4$NHCO(CH$_2$)$_5$— |
| 55-99 | 0-3 | —(CH$_2$)$_5$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 55-100 | 0-3 | —(CH$_2$)$_5$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_5$— |
| 55-101 | 0-3 | —(CH$_2$)$_5$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_5$— |
| 55-102 | 0-3 | —(CH$_2$)$_5$COOC$_2$H$_5$ | —CH$_3$ | —(CH$_2$)$_2$CONHC(COO$^-$)(CH$_2$)$_4$NHCO(CH$_2$)$_5$— |
| 55-103 | 0-3 | —CH$_3$ | —(CH$_2$)$_3$SO$_3$Na | —(CH$_2$)$_2$CONHC(COO$^-$)(CH$_2$)$_4$NHCO(CH$_2$)$_5$— |
| 55-104 | 0-3 | —CH$_3$ | —(CH$_2$)$_4$SO$_3$Na | —(CH$_2$)$_2$CONHC(COO$^-$)(CH$_2$)$_4$NHCO(CH$_2$)$_5$— |
| 55-105 | 0-3 | —CH$_3$ | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 55-106 | 0-3 | —CH$_3$ | —(CH$_2$)$_2$COOC$_2$H$_5$ | —(CH$_2$)$_2$CONHC(COO$^-$)(CH$_2$)$_4$NHCO(CH$_2$)$_5$— |
| 55-107 | 0-3 | —CH$_3$ | —(CH$_2$)$_5$COOC$_2$H$_5$ | —(CH$_2$)$_2$CONHC(COO$^-$)(CH$_2$)$_4$NHCO(CH$_2$)$_5$— |
| 55-108 | 0-3 | —CH$_3$ | —CH$_3$ | —(CH$_2$)$_2$CONHC(COO$^-$)(CH$_2$)$_4$NHCO(CH$_2$)$_5$— |
| 55-109 | 0-3 | —(CH$_2$)$_3$SO$_3$Na | —(CH$_2$)$_3$SO$_3$Na | —(CH$_2$)$_2$CONHC(COO$^-$)(CH$_2$)$_4$NHCO(CH$_2$)$_2$— |
| 55-110 | 0-3 | —(CH$_2$)$_3$SO$_3$Na | —(CH$_2$)$_4$SO$_3$Na | —(CH$_2$)$_2$CONHC(COO$^-$)(CH$_2$)$_4$NHCO(CH$_2$)$_2$— |
| 55-111 | 0-3 | —(CH$_2$)$_3$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 55-112 | 0-3 | —(CH$_2$)$_3$SO$_3$Na | —(CH$_2$)$_2$COOC$_2$H$_5$ | —(CH$_2$)$_2$CONHC(COO$^-$)(CH$_2$)$_4$NHCO(CH$_2$)$_2$— |
| 55-113 | 0-3 | —(CH$_2$)$_3$SO$_3$Na | —(CH$_2$)$_5$COOC$_2$H$_5$ | —(CH$_2$)$_2$CONHC(COO$^-$)(CH$_2$)$_4$NHCO(CH$_2$)$_2$— |
| 55-114 | 0-3 | —(CH$_2$)$_3$SO$_3$Na | —CH$_3$ | —(CH$_2$)$_2$CONHC(COO$^-$)(CH$_2$)$_4$NHCO(CH$_2$)$_2$— |
| 55-115 | 0-3 | —(CH$_2$)$_4$SO$_3$Na | —(CH$_2$)$_3$SO$_3$Na | —(CH$_2$)$_2$CONHC(COO$^-$)(CH$_2$)$_4$NHCO(CH$_2$)$_2$— |
| 55-116 | 0-3 | —(CH$_2$)$_4$SO$_3$Na | —(CH$_2$)$_4$SO$_3$Na | —(CH$_2$)$_2$CONHC(COO$^-$)(CH$_2$)$_4$NHCO(CH$_2$)$_2$— |
| 55-117 | 0-3 | —(CH$_2$)$_4$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 55-118 | 0-3 | —(CH$_2$)$_4$SO$_3$Na | —(CH$_2$)$_2$COOC$_2$H$_5$ | —(CH$_2$)$_2$CONHC(COO$^-$)(CH$_2$)$_4$NHCO(CH$_2$)$_2$— |
| 55-119 | 0-3 | —(CH$_2$)$_4$SO$_3$Na | —(CH$_2$)$_5$COOC$_2$H$_5$ | —(CH$_2$)$_2$CONHC(COO$^-$)(CH$_2$)$_4$NHCO(CH$_2$)$_2$— |
| 55-120 | 0-3 | —(CH$_2$)$_4$SO$_3$Na | —CH$_3$ | —(CH$_2$)$_2$CONHC(COO$^-$)(CH$_2$)$_4$NHCO(CH$_2$)$_2$— |

TABLE 12

|  | n | R4" | R6" | T |
|---|---|---|---|---|
| 55-121 | 0-3 | —(CH$_2$)$_2$CH(CH$_3$)SO$_3$Na | —(CH$_2$)$_3$SO$_3$Na | —(CH$_2$)$_2$CONHC(COO$^-$)(CH$_2$)$_4$NHCO(CH$_2$)$_2$— |
| 55-122 | 0-3 | —(CH$_2$)$_2$CH(CH$_3$)SO$_3$Na | —(CH$_2$)$_4$SO$_3$Na | —(CH$_2$)$_2$CONHC(COO$^-$)(CH$_2$)$_4$NHCO(CH$_2$)$_2$— |
| 55-123 | 0-3 | —(CH$_2$)$_2$CH(CH$_3$)SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 55-124 | 0-3 | —(CH$_2$)$_2$CH(CH$_3$)SO$_3$Na | —(CH$_2$)$_2$COOC$_2$H$_5$ | —(CH$_2$)$_2$CONHC(COO$^-$)(CH$_2$)$_4$NHCO(CH$_2$)$_2$— |
| 55-125 | 0-3 | —(CH$_2$)$_2$CH(CH$_3$)SO$_3$Na | —(CH$_2$)$_5$COOC$_2$H$_5$ | —(CH$_2$)$_2$CONHC(COO$^-$)(CH$_2$)$_4$NHCO(CH$_2$)$_2$— |
| 55-126 | 0-3 | —(CH$_2$)$_2$CH(CH$_3$)SO$_3$Na | —CH$_3$ | —(CH$_2$)$_2$CONHC(COO$^-$)(CH$_2$)$_4$NHCO(CH$_2$)$_2$— |
| 55-127 | 0-3 | —(CH$_2$)$_2$COOC$_2$H$_5$ | —(CH$_2$)$_3$SO$_3$Na | —(CH$_2$)$_2$CONHC(COO$^-$)(CH$_2$)$_4$NHCO(CH$_2$)$_2$— |
| 55-128 | 0-3 | —(CH$_2$)$_2$COOC$_2$H$_5$ | —(CH$_2$)$_4$SO$_3$Na | —(CH$_2$)$_2$CONHC(COO$^-$)(CH$_2$)$_4$NHCO(CH$_2$)$_2$— |
| 55-129 | 0-3 | —(CH$_2$)$_2$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 55-130 | 0-3 | —(CH$_2$)$_2$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_2$— |
| 55-131 | 0-3 | —(CH$_2$)$_2$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_2$— |
| 55-132 | 0-3 | —(CH$_2$)$_2$COOC$_2$H$_5$ | —CH$_3$ | —(CH$_2$)$_2$CONHC(COO$^-$)(CH$_2$)$_4$NHCO(CH$_2$)$_2$— |
| 55-133 | 0-3 | —(CH$_2$)$_5$COOC$_2$H$_5$ | —(CH$_2$)$_3$SO$_3$Na | —(CH$_2$)$_2$CONHC(COO$^-$)(CH$_2$)$_4$NHCO(CH$_2$)$_2$— |

TABLE 12-continued

| | n | R$^{4''}$ | R$^{6''}$ | T |
|---|---|---|---|---|
| 55-134 | 0-3 | —(CH$_2$)$_5$COOC$_2$H$_5$ | —(CH$_2$)$_4$SO$_3$Na | —(CH$_2$)$_2$CONHC(COO$^-$)(CH$_2$)$_4$NHCO(CH$_2$)$_2$— |
| 55-135 | 0-3 | —(CH$_2$)$_5$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 55-136 | 0-3 | —(CH$_2$)$_5$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_2$— |
| 55-137 | 0-3 | —(CH$_2$)$_5$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_2$— |
| 55-138 | 0-3 | —(CH$_2$)$_5$COOC$_2$H$_5$ | —CH$_3$ | —(CH$_2$)$_2$CONHC(COO$^-$)(CH$_2$)$_4$NHCO(CH$_2$)$_2$— |
| 55-139 | 0-3 | —CH$_3$ | —(CH$_2$)$_3$SO$_3$Na | —(CH$_2$)$_2$CONHC(COO$^-$)(CH$_2$)$_4$NHCO(CH$_2$)$_2$— |
| 55-140 | 0-3 | —CH$_3$ | —(CH$_2$)$_4$SO$_3$Na | —(CH$_2$)$_2$CONHC(COO$^-$)(CH$_2$)$_4$NHCO(CH$_2$)$_2$— |
| 55-141 | 0-3 | —CH$_3$ | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 55-142 | 0-3 | —CH$_3$ | —(CH$_2$)$_2$COOC$_2$H$_5$ | —(CH$_2$)$_2$CONHC(COO$^-$)(CH$_2$)$_4$NHCO(CH$_2$)$_2$— |
| 55-143 | 0-3 | —CH$_3$ | —(CH$_2$)$_5$COOC$_2$H$_5$ | —(CH$_2$)$_2$CONHC(COO$^-$)(CH$_2$)$_4$NHCO(CH$_2$)$_2$— |
| 55-144 | 0-3 | —CH$_3$ | —CH$_3$ | —(CH$_2$)$_2$CONHC(COO$^-$)(CH$_2$)$_4$NHCO(CH$_2$)$_2$— |

Preferable specific examples of the compounds represented by the general formula [56], includes for example, those represented by the following Tables 13 to 16. It should be noted that, in Tables 13 to 16, R$^{3''}$, R$^{6''}$ and R$^{10''}$ in the general formula [56] are —CH$_3$ groups; R$^{7''}$, R$^{9''}$ and R$^{10''}$ are hydrogen atoms; and is —SO$_3$Na group.

TABLE 13

| | n | R$^{1''}$ | R$^{2''}$ | T |
|---|---|---|---|---|
| 56-1 | 0-3 | —(CH$_2$)$_3$SO$_3$Na | —(CH$_2$)$_3$SO$_3$Na | —(CH$_2$)$_5$CONHC(COO$^-$)(CH$_2$)$_4$NHCO(CH$_2$)$_5$— |
| 56-2 | 0-3 | —(CH$_2$)$_3$SO$_3$Na | —(CH$_2$)$_4$SO$_3$Na | —(CH$_2$)$_5$CONHC(COO$^-$)(CH$_2$)$_4$NHCO(CH$_2$)$_5$— |
| 56-3 | 0-3 | —(CH$_2$)$_3$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 56-4 | 0-3 | —(CH$_2$)$_3$SO$_3$Na | —(CH$_2$)$_2$COOC$_2$H$_5$ | —(CH$_2$)$_5$CONHC(COO$^-$)(CH$_2$)$_4$NHCO(CH$_2$)$_5$— |
| 56-5 | 0-3 | —(CH$_2$)$_3$SO$_3$Na | —(CH$_2$)$_5$COOC$_2$H$_5$ | —(CH$_2$)$_5$CONHC(COO$^-$)(CH$_2$)$_4$NHCO(CH$_2$)$_5$— |
| 56-6 | 0-3 | —(CH$_2$)$_3$SO$_3$Na | —CH$_3$ | —(CH$_2$)$_5$CONHC(COO$^-$)(CH$_2$)$_4$NHCO(CH$_2$)$_5$— |
| 56-7 | 0-3 | —(CH$_2$)$_4$SO$_3$Na | —(CH$_2$)$_3$SO$_3$Na | —(CH$_2$)$_5$CONHC(COO$^-$)(CH$_2$)$_4$NHCO(CH$_2$)$_5$— |
| 56-8 | 0-3 | —(CH$_2$)$_4$SO$_3$Na | —(CH$_2$)$_4$SO$_3$Na | —(CH$_2$)$_5$CONHC(COO$^-$)(CH$_2$)$_4$NHCO(CH$_2$)$_5$— |
| 56-9 | 0-3 | —(CH$_2$)$_4$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 56-10 | 0-3 | —(CH$_2$)$_4$SO$_3$Na | —(CH$_2$)$_2$COOC$_2$H$_5$ | —(CH$_2$)$_5$CONHC(COO$^-$)(CH$_2$)$_4$NHCO(CH$_2$)$_5$— |
| 56-11 | 0-3 | —(CH$_2$)$_4$SO$_3$Na | —(CH$_2$)$_5$COOC$_2$H$_5$ | —(CH$_2$)$_5$CONHC(COO$^-$)(CH$_2$)$_4$NHCO(CH$_2$)$_5$— |
| 56-12 | 0-3 | —(CH$_2$)$_4$SO$_3$Na | —CH$_3$ | —(CH$_2$)$_5$CONHC(COO$^-$)(CH$_2$)$_4$NHCO(CH$_2$)$_5$— |
| 56-13 | 0-3 | —(CH$_2$)$_2$CH(CH$_3$)SO$_3$Na | —(CH$_2$)$_3$SO$_3$Na | —(CH$_2$)$_5$CONHC(COO$^-$)(CH$_2$)$_4$NHCO(CH$_2$)$_5$— |
| 56-14 | 0-3 | —(CH$_2$)$_2$CH(CH$_3$)SO$_3$Na | —(CH$_2$)$_4$SO$_3$Na | —(CH$_2$)$_5$CONHC(COO$^-$)(CH$_2$)$_4$NHCO(CH$_2$)$_5$— |
| 56-15 | 0-3 | —(CH$_2$)$_2$CH(CH$_3$)SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 56-16 | 0-3 | —(CH$_2$)$_2$CH(CH$_3$)SO$_3$Na | —(CH$_2$)$_2$COOC$_2$H$_5$ | —(CH$_2$)$_5$CONHC(COO$^-$)(CH$_2$)$_4$NHCO(CH$_2$)$_5$— |
| 56-17 | 0-3 | —(CH$_2$)$_2$CH(CH$_3$)SO$_3$Na | —(CH$_2$)$_5$COOC$_2$H$_5$ | —(CH$_2$)$_5$CONHC(COO$^-$)(CH$_2$)$_4$NHCO(CH$_2$)$_5$— |
| 56-18 | 0-3 | —(CH$_2$)$_2$CH(CH$_3$)SO$_3$Na | —CH$_3$ | —(CH$_2$)$_5$CONHC(COO$^-$)(CH$_2$)$_4$NHCO(CH$_2$)$_5$— |
| 56-19 | 0-3 | —(CH$_2$)$_2$COOC$_2$H$_5$ | —(CH$_2$)$_3$SO$_3$Na | —(CH$_2$)$_5$CONHC(COO$^-$)(CH$_2$)$_4$NHCO(CH$_2$)$_5$— |
| 56-20 | 0-3 | —(CH$_2$)$_2$COOC$_2$H$_5$ | —(CH$_2$)$_4$SO$_3$Na | —(CH$_2$)$_5$CONHC(COO$^-$)(CH$_2$)$_4$NHCO(CH$_2$)$_5$— |
| 56-21 | 0-3 | —(CH$_2$)$_2$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 56-22 | 0-3 | —(CH$_2$)$_2$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_5$— |
| 56-23 | 0-3 | —(CH$_2$)$_2$COOC$_2$H$_5$ | —(CH$_2$)$_5$COOC$_2$H$_5$ | —(CH$_2$)$_5$CONHC(COO$^-$)(CH$_2$)$_4$NHCO(CH$_2$)$_5$— |
| 56-24 | 0-3 | —(CH$_2$)$_2$COOC$_2$H$_5$ | —CH$_3$ | —(CH$_2$)$_5$CONHC(COO$^-$)(CH$_2$)$_4$NHCO(CH$_2$)$_5$— |
| 56-25 | 0-3 | —(CH$_2$)$_5$COOC$_2$H$_5$ | —(CH$_2$)$_3$SO$_3$Na | —(CH$_2$)$_5$CONHC(COO$^-$)(CH$_2$)$_4$NHCO(CH$_2$)$_5$— |
| 56-26 | 0-3 | —(CH$_2$)$_5$COOC$_2$H$_5$ | —(CH$_2$)$_4$SO$_3$Na | —(CH$_2$)$_5$CONHC(COO$^-$)(CH$_2$)$_4$NHCO(CH$_2$)$_5$— |
| 56-27 | 0-3 | —(CH$_2$)$_5$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 56-28 | 0-3 | —(CH$_2$)$_5$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_5$— |
| 56-29 | 0-3 | —(CH$_2$)$_5$COOC$_2$H$_5$ | —(CH$_2$)$_5$COOC$_2$H$_5$ | —(CH$_2$)$_5$CONHC(COO$^-$)(CH$_2$)$_4$NHCO(CH$_2$)$_5$— |
| 56-30 | 0-3 | —(CH$_2$)$_5$COOC$_2$H$_5$ | —CH$_3$ | —(CH$_2$)$_5$CONHC(COO$^-$)(CH$_2$)$_4$NHCO(CH$_2$)$_5$— |
| 56-31 | 0-3 | —CH$_3$ | —(CH$_2$)$_3$SO$_3$Na | —(CH$_2$)$_5$CONHC(COO$^-$)(CH$_2$)$_4$NHCO(CH$_2$)$_5$— |
| 56-32 | 0-3 | —CH$_3$ | —(CH$_2$)$_4$SO$_3$Na | —(CH$_2$)$_5$CONHC(COO$^-$)(CH$_2$)$_4$NHCO(CH$_2$)$_5$— |
| 56-33 | 0-3 | —CH$_3$ | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 56-34 | 0-3 | —CH$_3$ | —(CH$_2$)$_2$COOC$_2$H$_5$ | —(CH$_2$)$_5$CONHC(COO$^-$)(CH$_2$)$_4$NHCO(CH$_2$)$_5$— |
| 56-35 | 0-3 | —CH$_3$ | —(CH$_2$)$_5$COOC$_2$H$_5$ | —(CH$_2$)$_5$CONHC(COO$^-$)(CH$_2$)$_4$NHCO(CH$_2$)$_5$— |
| 56-36 | 0-3 | —CH$_3$ | —CH$_3$ | —(CH$_2$)$_5$CONHC(COO$^-$)(CH$_2$)$_4$NHCO(CH$_2$)$_5$— |
| 56-37 | 0-3 | —(CH$_2$)$_3$SO$_3$Na | —(CH$_2$)$_3$SO$_3$Na | —(CH$_2$)$_5$CONHC(COO$^-$)(CH$_2$)$_4$NHCO(CH$_2$)$_2$— |
| 56-38 | 0-3 | —(CH$_2$)$_3$SO$_3$Na | —(CH$_2$)$_4$SO$_3$Na | —(CH$_2$)$_5$CONHC(COO$^-$)(CH$_2$)$_4$NHCO(CH$_2$)$_2$— |
| 56-39 | 0-3 | —(CH$_2$)$_3$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 56-40 | 0-3 | —(CH$_2$)$_3$SO$_3$Na | —(CH$_2$)$_2$COOC$_2$H$_5$ | —(CH$_2$)$_5$CONHC(COO$^-$)(CH$_2$)$_4$NHCO(CH$_2$)$_2$— |

TABLE 14

| | n | R$^{1''}$ | R$^{2''}$ | T |
|---|---|---|---|---|
| 56-41 | 0-3 | —(CH$_2$)$_3$SO$_3$Na | —(CH$_2$)$_5$COOC$_2$H$_5$ | —(CH$_2$)$_5$CONHC(COO$^-$)(CH$_2$)$_4$NHCO(CH$_2$)$_2$— |
| 56-42 | 0-3 | —(CH$_2$)$_3$SO$_3$Na | —CH$_3$ | —(CH$_2$)$_5$CONHC(COO$^-$)(CH$_2$)$_4$NHCO(CH$_2$)$_2$— |
| 56-43 | 0-3 | —(CH$_2$)$_4$SO$_3$Na | —(CH$_2$)$_3$SO$_3$Na | —(CH$_2$)$_5$CONHC(COO$^-$)(CH$_2$)$_4$NHCO(CH$_2$)$_2$— |
| 56-44 | 0-3 | —(CH$_2$)$_4$SO$_3$Na | —(CH$_2$)$_4$SO$_3$Na | —(CH$_2$)$_5$CONHC(COO$^-$)(CH$_2$)$_4$NHCO(CH$_2$)$_2$— |
| 56-45 | 0-3 | —(CH$_2$)$_4$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 56-46 | 0-3 | —(CH$_2$)$_4$SO$_3$Na | —(CH$_2$)$_2$COOC$_2$H$_5$ | —(CH$_2$)$_5$CONHC(COO$^-$)(CH$_2$)$_4$NHCO(CH$_2$)$_2$— |
| 56-47 | 0-3 | —(CH$_2$)$_4$SO$_3$Na | —(CH$_2$)$_5$COOC$_2$H$_5$ | —(CH$_2$)$_5$CONHC(COO$^-$)(CH$_2$)$_4$NHCO(CH$_2$)$_2$— |
| 56-48 | 0-3 | —(CH$_2$)$_4$SO$_3$Na | —CH$_3$ | —(CH$_2$)$_5$CONHC(COO$^-$)(CH$_2$)$_4$NHCO(CH$_2$)$_2$— |

TABLE 14-continued

| | n | R$^{1''}$ | R$^{2''}$ | T |
|---|---|---|---|---|
| 56-49 | 0-3 | —(CH$_2$)$_2$CH(CH$_3$)SO$_3$Na | —(CH$_2$)$_3$SO$_3$Na | —(CH$_2$)$_5$CONHC(COO$^-$)(CH$_2$)$_4$NHCO(CH$_2$)$_2$— |
| 56-50 | 0-3 | —(CH$_2$)$_2$CH(CH$_3$)SO$_3$Na | —(CH$_2$)$_4$SO$_3$Na | —(CH$_2$)$_5$CONHC(COO$^-$)(CH$_2$)$_4$NHCO(CH$_2$)$_2$— |
| 56-51 | 0-3 | —(CH$_2$)$_2$CH(CH$_3$)SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 56-52 | 0-3 | —(CH$_2$)$_2$CH(CH$_3$)SO$_3$Na | —(CH$_2$)$_2$COOC$_2$H$_5$ | —(CH$_2$)$_5$CONHC(COO$^-$)(CH$_2$)$_4$NHCO(CH$_2$)$_2$— |
| 56-53 | 0-3 | —(CH$_2$)$_2$CH(CH$_3$)SO$_3$Na | —(CH$_2$)$_5$COOC$_2$H$_5$ | —(CH$_2$)$_5$CONHC(COO$^-$)(CH$_2$)$_4$NHCO(CH$_2$)$_2$— |
| 56-54 | 0-3 | —(CH$_2$)$_2$CH(CH$_3$)SO$_3$Na | —CH$_3$ | —(CH$_2$)$_5$CONHC(COO$^-$)(CH$_2$)$_4$NHCO(CH$_2$)$_2$— |
| 56-55 | 0-3 | —(CH$_2$)$_2$COOC$_2$H$_5$ | —(CH$_2$)$_3$SO$_3$Na | —(CH$_2$)$_5$CONHC(COO$^-$)(CH$_2$)$_4$NHCO(CH$_2$)$_2$— |
| 56-56 | 0-3 | —(CH$_2$)$_2$COOC$_2$H$_5$ | —(CH$_2$)$_4$SO$_3$Na | —(CH$_2$)$_5$CONHC(COO$^-$)(CH$_2$)$_4$NHCO(CH$_2$)$_2$— |
| 56-57 | 0-3 | —(CH$_2$)$_2$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 56-58 | 0-3 | —(CH$_2$)$_2$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_2$— |
| 56-59 | 0-3 | —(CH$_2$)$_2$COOC$_2$H$_5$ | —(CH$_2$)$_5$COOC$_2$H$_5$ | —(CH$_2$)$_5$CONHC(COO$^-$)(CH$_2$)$_4$NHCO(CH$_2$)$_2$— |
| 56-60 | 0-3 | —(CH$_2$)$_2$COOC$_2$H$_5$ | —CH$_3$ | —(CH$_2$)$_5$CONHC(COO$^-$)(CH$_2$)$_4$NHCO(CH$_2$)$_2$— |
| 56-61 | 0-3 | —(CH$_2$)$_5$COOC$_2$H$_5$ | —(CH$_2$)$_3$SO$_3$Na | —(CH$_2$)$_5$CONHC(COO$^-$)(CH$_2$)$_4$NHCO(CH$_2$)$_2$— |
| 56-62 | 0-3 | —(CH$_2$)$_5$COOC$_2$H$_5$ | —(CH$_2$)$_4$SO$_3$Na | —(CH$_2$)$_5$CONHC(COO$^-$)(CH$_2$)$_4$NHCO(CH$_2$)$_2$— |
| 56-63 | 0-3 | —(CH$_2$)$_5$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 56-64 | 0-3 | —(CH$_2$)$_5$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_2$— |
| 56-65 | 0-3 | —(CH$_2$)$_5$COOC$_2$H$_5$ | —(CH$_2$)$_5$COOC$_2$H$_5$ | —(CH$_2$)$_5$CONHC(COO$^-$)(CH$_2$)$_4$NHCO(CH$_2$)$_2$— |
| 56-66 | 0-3 | —(CH$_2$)$_5$COOC$_2$H$_5$ | —CH$_3$ | —(CH$_2$)$_5$CONHC(COO$^-$)(CH$_2$)$_4$NHCO(CH$_2$)$_2$— |
| 56-67 | 0-3 | —CH$_3$ | —(CH$_2$)$_3$SO$_3$Na | —(CH$_2$)$_5$CONHC(COO$^-$)(CH$_2$)$_4$NHCO(CH$_2$)$_2$— |
| 56-68 | 0-3 | —CH$_3$ | —(CH$_2$)$_4$SO$_3$Na | —(CH$_2$)$_5$CONHC(COO$^-$)(CH$_2$)$_4$NHCO(CH$_2$)$_2$— |
| 56-69 | 0-3 | —CH$_3$ | —(CH$_2$)$_2$CH(CH$_3$)SO$_3$Na | —(CH$_2$)$_5$CONHC(COO$^-$)(CH$_2$)$_4$NHCO(CH$_2$)$_2$— |
| 56-70 | 0-3 | —CH$_3$ | —(CH$_2$)$_2$COOC$_2$H$_5$ | —(CH$_2$)$_5$CONHC(COO$^-$)(CH$_2$)$_4$NHCO(CH$_2$)$_2$— |
| 56-71 | 0-3 | —CH$_3$ | —(CH$_2$)$_5$COOC$_2$H$_5$ | —(CH$_2$)$_5$CONHC(COO$^-$)(CH$_2$)$_4$NHCO(CH$_2$)$_2$— |
| 56-72 | 0-3 | —CH$_3$ | —CH$_3$ | —(CH$_2$)$_5$CONHC(COO$^-$)(CH$_2$)$_4$NHCO(CH$_2$)$_2$— |
| 56-73 | 0-3 | —(CH$_2$)$_3$SO$_3$Na | —(CH$_2$)$_3$SO$_3$Na | —(CH$_2$)$_2$CONHC(COO$^-$)(CH$_2$)$_4$NHCO(CH$_2$)$_5$— |
| 56-74 | 0-3 | —(CH$_2$)$_3$SO$_3$Na | —(CH$_2$)$_4$SO$_3$Na | —(CH$_2$)$_2$CONHC(COO$^-$)(CH$_2$)$_4$NHCO(CH$_2$)$_5$— |
| 56-75 | 0-3 | —(CH$_2$)$_3$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 56-76 | 0-3 | —(CH$_2$)$_3$SO$_3$Na | —(CH$_2$)$_2$COOC$_2$H$_5$ | —(CH$_2$)$_2$CONHC(COO$^-$)(CH$_2$)$_4$NHCO(CH$_2$)$_5$— |
| 56-77 | 0-3 | —(CH$_2$)$_3$SO$_3$Na | —(CH$_2$)$_5$COOC$_2$H$_5$ | —(CH$_2$)$_2$CONHC(COO$^-$)(CH$_2$)$_4$NHCO(CH$_2$)$_5$— |
| 56-78 | 0-3 | —(CH$_2$)$_3$SO$_3$Na | —CH$_3$ | —(CH$_2$)$_2$CONHC(COO$^-$)(CH$_2$)$_4$NHCO(CH$_2$)$_5$— |
| 56-79 | 0-3 | —(CH$_2$)$_4$SO$_3$Na | —(CH$_2$)$_3$SO$_3$Na | —(CH$_2$)$_2$CONHC(COO$^-$)(CH$_2$)$_4$NHCO(CH$_2$)$_5$— |
| 56-80 | 0-3 | —(CH$_2$)$_4$SO$_3$Na | —(CH$_2$)$_4$SO$_3$Na | —(CH$_2$)$_2$CONHC(COO$^-$)(CH$_2$)$_4$NHCO(CH$_2$)$_5$— |

TABLE 15

| | n | R$^{1''}$ | R$^{2''}$ | T |
|---|---|---|---|---|
| 56-81 | 0-3 | —(CH$_2$)$_4$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 56-82 | 0-3 | —(CH$_2$)$_4$SO$_3$Na | —(CH$_2$)$_2$COOC$_2$H$_5$ | —(CH$_2$)$_2$CONHC(COO$^-$)(CH$_2$)$_4$NHCO(CH$_2$)$_5$— |
| 56-83 | 0-3 | —(CH$_2$)$_4$SO$_3$Na | —(CH$_2$)$_5$COOC$_2$H$_5$ | —(CH$_2$)$_2$CONHC(COO$^-$)(CH$_2$)$_4$NHCO(CH$_2$)$_5$— |
| 56-84 | 0-3 | —(CH$_2$)$_4$SO$_3$Na | —CH$_3$ | —(CH$_2$)$_2$CONHC(COO$^-$)(CH$_2$)$_4$NHCO(CH$_2$)$_5$— |
| 56-85 | 0-3 | —(CH$_2$)$_2$CH(CH$_3$)SO$_3$Na | —(CH$_2$)$_3$SO$_3$Na | —(CH$_2$)$_2$CONHC(COO$^-$)(CH$_2$)$_4$NHCO(CH$_2$)$_5$— |
| 56-86 | 0-3 | —(CH$_2$)$_2$CH(CH$_3$)SO$_3$Na | —(CH$_2$)$_4$SO$_3$Na | —(CH$_2$)$_2$CONHC(COO$^-$)(CH$_2$)$_4$NHCO(CH$_2$)$_5$— |
| 56-87 | 0-3 | —(CH$_2$)$_2$CH(CH$_3$)SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 56-88 | 0-3 | —(CH$_2$)$_2$CH(CH$_3$)SO$_3$Na | —(CH$_2$)$_2$COOC$_2$H$_5$ | —(CH$_2$)$_2$CONHC(COO$^-$)(CH$_2$)$_4$NHCO(CH$_2$)$_5$— |
| 56-89 | 0-3 | —(CH$_2$)$_2$CH(CH$_3$)SO$_3$Na | —(CH$_2$)$_5$COOC$_2$H$_5$ | —(CH$_2$)$_2$CONHC(COO$^-$)(CH$_2$)$_4$NHCO(CH$_2$)$_5$— |
| 56-90 | 0-3 | —(CH$_2$)$_2$CH(CH$_3$)SO$_3$Na | —CH$_3$ | —(CH$_2$)$_2$CONHC(COO$^-$)(CH$_2$)$_4$NHCO(CH$_2$)$_5$— |
| 56-91 | 0-3 | —(CH$_2$)$_2$COOC$_2$H$_5$ | —(CH$_2$)$_3$SO$_3$Na | —(CH$_2$)$_2$CONHC(COO$^-$)(CH$_2$)$_4$NHCO(CH$_2$)$_5$— |
| 56-92 | 0-3 | —(CH$_2$)$_2$COOC$_2$H$_5$ | —(CH$_2$)$_4$SO$_3$Na | —(CH$_2$)$_2$CONHC(COO$^-$)(CH$_2$)$_4$NHCO(CH$_2$)$_5$— |
| 56-93 | 0-3 | —(CH$_2$)$_2$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 56-94 | 0-3 | —(CH$_2$)$_2$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_5$— |
| 56-95 | 0-3 | —(CH$_2$)$_2$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_5$— |
| 56-96 | 0-3 | —(CH$_2$)$_2$COOC$_2$H$_5$ | —CH$_3$ | —(CH$_2$)$_2$CONHC(COO$^-$)(CH$_2$)$_4$NHCO(CH$_2$)$_5$— |
| 56-97 | 0-3 | —(CH$_2$)$_5$COOC$_2$H$_5$ | —(CH$_2$)$_3$SO$_3$Na | —(CH$_2$)$_2$CONHC(COO$^-$)(CH$_2$)$_4$NHCO(CH$_2$)$_5$— |
| 56-98 | 0-3 | —(CH$_2$)$_5$COOC$_2$H$_5$ | —(CH$_2$)$_4$SO$_3$Na | —(CH$_2$)$_2$CONHC(COO$^-$)(CH$_2$)$_4$NHCO(CH$_2$)$_5$— |
| 56-99 | 0-3 | —(CH$_2$)$_5$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 56-100 | 0-3 | —(CH$_2$)$_5$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_5$— |
| 56-101 | 0-3 | —(CH$_2$)$_5$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_5$— |
| 56-102 | 0-3 | —(CH$_2$)$_5$COOC$_2$H$_5$ | —CH$_3$ | —(CH$_2$)$_2$CONHC(COO$^-$)(CH$_2$)$_4$NHCO(CH$_2$)$_5$— |
| 56-103 | 0-3 | —CH$_3$ | —(CH$_2$)$_3$SO$_3$Na | —(CH$_2$)$_2$CONHC(COO$^-$)(CH$_2$)$_4$NHCO(CH$_2$)$_5$— |
| 56-104 | 0-3 | —CH$_3$ | —(CH$_2$)$_4$SO$_3$Na | —(CH$_2$)$_2$CONHC(COO$^-$)(CH$_2$)$_4$NHCO(CH$_2$)$_5$— |
| 56-105 | 0-3 | —CH$_3$ | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 56-106 | 0-3 | —CH$_3$ | —(CH$_2$)$_2$COOC$_2$H$_5$ | —(CH$_2$)$_2$CONHC(COO$^-$)(CH$_2$)$_4$NHCO(CH$_2$)$_5$— |
| 56-107 | 0-3 | —CH$_3$ | —(CH$_2$)$_5$COOC$_2$H$_5$ | —(CH$_2$)$_2$CONHC(COO$^-$)(CH$_2$)$_4$NHCO(CH$_2$)$_5$— |
| 56-108 | 0-3 | —CH$_3$ | —CH$_3$ | —(CH$_2$)$_2$CONHC(COO$^-$)(CH$_2$)$_4$NHCO(CH$_2$)$_5$— |
| 56-109 | 0-3 | —(CH$_2$)$_3$SO$_3$Na | —(CH$_2$)$_3$SO$_3$Na | —(CH$_2$)$_2$CONHC(COO$^-$)(CH$_2$)$_4$NHCO(CH$_2$)$_2$— |
| 56-110 | 0-3 | —(CH$_2$)$_3$SO$_3$Na | —(CH$_2$)$_4$SO$_3$Na | —(CH$_2$)$_2$CONHC(COO$^-$)(CH$_2$)$_4$NHCO(CH$_2$)$_2$— |
| 56-111 | 0-3 | —(CH$_2$)$_3$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 56-112 | 0-3 | —(CH$_2$)$_3$SO$_3$Na | —(CH$_2$)$_2$COOC$_2$H$_5$ | —(CH$_2$)$_2$CONHC(COO$^-$)(CH$_2$)$_4$NHCO(CH$_2$)$_2$— |
| 56-113 | 0-3 | —(CH$_2$)$_3$SO$_3$Na | —(CH$_2$)$_5$COOC$_2$H$_5$ | —(CH$_2$)$_2$CONHC(COO$^-$)(CH$_2$)$_4$NHCO(CH$_2$)$_2$— |
| 56-114 | 0-3 | —(CH$_2$)$_3$SO$_3$Na | —CH$_3$ | —(CH$_2$)$_2$CONHC(COO$^-$)(CH$_2$)$_4$NHCO(CH$_2$)$_2$— |
| 56-115 | 0-3 | —(CH$_2$)$_4$SO$_3$Na | —(CH$_2$)$_3$SO$_3$Na | —(CH$_2$)$_2$CONHC(COO$^-$)(CH$_2$)$_4$NHCO(CH$_2$)$_2$— |
| 56-116 | 0-3 | —(CH$_2$)$_4$SO$_3$Na | —(CH$_2$)$_4$SO$_3$Na | —(CH$_2$)$_2$CONHC(COO$^-$)(CH$_2$)$_4$NHCO(CH$_2$)$_2$— |
| 56-117 | 0-3 | —(CH$_2$)$_4$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 56-118 | 0-3 | —(CH$_2$)$_4$SO$_3$Na | —(CH$_2$)$_2$COOC$_2$H$_5$ | —(CH$_2$)$_2$CONHC(COO$^-$)(CH$_2$)$_4$NHCO(CH$_2$)$_2$— |

TABLE 15-continued

| | n | R$^{1'''}$ | R$^{2'''}$ | T |
|---|---|---|---|---|
| 56-119 | 0-3 | —(CH$_2$)$_4$SO$_3$Na | —(CH$_2$)$_5$COOC$_2$H$_5$ | —(CH$_2$)$_2$CONHC(COO$^-$)(CH$_2$)$_4$NHCO(CH$_2$)$_2$— |
| 56-120 | 0-3 | —(CH$_2$)$_4$SO$_3$Na | —CH$_3$ | —(CH$_2$)$_2$CONHC(COO$^-$)(CH$_2$)$_4$NHCO(CH$_2$)$_2$— |

TABLE 16

| | n | R$^{1'''}$ | R$^{2'''}$ | T |
|---|---|---|---|---|
| 56-121 | 0-3 | —(CH$_2$)$_2$CH(CH$_3$)SO$_3$Na | —(CH$_2$)$_3$SO$_3$Na | —(CH$_2$)$_2$CONHC(COO$^-$)(CH$_2$)$_4$NHCO(CH$_2$)$_2$— |
| 56-122 | 0-3 | —(CH$_2$)$_2$CH(CH$_3$)SO$_3$Na | —(CH$_2$)$_4$SO$_3$Na | —(CH$_2$)$_2$CONHC(COO$^-$)(CH$_2$)$_4$NHCO(CH$_2$)$_2$— |
| 56-123 | 0-3 | —(CH$_2$)$_2$CH(CH$_3$)SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 56-124 | 0-3 | —(CH$_2$)$_2$CH(CH$_3$)SO$_3$Na | —(CH$_2$)$_2$COOC$_2$H$_5$ | —(CH$_2$)$_2$CONHC(COO$^-$)(CH$_2$)$_4$NHCO(CH$_2$)$_2$— |
| 56-125 | 0-3 | —(CH$_2$)$_2$CH(CH$_3$)SO$_3$Na | —(CH$_2$)$_5$COOC$_2$H$_5$ | —(CH$_2$)$_2$CONHC(COO$^-$)(CH$_2$)$_4$NHCO(CH$_2$)$_2$— |
| 56-126 | 0-3 | —(CH$_2$)$_2$CH(CH$_3$)SO$_3$Na | —CH$_3$ | —(CH$_2$)$_2$CONHC(COO$^-$)(CH$_2$)$_4$NHCO(CH$_2$)$_2$— |
| 56-127 | 0-3 | —(CH$_2$)$_2$COOC$_2$H$_5$ | —(CH$_2$)$_3$SO$_3$Na | —(CH$_2$)$_2$CONHC(COO$^-$)(CH$_2$)$_4$NHCO(CH$_2$)$_2$— |
| 56-128 | 0-3 | —(CH$_2$)$_2$COOC$_2$H$_5$ | —(CH$_2$)$_4$SO$_3$Na | —(CH$_2$)$_2$CONHC(COO$^-$)(CH$_2$)$_4$NHCO(CH$_2$)$_2$— |
| 56-129 | 0-3 | —(CH$_2$)$_2$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 56-130 | 0-3 | —(CH$_2$)$_2$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_2$— |
| 56-131 | 0-3 | —(CH$_2$)$_2$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_2$— |
| 56-132 | 0-3 | —(CH$_2$)$_2$COOC$_2$H$_5$ | —CH$_3$ | —(CH$_2$)$_2$CONHC(COO$^-$)(CH$_2$)$_4$NHCO(CH$_2$)$_2$— |
| 56-133 | 0-3 | —(CH$_2$)$_5$COOC$_2$H$_5$ | —(CH$_2$)$_3$SO$_3$Na | —(CH$_2$)$_2$CONHC(COO$^-$)(CH$_2$)$_4$NHCO(CH$_2$)$_2$— |
| 56-134 | 0-3 | —(CH$_2$)$_5$COOC$_2$H$_5$ | —(CH$_2$)$_4$SO$_3$Na | —(CH$_2$)$_2$CONHC(COO$^-$)(CH$_2$)$_4$NHCO(CH$_2$)$_2$— |
| 56-135 | 0-3 | —(CH$_2$)$_5$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 56-136 | 0-3 | —(CH$_2$)$_5$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_2$— |
| 56-137 | 0-3 | —(CH$_2$)$_5$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_2$— |
| 56-138 | 0-3 | —(CH$_2$)$_5$COOC$_2$H$_5$ | —CH$_3$ | —(CH$_2$)$_2$CONHC(COO$^-$)(CH$_2$)$_4$NHCO(CH$_2$)$_2$— |
| 56-139 | 0-3 | —CH$_3$ | —(CH$_2$)$_3$SO$_3$Na | —(CH$_2$)$_2$CONHC(COO$^-$)(CH$_2$)$_4$NHCO(CH$_2$)$_2$— |
| 56-140 | 0-3 | —CH$_3$ | —(CH$_2$)$_4$SO$_3$Na | —(CH$_2$)$_2$CONHC(COO$^-$)(CH$_2$)$_4$NHCO(CH$_2$)$_2$— |
| 56-141 | 0-3 | —CH$_3$ | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 56-142 | 0-3 | —CH$_3$ | —(CH$_2$)$_2$COOC$_2$H$_5$ | —(CH$_2$)$_2$CONHC(COO$^-$)(CH$_2$)$_4$NHCO(CH$_2$)$_2$— |
| 56-143 | 0-3 | —CH$_3$ | —(CH$_2$)$_5$COOC$_2$H$_5$ | —(CH$_2$)$_2$CONHC(COO$^-$)(CH$_2$)$_4$NHCO(CH$_2$)$_2$— |
| 56-144 | 0-3 | —CH$_3$ | —CH$_3$ | —(CH$_2$)$_2$CONHC(COO$^-$)(CH$_2$)$_4$NHCO(CH$_2$)$_2$— |

Preferable specific examples of the compounds represented by the general formula [57], includes for example, those represented by the following Tables 17 to 20. It should be noted that, in Tables 17 to 20, R$^{3'''}$, R$^{5'''}$ and R$^{11'''}$ in the general formula [57] are —CH$_3$ groups; R$^{7'''}$, R$^{9'''}$ and R$^{10'''}$ are hydrogen atoms; and R$^{8'''}$ is —SO$_3$Na group.

TABLE 17

| | n | R$^{2'''}$ | R$^{4'''}$ | T |
|---|---|---|---|---|
| 57-1 | 0-3 | —(CH$_2$)$_3$SO$_3$Na | —(CH$_2$)$_3$SO$_3$Na | —(CH$_2$)$_5$CONHC(COO$^-$)(CH$_2$)$_4$NHCO(CH$_2$)$_5$— |
| 57-2 | 0-3 | —(CH$_2$)$_3$SO$_3$Na | —(CH$_2$)$_4$SO$_3$Na | —(CH$_2$)$_5$CONHC(COO$^-$)(CH$_2$)$_4$NHCO(CH$_2$)$_5$— |
| 57-3 | 0-3 | —(CH$_2$)$_3$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 57-4 | 0-3 | —(CH$_2$)$_3$SO$_3$Na | —(CH$_2$)$_2$COOC$_2$H$_5$ | —(CH$_2$)$_5$CONHC(COO$^-$)(CH$_2$)$_4$NHCO(CH$_2$)$_5$— |
| 57-5 | 0-3 | —(CH$_2$)$_3$SO$_3$Na | —(CH$_2$)$_5$COOC$_2$H$_5$ | —(CH$_2$)$_5$CONHC(COO$^-$)(CH$_2$)$_4$NHCO(CH$_2$)$_5$— |
| 57-6 | 0-3 | —(CH$_2$)$_3$SO$_3$Na | —CH$_3$ | —(CH$_2$)$_5$CONHC(COO$^-$)(CH$_2$)$_4$NHCO(CH$_2$)$_5$— |
| 57-7 | 0-3 | —(CH$_2$)$_4$SO$_3$Na | —(CH$_2$)$_3$SO$_3$Na | —(CH$_2$)$_5$CONHC(COO$^-$)(CH$_2$)$_4$NHCO(CH$_2$)$_5$— |
| 57-8 | 0-3 | —(CH$_2$)$_4$SO$_3$Na | —(CH$_2$)$_4$SO$_3$Na | —(CH$_2$)$_5$CONHC(COO$^-$)(CH$_2$)$_4$NHCO(CH$_2$)$_5$— |
| 57-9 | 0-3 | —(CH$_2$)$_4$SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 57-10 | 0-3 | —(CH$_2$)$_4$SO$_3$Na | —(CH$_2$)$_2$COOC$_2$H$_5$ | —(CH$_2$)$_5$CONHC(COO$^-$)(CH$_2$)$_4$NHCO(CH$_2$)$_5$— |
| 57-11 | 0-3 | —(CH$_2$)$_4$SO$_3$Na | —(CH$_2$)$_5$COOC$_2$H$_5$ | —(CH$_2$)$_5$CONHC(COO$^-$)(CH$_2$)$_4$NHCO(CH$_2$)$_5$— |
| 57-12 | 0-3 | —(CH$_2$)$_4$SO$_3$Na | —CH$_3$ | —(CH$_2$)$_5$CONHC(COO$^-$)(CH$_2$)$_4$NHCO(CH$_2$)$_5$— |
| 57-13 | 0-3 | —(CH$_2$)$_2$CH(CH$_3$)SO$_3$Na | —(CH$_2$)$_3$SO$_3$Na | —(CH$_2$)$_5$CONHC(COO$^-$)(CH$_2$)$_4$NHCO(CH$_2$)$_5$— |
| 57-14 | 0-3 | —(CH$_2$)$_2$CH(CH$_3$)SO$_3$Na | —(CH$_2$)$_4$SO$_3$Na | —(CH$_2$)$_5$CONHC(COO$^-$)(CH$_2$)$_4$NHCO(CH$_2$)$_5$— |
| 57-15 | 0-3 | —(CH$_2$)$_2$CH(CH$_3$)SO$_3$Na | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 57-16 | 0-3 | —(CH$_2$)$_2$CH(CH$_3$)SO$_3$Na | —(CH$_2$)$_2$COOC$_2$H$_5$ | —(CH$_2$)$_5$CONHC(COO$^-$)(CH$_2$)$_4$NHCO(CH$_2$)$_5$— |
| 57-17 | 0-3 | —(CH$_2$)$_2$CH(CH$_3$)SO$_3$Na | —(CH$_2$)$_5$COOC$_2$H$_5$ | —(CH$_2$)$_5$CONHC(COO$^-$)(CH$_2$)$_4$NHCO(CH$_2$)$_5$— |
| 57-18 | 0-3 | —(CH$_2$)$_2$CH(CH$_3$)SO$_3$Na | —CH$_3$ | —(CH$_2$)$_5$CONHC(COO$^-$)(CH$_2$)$_4$NHCO(CH$_2$)$_5$— |
| 57-19 | 0-3 | —(CH$_2$)$_2$COOC$_2$H$_5$ | —(CH$_2$)$_3$SO$_3$Na | —(CH$_2$)$_5$CONHC(COO$^-$)(CH$_2$)$_4$NHCO(CH$_2$)$_5$— |
| 57-20 | 0-3 | —(CH$_2$)$_2$COOC$_2$H$_5$ | —(CH$_2$)$_4$SO$_3$Na | —(CH$_2$)$_5$CONHC(COO$^-$)(CH$_2$)$_4$NHCO(CH$_2$)$_5$— |
| 57-21 | 0-3 | —(CH$_2$)$_2$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 57-22 | 0-3 | —(CH$_2$)$_2$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_5$— |
| 57-23 | 0-3 | —(CH$_2$)$_5$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_5$— |
| 57-24 | 0-3 | —(CH$_2$)$_2$COOC$_2$H$_5$ | —CH$_3$ | —(CH$_2$)$_5$CONHC(COO$^-$)(CH$_2$)$_4$NHCO(CH$_2$)$_5$— |
| 57-25 | 0-3 | —(CH$_2$)$_5$COOC$_2$H$_5$ | —(CH$_2$)$_3$SO$_3$Na | —(CH$_2$)$_5$CONHC(COO$^-$)(CH$_2$)$_4$NHCO(CH$_2$)$_5$— |
| 57-26 | 0-3 | —(CH$_2$)$_5$COOC$_2$H$_5$ | —(CH$_2$)$_4$SO$_3$Na | —(CH$_2$)$_5$CONHC(COO$^-$)(CH$_2$)$_4$NHCO(CH$_2$)$_5$— |
| 57-27 | 0-3 | —(CH$_2$)$_5$COOC$_2$H$_5$ | —(CH$_2$)$_2$CH(CH$_3$)SO$_3$Na | —(CH$_2$)$_5$CONHC(COO$^-$)(CH$_2$)$_4$NHCO(CH$_2$)$_5$— |
| 57-28 | 0-3 | —(CH$_2$)$_5$COOC$_2$H$_5$ | —(CH$_2$)$_2$COOC$_2$H$_5$ | —(CH$_2$)$_5$CONHC(COO$^-$)(CH$_2$)$_4$NHCO(CH$_2$)$_5$— |
| 57-29 | 0-3 | —(CH$_2$)$_5$COOC$_2$H$_5$ | —(CH$_2$)$_5$COOC$_2$H$_5$ | —(CH$_2$)$_5$CONHC(COO$^-$)(CH$_2$)$_4$NHCO(CH$_2$)$_5$— |
| 57-30 | 0-3 | —(CH$_2$)$_5$COOC$_2$H$_5$ | —CH$_3$ | —(CH$_2$)$_5$CONHC(COO$^-$)(CH$_2$)$_4$NHCO(CH$_2$)$_5$— |
| 57-31 | 0-3 | —CH$_3$ | —(CH$_2$)$_3$SO$_3$Na | —(CH$_2$)$_5$CONHC(COO$^-$)(CH$_2$)$_4$NHCO(CH$_2$)$_5$— |
| 57-32 | 0-3 | —CH$_3$ | —(CH$_2$)$_4$SO$_3$Na | —(CH$_2$)$_5$CONHC(COO$^-$)(CH$_2$)$_4$NHCO(CH$_2$)$_5$— |
| 57-33 | 0-3 | —CH$_3$ | —(CH$_2$)$_2$CH(CH$_3$)SO$_3$Na | —(CH$_2$)$_5$CONHC(COO$^-$)(CH$_2$)$_4$NHCO(CH$_2$)$_5$— |

TABLE 17-continued

|  | n | R²" | R⁴" | T |
|---|---|---|---|---|
| 57-34 | 0-3 | —CH₃ | —(CH₂)₂COOC₂H₅ | —(CH₂)₅CONHC(COO⁻)(CH₂)₄NHCO(CH₂)₅— |
| 57-35 | 0-3 | —CH₃ | —(CH₂)₅COOC₂H₅ | —(CH₂)₅CONHC(COO⁻)(CH₂)₄NHCO(CH₂)₅— |
| 57-36 | 0-3 | —CH₃ | —CH₃ | —(CH₂)₅CONHC(COO⁻)(CH₂)₄NHCO(CH₂)₅— |
| 57-37 | 0-3 | —(CH₂)₃SO₃Na | —(CH₂)₃SO₃Na | —(CH₂)₅CONHC(COO⁻)(CH₂)₄NHCO(CH₂)₂— |
| 57-38 | 0-3 | —(CH₂)₃SO₃Na | —(CH₂)₄SO₃Na | —(CH₂)₅CONHC(COO⁻)(CH₂)₄NHCO(CH₂)₂— |
| 57-39 | 0-3 | —(CH₂)₃SO₃Na | —(CH₂)₂CH(CH₃)SO₃Na | —(CH₂)₅CONHC(COO⁻)(CH₂)₄NHCO(CH₂)₂— |
| 57-40 | 0-3 | —(CH₂)₃SO₃Na | —(CH₂)₂COOC₂H₅ | —(CH₂)₅CONHC(COO⁻)(CH₂)₄NHCO(CH₂)₂— |

TABLE 18

|  | n | R²" | R⁴" | T |
|---|---|---|---|---|
| 57-41 | 0-3 | —(CH₂)₃SO₃Na | —(CH₂)₅COOC₂H₅ | —(CH₂)₅CONHC(COO⁻)(CH₂)₄NHCO(CH₂)₂— |
| 57-42 | 0-3 | —(CH₂)₃SO₃Na | —CH₃ | —(CH₂)₅CONHC(COO⁻)(CH₂)₄NHCO(CH₂)₂— |
| 57-43 | 0-3 | —(CH₂)₄SO₃Na | —(CH₂)₃SO₃Na | —(CH₂)₅CONHC(COO⁻)(CH₂)₄NHCO(CH₂)₂— |
| 57-44 | 0-3 | —(CH₂)₄SO₃Na | —(CH₂)₄SO₃Na | —(CH₂)₅CONHC(COO⁻)(CH₂)₄NHCO(CH₂)₂— |
| 57-45 | 0-3 | —(CH₂)₄SO₃Na | —(CH₂)₂CH(CH₃)SO₃Na | —(CH₂)₅CONHC(COO⁻)(CH₂)₄NHCO(CH₂)₂— |
| 57-46 | 0-3 | —(CH₂)₄SO₃Na | —(CH₂)₂COOC₂H₅ | —(CH₂)₅CONHC(COO⁻)(CH₂)₄NHCO(CH₂)₂— |
| 57-47 | 0-3 | —(CH₂)₄SO₃Na | —(CH₂)₅COOC₂H₅ | —(CH₂)₅CONHC(COO⁻)(CH₂)₄NHCO(CH₂)₂— |
| 57-48 | 0-3 | —(CH₂)₄SO₃Na | —CH₃ | —(CH₂)₅CONHC(COO⁻)(CH₂)₄NHCO(CH₂)₂— |
| 57-49 | 0-3 | —(CH₂)₂CH(CH₃)SO₃Na | —(CH₂)₃SO₃Na | —(CH₂)₅CONHC(COO⁻)(CH₂)₄NHCO(CH₂)₂— |
| 57-50 | 0-3 | —(CH₂)₂CH(CH₃)SO₃Na | —(CH₂)₄SO₃Na | —(CH₂)₅CONHC(COO⁻)(CH₂)₄NHCO(CH₂)₂— |
| 57-51 | 0-3 | —(CH₂)₂CH(CH₃)SO₃Na | —(CH₂)₂CH(CH₃)SO₃Na | —(CH₂)₅CONHC(COO⁻)(CH₂)₄NHCO(CH₂)₂— |
| 57-52 | 0-3 | —(CH₂)₂CH(CH₃)SO₃Na | —(CH₂)₂COOC₂H₅ | —(CH₂)₅CONHC(COO⁻)(CH₂)₄NHCO(CH₂)₂— |
| 57-53 | 0-3 | —(CH₂)₂CH(CH₃)SO₃Na | —(CH₂)₅COOC₂H₅ | —(CH₂)₅CONHC(COO⁻)(CH₂)₄NHCO(CH₂)₂— |
| 57-54 | 0-3 | —(CH₂)₂CH(CH₃)SO₃Na | —CH₃ | —(CH₂)₅CONHC(COO⁻)(CH₂)₄NHCO(CH₂)₂— |
| 57-55 | 0-3 | —(CH₂)₂COOC₂H₅ | —(CH₂)₃SO₃Na | —(CH₂)₅CONHC(COO⁻)(CH₂)₄NHCO(CH₂)₂— |
| 57-56 | 0-3 | —(CH₂)₂COOC₂H₅ | —(CH₂)₄SO₃Na | —(CH₂)₅CONHC(COO⁻)(CH₂)₄NHCO(CH₂)₂— |
| 57-57 | 0-3 | —(CH₂)₂COOC₂H₅ | —(CH₂)₂CH(CH₃)SO₃Na | —(CH₂)₅CONHC(COO⁻)(CH₂)₄NHCO(CH₂)₂— |
| 57-58 | 0-3 | —(CH₂)₂COOC₂H₅ | —(CH₂)₂COOC₂H₅ | —(CH₂)₅CONHC(COO⁻)(CH₂)₄NHCO(CH₂)₂— |
| 57-59 | 0-3 | —(CH₂)₂COOC₂H₅ | —(CH₂)₅COOC₂H₅ | —(CH₂)₅CONHC(COO⁻)(CH₂)₄NHCO(CH₂)₂— |
| 57-60 | 0-3 | —(CH₂)₂COOC₂H₅ | —CH₃ | —(CH₂)₅CONHC(COO⁻)(CH₂)₄NHCO(CH₂)₂— |
| 57-61 | 0-3 | —(CH₂)₅COOC₂H₅ | —(CH₂)₃SO₃Na | —(CH₂)₅CONHC(COO⁻)(CH₂)₄NHCO(CH₂)₂— |
| 57-62 | 0-3 | —(CH₂)₅COOC₂H₅ | —(CH₂)₄SO₃Na | —(CH₂)₅CONHC(COO⁻)(CH₂)₄NHCO(CH₂)₂— |
| 57-63 | 0-3 | —(CH₂)₅COOC₂H₅ | —(CH₂)₂CH(CH₃)SO₃Na | —(CH₂)₅CONHC(COO⁻)(CH₂)₄NHCO(CH₂)₂— |
| 57-64 | 0-3 | —(CH₂)₅COOC₂H₅ | —(CH₂)₂COOC₂H₅ | —(CH₂)₅CONHC(COO⁻)(CH₂)₄NHCO(CH₂)₂— |
| 57-65 | 0-3 | —(CH₂)₅COOC₂H₅ | —(CH₂)₅COOC₂H₅ | —(CH₂)₅CONHC(COO⁻)(CH₂)₄NHCO(CH₂)₂— |
| 57-66 | 0-3 | —(CH₂)₅COOC₂H₅ | —CH₃ | —(CH₂)₅CONHC(COO⁻)(CH₂)₄NHCO(CH₂)₂— |
| 57-67 | 0-3 | —CH₃ | —(CH₂)₃SO₃Na | —(CH₂)₅CONHC(COO⁻)(CH₂)₄NHCO(CH₂)₂— |
| 57-68 | 0-3 | —CH₃ | —(CH₂)₄SO₃Na | —(CH₂)₅CONHC(COO⁻)(CH₂)₄NHCO(CH₂)₂— |
| 57-69 | 0-3 | —CH₃ | —(CH₂)₂CH(CH₃)SO₃Na | —(CH₂)₅CONHC(COO⁻)(CH₂)₄NHCO(CH₂)₂— |
| 57-70 | 0-3 | —CH₃ | —(CH₂)₂COOC₂H₅ | —(CH₂)₅CONHC(COO⁻)(CH₂)₄NHCO(CH₂)₂— |
| 57-71 | 0-3 | —CH₃ | —(CH₂)₅COOC₂H₅ | —(CH₂)₅CONHC(COO⁻)(CH₂)₄NHCO(CH₂)₂— |
| 57-72 | 0-3 | —CH₃ | —CH₃ | —(CH₂)₅CONHC(COO⁻)(CH₂)₄NHCO(CH₂)₂— |
| 57-73 | 0-3 | —(CH₂)₃SO₃Na | —(CH₂)₃SO₃Na | —(CH₂)₂CONHC(COO⁻)(CH₂)₄NHCO(CH₂)₅— |
| 57-74 | 0-3 | —(CH₂)₃SO₃Na | —(CH₂)₄SO₃Na | —(CH₂)₂CONHC(COO⁻)(CH₂)₄NHCO(CH₂)₅— |
| 57-75 | 0-3 | —(CH₂)₃SO₃Na | —(CH₂)₂CH(CH₃)SO₃Na | —(CH₂)₂CONHC(COO⁻)(CH₂)₄NHCO(CH₂)₅— |
| 57-76 | 0-3 | —(CH₂)₃SO₃Na | —(CH₂)₂COOC₂H₅ | —(CH₂)₂CONHC(COO⁻)(CH₂)₄NHCO(CH₂)₅— |
| 57-77 | 0-3 | —(CH₂)₃SO₃Na | —(CH₂)₅COOC₂H₅ | —(CH₂)₂CONHC(COO⁻)(CH₂)₄NHCO(CH₂)₅— |
| 57-78 | 0-3 | —(CH₂)₃SO₃Na | —CH₃ | —(CH₂)₂CONHC(COO⁻)(CH₂)₄NHCO(CH₂)₅— |
| 57-79 | 0-3 | —(CH₂)₄SO₃Na | —(CH₂)₃SO₃Na | —(CH₂)₂CONHC(COO⁻)(CH₂)₄NHCO(CH₂)₅— |
| 57-80 | 0-3 | —(CH₂)₄SO₃Na | —(CH₂)₄SO₃Na | —(CH₂)₂CONHC(COO⁻)(CH₂)₄NHCO(CH₂)₅— |

TABLE 19

|  | n | R²" | R⁴" | T |
|---|---|---|---|---|
| 57-81 | 0-3 | —(CH₂)₄SO₃Na | —(CH₂)₂CH(CH₃)SO₃Na | —(CH₂)₂CONHC(COO⁻)(CH₂)₄NHCO(CH₂)₅— |
| 57-82 | 0-3 | —(CH₂)₄SO₃Na | —(CH₂)₂COOC₂H₅ | —(CH₂)₂CONHC(COO⁻)(CH₂)₄NHCO(CH₂)₅— |
| 57-83 | 0-3 | —(CH₂)₄SO₃Na | —(CH₂)₅COOC₂H₅ | —(CH₂)₂CONHC(COO⁻)(CH₂)₄NHCO(CH₂)₅— |
| 57-84 | 0-3 | —(CH₂)₄SO₃Na | —CH₃ | —(CH₂)₂CONHC(COO⁻)(CH₂)₄NHCO(CH₂)₅— |
| 57-85 | 0-3 | —(CH₂)₂CH(CH₃)SO₃Na | —(CH₂)₃SO₃Na | —(CH₂)₂CONHC(COO⁻)(CH₂)₄NHCO(CH₂)₅— |
| 57-86 | 0-3 | —(CH₂)₂CH(CH₃)SO₃Na | —(CH₂)₄SO₃Na | —(CH₂)₂CONHC(COO⁻)(CH₂)₄NHCO(CH₂)₅— |
| 57-87 | 0-3 | —(CH₂)₂CH(CH₃)SO₃Na | —(CH₂)₂CH(CH₃)SO₃Na | —(CH₂)₂CONHC(COO⁻)(CH₂)₄NHCO(CH₂)₅— |
| 57-88 | 0-3 | —(CH₂)₂CH(CH₃)SO₃Na | —(CH₂)₂COOC₂H₅ | —(CH₂)₂CONHC(COO⁻)(CH₂)₄NHCO(CH₂)₅— |
| 57-89 | 0-3 | —(CH₂)₂CH(CH₃)SO₃Na | —(CH₂)₅COOC₂H₅ | —(CH₂)₂CONHC(COO⁻)(CH₂)₄NHCO(CH₂)₅— |
| 57-90 | 0-3 | —(CH₂)₂CH(CH₃)SO₃Na | —CH₃ | —(CH₂)₂CONHC(COO⁻)(CH₂)₄NHCO(CH₂)₅— |
| 57-91 | 0-3 | —(CH₂)₂COOC₂H₅ | —(CH₂)₃SO₃Na | —(CH₂)₂CONHC(COO⁻)(CH₂)₄NHCO(CH₂)₅— |
| 57-92 | 0-3 | —(CH₂)₂COOC₂H₅ | —(CH₂)₄SO₃Na | —(CH₂)₂CONHC(COO⁻)(CH₂)₄NHCO(CH₂)₅— |
| 57-93 | 0-3 | —(CH₂)₂COOC₂H₅ | —(CH₂)₂CH(CH₃)SO₃Na | —(CH₂)₂CONHC(COO⁻)(CH₂)₄NHCO(CH₂)₅— |
| 57-94 | 0-3 | —(CH₂)₂COOC₂H₅ | —(CH₂)₂COOC₂H₅ | —(CH₂)₂CONHC(COO⁻)(CH₂)₄NHCO(CH₂)₅— |
| 57-95 | 0-3 | —(CH₂)₂COOC₂H₅ | —(CH₂)₅COOC₂H₅ | —(CH₂)₂CONHC(COO⁻)(CH₂)₄NHCO(CH₂)₅— |
| 57-96 | 0-3 | —(CH₂)₂COOC₂H₅ | —CH₃ | —(CH₂)₂CONHC(COO⁻)(CH₂)₄NHCO(CH₂)₅— |

TABLE 19-continued

|  | n | $R^{2''}$ | $R^{4''}$ | T |
|---|---|---|---|---|
| 57-97 | 0-3 | $-(CH_2)_5COOC_2H_5$ | $-(CH_2)_3SO_3Na$ | $-(CH_2)_2CONHC(COO^-)(CH_2)_4NHCO(CH_2)_5-$ |
| 57-98 | 0-3 | $-(CH_2)_5COOC_2H_5$ | $-(CH_2)_4SO_3Na$ | $-(CH_2)_2CONHC(COO^-)(CH_2)_4NHCO(CH_2)_5-$ |
| 57-99 | 0-3 | $-(CH_2)_5COOC_2H_5$ | $-(CH_2)_2CH(CH_3)SO_3Na$ | $-(CH_2)_2CONHC(COO^-)(CH_2)_4NHCO(CH_2)_5-$ |
| 57-100 | 0-3 | $-(CH_2)_5COOC_2H_5$ | $-(CH_2)_2COOC_2H_5$ | $-(CH_2)_2CONHC(COO^-)(CH_2)_4NHCO(CH_2)_5-$ |
| 57-101 | 0-3 | $-(CH_2)_5COOC_2H_5$ | $-(CH_2)_5COOC_2H_5$ | $-(CH_2)_2CONHC(COO^-)(CH_2)_4NHCO(CH_2)_5-$ |
| 57-102 | 0-3 | $-(CH_2)_5COOC_2H_5$ | $-CH_3$ | $-(CH_2)_2CONHC(COO^-)(CH_2)_4NHCO(CH_2)_5-$ |
| 57-103 | 0-3 | $-CH_3$ | $-(CH_2)_3SO_3Na$ | $-(CH_2)_2CONHC(COO^-)(CH_2)_4NHCO(CH_2)_5-$ |
| 57-104 | 0-3 | $-CH_3$ | $-(CH_2)_4SO_3Na$ | $-(CH_2)_2CONHC(COO^-)(CH_2)_4NHCO(CH_2)_5-$ |
| 57-105 | 0-3 | $-CH_3$ | $-(CH_2)_2CH(CH_3)SO_3Na$ | $-(CH_2)_2CONHC(COO^-)(CH_2)_4NHCO(CH_2)_5-$ |
| 57-106 | 0-3 | $-CH_3$ | $-(CH_2)_2COOC_2H_5$ | $-(CH_2)_2CONHC(COO^-)(CH_2)_4NHCO(CH_2)_5-$ |
| 57-107 | 0-3 | $-CH_3$ | $-(CH_2)_5COOC_2H_5$ | $-(CH_2)_2CONHC(COO^-)(CH_2)_4NHCO(CH_2)_5-$ |
| 57-108 | 0-3 | $-CH_3$ | $-CH_3$ | $-(CH_2)_2CONHC(COO^-)(CH_2)_4NHCO(CH_2)_5-$ |
| 57-109 | 0-3 | $-(CH_2)_3SO_3Na$ | $-(CH_2)_3SO_3Na$ | $-(CH_2)_2CONHC(COO^-)(CH_2)_4NHCO(CH_2)_2-$ |
| 57-110 | 0-3 | $-(CH_2)_3SO_3Na$ | $-(CH_2)_4SO_3Na$ | $-(CH_2)_2CONHC(COO^-)(CH_2)_4NHCO(CH_2)_2-$ |
| 57-111 | 0-3 | $-(CH_2)_3SO_3Na$ | $-(CH_2)_2CH(CH_3)SO_3Na$ | $-(CH_2)_2CONHC(COO^-)(CH_2)_4NHCO(CH_2)_2-$ |
| 57-112 | 0-3 | $-(CH_2)_3SO_3Na$ | $-(CH_2)_2COOC_2H_5$ | $-(CH_2)_2CONHC(COO^-)(CH_2)_4NHCO(CH_2)_2-$ |
| 57-113 | 0-3 | $-(CH_2)_3SO_3Na$ | $-(CH_2)_5COOC_2H_5$ | $-(CH_2)_2CONHC(COO^-)(CH_2)_4NHCO(CH_2)_2-$ |
| 57-114 | 0-3 | $-(CH_2)_3SO_3Na$ | $-CH_3$ | $-(CH_2)_2CONHC(COO^-)(CH_2)_4NHCO(CH_2)_2-$ |
| 57-115 | 0-3 | $-(CH_2)_4SO_3Na$ | $-(CH_2)_3SO_3Na$ | $-(CH_2)_2CONHC(COO^-)(CH_2)_4NHCO(CH_2)_2-$ |
| 57-116 | 0-3 | $-(CH_2)_4SO_3Na$ | $-(CH_2)_4SO_3Na$ | $-(CH_2)_2CONHC(COO^-)(CH_2)_4NHCO(CH_2)_2-$ |
| 57-117 | 0-3 | $-(CH_2)_4SO_3Na$ | $-(CH_2)_2CH(CH_3)SO_3Na$ | $-(CH_2)_2CONHC(COO^-)(CH_2)_4NHCO(CH_2)_2-$ |
| 57-118 | 0-3 | $-(CH_2)_4SO_3Na$ | $-(CH_2)_2COOC_2H_5$ | $-(CH_2)_2CONHC(COO^-)(CH_2)_4NHCO(CH_2)_2-$ |
| 57-119 | 0-3 | $-(CH_2)_4SO_3Na$ | $-(CH_2)_5COOC_2H_5$ | $-(CH_2)_2CONHC(COO^-)(CH_2)_4NHCO(CH_2)_2-$ |
| 57-120 | 0-3 | $-(CH_2)_4SO_3Na$ | $-CH_3$ | $-(CH_2)_2CONHC(COO^-)(CH_2)_4NHCO(CH_2)_2-$ |

TABLE 20

|  | n | $R^{2''}$ | $R^{4''}$ | T |
|---|---|---|---|---|
| 57-121 | 0-3 | $-(CH_2)_2CH(CH_3)SO_3Na$ | $-(CH_2)_3SO_3Na$ | $-(CH_2)_2CONHC(COO^-)(CH_2)_4NHCO(CH_2)_2-$ |
| 57-122 | 0-3 | $-(CH_2)_2CH(CH_3)SO_3Na$ | $-(CH_2)_4SO_3Na$ | $-(CH_2)_2CONHC(COO^-)(CH_2)_4NHCO(CH_2)_2-$ |
| 57-123 | 0-3 | $-(CH_2)_2CH(CH_3)SO_3Na$ | $-(CH_2)_2CH(CH_3)SO_3Na$ | $-(CH_2)_2CONHC(COO^-)(CH_2)_4NHCO(CH_2)_2-$ |
| 57-124 | 0-3 | $-(CH_2)_2CH(CH_3)SO_3Na$ | $-(CH_2)_2COOC_2H_5$ | $-(CH_2)_2CONHC(COO^-)(CH_2)_4NHCO(CH_2)_2-$ |
| 57-125 | 0-3 | $-(CH_2)_2CH(CH_3)SO_3Na$ | $-(CH_2)_5COOC_2H_5$ | $-(CH_2)_2CONHC(COO^-)(CH_2)_4NHCO(CH_2)_2-$ |
| 57-126 | 0-3 | $-(CH_2)_2CH(CH_3)SO_3Na$ | $-CH_3$ | $-(CH_2)_2CONHC(COO^-)(CH_2)_4NHCO(CH_2)_2-$ |
| 57-127 | 0-3 | $-(CH_2)_2COOC_2H_5$ | $-(CH_2)_3SO_3Na$ | $-(CH_2)_2CONHC(COO^-)(CH_2)_4NHCO(CH_2)_2-$ |
| 57-128 | 0-3 | $-(CH_2)_2COOC_2H_5$ | $-(CH_2)_4SO_3Na$ | $-(CH_2)_2CONHC(COO^-)(CH_2)_4NHCO(CH_2)_2-$ |
| 57-129 | 0-3 | $-(CH_2)_2COOC_2H_5$ | $-(CH_2)_2CH(CH_3)SO_3Na$ | $-(CH_2)_2CONHC(COO^-)(CH_2)_4NHCO(CH_2)_2-$ |
| 57-130 | 0-3 | $-(CH_2)_2COOC_2H_5$ | $-(CH_2)_2COOC_2H_5$ | $-(CH_2)_2CONHC(COO^-)(CH_2)_4NHCO(CH_2)_2-$ |
| 57-131 | 0-3 | $-(CH_2)_2COOC_2H_5$ | $-(CH_2)_5COOC_2H_5$ | $-(CH_2)_2CONHC(COO^-)(CH_2)_4NHCO(CH_2)_2-$ |
| 57-132 | 0-3 | $-(CH_2)_2COOC_2H_5$ | $-CH_3$ | $-(CH_2)_2CONHC(COO^-)(CH_2)_4NHCO(CH_2)_2-$ |
| 57-133 | 0-3 | $-(CH_2)_5COOC_2H_5$ | $-(CH_2)_3SO_3Na$ | $-(CH_2)_2CONHC(COO^-)(CH_2)_4NHCO(CH_2)_2-$ |
| 57-134 | 0-3 | $-(CH_2)_5COOC_2H_5$ | $-(CH_2)_4SO_3Na$ | $-(CH_2)_2CONHC(COO^-)(CH_2)_4NHCO(CH_2)_2-$ |
| 57-135 | 0-3 | $-(CH_2)_5COOC_2H_5$ | $-(CH_2)_2CH(CH_3)SO_3Na$ | $-(CH_2)_2CONHC(COO^-)(CH_2)_4NHCO(CH_2)_2-$ |
| 57-136 | 0-3 | $-(CH_2)_5COOC_2H_5$ | $-(CH_2)_2COOC_2H_5$ | $-(CH_2)_2CONHC(COO^-)(CH_2)_4NHCO(CH_2)_2-$ |
| 57-137 | 0-3 | $-(CH_2)_5COOC_2H_5$ | $-(CH_2)_5COOC_2H_5$ | $-(CH_2)_2CONHC(COO^-)(CH_2)_4NHCO(CH_2)_2-$ |
| 57-138 | 0-3 | $-(CH_2)_5COOC_2H_5$ | $-CH_3$ | $-(CH_2)_2CONHC(COO^-)(CH_2)_4NHCO(CH_2)_2-$ |
| 57-139 | 0-3 | $-CH_3$ | $-(CH_2)_3SO_3Na$ | $-(CH_2)_2CONHC(COO^-)(CH_2)_4NHCO(CH_2)_2-$ |
| 57-140 | 0-3 | $-CH_3$ | $-(CH_2)_4SO_3Na$ | $-(CH_2)_2CONHC(COO^-)(CH_2)_4NHCO(CH_2)_2-$ |
| 57-141 | 0-3 | $-CH_3$ | $-(CH_2)_2CH(CH_3)SO_3Na$ | $-(CH_2)_2CONHC(COO^-)(CH_2)_4NHCO(CH_2)_2-$ |
| 57-142 | 0-3 | $-CH_3$ | $-(CH_2)_2COOC_2H_5$ | $-(CH_2)_2CONHC(COO^-)(CH_2)_4NHCO(CH_2)_2-$ |
| 57-143 | 0-3 | $-CH_3$ | $-(CH_2)_5COOC_2H_5$ | $-(CH_2)_2CONHC(COO^-)(CH_2)_4NHCO(CH_2)_2-$ |
| 57-144 | 0-3 | $-CH_3$ | $-CH_3$ | $-(CH_2)_2CONHC(COO^-)(CH_2)_4NHCO(CH_2)_2-$ |

Preferable specific examples of the compounds represented by the general formula [58], includes for example, those represented by the following Tables 21 to 24. It should be noted that, in Tables 21 to 24, $R^{3''}$, $R^{5''}$ and $R^{11''}$ in the general formula [58] are $-CH_3$ groups; $R^{7''}$, $R^{9''}$ and $R^{10''}$ are hydrogen atoms; and $R^{8''}$ is $-SO_3Na$ group.

TABLE 21

|  | n | $R^{1''}$ | $R^{6''}$ | T |
|---|---|---|---|---|
| 58-1 | 0-3 | $-(CH_2)_3SO_3Na$ | $-(CH_2)_3SO_3Na$ | $-(CH_2)_5CONHC(COO^-)(CH_2)_4NHCO(CH_2)_5-$ |
| 58-2 | 0-3 | $-(CH_2)_3SO_3Na$ | $-(CH_2)_4SO_3Na$ | $-(CH_2)_5CONHC(COO^-)(CH_2)_4NHCO(CH_2)_5-$ |
| 58-3 | 0-3 | $-(CH_2)_3SO_3Na$ | $-(CH_2)_2CH(CH_3)SO_3Na$ | $-(CH_2)_5CONHC(COO^-)(CH_2)_4NHCO(CH_2)_5-$ |
| 58-4 | 0-3 | $-(CH_2)_3SO_3Na$ | $-(CH_2)_2COOC_2H_5$ | $-(CH_2)_5CONHC(COO^-)(CH_2)_4NHCO(CH_2)_5-$ |
| 58-5 | 0-3 | $-(CH_2)_3SO_3Na$ | $-(CH_2)_5COOC_2H_5$ | $-(CH_2)_5CONHC(COO^-)(CH_2)_4NHCO(CH_2)_5-$ |
| 58-6 | 0-3 | $-(CH_2)_3SO_3Na$ | $-CH_3$ | $-(CH_2)_5CONHC(COO^-)(CH_2)_4NHCO(CH_2)_5-$ |
| 58-7 | 0-3 | $-(CH_2)_4SO_3Na$ | $-(CH_2)_3SO_3Na$ | $-(CH_2)_5CONHC(COO^-)(CH_2)_4NHCO(CH_2)_5-$ |
| 58-8 | 0-3 | $-(CH_2)_4SO_3Na$ | $-(CH_2)_4SO_3Na$ | $-(CH_2)_5CONHC(COO^-)(CH_2)_4NHCO(CH_2)_5-$ |
| 58-9 | 0-3 | $-(CH_2)_4SO_3Na$ | $-(CH_2)_2CH(CH_3)SO_3Na$ | $-(CH_2)_5CONHC(COO^-)(CH_2)_4NHCO(CH_2)_5-$ |
| 58-10 | 0-3 | $-(CH_2)_4SO_3Na$ | $-(CH_2)_2COOC_2H_5$ | $-(CH_2)_5CONHC(COO^-)(CH_2)_4NHCO(CH_2)_5-$ |
| 58-11 | 0-3 | $-(CH_2)_4SO_3Na$ | $-(CH_2)_5COOC_2H_5$ | $-(CH_2)_5CONHC(COO^-)(CH_2)_4NHCO(CH_2)_5-$ |

TABLE 21-continued

|  | n | $R^{1''}$ | $R^{6''}$ | T |
|---|---|---|---|---|
| 58-12 | 0-3 | —$(CH_2)_4SO_3Na$ | —$CH_3$ | —$(CH_2)_5CONHC(COO^-)(CH_2)_4NHCO(CH_2)_5$— |
| 58-13 | 0-3 | —$(CH_2)_2CH(CH_3)SO_3Na$ | —$(CH_2)_3SO_3Na$ | —$(CH_2)_5CONHC(COO^-)(CH_2)_4NHCO(CH_2)_5$— |
| 58-14 | 0-3 | —$(CH_2)_2CH(CH_3)SO_3Na$ | —$(CH_2)_4SO_3Na$ | —$(CH_2)_5CONHC(COO^-)(CH_2)_4NHCO(CH_2)_5$— |
| 58-15 | 0-3 | —$(CH_2)_2CH(CH_3)SO_3Na$ | —$(CH_2)_2CH(CH_3)SO_3Na$ | —$(CH_2)_5CONHC(COO^-)(CH_2)_4NHCO(CH_2)_5$— |
| 58-16 | 0-3 | —$(CH_2)_2CH(CH_3)SO_3Na$ | —$(CH_2)_2COOC_2H_5$ | —$(CH_2)_5CONHC(COO^-)(CH_2)_4NHCO(CH_2)_5$— |
| 58-17 | 0-3 | —$(CH_2)_2CH(CH_3)SO_3Na$ | —$(CH_2)_5COOC_2H_5$ | —$(CH_2)_5CONHC(COO^-)(CH_2)_4NHCO(CH_2)_5$— |
| 58-18 | 0-3 | —$(CH_2)_2CH(CH_3)SO_3Na$ | —$CH_3$ | —$(CH_2)_5CONHC(COO^-)(CH_2)_4NHCO(CH_2)_5$— |
| 58-19 | 0-3 | —$(CH_2)_2COOC_2H_5$ | —$(CH_2)_3SO_3Na$ | —$(CH_2)_5CONHC(COO^-)(CH_2)_4NHCO(CH_2)_5$— |
| 58-20 | 0-3 | —$(CH_2)_2COOC_2H_5$ | —$(CH_2)_4SO_3Na$ | —$(CH_2)_5CONHC(COO^-)(CH_2)_4NHCO(CH_2)_5$— |
| 58-21 | 0-3 | —$(CH_2)_2COOC_2H_5$ | —$(CH_2)_2CH(CH_3)SO_3Na$ | —$(CH_2)_5CONHC(COO^-)(CH_2)_4NHCO(CH_2)_5$— |
| 58-22 | 0-3 | —$(CH_2)_2COOC_2H_5$ | —$(CH_2)_2COOC_2H_5$ | —$(CH_2)_5CONHC(COO^-)(CH_2)_4NHCO(CH_2)_5$— |
| 58-23 | 0-3 | —$(CH_2)_2COOC_2H_5$ | —$(CH_2)_5COOC_2H_5$ | —$(CH_2)_5CONHC(COO^-)(CH_2)_4NHCO(CH_2)_5$— |
| 58-24 | 0-3 | —$(CH_2)_2COOC_2H_5$ | —$CH_3$ | —$(CH_2)_5CONHC(COO^-)(CH_2)_4NHCO(CH_2)_5$— |
| 58-25 | 0-3 | —$(CH_2)_5COOC_2H_5$ | —$(CH_2)_3SO_3Na$ | —$(CH_2)_5CONHC(COO^-)(CH_2)_4NHCO(CH_2)_5$— |
| 58-26 | 0-3 | —$(CH_2)_5COOC_2H_5$ | —$(CH_2)_4SO_3Na$ | —$(CH_2)_5CONHC(COO^-)(CH_2)_4NHCO(CH_2)_5$— |
| 58-27 | 0-3 | —$(CH_2)_5COOC_2H_5$ | —$(CH_2)_2CH(CH_3)SO_3Na$ | —$(CH_2)_5CONHC(COO^-)(CH_2)_4NHCO(CH_2)_5$— |
| 58-28 | 0-3 | —$(CH_2)_5COOC_2H_5$ | —$(CH_2)_2COOC_2H_5$ | —$(CH_2)_5CONHC(COO^-)(CH_2)_4NHCO(CH_2)_5$— |
| 58-29 | 0-3 | —$(CH_2)_5COOC_2H_5$ | —$(CH_2)_5COOC_2H_5$ | —$(CH_2)_5CONHC(COO^-)(CH_2)_4NHCO(CH_2)_5$— |
| 58-30 | 0-3 | —$(CH_2)_5COOC_2H_5$ | —$CH_3$ | —$(CH_2)_5CONHC(COO^-)(CH_2)_4NHCO(CH_2)_5$— |
| 58-31 | 0-3 | —$CH_3$ | —$(CH_2)_3SO_3Na$ | —$(CH_2)_5CONHC(COO^-)(CH_2)_4NHCO(CH_2)_5$— |
| 58-32 | 0-3 | —$CH_3$ | —$(CH_2)_4SO_3Na$ | —$(CH_2)_5CONHC(COO^-)(CH_2)_4NHCO(CH_2)_5$— |
| 58-33 | 0-3 | —$CH_3$ | —$(CH_2)_2CH(CH_3)SO_3Na$ | —$(CH_2)_5CONHC(COO^-)(CH_2)_4NHCO(CH_2)_5$— |
| 58-34 | 0-3 | —$CH_3$ | —$(CH_2)_2COOC_2H_5$ | —$(CH_2)_5CONHC(COO^-)(CH_2)_4NHCO(CH_2)_5$— |
| 58-35 | 0-3 | —$CH_3$ | —$(CH_2)_5COOC_2H_5$ | —$(CH_2)_5CONHC(COO^-)(CH_2)_4NHCO(CH_2)_5$— |
| 58-36 | 0-3 | —$CH_3$ | —$CH_3$ | —$(CH_2)_5CONHC(COO^-)(CH_2)_4NHCO(CH_2)_5$— |
| 58-37 | 0-3 | —$(CH_2)_3SO_3Na$ | —$(CH_2)_3SO_3Na$ | —$(CH_2)_5CONHC(COO^-)(CH_2)_4NHCO(CH_2)_2$— |
| 58-38 | 0-3 | —$(CH_2)_3SO_3Na$ | —$(CH_2)_4SO_3Na$ | —$(CH_2)_5CONHC(COO^-)(CH_2)_4NHCO(CH_2)_2$— |
| 58-39 | 0-3 | —$(CH_2)_3SO_3Na$ | —$(CH_2)_2CH(CH_3)SO_3Na$ | —$(CH_2)_5CONHC(COO^-)(CH_2)_4NHCO(CH_2)_2$— |
| 58-40 | 0-3 | —$(CH_2)_3SO_3Na$ | —$(CH_2)_2COOC_2H_5$ | —$(CH_2)_5CONHC(COO^-)(CH_2)_4NHCO(CH_2)_2$— |

TABLE 22

|  | n | $R^{1''}$ | $R^{6''}$ | T |
|---|---|---|---|---|
| 58-41 | 0-3 | —$(CH_2)_3SO_3Na$ | —$(CH_2)_5COOC_2H_5$ | —$(CH_2)_5CONHC(COO^-)(CH_2)_4NHCO(CH_2)_2$— |
| 58-42 | 0-3 | —$(CH_2)_3SO_3Na$ | —$CH_3$ | —$(CH_2)_5CONHC(COO^-)(CH_2)_4NHCO(CH_2)_2$— |
| 58-43 | 0-3 | —$(CH_2)_4SO_3Na$ | —$(CH_2)_3SO_3Na$ | —$(CH_2)_5CONHC(COO^-)(CH_2)_4NHCO(CH_2)_2$— |
| 58-44 | 0-3 | —$(CH_2)_4SO_3Na$ | —$(CH_2)_4SO_3Na$ | —$(CH_2)_5CONHC(COO^-)(CH_2)_4NHCO(CH_2)_2$— |
| 58-45 | 0-3 | —$(CH_2)_4SO_3Na$ | —$(CH_2)_2CH(CH_3)SO_3Na$ | —$(CH_2)_5CONHC(COO^-)(CH_2)_4NHCO(CH_2)_2$— |
| 58-46 | 0-3 | —$(CH_2)_4SO_3Na$ | —$(CH_2)_2COOC_2H_5$ | —$(CH_2)_5CONHC(COO^-)(CH_2)_4NHCO(CH_2)_2$— |
| 58-47 | 0-3 | —$(CH_2)_4SO_3Na$ | —$(CH_2)_5COOC_2H_5$ | —$(CH_2)_5CONHC(COO^-)(CH_2)_4NHCO(CH_2)_2$— |
| 58-48 | 0-3 | —$(CH_2)_4SO_3Na$ | —$CH_3$ | —$(CH_2)_5CONHC(COO^-)(CH_2)_4NHCO(CH_2)_2$— |
| 58-49 | 0-3 | —$(CH_2)_2CH(CH_3)SO_3Na$ | —$(CH_2)_3SO_3Na$ | —$(CH_2)_5CONHC(COO^-)(CH_2)_4NHCO(CH_2)_2$— |
| 58-50 | 0-3 | —$(CH_2)_2CH(CH_3)SO_3Na$ | —$(CH_2)_4SO_3Na$ | —$(CH_2)_5CONHC(COO^-)(CH_2)_4NHCO(CH_2)_2$— |
| 58-51 | 0-3 | —$(CH_2)_2CH(CH_3)SO_3Na$ | —$(CH_2)_2CH(CH_3)SO_3Na$ | —$(CH_2)_5CONHC(COO^-)(CH_2)_4NHCO(CH_2)_2$— |
| 58-52 | 0-3 | —$(CH_2)_2CH(CH_3)SO_3Na$ | —$(CH_2)_2COOC_2H_5$ | —$(CH_2)_5CONHC(COO^-)(CH_2)_4NHCO(CH_2)_2$— |
| 58-53 | 0-3 | —$(CH_2)_2CH(CH_3)SO_3Na$ | —$(CH_2)_5COOC_2H_5$ | —$(CH_2)_5CONHC(COO^-)(CH_2)_4NHCO(CH_2)_2$— |
| 58-54 | 0-3 | —$(CH_2)_2CH(CH_3)SO_3Na$ | —$CH_3$ | —$(CH_2)_5CONHC(COO^-)(CH_2)_4NHCO(CH_2)_2$— |
| 58-55 | 0-3 | —$(CH_2)_2COOC_2H_5$ | —$(CH_2)_3SO_3Na$ | —$(CH_2)_5CONHC(COO^-)(CH_2)_4NHCO(CH_2)_2$— |
| 58-56 | 0-3 | —$(CH_2)_2COOC_2H_5$ | —$(CH_2)_4SO_3Na$ | —$(CH_2)_5CONHC(COO^-)(CH_2)_4NHCO(CH_2)_2$— |
| 58-57 | 0-3 | —$(CH_2)_2COOC_2H_5$ | —$(CH_2)_2CH(CH_3)SO_3Na$ | —$(CH_2)_5CONHC(COO^-)(CH_2)_4NHCO(CH_2)_2$— |
| 58-58 | 0-3 | —$(CH_2)_2COOC_2H_5$ | —$(CH_2)_2COOC_2H_5$ | —$(CH_2)_5CONHC(COO^-)(CH_2)_4NHCO(CH_2)_2$— |
| 58-59 | 0-3 | —$(CH_2)_2COOC_2H_5$ | —$(CH_2)_5COOC_2H_5$ | —$(CH_2)_5CONHC(COO^-)(CH_2)_4NHCO(CH_2)_2$— |
| 58-60 | 0-3 | —$(CH_2)_2COOC_2H_5$ | —$CH_3$ | —$(CH_2)_5CONHC(COO^-)(CH_2)_4NHCO(CH_2)_2$— |
| 58-61 | 0-3 | —$(CH_2)_5COOC_2H_5$ | —$(CH_2)_3SO_3Na$ | —$(CH_2)_5CONHC(COO^-)(CH_2)_4NHCO(CH_2)_2$— |
| 58-62 | 0-3 | —$(CH_2)_5COOC_2H_5$ | —$(CH_2)_4SO_3Na$ | —$(CH_2)_5CONHC(COO^-)(CH_2)_4NHCO(CH_2)_2$— |
| 58-63 | 0-3 | —$(CH_2)_5COOC_2H_5$ | —$(CH_2)_2CH(CH_3)SO_3Na$ | —$(CH_2)_5CONHC(COO^-)(CH_2)_4NHCO(CH_2)_2$— |
| 58-64 | 0-3 | —$(CH_2)_5COOC_2H_5$ | —$(CH_2)_2COOC_2H_5$ | —$(CH_2)_5CONHC(COO^-)(CH_2)_4NHCO(CH_2)_2$— |
| 58-65 | 0-3 | —$(CH_2)_5COOC_2H_5$ | —$(CH_2)_5COOC_2H_5$ | —$(CH_2)_5CONHC(COO^-)(CH_2)_4NHCO(CH_2)_2$— |
| 58-66 | 0-3 | —$(CH_2)_5COOC_2H_5$ | —$CH_3$ | —$(CH_2)_5CONHC(COO^-)(CH_2)_4NHCO(CH_2)_2$— |
| 58-67 | 0-3 | —$CH_3$ | —$(CH_2)_3SO_3Na$ | —$(CH_2)_5CONHC(COO^-)(CH_2)_4NHCO(CH_2)_2$— |
| 58-68 | 0-3 | —$CH_3$ | —$(CH_2)_4SO_3Na$ | —$(CH_2)_5CONHC(COO^-)(CH_2)_4NHCO(CH_2)_2$— |
| 58-69 | 0-3 | —$CH_3$ | —$(CH_2)_2CH(CH_3)SO_3Na$ | —$(CH_2)_5CONHC(COO^-)(CH_2)_4NHCO(CH_2)_2$— |
| 58-70 | 0-3 | —$CH_3$ | —$(CH_2)_2COOC_2H_5$ | —$(CH_2)_5CONHC(COO^-)(CH_2)_4NHCO(CH_2)_2$— |
| 58-71 | 0-3 | —$CH_3$ | —$(CH_2)_5COOC_2H_5$ | —$(CH_2)_5CONHC(COO^-)(CH_2)_4NHCO(CH_2)_2$— |
| 58-72 | 0-3 | —$CH_3$ | —$CH_3$ | —$(CH_2)_5CONHC(COO^-)(CH_2)_4NHCO(CH_2)_2$— |
| 58-73 | 0-3 | —$(CH_2)_3SO_3Na$ | —$(CH_2)_3SO_3Na$ | —$(CH_2)_2CONHC(COO^-)(CH_2)_4NHCO(CH_2)_5$— |
| 58-74 | 0-3 | —$(CH_2)_3SO_3Na$ | —$(CH_2)_4SO_3Na$ | —$(CH_2)_2CONHC(COO^-)(CH_2)_4NHCO(CH_2)_5$— |
| 58-75 | 0-3 | —$(CH_2)_3SO_3Na$ | —$(CH_2)_2CH(CH_3)SO_3Na$ | —$(CH_2)_2CONHC(COO^-)(CH_2)_4NHCO(CH_2)_5$— |
| 58-76 | 0-3 | —$(CH_2)_3SO_3Na$ | —$(CH_2)_2COOC_2H_5$ | —$(CH_2)_2CONHC(COO^-)(CH_2)_4NHCO(CH_2)_5$— |
| 58-77 | 0-3 | —$(CH_2)_3SO_3Na$ | —$(CH_2)_5COOC_2H_5$ | —$(CH_2)_2CONHC(COO^-)(CH_2)_4NHCO(CH_2)_5$— |
| 58-78 | 0-3 | —$(CH_2)_3SO_3Na$ | —$CH_3$ | —$(CH_2)_2CONHC(COO^-)(CH_2)_4NHCO(CH_2)_5$— |
| 58-79 | 0-3 | —$(CH_2)_4SO_3Na$ | —$(CH_2)_3SO_3Na$ | —$(CH_2)_2CONHC(COO^-)(CH_2)_4NHCO(CH_2)_5$— |
| 58-80 | 0-3 | —$(CH_2)_4SO_3Na$ | —$(CH_2)_4SO_3Na$ | —$(CH_2)_2CONHC(COO^-)(CH_2)_4NHCO(CH_2)_5$— |

TABLE 23

| | n | R$^{1''}$ | R$^{6''}$ | T |
|---|---|---|---|---|
| 58-81 | 0-3 | —(CH$_2$)$_4$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 58-82 | 0-3 | —(CH$_2$)$_4$SO$_3$Na | —(CH$_2$)$_2$COOC$_2$H$_5$ | —(CH$_2$)$_2$CONHC(COO$^-$)(CH$_2$)$_4$NHCO(CH$_2$)$_5$— |
| 58-83 | 0-3 | —(CH$_2$)$_4$SO$_3$Na | —(CH$_2$)$_5$COOC$_2$H$_5$ | —(CH$_2$)$_2$CONHC(COO$^-$)(CH$_2$)$_4$NHCO(CH$_2$)$_5$— |
| 58-84 | 0-3 | —(CH$_2$)$_4$SO$_3$Na | —CH$_3$ | —(CH$_2$)$_2$CONHC(COO$^-$)(CH$_2$)$_4$NHCO(CH$_2$)$_5$— |
| 58-85 | 0-3 | —(CH$_2$)$_2$CH(CH$_3$)SO$_3$Na | —(CH$_2$)$_3$SO$_3$Na | —(CH$_2$)$_2$CONHC(COO$^-$)(CH$_2$)$_4$NHCO(CH$_2$)$_5$— |
| 58-86 | 0-3 | —(CH$_2$)$_2$CH(CH$_3$)SO$_3$Na | —(CH$_2$)$_4$SO$_3$Na | —(CH$_2$)$_2$CONHC(COO$^-$)(CH$_2$)$_4$NHCO(CH$_2$)$_5$— |
| 58-87 | 0-3 | —(CH$_2$)$_2$CH(CH$_3$)SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 58-88 | 0-3 | —(CH$_2$)$_2$CH(CH$_3$)SO$_3$Na | —(CH$_2$)$_2$COOC$_2$H$_5$ | —(CH$_2$)$_2$CONHC(COO$^-$)(CH$_2$)$_4$NHCO(CH$_2$)$_5$— |
| 58-89 | 0-3 | —(CH$_2$)$_2$CH(CH$_3$)SO$_3$Na | —(CH$_2$)$_5$COOC$_2$H$_5$ | —(CH$_2$)$_2$CONHC(COO$^-$)(CH$_2$)$_4$NHCO(CH$_2$)$_5$— |
| 58-90 | 0-3 | —(CH$_2$)$_2$CH(CH$_3$)SO$_3$Na | —CH$_3$ | —(CH$_2$)$_2$CONHC(COO$^-$)(CH$_2$)$_4$NHCO(CH$_2$)$_5$— |
| 58-91 | 0-3 | —(CH$_2$)$_2$COOC$_2$H$_5$ | —(CH$_2$)$_3$SO$_3$Na | —(CH$_2$)$_2$CONHC(COO$^-$)(CH$_2$)$_4$NHCO(CH$_2$)$_5$— |
| 58-92 | 0-3 | —(CH$_2$)$_2$COOC$_2$H$_5$ | —(CH$_2$)$_4$SO$_3$Na | —(CH$_2$)$_2$CONHC(COO$^-$)(CH$_2$)$_4$NHCO(CH$_2$)$_5$— |
| 58-93 | 0-3 | —(CH$_2$)$_2$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 58-94 | 0-3 | —(CH$_2$)$_2$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_5$— |
| 58-95 | 0-3 | —(CH$_2$)$_2$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_5$— |
| 58-96 | 0-3 | —(CH$_2$)$_2$COOC$_2$H$_5$ | —CH$_3$ | —(CH$_2$)$_2$CONHC(COO$^-$)(CH$_2$)$_4$NHCO(CH$_2$)$_5$— |
| 58-97 | 0-3 | —(CH$_2$)$_5$COOC$_2$H$_5$ | —(CH$_2$)$_3$SO$_3$Na | —(CH$_2$)$_2$CONHC(COO$^-$)(CH$_2$)$_4$NHCO(CH$_2$)$_5$— |
| 58-98 | 0-3 | —(CH$_2$)$_5$COOC$_2$H$_5$ | —(CH$_2$)$_4$SO$_3$Na | —(CH$_2$)$_2$CONHC(COO$^-$)(CH$_2$)$_4$NHCO(CH$_2$)$_5$— |
| 58-99 | 0-3 | —(CH$_2$)$_5$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 58-100 | 0-3 | —(CH$_2$)$_5$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_5$— |
| 58-101 | 0-3 | —(CH$_2$)$_5$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_5$— |
| 58-102 | 0-3 | —(CH$_2$)$_5$COOC$_2$H$_5$ | —CH$_3$ | —(CH$_2$)$_2$CONHC(COO$^-$)(CH$_2$)$_4$NHCO(CH$_2$)$_5$— |
| 58-103 | 0-3 | —CH$_3$ | —(CH$_2$)$_3$SO$_3$Na | —(CH$_2$)$_2$CONHC(COO$^-$)(CH$_2$)$_4$NHCO(CH$_2$)$_5$— |
| 58-104 | 0-3 | —CH$_3$ | —(CH$_2$)$_4$SO$_3$Na | —(CH$_2$)$_2$CONHC(COO$^-$)(CH$_2$)$_4$NHCO(CH$_2$)$_5$— |
| 58-105 | 0-3 | —CH$_3$ | —(CH$_2$)$_2$CH(CH$_3$)SO$_3$Na | —(CH$_2$)$_2$CONHC(COO$^-$)(CH$_2$)$_4$NHCO(CH$_2$)$_5$— |
| 58-106 | 0-3 | —CH$_3$ | —(CH$_2$)$_2$COOC$_2$H$_5$ | —(CH$_2$)$_2$CONHC(COO$^-$)(CH$_2$)$_4$NHCO(CH$_2$)$_5$— |
| 58-107 | 0-3 | —CH$_3$ | —(CH$_2$)$_5$COOC$_2$H$_5$ | —(CH$_2$)$_2$CONHC(COO$^-$)(CH$_2$)$_4$NHCO(CH$_2$)$_5$— |
| 58-108 | 0-3 | —CH$_3$ | —CH$_3$ | —(CH$_2$)$_2$CONHC(COO$^-$)(CH$_2$)$_4$NHCO(CH$_2$)$_5$— |
| 58-109 | 0-3 | —(CH$_2$)$_3$SO$_3$Na | —(CH$_2$)$_3$SO$_3$Na | —(CH$_2$)$_2$CONHC(COO$^-$)(CH$_2$)$_4$NHCO(CH$_2$)$_2$— |
| 58-110 | 0-3 | —(CH$_2$)$_3$SO$_3$Na | —(CH$_2$)$_4$SO$_3$Na | —(CH$_2$)$_2$CONHC(COO$^-$)(CH$_2$)$_4$NHCO(CH$_2$)$_2$— |
| 58-111 | 0-3 | —(CH$_2$)$_3$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 58-112 | 0-3 | —(CH$_2$)$_3$SO$_3$Na | —(CH$_2$)$_2$COOC$_2$H$_5$ | —(CH$_2$)$_2$CONHC(COO$^-$)(CH$_2$)$_4$NHCO(CH$_2$)$_2$— |
| 58-113 | 0-3 | —(CH$_2$)$_3$SO$_3$Na | —(CH$_2$)$_5$COOC$_2$H$_5$ | —(CH$_2$)$_2$CONHC(COO$^-$)(CH$_2$)$_4$NHCO(CH$_2$)$_2$— |
| 58-114 | 0-3 | —(CH$_2$)$_3$SO$_3$Na | —CH$_3$ | —(CH$_2$)$_2$CONHC(COO$^-$)(CH$_2$)$_4$NHCO(CH$_2$)$_2$— |
| 58-115 | 0-3 | —(CH$_2$)$_4$SO$_3$Na | —(CH$_2$)$_3$SO$_3$Na | —(CH$_2$)$_2$CONHC(COO$^-$)(CH$_2$)$_4$NHCO(CH$_2$)$_2$— |
| 58-116 | 0-3 | —(CH$_2$)$_4$SO$_3$Na | —(CH$_2$)$_4$SO$_3$Na | —(CH$_2$)$_2$CONHC(COO$^-$)(CH$_2$)$_4$NHCO(CH$_2$)$_2$— |
| 58-117 | 0-3 | —(CH$_2$)$_4$SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 58-118 | 0-3 | —(CH$_2$)$_4$SO$_3$Na | —(CH$_2$)$_2$COOC$_2$H$_5$ | —(CH$_2$)$_2$CONHC(COO$^-$)(CH$_2$)$_4$NHCO(CH$_2$)$_2$— |
| 58-119 | 0-3 | —(CH$_2$)$_4$SO$_3$Na | —(CH$_2$)$_5$COOC$_2$H$_5$ | —(CH$_2$)$_2$CONHC(COO$^-$)(CH$_2$)$_4$NHCO(CH$_2$)$_2$— |
| 58-120 | 0-3 | —(CH$_2$)$_4$SO$_3$Na | —CH$_3$ | —(CH$_2$)$_2$CONHC(COO$^-$)(CH$_2$)$_4$NHCO(CH$_2$)$_2$— |

TABLE 24

| | n | R$^{1''}$ | R$^{6''}$ | T |
|---|---|---|---|---|
| 58-121 | 0-3 | —(CH$_2$)$_2$CH(CH$_3$)SO$_3$Na | —(CH$_2$)$_3$SO$_3$Na | —(CH$_2$)$_2$CONHC(COO$^-$)(CH$_2$)$_4$NHCO(CH$_2$)$_2$— |
| 58-122 | 0-3 | —(CH$_2$)$_2$CH(CH$_3$)SO$_3$Na | —(CH$_2$)$_4$SO$_3$Na | —(CH$_2$)$_2$CONHC(COO$^-$)(CH$_2$)$_4$NHCO(CH$_2$)$_2$— |
| 58-123 | 0-3 | —(CH$_2$)$_2$CH(CH$_3$)SO$_3$Na | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 58-124 | 0-3 | —(CH$_2$)$_2$CH(CH$_3$)SO$_3$Na | —(CH$_2$)$_2$COOC$_2$H$_5$ | —(CH$_2$)$_2$CONHC(COO$^-$)(CH$_2$)$_4$NHCO(CH$_2$)$_2$— |
| 58-125 | 0-3 | —(CH$_2$)$_2$CH(CH$_3$)SO$_3$Na | —(CH$_2$)$_5$COOC$_2$H$_5$ | —(CH$_2$)$_2$CONHC(COO$^-$)(CH$_2$)$_4$NHCO(CH$_2$)$_2$— |
| 58-126 | 0-3 | —(CH$_2$)$_2$CH(CH$_3$)SO$_3$Na | —CH$_3$ | —(CH$_2$)$_2$CONHC(COO$^-$)(CH$_2$)$_4$NHCO(CH$_2$)$_2$— |
| 58-127 | 0-3 | —(CH$_2$)$_2$COOC$_2$H$_5$ | —(CH$_2$)$_3$SO$_3$Na | —(CH$_2$)$_2$CONHC(COO$^-$)(CH$_2$)$_4$NHCO(CH$_2$)$_2$— |
| 58-128 | 0-3 | —(CH$_2$)$_2$COOC$_2$H$_5$ | —(CH$_2$)$_4$SO$_3$Na | —(CH$_2$)$_2$CONHC(COO$^-$)(CH$_2$)$_4$NHCO(CH$_2$)$_2$— |
| 58-129 | 0-3 | —(CH$_2$)$_2$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 58-130 | 0-3 | —(CH$_2$)$_2$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_2$— |
| 58-131 | 0-3 | —(CH$_2$)$_2$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_2$— |
| 58-132 | 0-3 | —(CH$_2$)$_2$COOC$_2$H$_5$ | —CH$_3$ | —(CH$_2$)$_2$CONHC(COO$^-$)(CH$_2$)$_4$NHCO(CH$_2$)$_2$— |
| 58-133 | 0-3 | —(CH$_2$)$_5$COOC$_2$H$_5$ | —(CH$_2$)$_3$SO$_3$Na | —(CH$_2$)$_2$CONHC(COO$^-$)(CH$_2$)$_4$NHCO(CH$_2$)$_2$— |
| 58-134 | 0-3 | —(CH$_2$)$_5$COOC$_2$H$_5$ | —(CH$_2$)$_4$SO$_3$Na | —(CH$_2$)$_2$CONHC(COO$^-$)(CH$_2$)$_4$NHCO(CH$_2$)$_2$— |
| 58-135 | 0-3 | —(CH$_2$)$_5$COOC$_2$H$_5$ | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 58-136 | 0-3 | —(CH$_2$)$_5$COOC$_2$H$_5$ | —(CH$_2$)$_2$COOC$_2$H$_5$ | —(CH$_2$)$_2$CONHC(COO$^-$)(CH$_2$)$_4$NHCO(CH$_2$)$_2$— |
| 58-137 | 0-3 | —(CH$_2$)$_5$COOC$_2$H$_5$ | —(CH$_2$)$_5$COOC$_2$H$_5$ | —(CH$_2$)$_2$CONHC(COO$^-$)(CH$_2$)$_4$NHCO(CH$_2$)$_2$— |
| 58-138 | 0-3 | —(CH$_2$)$_5$COOC$_2$H$_5$ | —CH$_3$ | —(CH$_2$)$_2$CONHC(COO$^-$)(CH$_2$)$_4$NHCO(CH$_2$)$_2$— |
| 58-139 | 0-3 | —CH$_3$ | —(CH$_2$)$_3$SO$_3$Na | —(CH$_2$)$_2$CONHC(COO$^-$)(CH$_2$)$_4$NHCO(CH$_2$)$_2$— |
| 58-140 | 0-3 | —CH$_3$ | —(CH$_2$)$_4$SO$_3$Na | —(CH$_2$)$_2$CONHC(COO$^-$)(CH$_2$)$_4$NHCO(CH$_2$)$_2$— |
| 58-141 | 0-3 | —CH$_3$ | —(CH$_2$)$_2$CH(CH$_3$)SO$_3$Na | —(CH$_2$)$_2$CONHC(COO$^-$)(CH$_2$)$_4$NHCO(CH$_2$)$_2$— |
| 58-142 | 0-3 | —CH$_3$ | —(CH$_2$)$_2$COOC$_2$H$_5$ | —(CH$_2$)$_2$CONHC(COO$^-$)(CH$_2$)$_4$NHCO(CH$_2$)$_2$— |
| 58-143 | 0-3 | —CH$_3$ | —(CH$_2$)$_5$COOC$_2$H$_5$ | —(CH$_2$)$_2$CONHC(COO$^-$)(CH$_2$)$_4$NHCO(CH$_2$)$_2$— |
| 58-144 | 0-3 | —CH$_3$ | —CH$_3$ | —(CH$_2$)$_2$CONHC(COO$^-$)(CH$_2$)$_4$NHCO(CH$_2$)$_2$— |

In addition, in the case where a reactive group of the present invention, contained in a compound of the present invention, is subjected to binding, for example, to a substance to be labeled or the like, such a group that enhances (activates) binding ability to a functional group to be contained in a substance to be labeled (for example, amino group, carboxyl group, thiol group, hydroxyl group, formyl group or the like) (hereinafter may be abbreviated as "a functional group of a substance to be labeled") may be introduced further to the reactive group.

It should be noted that one introduced with such a reaction activation group of the present invention, that is, one where such a group that enhances binding ability to a functional group of a substance to be labeled is introduced to a reactive group of the present invention, is also included in the reactive group of the present invention.

As such a reaction activation group, it is not especially limited, as long as it is one enabling to make binding to a functional group of a substance to be labeled, and all of those usually used in this field are included.

As the reaction activation group of the present invention, it is not especially limited as long as it is one capable of binding to a functional group of a substance to be labeled, and all those usually used in this field are included, for example, one activating reactivity with an amino group (hereinafter referred to as "a reaction activation group to an amino group"), one activating reactivity with a thiol group (hereinafter referred to as "a reaction activation group to a thiol group"), one activating reactivity with a hydroxyl group (hereinafter referred to as "a reaction activation group to a hydroxyl group"), one activating reactivity with a formyl group (hereinafter referred to as "a reaction activation group to a formyl group") or the like.

A preferable specific example of the reaction activation group to an amino group, includes, for example, succinimide group, sulfosuccinimide group, norbornene group, 4-nitrophenoxy group, a group derived from a carboxylic anhydride (for example, acetoxycarbonylmethyl group, propionyloxycarbonylethyl group, benzoyloxybenzyl group, or the like), $C_1$ to $C_3$ halosulfonyl alkyl group (for example, fluorosulfonylmethyl group, fluorosulfonylethyl group, fluorosulfonylpropyl group, chlorosulfonylmethyl group, chlorosulfonylethyl group, chlorosulfonylpropyl group, bromosulfonylmethyl group, bromosulfonylethyl group, bromosulfonylpropyl group, iodosulfonylmethyl group, iodosulfonylethyl group, iodosulfonylpropyl group, or the like), halosulfonylaryl group (for example, fluorosulfonylphenyl group, chlorosulfonylphenyl group, bromosulfonylphenyl group, iodosulfonylphenyl group, or the like); $C_1$ to $C_3$ halocarbonyl alkyl group (for example, fluorocarbonylmethyl group, fluorocarbonylethyl group, fluorocarbonylpropyl group, chlorocarbonylmethyl group, chlorocarbonylethyl group, chlorocarbonylpropyl group, bromocarbonylmethyl group, bromocarbonylethyl group, bromocarbonylpropyl group, iodocarbonylmethyl group, iodocarbonylethyl group, iodocarbonylpropyl group, or the like); halocarbonylaryl group (for example, fluorocarbonylphenyl group, chlorocarbonylphenyl group, bromocarbonylphenyl group, iodocarbonylphenyl group, or the like); phosphoamidite group, isothiocyanate group, isocyanate group, monohalogen (for example, F, Cl, Br, I, or the like) substituted triazino group, dihalogen (for example, F, Cl, Br, I, or the like) substituted triazino group, monohalogen (for example, F, Cl, Br, I, or the like) substituted pyrimidino group, dihalogen (for example, F, Cl, Br, I, or the like) substituted pyrimidino group, monohalogen (for example, F, Cl, Br, I, or the like) substituted pyridino group, dihalogen (for example, F, Cl, Br, I, or the like) substituted pyridino group, phosphoryl halide (for example, F, Cl, Br, I, or the like) or the like.

A preferable specific example of the reaction activation group to a thiol group, includes, for example, carboxylic anhydride derived group (example, acetoxycarbonylmethyl group, propionyloxycarbonylethyl group, benzoyloxybenzyl group or the like); maleimide group, sulfomaleimide group, sulfonylhalide group (for example, F, Cl, Br, I, or the like); α-halogeno (for example, F, Cl, Br, I, or the like) acetamide group; $C_1$ to $C_3$ halocarbonyl alkyl group (for example, fluorocarbonylmethyl group, fluorocarbonylethyl group, fluorocarbonylpropyl group, chlorocarbonylmethyl group, chlorocarbonylethyl group, chlorocarbonylpropyl group, bromocarbonylmethyl group, bromocarbonylethyl group, bromocarbonylpropyl group, iodocarbonylmethyl group, iodocarbonylethyl group, iodocarbonylpropyl group, or the like); halocarbonylaryl group (for example, fluorocarbonylphenyl group, chlorocarbonylphenyl group, bromocarbonylphenyl group, iodocarbonylphenyl group, or the like); isothiocyanate group, isocyanate group, 2-pyridyldithio group; or the like.

A preferable specific example of the reaction activation group to a hydroxyl group, includes, for example, carboxylic anhydride derived group (for example, acetoxycarbonylmethyl group, propionyloxycarbonylethyl group, benzoyloxybenzyl group or the like); $C_1$ to $C_3$ halosulfonyl alkyl group (for example, fluorosulfonylmethyl group, fluorosulfonylethyl group, fluorosulfonylpropyl group, chlorosulfonylmethyl group, chlorosulfonylethyl group, chlorosulfonylpropyl group, bromosulfonylmethyl group, bromosulfonylethyl group, bromosulfonylpropyl group, iodosulfonylmethyl group, iodosulfonylethyl group, iodosulfonylpropyl group, or the like); halosulfonylaryl group (for example, fluorosulfonylphenyl group, chlorosulfonylphenyl group, bromosulfonylphenyl group, iodosulfonylphenyl group, or the like); phosphoamidite group; $C_1$ to $C_3$ halocarbonyl alkyl group (for example, fluorocarbonylmethyl group, fluorocarbonylethyl group, fluorocarbonylpropyl group, chlorocarbonylmethyl group, chlorocarbonylethyl group, chlorocarbonylpropyl group, bromocarbonylmethyl group, bromocarbonylethyl group, bromocarbonylpropyl group, iodocarbonylmethyl group, iodocarbonylethyl group, iodocarbonylpropyl group, or the like); halocarbonylaryl group (for example, fluorocarbonylphenyl group, chlorocarbonylphenyl group, bromocarbonylphenyl group, iodocarbonylphenyl group, or the like); isothiocyanate group, isocyanate group; phosphoryl halide group (for example, F, Cl, Br, I or the like); or the like.

A preferable specific example of the reaction activation group to a formyl group, includes, for example, hydrazide group or the like.

In addition, it is also possible to label a substance to be labeled, after introducing the above reaction activation group to a functional group of a substance to be labeled, by subjecting it to a reaction with the reactive group of the present invention, and a reaction activation group of a functional group of a substance to be labeled in this case, includes also similar one as the above reaction activation group of the present invention.

In the reaction activation group of the present invention, for example, a succinimide (Su) group, a maleimide (Ma) group or the like is preferable.

A preferable specific example of a group where the reaction activation group is introduced to the reactive group of the present invention, includes, for example, —COOSu group, —CONH(CH$_2$)$_4$Ma group or the like. Such a compound containing the reaction activation group of the present invention is also included in the compound of the present invention represented by the general formula [51].

A specific example of a compound of the present invention containing such a reaction activation group of the present invention includes all of the compounds where the above reaction activation group of the present invention is further introduced to the reactive group of the present invention in the compound of the present invention, for example, one where the above reaction activation group is contained in the bivalent group represented by T in the general formulae [55] to [58], and in particular, one where the above reaction activation group is introduced in the reactive group of the present invention represented by $R^{20}$ in the general formula [60] is preferable.

An example of the compound of the present invention introduced with such a reaction activation group of the present invention will be shown below.

A preferable specific example of the compound represented by the general formula [55], containing the reaction activation group of the present invention, includes for example, one shown in the following Table 25. It should be noted that, in Table 25, $R^{3'''}$, $R^{5'''}$ and $R^{11'''}$ represented by the general formula [55] represent —$CH_3$ groups; $R^{7'''}$, $R^{9'''}$ and $R^{10'''}$ represent hydrogen atoms; and $R^{8'''}$ represents a —$SO_3Na$ group.

A preferable specific example of the compound represented by the general formula [58], containing the reaction activation group of the present invention, includes for example, one shown in the following Table 28. It should be noted that, in Table 28, $R^{3'''}$, $R^{5'''}$ and $R^{11'''}$ represented by the general formula [58] represent —$CH_3$ groups; $R^{7'''}$, $R^{9'''}$ and $R^{10'''}$ represent hydrogen atoms; and $R^{8'''}$ represents a —$SO_3Na$ group.

TABLE 28

|  | n | $R^{1'''}$ | $R^{6'''}$ | T |
|---|---|---|---|---|
| 58-1-1 | 0-3 | —$(CH_2)_3SO_3Na$ | —$(CH_2)_3SO_3Na$ | —$(CH_2)_5CONHC(COOSu)(CH_2)_4NHCO(CH_2)_5$— |
| 58-1-2 | 0-3 | —$(CH_2)_3SO_3Na$ | —$(CH_2)_3SO_3Na$ | —$(CH_2)_5CONHC[CONH(CH_2)_4Ma](CH_2)_4NHCO(CH_2)_5$— |

In this way, a compound wherein the reactive activation group is introduced with a reactive group of the present invention is also included in the compound group of the present invention.

3-2. A Synthesis Method for the Compound [51] of the Present Invention

TABLE 25

|  | n | $R^{4'''}$ | $R^{6'''}$ | T |
|---|---|---|---|---|
| 55-1-1 | 0-3 | —$(CH_2)_3SO_3Na$ | —$(CH_2)_3SO_3Na$ | —$(CH_2)_5CONHC(COOSu)(CH_2)_4NHCO(CH_2)_5$— |
| 55-1-2 | 0-3 | —$(CH_2)_3SO_3Na$ | —$(CH_2)_3SO_3Na$ | —$(CH_2)_5CONHC[CONH(CH_2)_4Ma](CH_2)_4NHCO(CH_2)_5$— |
| 55-139-1 | 0-3 | —$CH_3$ | —$(CH_2)_3SO_3Na$ | —$(CH_2)_2CONHC(COOSu)(CH_2)_4NHCO(CH_2)_2$— |
| 55-139-2 | 0-3 | —$CH_3$ | —$(CH_2)_3SO_3Na$ | —$(CH_2)_2CONHC[CONH(CH_2)_4Ma](CH_2)_4NHCO(CH_2)_2$— |

A preferable specific example of the compound represented by the general formula [56], containing the reaction activation group of the present invention, includes for example, one shown in the following Table 26. It should be noted that, in Table 26, $R^{3'''}$, $R^{6'''}$ and $R^{11'''}$ represented by the general formula [56] represent —$CH_3$ groups; $R^{7'''}$, $R^{9'''}$ and $R^{10'''}$ represent hydrogen atoms; and $R^{8'''}$ represents a —$SO_3Na$ group.

3-2-1. Synthesis of an Indolenine Compound—Pyrazole Compound Complex (it Corresponds to the Compound Represented by the General Formula [51] of the Present Invention)

The compound represented by the general formula [51] can be synthesized, for example, by the following method.

TABLE 26

|  | n | $R^{1'''}$ | $R^{2'''}$ | T |
|---|---|---|---|---|
| 56-1-1 | 0-3 | —$(CH_2)_3SO_3Na$ | —$(CH_2)_3SO_3Na$ | —$(CH_2)_5CONHC(COOSu)(CH_2)_4NHCO(CH_2)_5$— |
| 56-1-2 | 0-3 | —$(CH_2)_3SO_3Na$ | —$(CH_2)_3SO_3Na$ | —$(CH_2)_5CONHC[CONH(CH_2)_4Ma](CH_2)_4NHCO(CH_2)_5$— |

A preferable specific example of the compound represented by the general formula [57], containing the reaction activation group of the present invention, includes for example, one shown in the following Table 27. It should be noted that, in Table 27, $R^{3'''}$, $R^{5'''}$ and $R^{11'''}$ represented by the general formula [57] represent —$CH_3$ groups; $R^{7'''}$, $R^{9'''}$ and $R^{10'''}$ represent hydrogen atoms; and $R^{8'''}$ represents a —$SO_3Na$ group.

Explanation will be given on a method for synthesizing the compound represented by the general formula [51] (in detail, the compound represented by the general formulae [55] to [58]), with reference to an example of the case using the compound represented by the general formula [55] (that is, it corresponds to one where $R^{1'''}$ and $R^{2'''}$ in the general formula [51] form the bivalent group represented by T).

TABLE 27

|  | n | $R^{2'''}$ | $R^{4'''}$ | T |
|---|---|---|---|---|
| 57-37-1 | 0-3 | —$(CH_2)_3SO_3^-$ | —$(CH_2)_3SO_3Na$ | —$(CH_2)_5CONHC(COOSu)(CH_2)_4NHCO(CH_2)_2$— |
| 57-37-2 | 0-3 | —$(CH_2)_3SO_3^-$ | —$(CH_2)_3SO_3Na$ | —$(CH_2)_5CONHC[CONH(CH_2)_4Ma](CH_2)_4NHCO(CH_2)_2$— |

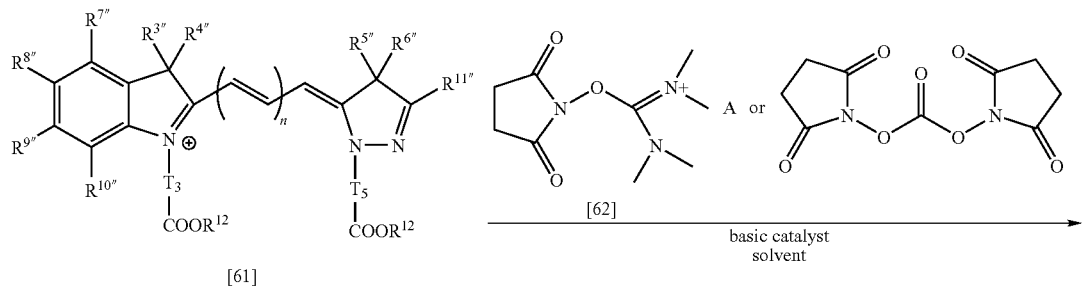

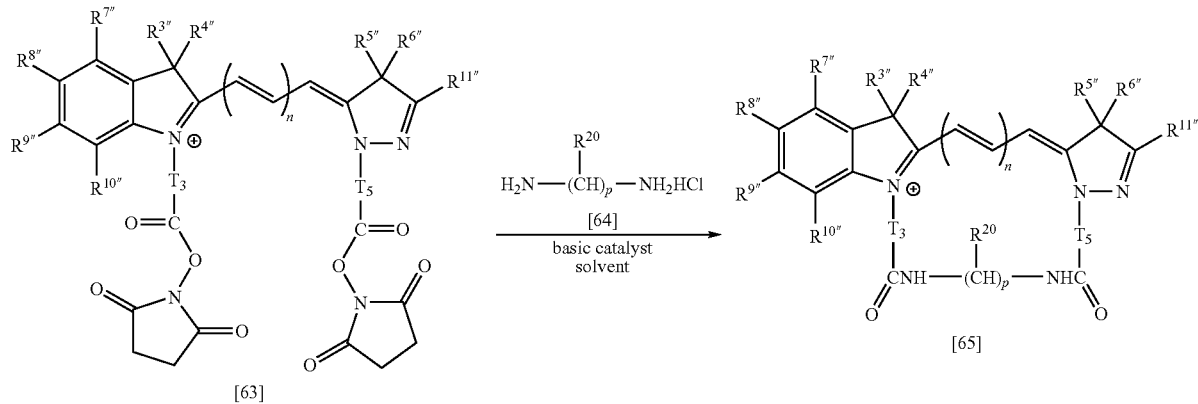

(wherein A represents tetrafluoroborate or hexafluorophosphate; and $R^{3''}$ to $R^{6''}$, $R^{7''}$ to $R^{11''}$, $R^{12''}$, $R^{20''}$, $T_3$, T5, n and p are the same as above).

It should be noted that the compound represented by the general formula [61] corresponds to a compound, among the compounds represented by the general formula [51], wherein $R^{1''}$ is an alkyl group having as a substituent the group represented by the general formula [2] (that is, a $-T_3-COOR^{12}$ group), and $R^{2''}$ is an alkyl group having as a substituent the group represented by the general formula [2] (that is a $-T_5-COOR^{12}$ group).

In addition, the compound represented by the general formula [65] corresponds to the case, among the compounds represented by the general formula [55], wherein T is the group represented by the general formula [63] (where $R^{18}$ and $R^{19}$ are —CONH— groups).

That is, the compound represented by the general formula [61] (a compound having the reactive group of the present invention) is subjected to a reaction with the compound represented by the general formula [62] or disuccinimidyl carbonate (DSC) (from 2 to 20 times mole relative to the compound represented by the general formula [61]), at 0 to 40° C. for 0.1 to 12 hours, in the presence of a basic catalyst (organic amines such as N-ethyldiisopropylamine, pyridine, triethylamine, N,N-dimethylaniline, piperidine, 4-dimethylaminopyridine, 1,5-diazabicyclo [4.3.0] nona-5-ene, 1,8-diazabicyclo [5.4.0] undec-7-ene and tri-n-butylamine) in a suitable solvent (amides such as N,N-dimethylformamide (DMF), N,N-dimethylacetamide (DMA), acetamide and N-methylpyrrolidone) to obtain the compound represented by the general formula [63].

Then, the compound represented by the general formula [63] and the compound represented by the general formula [64] are subjected to a reaction at 0 to 40° C. for 0.1 to 12 hours, in the presence of a basic catalyst (e.g. alkali metal hydrogencarbonates such as sodium hydrogencarbonate and potassium hydrogencarbonate; organic amines such as N-ethyldiisopropylamine, pyridine, triethylamine, N,N-dimethylaniline, piperidine, 4-dimethylaminopyridine, 1,5-diazabicyclo [4.3.0] nona-5-ene, 1,8-diazabicyclo [5.4.0] undec-7-ene and tri-n-butylamine; or the like) in a suitable solvent (amides such as DMF, DMA, acetamide and N-methylpyrrolidone; water; or the like) to obtain the objective compound represented by the general formula [65].

Other compounds represented by the general formula [51] can be obtained also by using corresponding raw materials, and by subjecting them to synthesis as appropriate in accordance with the above method.

3-2-2. Synthesis of a Compound of the Present Invention Containing a Reaction Activation Group (a Group Obtained by Activating a Reactive Group of the Present Invention)

Explanation will be given on a method for introducing the reaction activation group of the present invention to the reactive group of the present invention, with reference to an example of the case, among the compounds represented by the general formula [51], of using the compound represented by the general formula [55] (that is, it corresponds to one where $R^{1''}$ and $R^{2''}$ in the general formula [51] form the bivalent group represented by T); and still more, among the compounds represented by the general formula [65], the case of using the compound where p is 5, one of the 5 $R^{20}$s is the group represented by the general formula [2] (that is, it corresponds to the compound represented by the following general formula [66]).

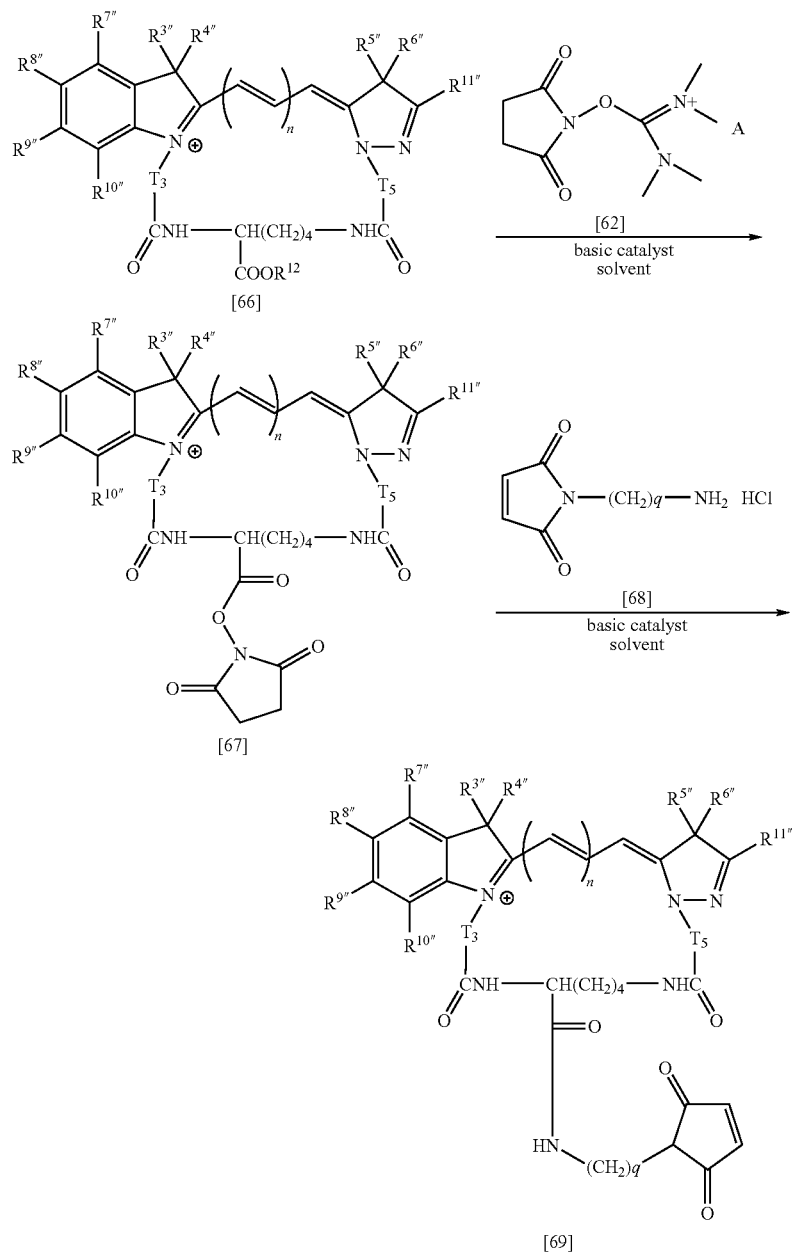

(wherein q represents an integer of from 2 to 10; and $R^{3''}$ to $R^{11''}$, $R^{12}$, $T_3$, $T_5$, A and n are the same as above).

It should be noted that the compound represented by the general formula [66] corresponds to a compound, among the compounds represented by the general formula [65], where p is 5, one of 5 $R^{20}$s is the group represented by the general formula [2], and other $R^{20}$s are hydrogen atoms.

In the general formula [68] and [69], q represents an integer of from 2 to 10.

That is, the compound represented by the general formula [66] (a compound having the reactive group of the present invention) is subjected to a reaction with a succinimidation reagent, for example, the compound represented by the general formula [62] or the like (from 1 to 10 times mole relative to the compound represented by the general formula [66]), at 0 to 40° C. for 0.1 to 12 hours, in the presence of a basic catalyst (e.g. organic amines such as N-ethyldiisopropylamine, pyridine, triethylamine, N,N-dimethylaniline, piperidine, 4-dimethylaminopyridine, 1,5-diazabicyclo [4.3.0] nona-5-ene, 1,8-diazabicyclo [5.4.0] undeca-7-ene and tri-n-butylamine, etc.) in a suitable solvent (e.g. amides such as DMF, DMA, acetamide, N-methylpyrrolidone, etc.) to obtain the compound represented by the general formula [67] (a compound having the succinimide group, which is a reaction activation group of the present invention).

The compound represented by the general formula [67] is subjected to a reaction with a maleimidation reagent, for example, the compound represented by the general formula [68] or the like (from 1 to 10 times mole relative to the compound represented by the general formula [67]), at 0 to 40° C. for 0.1 to 12 hours, in the presence of a basic catalyst (e.g. organic amines such as triethylamine, N-ethyldiisopropylamine, pyridine, N,N-dimethylaniline, piperidine, 4-dimethylaminopyridine, 1,5-diazabicyclo [4.3.0] nona-5-ene, 1,8-diazabicyclo [5.4.0] undeca-7-ene and tri-n-butylamine, etc.) in a suitable solvent (e.g. amides such as DMF, DMA, acetamide, N-methylpyrrolidone, etc.) to obtain the compound represented by the general formula [69] (a compound having the maleimide group, which is a reaction activation group of the present invention).

The succinimidation reagent relevant to the present invention, includes all of those used in this field without limiting to the compounds represented by the general formula [62], and for example, di(N-succinimidyl) carbonate (DSC), 2-succinimide-1,1,3,3-tetramethyluronium tetrafluoroborate (TSTU),2-(5-norbornene-2,3-dicarboxylmide)-1,1,3,3-tetramet hyluronium tetrafluoroborate (TNTU) or the like.

As a method for introducing a reaction activation group of the present invention, other than the above reaction activation groups, they can be obtained by using corresponding raw materials, and by subjecting them to synthesis as appropriate in accordance with the above method.

3-2-3. Synthesis of an Indolenine Compound—Pyrazole Compound Complex (a Compound Represented by the General Formula [75])

Explanation will be given below on a synthesis method for the compound represented by the general formula [75] (an indolenine compound—pyrazole compound complex).

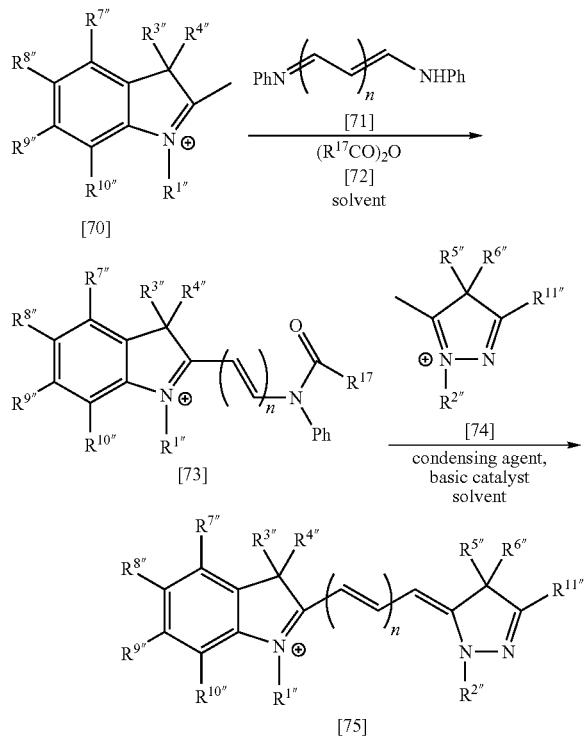

(wherein $R^{17}$ represents alkyl group or aryl group; and definitions of $R^{1''}$ to $R^{6''}$, $R^{11''}$, n and others are the same as above, provided that at least one of $R^{1''}$, $R^{3''}$ and $R^{4''}$ has as a substituent the group represented by the general formula [2], and at least one of $R^{2''}$, $R^{5''}$ and $R^{6''}$ has as a substituent the group represented by the general formula [2]).

In the general formulae [72] and [73], the alkyl group represented by $R^{17}$ may be any of straight-chained, branched and cyclic one, and includes one having usually $C_1$ to $C_{10}$; preferably $C_1$ to $C_3$, and specifically, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, sec-hexyl group, tert-hexyl group, neohexyl group, n-heptyl group, isoheptyl group, sec-heptyl group, tert-heptyl group, neoheptyl group, n-octyl group, isooctyl group, sec-octyl group, tert-octyl group, neooctyl group, n-nonyl group, isononyl group, sec-nonyl group, tert-nonyl group, neononyl group, n-decyl group, isodecyl group, sec-decyl group, tert-decyl group, neodecyl group, cyclopropyl group, cyclobutyl group, cyclopentyl group, cyclohexyl group, cycloheptyl group, cyclooctyl group, cyclononyl group, cyclodecyl group or the like.

The aryl group represented by $R^{17}$ includes usually one having $C_6$ to $C_{10}$, and specifically, for example, phenyl group, naphthyl group or the like.

That is, first of all, the indolenine compound represented by the general formula [70] (an indolenine skeleton part), the compound represented by the general formula [71] [from 1 to 2 times mole relative to the compound represented by the general formula [70]], and an acid anhydride represented by the general formula [72] [from 1 to 20 times mole relative to the compound represented by the general formula [70]] (for example, acetic anhydride, propionic anhydride, butyric anhydride, benzoic anhydride or the like) are dissolved, if necessary, in a solvent (carboxylic acids such as acetic acid, propionic acid and butyric acid; nitrites such as acetonitrile, propionitrile and n-butyronitrile; or the like), and are subjected to a reaction at 0 to 150° C. (preferably at 40 to 120° C.) for 0.1 to 24 hours (preferably for 0.5 to 12 hours, and more preferably for 1 to 8 hours) to obtain the compound represented by the general formula [73].

Then, the compound represented by the general formula [73] and the compound represented by the general formula [74] (a pyrazole skeleton part) [from 0.5 to 10 times mole, preferably from 1 to 5 times mole relative to the compound represented by the general formula [73]] are subjected to a reaction at 0 to 150° C. (preferably at 40 to 120° C.) for 0.1 to 24 hours (preferably for 0.5 to 12 hours, and more preferably for 1 to 8 hours) in the presence of a basic catalyst (e.g. organic amines such as pyridine, triethylamine, N,N-dimethylaniline, piperidine, pyridine, 4-dimethylaminopyridine, 1,5-diazabicyclo [4.3.0] nona-5-ene, 1,8-diazabicyclo [5.4.0] undeca-7-ene and tri-n-butylamine; metal hydrides such as sodium hydride; basic alkali metal compounds such as n-butyllithium, etc.), by using dehydrating condensing agent (e.g. inorganic dehydrating agents such as concentrated sulfuric acid, diphosphorus pentaoxide and anhydrous zinc chloride; carbodiimides such as dicyclohexylcarbodiimide, diisopropylcarbodiimide, 1-ethyl-3-(3-dimethylaminopropyl)carbodiimide hydrochloride; acetic anhydride, polyphosphoric acid, carbonyldiimidazole, p-toluenesulfonylchloride, etc.), and, if necessary, in a solvent (e.g. amides such as N,N-dimethylformamide(DMF), N,N-dimethylacetamide (DMA), acetamide and N-methylpyrrolidone; nitriles such as acetonitrile, propionitrile and n-butyronitrile and the like; alcohols such as methanol, ethanol, propanol, isopropanol, butanol, ethylene glycol and 1,4-butanediol; ethers such as tetrahydrofuran, dioxane, anisole and ethylene glycol monoethyl ether; sulfoxides such as dimethylsulfoxide, etc.) to obtain the compound represented by the general formula [75].

3-2-4 Synthesis of an Indolenine Skeleton Part (the Compound Represented by the General Formula [70])

Explanation will be given below on a synthesis method for the compounds represented by the general formula [70] (an indolenine skeleton part).

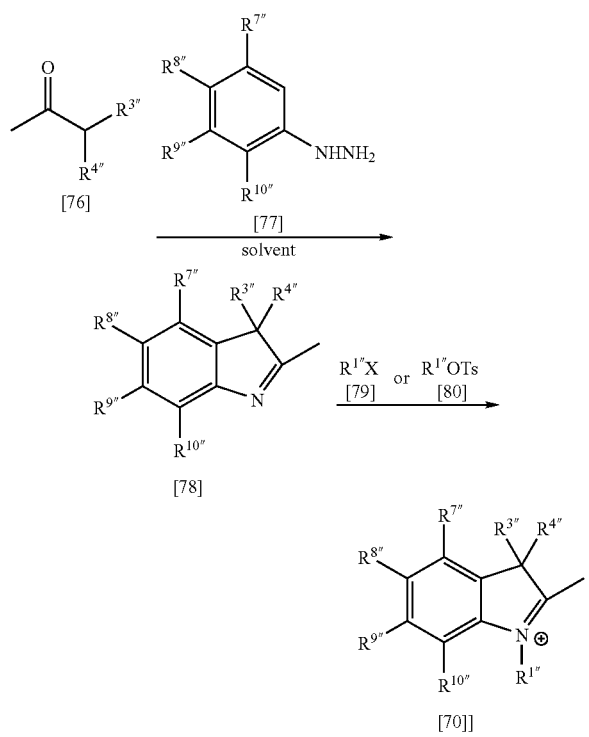

(wherein X represents a halogen atom; and $R^{1''}$, $R^{3''}$, $R^{4''}$ and $R^{7''}$ to $R^{10''}$ are the same as above).

In the general formula [79], the halogen atom represented by X, includes, for example, fluorine atom, chlorine atom, bromine atom, iodine atom or the like.

That is, the ketone compound represented by the general formula [76] and the compound represented by the general formula [77] are subjected to a reaction at 40 to 250° C. for 0.1 to 24 hours, in a suitable solvent (e.g. carboxylic acids such as acetic acid and propionic acid; alcohols such as ethylene glycol and 1,4-butanediol, etc.) to obtain the compound represented by the general formula [78] (see for example, Journal of Organic Chemistry, 42 (14), 2474-80, 1977 or the like).

Then, the compound represented by the general formula [78] and the halide compound represented by the general formula [79] or the tosylate compound represented by the general formula [80] are dissolved in a suitable solvent (e.g. halogenated aromatic hydrocarbons such as chlorobenzene and 1,2-dichlorobenzene; halogenated hydrocarbons such as 1,2-dichloroethane; aromatic hydrocarbons such as toluene, xylene and benzene; amides such as DMA, DMF, acetamide and N-methylpyrrolidone, etc.), and are subjected to a reaction at 40 to 200° C. for 1 to 24 hours to obtain the compound represented by the general formula [70] (see for example, J. Chem. Soc., Perkin Trans. 1. 947-952, 1984 or the like).

The ketone compound represented by the general formula [76] may use a commercial product (for example, 3-methyl-2-butanone, 3-methyl-2-pentanone, 3-methyl-2-hexanone, 1-cyclopropylethanone, 1-cyclobutylethanone or the like), or one synthesized as appropriate by a usual method: Specifically, includes, for example, a method where ethyl 2-methylacetoacetate and a compound having a leaving group (for example, halogen atom, tosylate group, or the like) are subjected to a reaction at −80 to 100° C. for 0.1 to 24 hours, in the presence of a basic catalyst (e.g. metal hydrides such as sodium hydride and potassium hydride; alkali metal carbonates such as lithium carbonate, sodium carbonate and potassium carbonate; alkali metal alkoxides such as sodium methoxide, sodium ethoxide and potassium tert-butoxide; basic alkali metal compounds such as n-butyllithium; alkali metal amides such as lithium diisopropylamide, etc.), in a suitable solvent (e.g. amides such as DMF, DMA, acetamide and N-methylpyrrolidone; alcohols such as methanol, ethanol, propanol, isopropanol, butanol and ethylene glycol; ethers such as tetrahydrofuran, dioxane and ethylene glycol monoethyl ether; sulfoxides such as dimethylsulfoxide, etc.), and then the resulting solution is subjected to a decarbonation by using an acid catalyst (refer to, for example, Modern Synthetic Reactions, California, $2^{nd}$ ed., pages 492, 510 and 756 (1972) or the like) or the like.

The compound represented by the general formula [77], may use a commercial product, or one synthesized as appropriate by a usual method.

3-2-5. Synthesis of a Pyrazole Skeleton Part (a Compound Represented by the General Formula [74])

Explanation will be given below on a synthesis method for the compound represented by the general formula [74] (a pyrazole skeleton part).

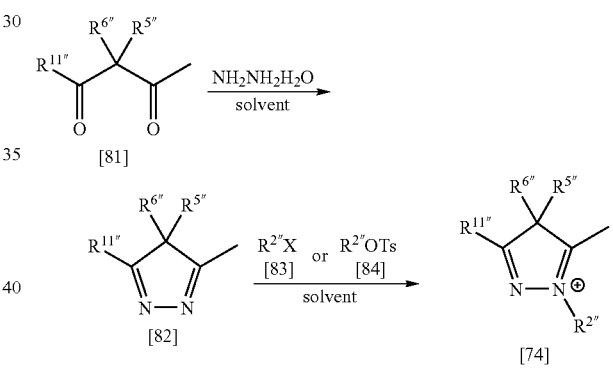

(wherein $R^{2''}$, $R^{5''}$ to $R^{6''}$, $R^{11''}$ and X are the same as above)

That is, the diketone compound represented by the general formula [81] and hydrazine are subjected to a dehydration reaction at 60 to 100° C. for 1 to 4 hours in a suitable solvent (e.g. alcohols such as methanol, ethanol, propanol, isopropanol, butanol and ethylene glycol, etc.), to obtain a 4H-pyrazole compound represented by the general formula [82] (see for example, Adv. Heterocycle Chem., Vol. 34, 53-78, 1983 or the like).

Then, the 4H-pyrazole represented by the general formula [82] is subjected to an N-alkylation reaction with a halide compound represented by the general formula [83] or the tosylate compound represented by the general formula [84], at 80 to 140° C. for 1 to 12 hours in a suitable solvent (e.g. halogenated aromatic hydrocarbons such as chlorobenzene and 1,2-dichlorobenzene; halogenated hydrocarbons such as 1,2-dichloroethane; aromatic hydrocarbons such as toluene, xylene and benzene; amides such as DMF, DMA, acetamide and N-methylpyrrolidone, etc.), to obtain the compound represented by the general formula [74] (see for example, J. Chem. Soc., Perkin Trans. 1. 947-952, 1984 or the like).

The diketone compound represented by the general formula [81], may use a commercial product (for example, 3,3- dimethyl-2,4-pentanedione or the like), or one synthesized as appropriate by a usual method: Specifically, includes, for example, a method where 3-methyl-2,4-pentanedione or 4-acetyl-5-oxohexanoic acid ethyl ester and a compound having a leaving group (for example, halogen atom, tosylate group, or the like) are subjected to a reaction at −80 to 100° C. for 0.1 to 24 hours, in the presence of a basic catalyst (metal hydrides such as sodium hydride, potassium hydride; alkali metal carbonates such as lithium carbonate, sodium carbonate, potassium carbonate; alkali metal alkoxides such as sodium methoxide, sodium ethoxide, potassium tert-butoxide; basic alkali metal compounds such as n-butyllithium; alkali metal amides such as lithium diisopropylamide; or the like), in a suitable solvent (amides such as DMF, DMA, acetamide, N-methylpyrrolidone; alcohols such as methanol, ethanol, propanol, isopropanol, butanol, ethylene glycol; ethers such as tetrahydrofuran, dioxane, ethylene glycol monoethyl ether; sulfoxides such as dimethylsulfoxide; or the like), (refer to, for example, Modern Synthetic Reactions, California, $2^{nd}$ ed., pages 492, 510 and 756 (1972) or the like) or the like.

3-3. Property of the Compound [51] of the Present Invention

The resulting compound [51] of the present invention is expected to be used as a fluorescent labeling substance of, for example, a nucleic acid extraction method, an immunoassay method or the like.

4. A Labeled Compound of the Present Invention, and a Labeling Method 4-1. A Labeled Compound of the Present Invention (a Compound Labeled with the Compound [51] of the Present Invention)

The labeled compound of the present invention includes one where the compound of the present invention (labeling substance) and the substance to be labeled are bound directly or indirectly, and specifically includes one where the group represented by the general formula [2] (for example, a carboxyl group or the like), the group represented by the general formula [3] (for example, a sulfo group or the like), amino group, hydroxyl group, thiol group, or formyl group, is bound directly or indirectly with a substance to be labeled.

As for the group represented by the general formula [2] (for example, a carboxyl group or the like), the group represented by the general formula [3] (for example, a sulfo group or the like), amino group, hydroxyl group, thiol group or formyl group (hereafter may be abbreviated as "reactive group of the present invention"), in the compound of the present invention to be bound to a substance to be labeled, it is preferable that they are contained usually in $R^{1''}$ to $R^{11''}$ in the general formula [1], or in a bivalent group formed by any of $R^{1''}$ and $R^{2''}$, $R^{4''}$ and $R^{5''}$, $R^{1''}$ and $R^{6''}$, and $R^{2''}$ and $R^{4''}$, (that is, a bivalent group represented by T in the general formulae [7] to [10]), preferably in a bivalent group represented by T in the general formulae [7] to [10], that is a bivalent group represented by the general formula [36], and more preferably in $R^{20}$ in the general formula [36].

A substance to be labeled by a compound of the present invention, includes, for example, all of those usually used as a substance to be labeled in this field, however, specifically includes, for example, biotin, avidin, streptavidin, amino acid, proteine, peptide, enzyme substrate, hormone, lymphokine, metabolite, receptor, ligand, agonist, antagonist, antigen, hapten, dendrimer, lectin, toxin, carbohydratem, saccharides such as fructose, polysaccharides and the like; nucleoside (for example, ribonucleoside, deoxyribonucleoside, or the like), nucleotide (for example, ribonucleotide, deoxyribonucleotide, or the like), nucleic acid (oligonucleotide, polynucleotide) [for example, deoxyribonucleic acid (DNA), ribonucleic acid(RNA), or the like], nucleic acid derivatives (for example, DNA fragment, RNA fragment, or the like), natural drugs, virus, virus components, yeast components, hemocyte, hemocyte components, biological cells, non-cellular hemocyte components, bacteria, bacteria components, natural and synthetic lipid cysts, synthetic and natural drugs, poisons, environmental pollutants, polymers, polymer particles, glass particles, glass surface materials, plastic particles, plastic surface materials, polymer films, conductors and semiconductors; along with antibody therefor and degradation products thereof (for example, Fab, Fab', F(ab')$_2$, and the like) or the like, and among these, for example, nucleotide, antibody or degradation products thereof or the like is preferable.

Nucleoside is composed of a purine base or a pyrimidine base, and pentose as a saccharide moiety, and specifically includes, ribonucleoside where, for example, the saccharide moiety is D-ribose; deoxyribonucleoside where, for example, the saccharide moiety is D-2-deoxyribose, or the like.

Nucleotide is composed of a purine base or a pyrimidine base, and pentose as a saccharide moiety, and phosphoric acid, and specifically includes, ribonucleotide where, for example, the saccharide moiety is D-ribose; deoxyribonucleotide where, for example, the saccharide moiety is D-2-deoxyribose, or the like.

In addition, the nucleoside and nucleotide, includes also, for example, like nucleoside antibiotics, one where a salt moiety as a fundamental part thereof is not a purine structure or a pyrimidine structure, one where these structures are modified, one where the saccharide moiety is not D-ribose or deoxy-D-ribose, one where they are modified, one where a phosphoric acid moiety (—OPO$_3^-$) is substituted with other element [for example, a sulfur atom (—OPO$_2$S$^-$) or the like), one where the phosphoric acid moiety is modified, or the like.

Nucleic acid has the nucleotide as a fundamental unit, and is a chain-like oligo- or polynucleotide, where this phosphoric acid is bound by a diester bond between 3' and 5' site carbons of the saccharide, in each of nucleotides, and specifically includes, ribonucleic acid (RNA) where, for example, the saccharide moiety is ribose; deoxyribonucleic acid (DNA) where, for example, the saccharide moiety is D-2-deoxyribose, or the like.

These nucleotide, nucleic acid and derivative nucleic acid may be those composed of nucleic acid chains of any of a single strand, a double strand or more than two strands. In addition, they may be modified as appropriate with a suitable one, as long as it is within a range where an object of the present invention can be attained.

"A compound of the present invention and a substance to be labeled are directly bound" means that, for example, the compound of the present invention (namely, a reactive group of the present invention in the compound) binds to a functional group in the substance to be labeled (for example, amino group, carboxyl group, thiol group, hydroxyl group, formyl group or the like) by, for example, an ionic bond, a covalent bond or the like. In addition, "a compound of the present invention and a substance to be labeled are indirectly bound" means that, for example, a reactive group of the present invention binds to the functional group in the substance to be labeled, via a linker or the like (for example, by an ionic bond, a covalent bond or the like). The linker used in the indirect binding, includes all of those usually used in this field.

4-2. A Labeling Method of the Present Invention

As for a method for labeling a substance to be labeled by using the compound [1] of the present invention, the labeling may be carried out by selecting, as appropriate, a known method itself, and the labeling may be easily carried out, for example, by subjecting the reactive group of the present invention [that is, the group represented by the general formula [2] (for example, a carboxyl group or the like), the group represented by the general formula [3] (for example, a sulfo group or the like), amino group, hydroxyl group, thiol group, or formyl group), contained in at least one of $R^1$ to $R^{11}$ in the general formula [51], or a bivalent group formed by any of $R^{1''}$ and $R^{2''}$, $R^{4''}$ and $R^{5''}$, $R^{1''}$ and $R^{6''}$, and $R^{2''}$ and $R^{4''}$, and a functional group of the substance to be labeled (for example, amino group, carboxyl group, thiol group, hydroxyl group, formyl group or the like), (hereafter may be abbreviated as "a functional group of the substance to be labeled"), to direct binding by, for example, an ionic bond, a covalent bond or the like; or binding via a linker introduced to a part of the substance to be labeled.

In addition, as for a method for labeling nucleotide (a substance to be labeled), labeling can be carried out easily by a method for using an enzyme, other than a method for labeling by using the above chemical reaction, and the enzyme used here, includes all of those usually used in this field.

The reactive group of the present invention may be introduced further with a group which enhances reactivity with a functional group of a substance to be labeled (a reaction activation group of the present invention).

It should be noted that, such a reaction activation group is included in a reactive group of the present invention, and a compound containing such a reaction activation group is also included in a compound of the present invention.

A specific example of a method for labeling a substance to be labeled, by using a compound of the present invention, includes, for example, (1) a labeling method by introducing further a reaction activation group of the present invention to a reactive group of the present invention, and then binding thereto a functional group of a substance to be labeled (hereafter may be abbreviated as simply "a functional group"), (2) a labeling method by introducing a reaction activation group of the present invention to a functional group of a substance to be labeled, and then binding thereto a reactive group of the present invention, (3) a labeling method by bonding a multivalent reactive linker reagent, usually used in this field, to a reactive group of the present invention and a functional group of a substance to be labeled, and (4) a labeling method by introducing the same or different reaction activation group to a reactive group of the present invention and a functional group of a substance to be labeled, and then binding thereto a linker, usually used in this field, or the like As the reaction activation group of the present invention, it is not especially limited as long as it is one capable of binding to a functional group of a substance to be labeled, and all those usually used in this field are included, for example, one activating reactivity with an amino group (hereafter referred to as "a reaction activation group to an amino group"), one activating reactivity with a thiol group (hereafter referred to as "a reaction activation group to a thiol group"), one activating reactivity with a hydroxyl group (hereafter referred to as "a reaction activation group to a hydroxyl group"), one activating reactivity with a formyl group (hereafter referred to as "a reaction activation group to a formyl group") or the like. A preferable specific example of these a reaction activation group is as described above.

In addition, it is also possible to label a substance to be labeled, after introducing the above reaction activation group to a functional group of a substance to be labeled, by subjecting it to a reaction with the reactive group of the present invention, and a reaction activation group of a functional group of a substance to be labeled in this case, includes also similar one to the above reaction activation group of the present invention.

In the reaction activation group of the present invention, for example, a succinimide (Su) group, a maleimide (Ma) group or the like is preferable.

A preferable specific example of a group where the reaction activation group is introduced to the reactive group of the present invention, includes, for example, —COOSu group, —CONH(CH$_2$)$_4$Ma group or the like. Such a compound containing the reaction activation group of the present invention is also included in the compound of the present invention represented by the general formula [1].

In the case where the reactive group of the present invention is the group represented by the general formula [2] (hereafter abbreviated as "a carboxyl group of the present invention"), and a substance to be labeled is binding thereto, it is preferable that it is bound to amino group, thiol group or hydroxyl group, which is a functional group of a substance to be labeled, or of a linker introduced thereto (hereafter abbreviated simply as "a substance to be labeled"), and there is included, as a method therefor, (i) a method for subjecting to a reaction by using, for example, a condensing reagent such as N-hydroxysuccinimide and carbodiimide, (ii) a method for forming a carboxylchloride by subjecting thionyl chloride to action to a carboxyl group of the present invention, and then subjecting it to a reaction with an amino group of a substance to be labeled, (iii) a method for subjecting to a reaction by the addition of hydrochloric acid and methanol to a carboxyl group of the present invention, and then subjecting to a reaction by the addition of hydrazine to form hydrazide, and subjecting to activation by the further addition of sodium nitrite and hydrochloric acid thereto to make acylazide, and then subjecting it to a reaction with amino group, thiol group or hydroxyl group of a substance to be labeled, (iv) a method for forming an anhydride from a carboxyl group of the present invention, and then subjecting it to a reaction with an amino group of a substance to be labeled (dehydrating condensation); or the like.

In addition, in the case where a reactive group of the present invention is the group represented by the general formula [3] (hereafter abbreviated as "a sulfo group of the present invention"), and a substance to be labeled is subjected to bond therewith, it is preferable to be subjected to binding to amino group, imidazole group, thiol group or phenol group of the substance to be labeled, and a method therefor, includes for example, (i) a method for subjecting chlorosulfonic acid to a reaction with the sulfo group of the present invention to form sulfochloride, and then subjecting it to a reaction with amino group, imidazole group, thiol group or phenol group of a substance to be labeled.

In the case where the reactive group of the present invention is an amino group (hereafter abbreviated as "an amino group of the present invention"), and a substance to be labeled is subjected to bond therewith, it is preferable to subject it to binding to carboxyl group, amino group, phenol group or thiol group, which is a functional group of a substance to be labeled or a linker thereof, and a method therefor, includes for example, (i) a method for subjecting the amino group of the present invention to binding to the amino group of a substance to be labeled or a linker thereof, by using a condensing reagent such as N-hydroxysuccinimide and carboxydiimide, (ii) a method for making phosgene to act to the amino group of the present invention to convert to an isocyanate, and then subjecting it to binding to the amino group of the substance to be labeled or the linker thereof, (iii) a method for subjecting glutaraldehyde to a reaction to the amino group of the present invention, and then subjecting it to a reaction with amino group, or phenol group of the substance to be labeled or the linker thereof, (iv) in the case where the substance to be labeled or the linker thereof is one derived from saccharide or saccharide protein, a method for subjecting it to a reaction with periodic acid in advance, and then subjecting it to a reaction with the amino group of the present invention, and further subjecting it to reduction by using sodium borohydride or the like and (v) a method for subjecting the amino group of the present invention to maleimidation or pyridyldithiosulfidation with a bivalent spacer having a maleimide group (for example, m-maleimidebenzoyl N-hydroxysuccinmide ester), or a bivalent spacer having a pyridyldithiosulfide group (for example, 4-succinimidyloxy-carbonyl-α-(2-pyridyldithio) toluene or the like), and then subjecting it to a reaction with the thiol group of the substance to be labeled or the linker thereof.

In the case where the reactive group of the present invention is a hydroxyl group (hereafter abbreviated as "a hydroxyl group of the present invention"), and a substance to be labeled is subjected to a reaction therewith, it is preferable to be subjected to binding to amino group, thiol group or hydroxyl group, which is a functional group of a substance to be labeled or a linker thereof, and a method therefor, includes for example, (i) a method for forming a triazinyl derivative by subjecting a cyanuric chloride group to action to the hydroxyl group of the present invention, and subjecting it to a reaction with the amino group of the substance to be labeled or a linker thereof, (ii) a method for subjecting the hydroxyl group of the present invention to acetylation, then bromination, bromine-iodine exchange by using sodium iodide, and then subjecting it to a reaction with the amino group, thiol group or hydroxyl group of the substance to be labeled or a linker thereof, (iii) a method for subjecting cyanogen bromide to action to the hydroxyl group of the present invention for activation thereof, and then subjecting it to a reaction with the amino group of the substance to be labeled or a linker thereof.

In the case where the reactive group of the present invention is a thiol group (hereafter abbreviated as "a thiol group of the present invention"), and a substance to be labeled is subjected to a reaction therewith, it is preferable to be subjected to binding to amino group, thiol group or hydroxyl group, which is a functional group of a substance to be labeled or a linker thereof, and a method therefor, includes for example, (i) a method for subjecting the amino group of the substance to be labeled or a linker thereof to maleimidation or pyridyldithiosulfidation with a bivalent spacer having a maleimide group (for example, m-maleimidebenzoyl N-hydroxysuccinmide ester) or a bivalent spacer having a pyridyldithiosulfide group (for example, 4-succinimidyloxy-carbonyl-α-(2-pyridyldithio)toluene or the like), and then subjecting the thiol group of the present invention to a reaction therewith, and (ii) a method for subjecting the thiol group of the present invention to a reaction with the thiol group of the substance to be labeled or a linker thereof, by using a bivalent spacer such as bismaleimidehexane, 1,4-di-[3'-2'-pyridyldithio(propionamide)]butane or the like.

In the case where the reactive group of the present invention is a formyl group (hereafter abbreviated as "a formyl group of the present invention"), and a substance to be labeled is subjected to a reaction therewith, it is preferable to be subjected to binding to amino group or the like, which is a functional group of a substance to be labeled or a linker thereof, and a method therefor, includes for example, (i) a method for subjecting the amino group of a substance to be labeled or a linker thereof to a direct reaction with the formyl group of the present invention, and then subjecting it to reduction by using sodium borohydride or the like.

A polyvalent reactive linker reagent, includes all of those usually used in this field, however, specifically, for example, a bivalent reagent in the case where one of the reactive group of the present invention and a functional group of a substance to be labeled is an amino group, and the other is a thiol group (hereafter abbreviated as "a bivalent reagent of amino group and thiol group"); a bivalent reagent in the case where one of the reactive group and the functional group is an amino group, and the other is the group represented by the general formula [2] (carboxyl group or the like)(hereafter abbreviated as "a bivalent reagent of amino group and carboxyl group"); a bivalent reagent in the case where one of the reactive group and the functional group is an thiol group, and the other is a hydroxyl group (hereafter abbreviated as "a bivalent reagent of thiol group and hydroxyl group"); a bivalent reagent in the case where both of the reactive group and the functional group are amino groups (hereafter abbreviated as "a bivalent reagent of amino group and amino group"); a bivalent reagent in the case where both of the reactive group and the functional group are thiol groups (hereafter abbreviated as "a bivalent reagent of thiol group and thiol group"); or the like.

A specific example of the bivalent reagent of amino group and thiol group includes, for example, N-(α-maleimideacetoxy)succinimide, N-[γ-maleimidebutyryloxy]succinimide, N-(6-maleimidecaproyloxy)succinimide, N-(8-maleimidecapryloxy)succinimide, N-(11-maleimideundecanoyloxy)succinimide, m-maleimidebenzoyl-N-hydroxysuccinimide, succinimidyl 4-[p-maleimidephenyl]butyrate, succinimidyl 4-[N-maleimidemethyl]cyclohexane-1-carboxylate, succinimidyl 6-[β-maleimidepropionamide]hexanoate, N-succinimidyl 3-(2-pyridyldithio)propionate or the like.

A specific example of the bivalent reagent of amino group and carboxyl group includes, for example, 3-[(2-aminoethyl)dithio]propionic acid hydrochloride, 1-ethyl-3-[3-dimethylaminopropyl]carbodiimide hydrochloride or the like.

A specific example of the bivalent reagent of thiol group and hydroxyl group includes, for example, N-[p-maleimidephenyl] isocyanate or the like.

A specific example of the bivalent reagent of amino group and amino group, includes, for example, methyl N-succinimidyl adipate, disuccinimidyl glutarate, disuccinimidyl suberate, ethylene glycol bis[succinimidyl succinate], dithiobis [succinimidyl propionate], disuccinimidyl tartrate, bis[2-(succinimideoxycarbonyloxy)ethyl]sulfone, 1,5-difluoro-2, 4-dinitrobenzene or the like.

A specific example of the bivalent reagent of thiol group and thiol group, includes, for example, bis-maleimideethane, 1,4-bis-maleimidebutane, bis-maleimidehexane, 1,4-bis-maleimidyl-2,3-dihydroxybutane, dithio-bis-maleimideethane, 1,6-hexane-bis-vinylsulfone, 1,8-bis-maleimide diethylene glycol, 1,11-bis-maleimidetriethylene glycol, 1,4-di-[3'-(2'-pyridyldithio)-propionamide]butane or the like.

4-3. Preparation of a Labeled Nucleotide Using a Compound of the Present Invention As a specific example of a method for labeling a substance to be labeled by using the compound [1] of the present invention, explanation will be given with reference to an example of the case of labeling nucleotide (a substance to be labeled).

That is, in the case of labeling nucleotide having an amino group on a base thereof (for example, cytidine, adenine, guanine or the like), the reactive group in the compound the present invention may be directly bound, or the group obtained by activating a reactive group of the compound the present invention (reaction activation group) may be bound, and among them, it is preferable to be subjected to binding to a group represented by the general formula [2], or a group introduced with the reaction activation group (activated ester group), and in particular, it is more preferable to be subjected to binding to the activated ester group.

In addition, in the case where the compound of the present invention is subjected to indirect binding to nucleotide, first, on a base or a hydroxyl group of the nucleotide, a derivative introduced with a linker having a functional group such as, for example, amino group, carboxyl group and thiol group (hereinafter abbreviated as "a nucleotide derivative") is synthesized, and then, in the case of subjecting, for example, to binding to the amino group in the nucleotide derivative, it may be subjected to binding to the reactive group or the reaction activation group in the compound of the present invention (in particular, carboxyl group or the activated ester group is preferable); in the case of subjecting to binding, for example, to the carboxyl group in the nucleotide derivative, it may be subjected to binding to the amino group, that is reactive group, in the compound of the present invention; and in the case of subjecting to binding, for example, to the thiol group in the nucleotide derivative, it may be subjected to binding to the maleimide group (reaction activation group) in the compound of the present invention. As the linker to be used, any one usually used in this field may be adopted, and an ester bond, an ether bond and/or an amide bond may also be contained in the linker.

Explanation will be given on a labeling method by using the compound [51] of the present invention, with reference to an example of one, among compounds of the present invention, where a carboxyalkyl group contained in $R^{1''}$ (that is, it corresponds to the case where $R^{1''}$ is an alkyl group having as a substituent the group represented by the general formula [2]) is indirectly bound to a nucleotide residue, via a linker or the like.

In the above case, as a linker, there can be used all of those that are used in this field, and specifically, there is included a linker with a structure represented by the following general formula (A):

-E-X-T10-Y—NH— (A)

(wherein E represents —CH=CH— or —C≡C—; X and Y each independently represent alkylene group; and T10 represents —O— or —NH—CO—).

In the general formula (A), the alkylene group represented by X, may be any of straight-chained, branched and cyclic one, and preferably straight-chained one, and includes one having usually $C_1$ to $C_{10}$, preferably $C_1$ to $C_6$, more preferably $C_1$ to $C_3$, and specifically, straight-chained alkylene group such as methylene group, ethylene group, trimethylene group, tetramethylene group, pentamethylene group, hexamethylene group, heptamethylene group, octamethylene group, nonamethylene group, decamethylene group; branched alkylene group such as ethylidene group, propylene group, isopropylidene group, 1-methyltrimethylene group, 2-methyltrimethylene group, 1,1-dimethylethylene group, 1,2-dimethylethylene group, ethylethylene group, 1-methyltetramethylene group, 1,1-dimethyltrimethylene group, 2,2-dimethyltrimethylene group, 2-ethyltrimethylene group, 1-methylpentamethylene group, 1-methylhexamethylene group, 1-methylheptamethylene group, 1,4-diethyltetramethylene group, 2,4-dimethylheptamethylene group, 1-methyloctamethylene group and 1-methylnonamethylene group; cyclic alkylene group such as cyclopropylene group, 1,3-cyclobutylene group, 1,3-cyclopentylene group, 1,4-cyclohexylene group, 1,5-cycloheptylene group, 1,5-cyclooctylene group, 1,5-cyclononylene group and 1,6-cyclodecalene group; or the like.

The alkylene group represented by Y, may be any of straight-chained, branched and cyclic one, and preferably straight-chained one, and includes one having usually $C_1$ to $C_{10}$, preferably $C_2$ to $C_8$, more preferably $C_2$ to $C_6$, and specifically, for example, straight-chained alkylene group such as methylene group, ethylene group, trimethylene group, tetramethylene group, pentamethylene group, hexamethylene group, heptamethylene group, octamethylene group, nonamethylene group, decamethylene group; branched alkylene group such as ethylidene group, propylene group, isopropylidene group, 1-methyltrimethylene group, 2-methyltrimethylene group, 1,1-dimethylethylene group, 1,2-dimethylethylene group, ethylethylene group, 1-methyltetramethylene group, 1,1-dimethyltrimethylene group, 2,2-dimethyltrimethylene group, 2-ethyltrimethylene group, 1-methylpentamethylene group, 1-methylhexamethylene group, 1-methylheptamethylene group, 1,4-diethyltetramethylene group, 2,4-dimethylheptamethylene group, 1-methyloctamethylene group, 1-methylnonamethylene group; cyclic alkylene group such as cyclopropylene group, 1,3-cyclobutylene group, 1,3-cyclopentylene group, 1,4-cyclohexylene group, 1,5-cycloheptylene group, 1,5-cyclooctylene group, 1,5-cyclononylene group, 1,6-cyclodecalene group; or the like.

The labeled nucleotide relevant to the present invention, includes a nucleotide residue labeled with the compound [51] of the present invention, directly or indirectly via linker or the like, specifically, for example, a nucleotide residue represented by the following general formula [74]:

Q1-V1-W2 [74]

[wherein Q1 represents a nucleotide residue; V1 represents a linker; and W2 represents the following general formula [51']:]

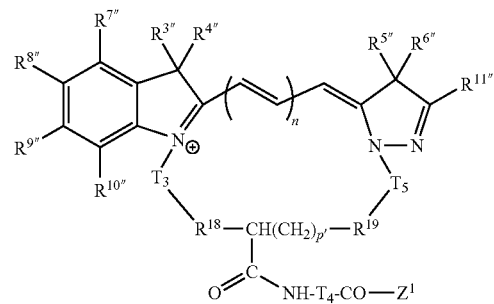

[51']

(where $Z^1$ represents a linker for binding to V1; p' represents an integer of from 1 to 19; and $R^{3''}$ to $R^{11''}$, $R^{18}$ to $R^{19}$, and $T_3$ to $T_5$ are the same as above).

It should be noted that the compound represented by the general formula [51'] corresponds to a compound derivative in the case where, among compounds represented by the general formula [51], a bivalent group formed by $R^{1''}$ and $R^{2''}$ is the group represented by the general formula [60], (where $R^{20}$ is a group represented by the general formula [73]).

The nucleotide residue represented by Q1 in the general formula [74], includes, for example, ribonucleotide residue, 2'-deoxyribonucleotide residue, 3'-deoxyribonucleotide residue, 5'-deoxyribonucleotide residue, 2',3'-dideoxyribonucleotide residue or the like.

Specifically, such a nucleotide residue, includes, for example, purinenucleotide residue represented by the general formula (i), (ii), (v), (vi), (vii), (viii), (xii) and (viii), or pyrimidine nucleotide residue represented by the general formula (iii), (iv), (x) and (xi).
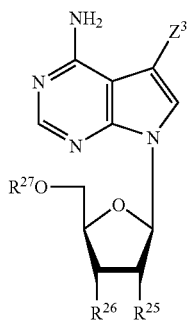
(i)
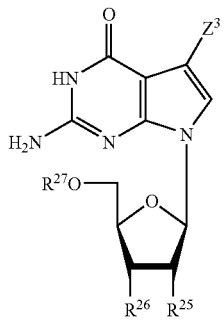
(ii)
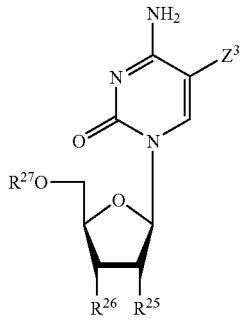
(iii)
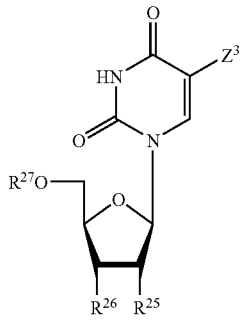
(iv)
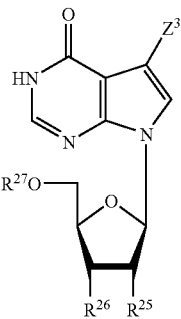
(v)
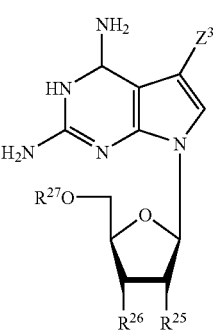
(vi)
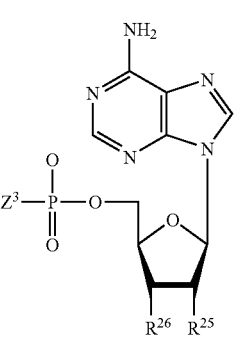
(vii)
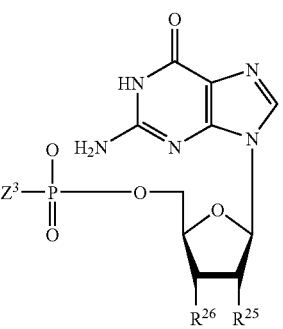
(viii)
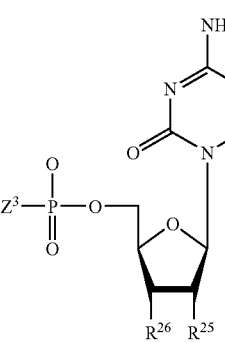
(ix)

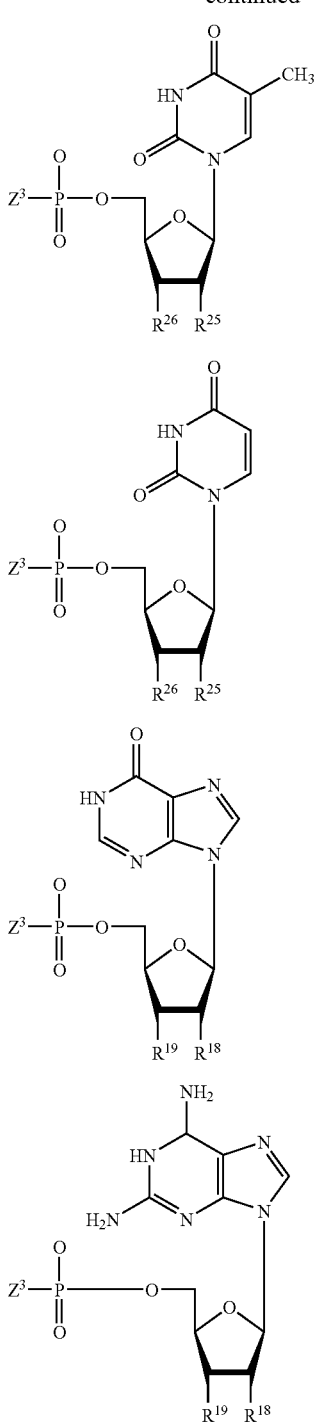

In the above general formula, $Z^3$ represents a linker for binding to V1; $R^{25}$ and $R^{26}$ each independently represent H, OH or O—; $R^{27}$ represents —$PO_2H$—, $PO_3H_2$—, $P_2O_6H_3$, —$P_3O_9H_4$, or a salt thereof. It should be noted that, a specific example of the salt, includes, an alkali metal salt such as, for example, sodium salt, potassium salt and lithium salt; an alkaline earth salt such as, for example, barium salt; ammonium salt; triethylammonium salt; an organic amine salt such as, for example, pyridine salt.

The linker represented by V1 in the general formula [74] is a linker for bonding the nucleotide residue represented by Q1 and the compound derivative (fluorescent labeling) of the present invention represented by W2 [the general formula [51']].

That is, as for a pyrimidine nucleotide residue, among nucleotide residues represented by the above Q1, one terminal of the linker is bound to 5 position of a pyrimidine ring thereof [in the case of the general formulae (iii) and (iv)], or to a phosphorus atom in a phosphate residue thereof [in the case of the general formulae (x) and (xi)]; and as for a purine nucleotide residue, it is bound to 7 position of a 7-deazapurine ring thereof [in the case of the general formulae (i), (ii), (v), and (vi)], or to a phosphorous atom of the phosphate residue of a purine ring thereof (or a 7-dezapurine ring) [in the case of the general formulae (vii), (viii), (ix), (xii) and (xiii)].

Still more, the other terminal of the linker is bound to a carbonyl group [a carbonyl group binding to $T_4$ in the general formula [51']] of the compound derivative (labeling substance) of the present invention represented by W2 [the general formula [51']].

As such a linker, there can be used all of those that are capable of bonding a carbonyl group [a carbonyl group binding to $T_4$ in the general formula [51']] of the compound derivative (labeling substance) of the present invention represented by W2 [the general formula [51']], and the nucleotide residue represented by Q1, and specifically includes a linker with a structure represented by the following general formula (A):

$$-E-X-T10-Y-NH-\qquad (A)$$

(wherein E, X, T10 and Y are the same as above, and specific examples and preferable examples thereof and the like are also as described above).

Therefore, as the nucleotide residue represented by the general formula [74], one each represented by the following general formula [74'] is preferable, and one represented by the following general formula [74"] is more preferable:

$$Q1-E-X1-T11-Y1-NH-W2 \qquad [74']$$

(wherein E1 represents —CH=CH— or —C≡C—; X1 and Y1 each independently represent alkylene group; and T11 represents —O— or —NH—CO—; in addition, Q1 and W2 are the same as above).

It should be noted that, in the above description, the alkylene group represented by X1 is the same as the above alkylene group represented by X, and specific examples and preferable examples thereof and the like are also the same as described above. In addition, the alkylene group represented by Y1 is the same as the above alkylene group represented by Y, and specific examples and preferable examples thereof and the like are also the same as described above.

$$Q1-E-(CH_2)_r-T11-(CH_2)_n-NH-W2 \qquad [74"]$$

(wherein r represents an integer of from 1 to 10, preferably from 1 to 6, more preferably from 1 to 4; s represents an integer of from 1 to 10, preferably from 2 to 8, more preferably from 2 to 4; in addition, Q1, W2, E1 and T11 are the same as above).

In the general formula [51'], $R^{3'}$ to $R^{11"}$, $R^{18}$ to $R^{19}$ and $T_3$ to $T_5$ are the same as above, and specific examples and preferable examples thereof and the like are also as described above.

The compound derivatives (labeling substance) of the present invention represented by W2 [the general formula [51'] are those derived from the compound [51] of the present invention as described above, and preferable specific examples thereof are also similar to the compound [51] of the present invention as described above.

A method for labeling the above described nucleotide with the compound [51] (labeling substance) relevant to the present invention, includes a direct labeling method or an indirect labeling method, known itself, [for example, a method described in WO96/17628 (JP-A-2002-12782), U.S. Pat. No. 6,974,873, JP-A-2002-193991, WO99/12544, JP-A-11-80189 or the like]

In addition, in labeling nucleotide with the compound [51] (labeling substance) relevant to the present invention, it is simpler and more convenient to use a commercially available standard labeling kit based on the labeling method as described above, except for using the compound [51] relevant to the present invention.

It should be noted that to utilize these methods in the present invention, it is required a labeled nucleotide bound to the compound [51] (labeling substance) relevant to the present invention, however, the labeled nucleotide can be prepared by a known method itself (for example, the above labeling method or the like).

Specifically, it can be prepared in accordance with a method described in, for example, JP-A-2002-193991 (paragraphs from to [0121]), and also can be prepared as follows:

That is, it can be obtained easily, for example, by subjecting a nucleotide derivative represented by the following general formula (a) to a reaction with the compound [51] (labeling substance) [succinimidyl ester substance] relevant to the present invention represented by the following general formula (b'):

Q-E-X-T10-Y1-NH$_2$ (a)

(wherein Q represents Q1; and Q1, E, X, T10 and Y are the same as above).

W'—OSu (b')

(wherein W' represents W2; Su represents a succinimide group; and W2 is the same a above).

In addition, in the case where T10 of the linker part represented by the general formula (a), as described above, is —NH—CO—, it can be prepared, for example, as follows:

That is, for example, first a part of a linker (a partial linker A) represented by the following general formula (c) is introduced, to be subjected further to a reaction with the succinimidyl ester substance of the remaining linker part (a partial linker B) to prepare a nucleotide derivative represented by the following general formula (d), which is introduced with the linker. Still more, it can be obtained easily by subjecting the nucleotide derivative represented by the following general formula (d) to a reaction with the compound [51] (labeling substance) [the succinimidyl ester substance] of the present invention represented by the following general formula (b').

-E-X—NH$_2$ (c)

(wherein E and X are the same as above).

Q-E-X—NH—CO—Y—NH$_2$ (d)

(wherein Q, E, X and Y are the same as above).

W'-OSu (b')

(wherein W' and Su are the same as above)

More specifically, among the labeled mononucleotides bound to the compound [51] (labeling substance) of the present invention as above, a fluorescent labeling, 2'-deoxycytidine-5'-triphophate derivative and a fluorescent labeling, 2'-deoxyuridine-5'-triphosphate derivative can be synthesized, for example, according to the following synthesis route.

It should be noted that abbreviated formal names used in the following synthesis route are as follows:

MeOTfa: methyl trifluoroacetate
-Tfa: trifluoroacetyl group
Bu$_3$SnH: tri(n-butyl)tin hydride
AIBN: azobisisobutyronitrile
Et$_3$N: triethylamine
HO-Su: N-hydroxysuccinimide
DMF: N,N-dimethylformamide
TMS-Acetamide: N,O-bis(trimethylsilyl)acetamide
PdCl$_2$(CH$_3$CN)$_2$: bis(acetonitrile)dichloropalladium(II)
tris(TBAPP): tris(tri-n-butylammonium) pyrophosphate
(EtO)$_3$PO: triethyl phosphate
TFP: tri-2-furylphosphine
Pd$_2$(dba) 3: tris(dibenzylideneacetone)dipalladium(0)

(1) Synthesis of the Partial Linker (A)

It should be noted that this compound is a compound corresponding to -E-X—NH— in the case where T10 is —NH—CO—, in the linker (-E-X-T10-Y—NH—) represented by the above general formula (A), and a compound where E is —CH=CH— and X is a methylene group.

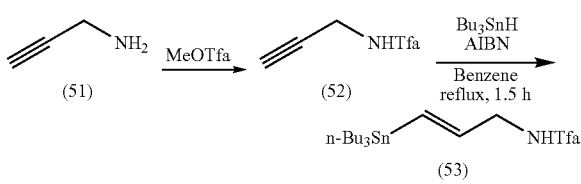

(2) Synthesis of a Partial Linker (B)

It should be noted that this compound is a compound corresponding to —CO—Y—NH— in the case where T10 is —NH—CO—, in the linker (-E-X-T10-Y—NH—) represented by the above general formula (A), and a compound where Y is a pentamethylene group.

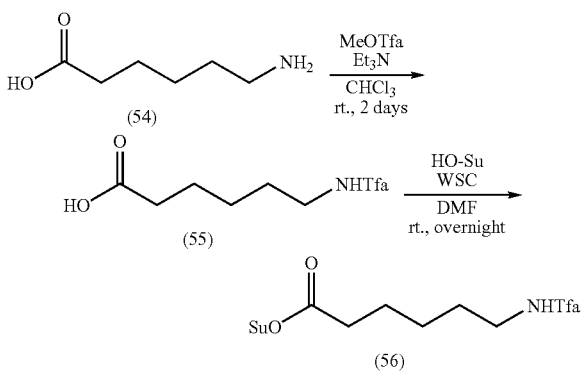

(3) Synthesis of a 2'-deoxycytidine-5'-triphosphate Derivative [a Compound of the General Formula (d)]

It should be noted that this compound is a compound corresponding to Q1-E1-X1-T11-yl-NH— of the general formula [74'] (Q1-E1-X1-T11-yl-NH—W2), and a compound where Q1 is 2'-deoxycytidine, E1 is —CH=CH—, X1 is a methylene group, T11 is —NH—CO—, and Y1 is a pentamethylene group.

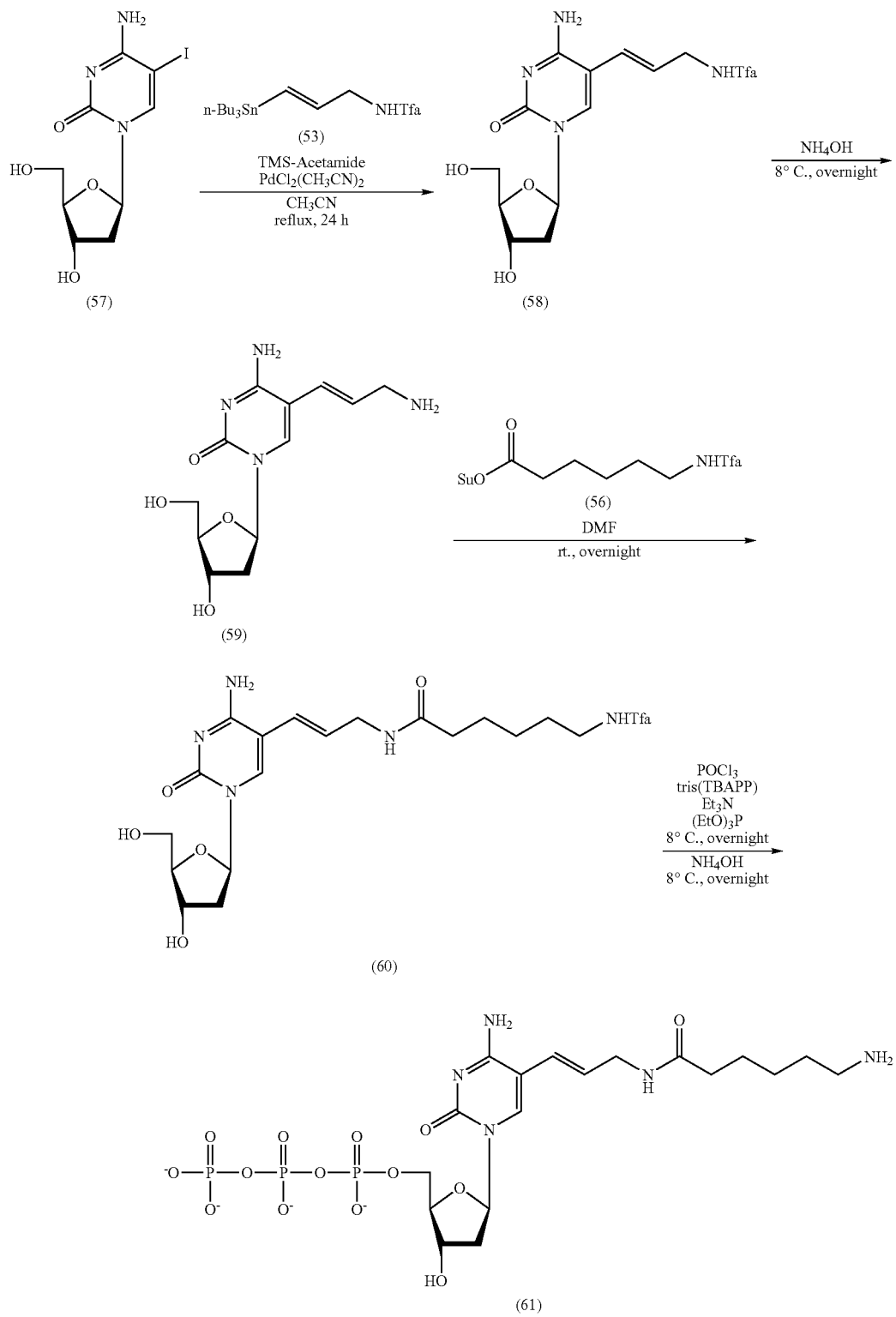

(4) Synthesis of the Fluorescent Labeling, 2'-deoxycytidine-5'-triphosphate derivative [mononucleotide Labeled with the Compound [51] (a Labeling Substance) of the Present Invention]

It should be noted that this compound is a compound, in the general formula [74'] (Q1-E1-X1-T11-Y1-NH—W2), where Q1 is 2'-deoxycytidine, E1 is —CH═CH—, X1 is a methylene group, T11 is —NH—CO—, Y1 is a pentamethylene group and W2 is the following compound (14) or (25):

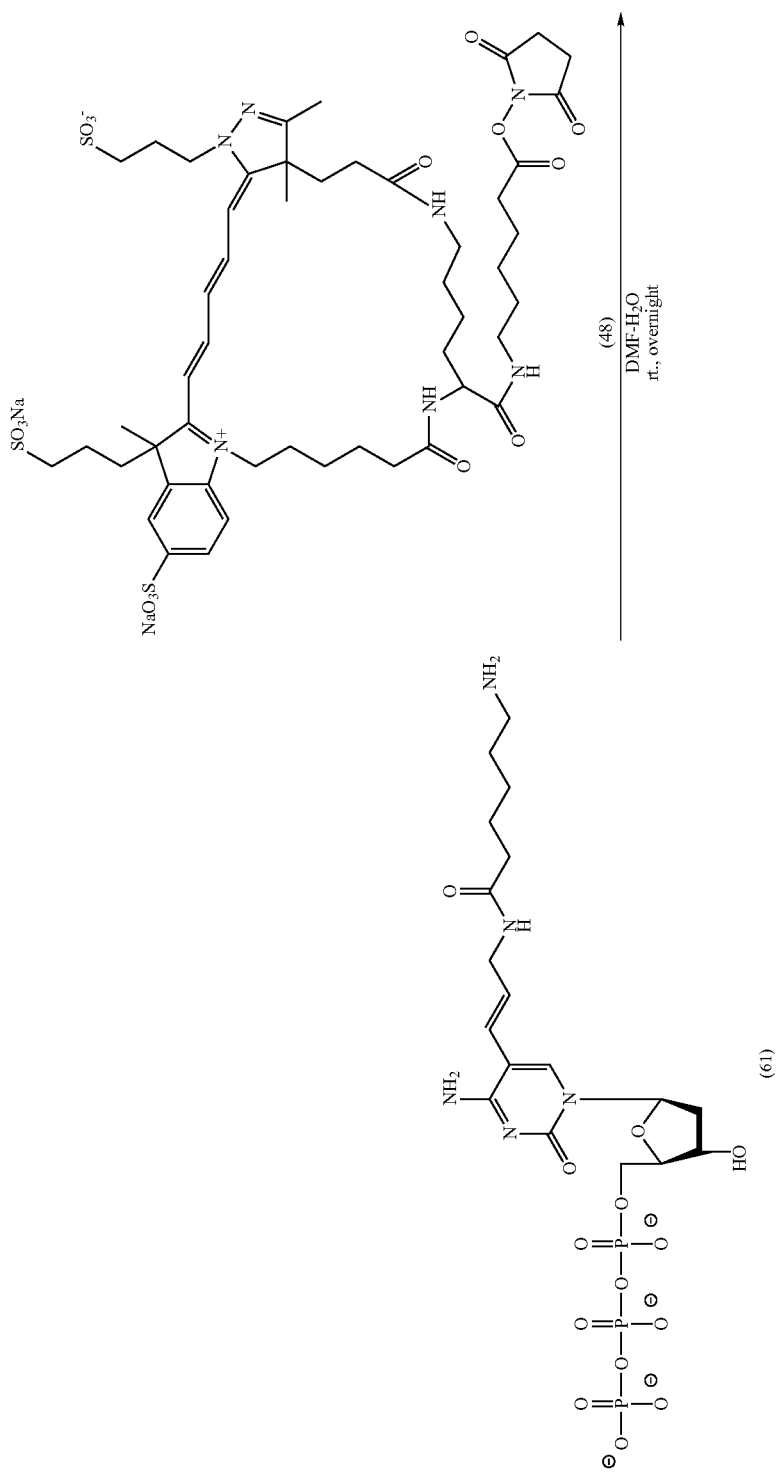

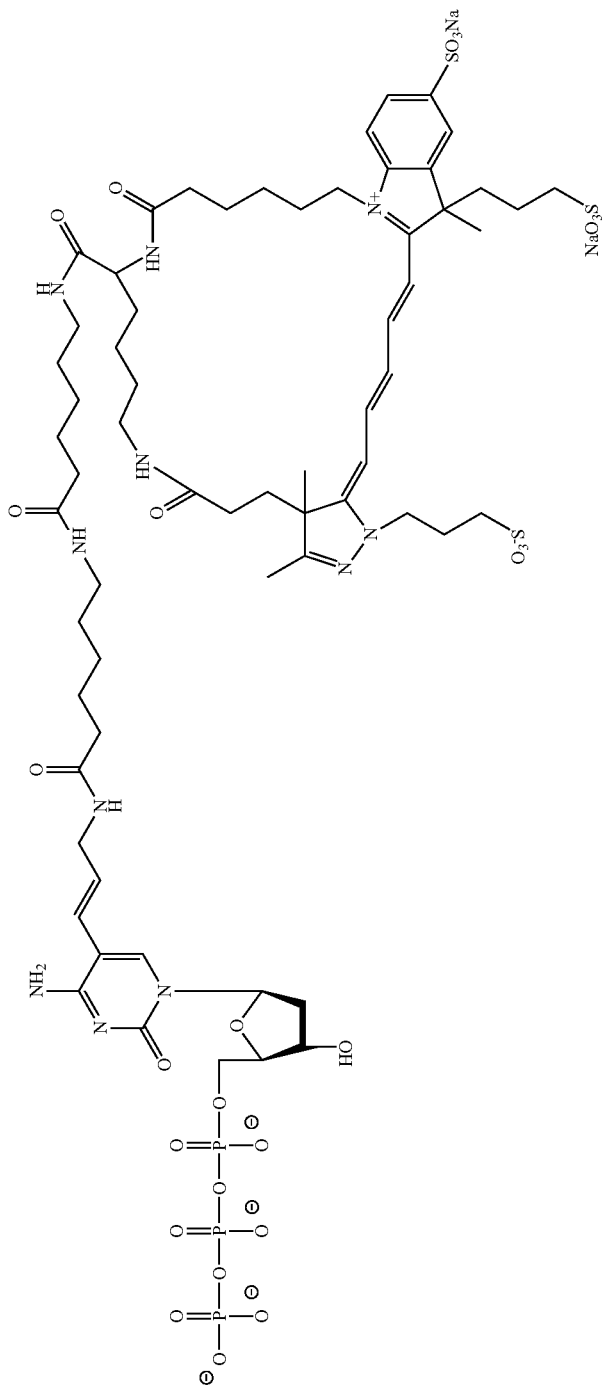

It should be noted that the labeled nucleotide other than the above can also be prepared as appropriate by using the corresponding materials in the same way as the above.

Because a pyrazole-based cyanine dye of the present invention (in particular, the compound [51] of the present invention) has a structure where a pyrazole skeleton and an indole skeleton are bound to a polymethine chain, and is still more cross-linked, and it exerts fluorescence characteristics in shorter wavelength region as compared with a conventional light source, and it becomes possible to use a light source of a short wavelength region with high energy efficiency. In addition, in the case where a measurement object is detected by using this as a labeling agent (a labeling substance), it becomes possible to detect the measurement object in high detection sensitivity, without having problems, for example, low water-solubility, reduced detection sensitivity by optical quenching caused by aggregation of dyes themselves and the like, which a conventional cyanine dye derivative had.

Explanation will be given below in further specifically on the present invention with reference to Examples and Comparative examples, however, the present invention should not be limited thereto.

EXAMPLES

Example 1

Synthesis of the Compounds (13) to (15) of the Present Invention

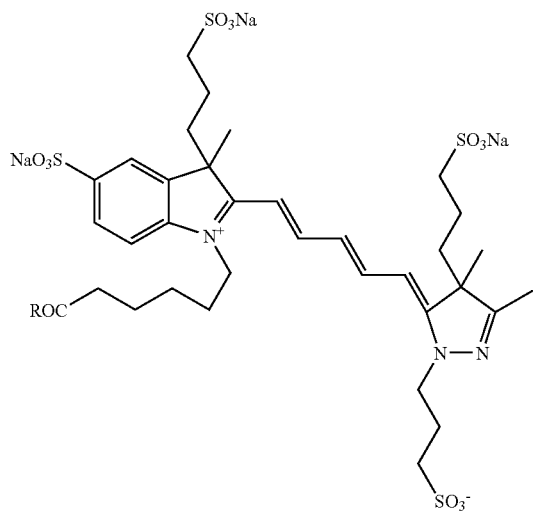

13, R = OH
14, R = OSu
15, R = NH(CH$_2$)$_4$Ma

* Su=a succinimide group, Ma=a maleimide group (1) Synthesis of an Indolenine Compound (8)

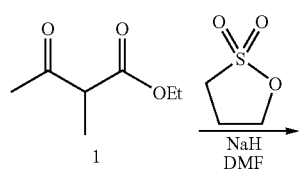

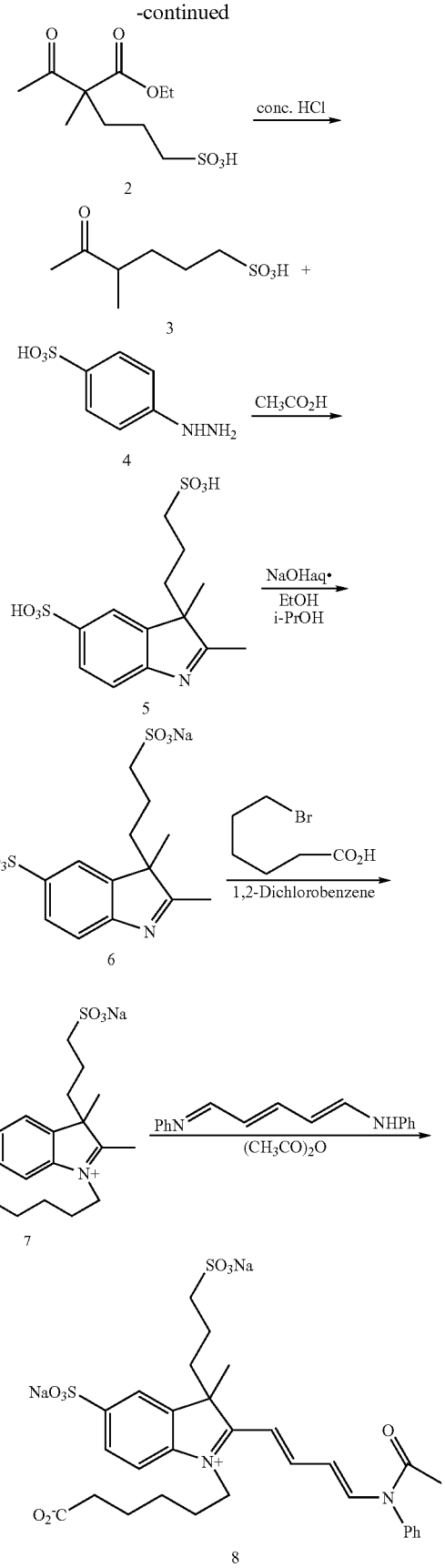

[Synthesis of the Compound (2)]

In N,N-dimethylformamide (DMF, 80 mL), ethyl 2-methylacetoacetate (1) (25.0 g, 0.173 mol), 1,3-propanesultone (23.3 g, 0.190 mol) and sodium hydride (8.5 g, 0.208 mol) were added a reaction under stirring at 90° C. overnight. After completion of the reaction, the solvent was removed under reduced pressure to be subjected to washing twice by the addition of water (200 mL) and diethyl ether (200 mL). After that, the water layer portion was removed under reduced pressure to give the compound (2) (42.1 g, yield; 91%).

[Synthesis of the Compound (3)]

In concentrated hydrochloric acid (60 mL), the compound (2) (40.5 g, 0.152 mol) was subjected to a reaction under stirring at 100° C. for 3 hours. After completion of the reaction, the solvent was removed under reduced pressure to be subjected to purification by using silica gel column chromatography (elution liquid: methanol) to give the compound (3) (16.6 g, yield; 56%).

[Synthesis of the Compound (5)]

In acetic acid (50 mL), the compound (3) (10.0 g, 0.051 mol) and the compound (4) (12.9 g, 0.066 mol) were subjected to refluxing under heating at 120° C. for 4 hours. After completion of the reaction, the solvent was removed under reduced pressure to be subjected to purification by using reversed phase column chromatography (elution liquid: water) to give the compound (5) (11.5 g, yield; 65%).

Property data: IR (KBr) (cm$^{-1}$): 3450, 1196

[Synthesis of the Compound (6)]

The compound (5) (11.5 g, 0.033 mol) was dissolved in water (50 mL) and ethanol (50 mL) to be subjected to a reaction under stirring at room temperature for 4 hours. After completion of the reaction, the solvent was removed under reduced pressure to be subjected to purification by using reversed phase column chromatography (elution liquid: water) to give the compound (6) (10.3 g, yield; 80%).

Property data: Mass (nega=346)

IR (KBr) (cm$^{-1}$): 3444, 1193

[Synthesis of the Compound (7)]

The compound (6) (10.0 g, 0.026 mol) and 6-bromohexanoic acid (9.97 g, 0.052 mol) were dissolved in 1,2-dichlorobenzene (100 mL) and subjected to a reaction under stirring at 120° C. overnight. After completion of the reaction, the solvent was removed under reduced pressure to be subjected to washing three times by using ethyl acetate to give the compound (7) (11.5 g, yield; 89%).

Property data: Mass (nega=460)

IR (KBr) (cm$^{-1}$): 3446, 1723, 1194

[Synthesis of the Compound (8)]

The compound (7) (1.5 g, 2.967 mmol) and malonic acid aldehyde anilide hydrochloride (0.77 g, 2.967 mmol) were dissolved in acetic anhydride (20 mL) and subjected to a reaction under stirring at 120° C. for 1 hour. After completion of the reaction, the solvent was removed under reduced pressure to be subjected to purification by using reversed phase column chromatography (elution liquid: 10% aqueous solution of acetonitrile) to give an indolenine compound (8) (0.18 g, yield; 10%).

Property data: Mass (nega: posi=631:633)

IR (KBr) (cm$^{-1}$): 3443, 1716, 1574, 1465, 1189

(2) Synthesis of the Pyrazole Compound (12)

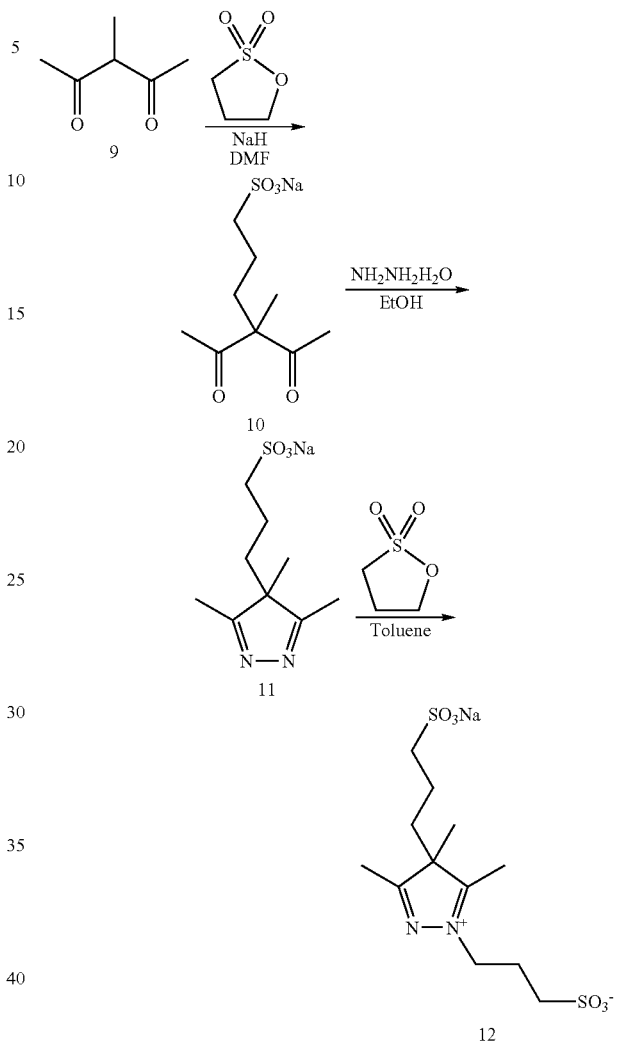

[Synthesis of the Compound (10)]

In DMF (100 mL), 3-methyl-2,4-pentanedione (compound (9)) (15.0 g, 0.13 mol), 1,3-propanesultone (16.1 g, 0.13 mol), and sodium hydride (5.0 g, 0.208 mol) were used to a reaction under stirring at 50° C. for 16 hours. After completion of the reaction, neutralization was carried out by using 1N sodium hydroxide, and the solvent was removed under reduced pressure to be subjected to washing twice by the addition of water (200 mL) and diethyl ether (200 mL). After that, the water layer portion was removed under reduced pressure to give the pyrazole compound (10) (32.2 g, yield; 96%).

Property data: IR (KBr) (cm$^{-1}$): 3474, 1695, 1665, 1191

[Synthesis of the Compound (11)]

The compound (10) (10.0 g, 0.042 mol) and hydrazine monohydrate (2.1 g, 0.042 mol) were dissolved in ethanol (EtOH, 150 mL), and were subjected to a reaction under stirring at 80° C. for 3 hours. After completion of the reaction, the solvent was removed under reduced pressure to be subjected to purification by using silica gel column chromatography (elution liquid: methanol/chloroform=1/1) to give the compound (11) (9.0 g, yield; 92%).

Property data: IR (KBr) (cm$^{-1}$): 3421, 1195

[Synthesis of the Compound (12)]

The compound (11) (4.8 g, 0.019 mol) and 1,3-propane sultone (2.5 g, 0.02 mol) were dissolved in dimethylacetoamide (30 mL), and were subjected to stirring at 140° C. for 4 hours. After completion of the reaction, ethyl acetate (200 mL) was added to deposit a crystal, which was filtered to give the pyrazole compound (12) (5.3 g, yield; 76%).

Property data: Mass (nega=352)

IR (KBr) (cm$^{-1}$): 3446, 1194

(3) Synthesis of Indolenine Compound—Pyrazole Compound Complexes (Compounds of the Present Invention) (13) to (15)

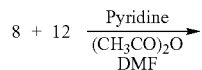

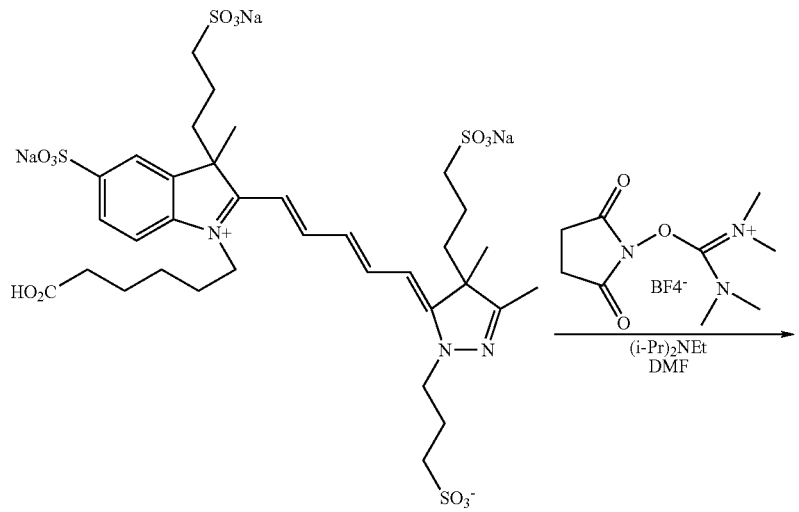

13

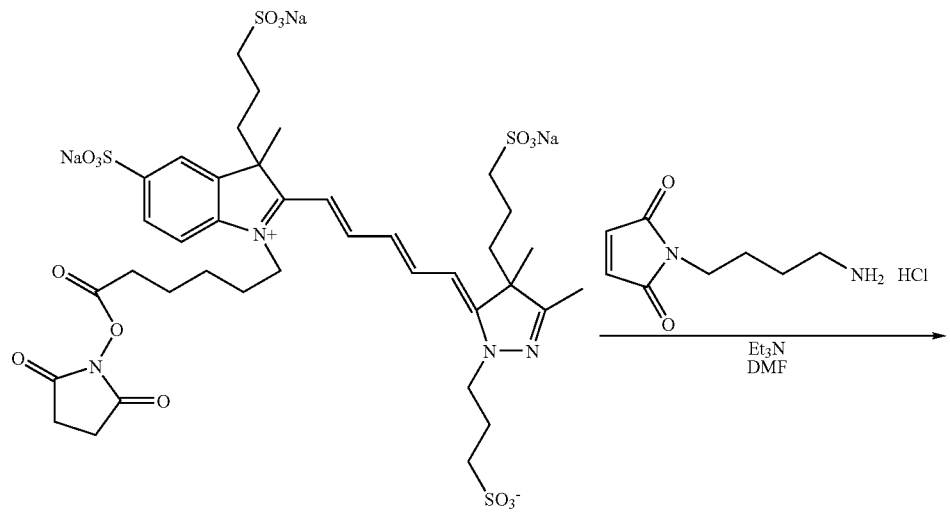

14

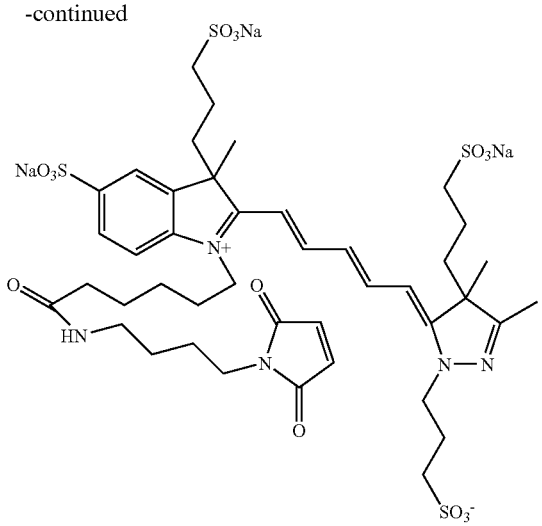

15

[Synthesis of the Compound (13)] (a Maleimide Substance of the Present Invention)

The resulting indolenine compound (8) in Example 1, (1) g, 0.158 mmol) and the resulting pyrazole compound (12) in Example 1, (2) (0.17 g, 0.474 mol) were dissolved in DMF (2 mL), and pyridine (1 mL) and acetic anhydride (0.5 mL) were added thereto to be subjected to stirring at 80° C. for 1 hour. After completion of the reaction, the solvent was removed under reduced pressure to be subjected to purification by using reversed phase column chromatography (elution liquid: 10% aqueous solution of methanol) and Sephadex LH-20 [manufactured by GE Healthcare Bioscience Co., Ltd., (former name: Amasham Bioscience Co., Ltd.)] (elution liquid: methanol) to give an compound (13) (15 mg, yield; 12%).

Property data: Mass (nega=850)
Fluorescence characteristics are shown below.

| | |
|---|---|
| Max. absorption wavelength (λmax) | 634 nm |
| Molar absorption coefficient (ε) | 230,000 $M^{-1}cm^{-1}$ |
| Max. excitation wavelength [Ex(max)] | 635 nm |
| Max. fluorescence wavelength [Em(max)] | 655 nm |

[Synthesis of the Compound (14)]

The compound (13) (13 mg, 0.015 mmol) was dissolved in DMF (0.6 mL), and 2-succinimide-1,1,3,3-tetramethyluronium tetrafluoroborate (TSTU) (46 mg), and N-ethyldiisopropylamine ((i-Pr)$_2$NEt) (600 µl) were added to stirring at room temperature for 1 hour. After completion of the reaction, ethyl acetate (15 mL) was added to deposit a crystal, which was subjected to centrifugal separation to give the compound (14) (13 mg, yield; 90%).

Property data: Mass (nega=947)

[Synthesis of the Compound (15)]

To the maleimidation reagent (N-(4-aminobutyl) maleimide hydrochloride) (6 mg), triethylamine (Et$_3$N) (10 µl)), DMF (1 mL) was added and stirred for 10 minutes. After that, a solution dissolved with the compound (14) (7 mg, 0.007 mmol) in DMF (1 mL) was slowly added to stirring at room temperature for 1 hour. After completion of the reaction, the solvent was removed under reduced pressure to be subjected to purification by using fractionated reversed phase HPLC to give the compound (15) (1.1 mg, yield; 15%).

Property data: Mass (nega=1000)

Example 2

Synthesis of the Compounds (20) to (22) of the Present Invention

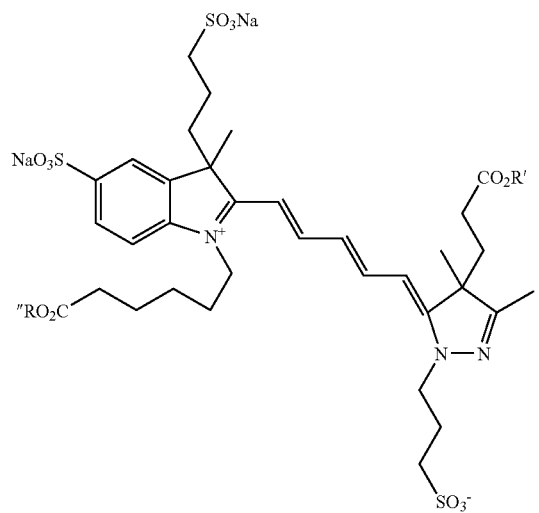

20, R' = ET, R'' = H
21, R' = R'' = H
22, R' = R'' = Su (1) Synthesis of the Pyrazole Compound (19)

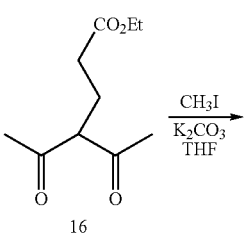

16

-continued

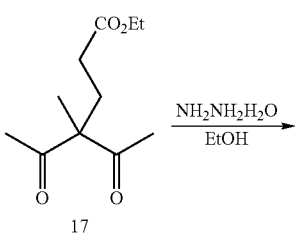

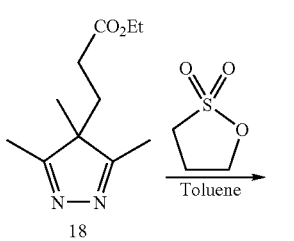

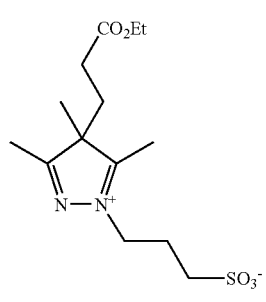

[Synthesis of the Compound (17)]

In tetrahydrofuran (THF) (100 mL), 4-acetyl-5-oxohexanoic acid ethyl ester (compound (16)) (10.0 g, 49.94 mmol), methyliodide (10.6 g, 74.91 mmol), and potassium carbonate (17.3 g, 0.125 mol) were added to stirring at room temperature overnight. After completion of the reaction, the solution was neutralized by using 1N hydrochloric acid, and subjected to washing twice by the addition of water (100 mL) and ethyl acetate (100 mL). After that, the ethyl acetate layer was washed twice with a saturated aqueous solution of sodium bicarbonate (100 mL) and a saturated aqueous solution of sodium chloride (100 mL). Then, the resulting ethyl acetate layer was removed under reduced pressure, to be subjected to purification by using silica gel column chromatography (elution liquid: ethyl acetate/hexane=1/3) to give the compound (17) (10.0 g, yield; 93%).

[Synthesis of the Compound (18)]

The compound (17) (10.0 g, 46.7 mmol) and hydrazine monohydrate (2.6 g, 51.4 mmol) were dissolved in ethanol (150 mL), and were subjected to stirring at 80° C. for 2 hours. After completion of the reaction, the solvent was removed under reduced pressure, to be subjected to purification by using silica gel column chromatography (elution liquid: methanol/chloroform=1/1) to give the compound (18) (9.3 g, yield; 95%).

[Synthesis of the Pyrazole Compound (19)]

The compound (18) (9.3 g, 44.2 mmol) and 1,3-propanesultone g, 44.9 mmol) were dissolved in toluene (150 mL), and were subjected to stirring at 120° C. for 5 hours. After completion of the reaction, ethyl acetate (200 mL) was added to deposit a crystal, which was filtered to give the compound (19) (10.6 g, yield; 72%).

Property data: Mass (nega=331)

IR (KBr) (cm$^{-1}$): 3436, 1726, 1211

(2) Synthesis of Indolenine Compound—Pyrazole Compound Complexes (Compounds of the Present Invention) (20) to (22)

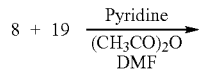

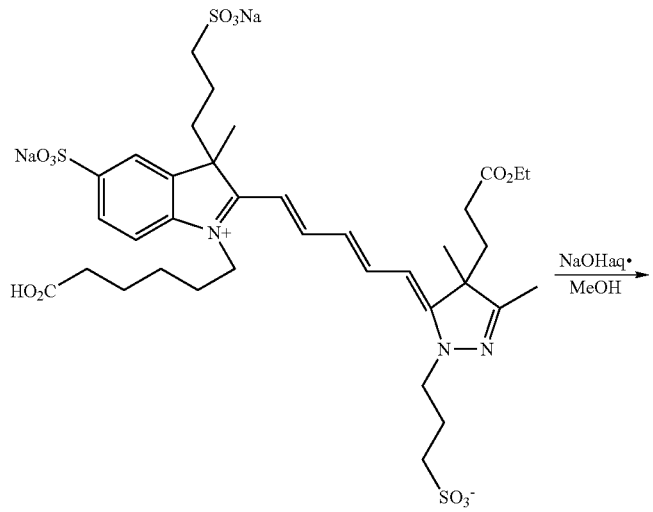

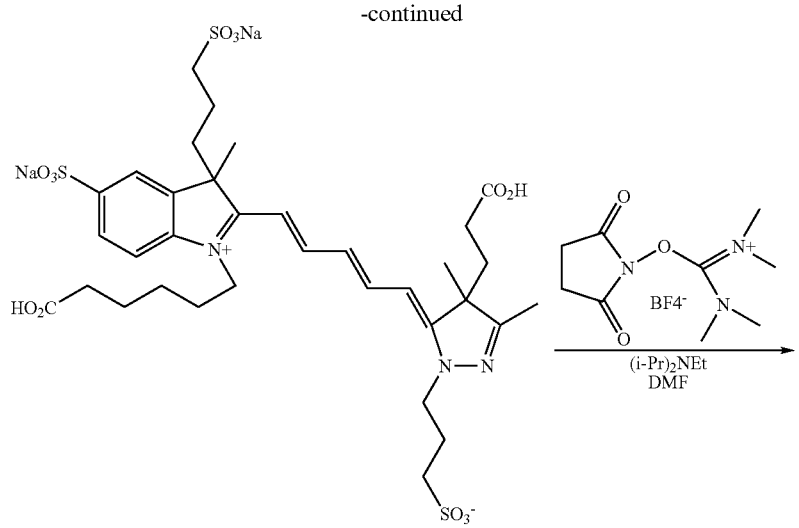

21

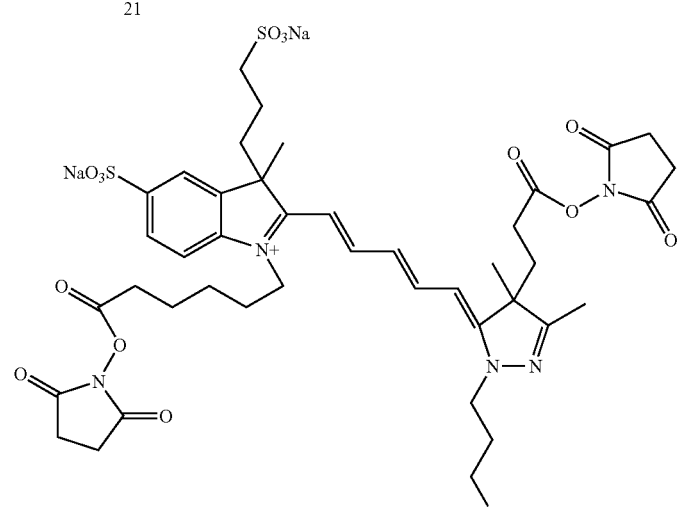

22

[Synthesis of the Compound (20)]

The resulting indolenine compound (8) in Example 1, (1) (0.15 g, 0.237 mmol) and the resulting pyrazole compound (19) in Example 2, (1) (0.24 g, 0.711 mmol) were dissolved in DMF (2 mL), and pyridine (1 mL) and acetic anhydride (0.5 mL) were added to stirring at 80° C. for 1 hour. After completion of the reaction, the solvent was removed under reduced pressure to be subjected to purification by using reversed phase column chromatography (elution liquid: 10% aqueous solution of methanol) and Sephadex LH-20 [manufactured by GE Healthcare Bioscience Co., Ltd.] (elution liquid: methanol) to give the compound (20) (52 mg, yield; 26%).

Property data: Mass (nega=828)

[Synthesis of the Compound (21)]

The compound (20) (53 mg, 0.064 mmol) was dissolved in methanol (MeOH, 3 mL), and a 1N aqueous solution of sodium hydroxide (1 mL) was added to stirring at 40° C. for 1 hour. After completion of the reaction, the solution was subjected to purification by using Sephadex LH-20 (elution liquid: methanol) to give the compound (21) (15 mg, yield; 29%).

Property data: Mass (nega=800)

Fluorescence characteristics are shown below.

| | |
|---|---:|
| Max. absorption wavelength (λmax) | 635 nm |
| Molar absorption coefficient (ε) | 219,000 $M^{-1}cm^{-1}$ |
| Max. excitation wavelength [Ex(max)] | 636 nm |
| Max. fluorescence wavelength [Em(max)] | 657 nm |

[Synthesis of the Compound (22)]

The compound (21) (15 mg, 0.019 mmol) was dissolved in DMF (1 mL), and 2-succinimide-1,1,3,3-tetramethyluronium tetrafluoroborate (TSTU) (113 mg, 0.337 mmol) and N-ethyl diisopropylamine (120 μl) were added to stirring at room temperature for 3 hours. After completion of the reaction, ethyl acetate (15 mL) was added to deposit a crystal, which was subjected to centrifugal separation to give the compound (22) (15 mg, yield; 81%).

Property data: Mass (nega=995)

Example 3

Synthesis of the Compounds (24) to (25) of the Present Invention

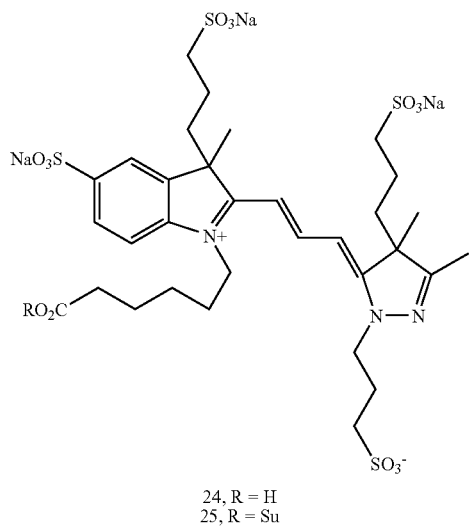

24, R = H
25, R = Su

(1) Synthesis of the Indolenine Compound (23)

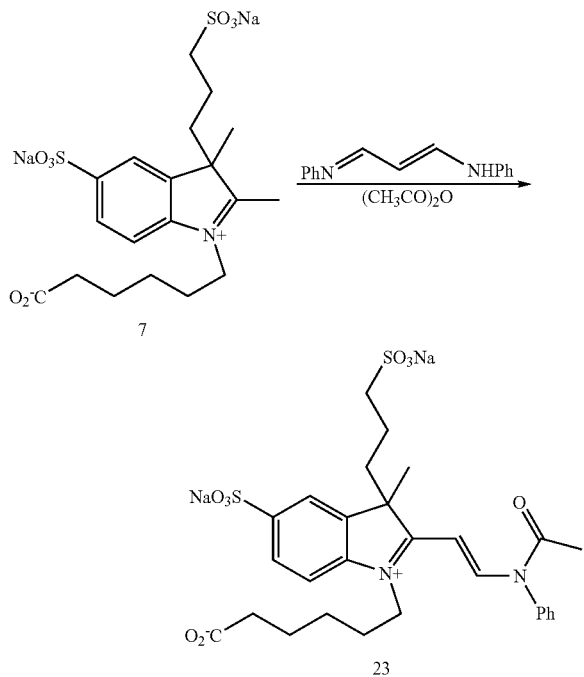

[Synthesis of the Compound (23)]

The resulting compound (7) in Example 1, (1) (5.0 g, 9.89 mmol) and N,N'-diphenyl formamidine (2.1 g, 9.89 mmol) were dissolved in acetic anhydride (50 mL), and was subjected to stirring at 120° C. for 1 hour. After completion of the reaction, ethyl acetate (200 mL) was added to the reaction solution to deposit a crystal, which was filtered to give the indolenine compound (23) (4.8 g, yield; 74%).

(2) Synthesis of Indolenine Compound—Pyrazole Compound Complexes (Compounds of the Present Invention) (24) to (25)

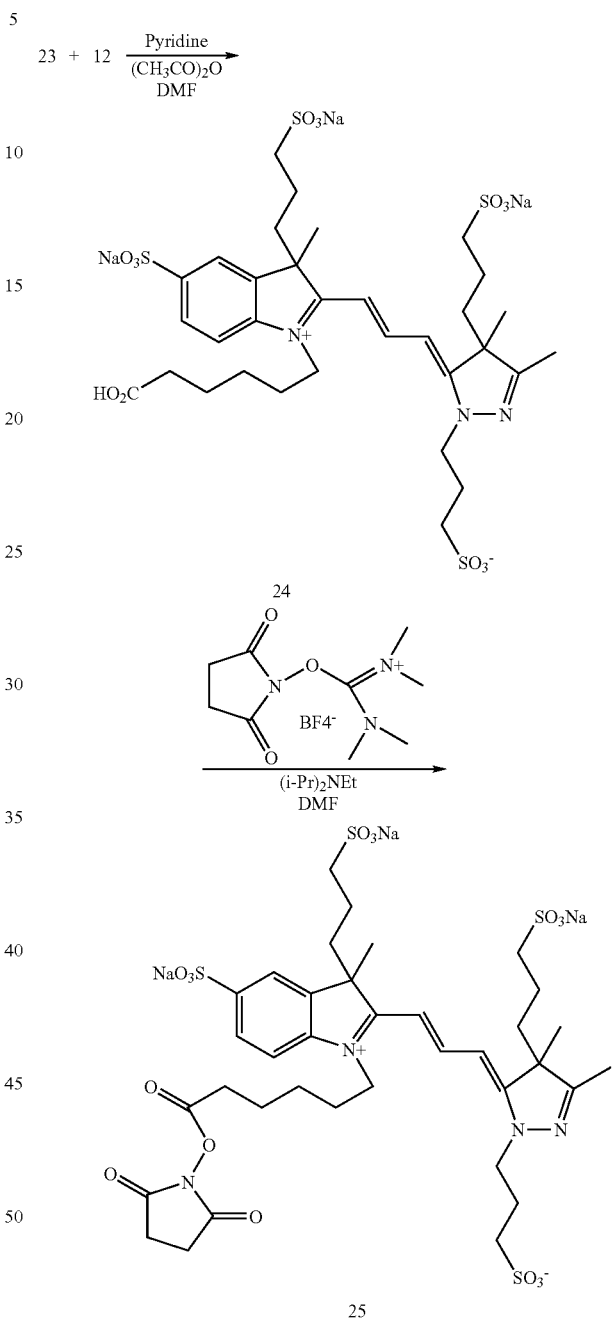

[Synthesis of the Compound (24)]

The resulting indolenine compound (23) obtained by (1) in Example 3 (60 mg, 0.092 mmol), and the resulting pyrazole compound (12) in Example 1, (2) (87 mg, 0.231 mmol) were dissolved in DMF (2 mL), and pyridine (0.5 mL) and acetic anhydride (0.2 mL) were added thereto to be subjected to stirring at 80° C. for 1 hour. After completion of the reaction, the solvent was removed under reduced pressure to be subjected to purification by using reversed phase column chromatography (elution liquid: water) and Sephadex LH-20 (elution liquid: methanol) to give the compound (24) (8 mg, yield; 10%).

Property data: Mass (nega/posi=824/826)

[Synthesis of the Compound (25)]

The compound (24) (6 mg, 0.007 mmol) was dissolved in DMF (300 μL), and 2-succinimide-1,1,3,3-tetramethyluronium tetrafluoroborate (TSTU) (20 mg, 0.07 mmol) and N-ethyl diisopropylamine (30 μl) were added to stirring at room temperature for 3 hours. After completion of the reaction, ethyl acetate (20 mL) was added to deposit a crystal, which was subjected to centrifugal separation to give the compound (25) (5 mg, yield; 81%).

Property data: Mass (nega=922)

Example 4

Synthesis of the Compounds (32) and (42) of the Present Invention

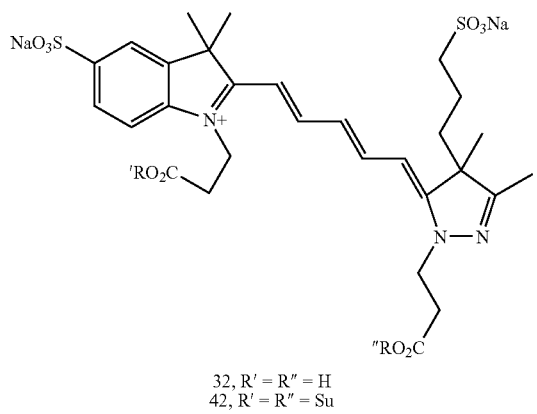

32, R' = R'' = H
42, R' = R'' = Su (1) Synthesis of the Indolenine Compound (30)

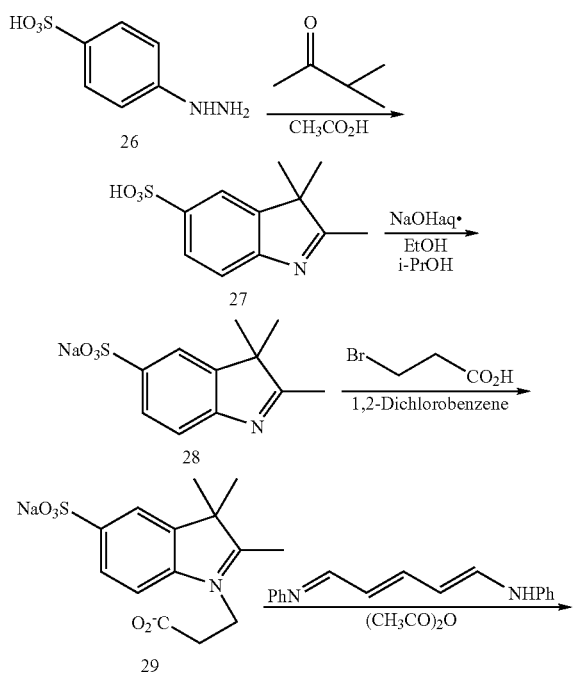

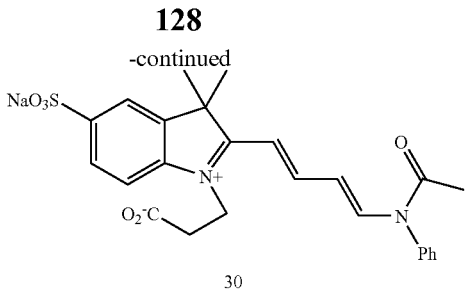

30

[Synthesis of the Compound (27)]

As starting raw materials, 4-hydrazinobenzenesulfonic acid 0.5 hydrate [compound (26)] (50.0 g, 0.253 mol), and 3-methyl-2-butanone (65.5 g, 0.759 mol) were used, which were subjected to stirring in acetic acid (200 mL) at 120° C. for 3 hours. After completion of the reaction, the solvent was cooled, and was subjected to washing twice by the addition of diethyl ether (300 mL) to give the compound (27) (52.0 g, yield; 86%).

Property data: Mass (nega=238)

[Synthesis of the Compound (28)]

The compound (27) (10.0 g, 0.042 mol) and sodium hydroxide (1.67 g, 0.042 mol) were subjected to stirring in a mixed solvent of ethanol (30 mL)/2-propanol (10 mL) at room temperature for 4 hours. After completion of the reaction, the solvent was removed under reduced pressure, and 2-propanol (100 mL) was added for washing twice to give the compound (28) (4.2 g, yield; 39%).

Property data: IR (cm$^{-1}$): 3206, 1205

[Synthesis of the Compound (29)]

The compound (28) (3.5 g, 0.013 mol) and 3-bromopropionic acid (2.5 g, 0.016 mol) were subjected to refluxing under heating in toluene (50 mL) at 110° C. overnight. After completion of the reaction, ethyl acetate (100 mL) was added for washing three times to give the compound (29) (1.7 g, yield; 41%).

Property data: Mass (nega=310)

[Synthesis of the Compound (30)]

The compound (29) (1.5 g, 4.50 mmol) and malonaldehyde dianilide hydrochloride (1.16 g, 4.50 mmol) and were dissolved in acetic anhydride (20 mL) to be subjected to stirring at 120° C. for 1 hour. After completion of the reaction, ethyl acetate (50 mL) was added for washing twice to give the indolenine compound (30) (1.59 g, yield; 70%).

Property data: Mass (nega=481)

(2) Synthesis of the Pyrazole Compound (31)

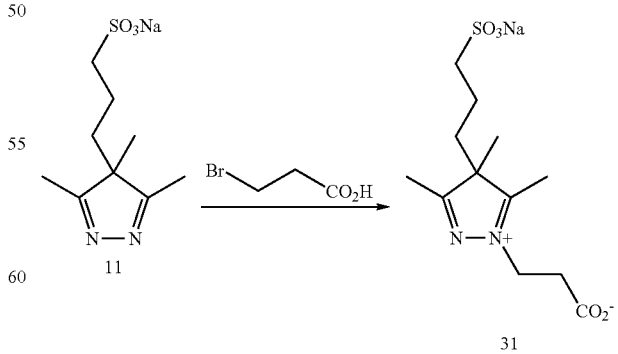

[Synthesis of the Compound (31)]

The resulting compound (10) in Example 1, (2) (0.59 g, 2.32 mmol) and 3-bromopropionic acid (0.39 g, 2.55 mmol)

were subjected to stirring at 140° C. overnight in non-solvent. After completion of the reaction, ethyl acetate (30 mL) was added for washing twice to give the compound (31) (0.73 g, yield; 96%).

Property data: Mass (nega=303)

(3) Synthesis of indolenine compound—pyrazole compound complex (32)

0.37 mmol) and pyridine (120 μl) were added to stirring at 40° C. for 4 hours. After completion of the reaction, ethyl acetate (15 mL) was added to deposit a crystal, which was subjected to washing to give the compound (42) (10 mg, yield; 79%).

Property data: Mass (nega=846)

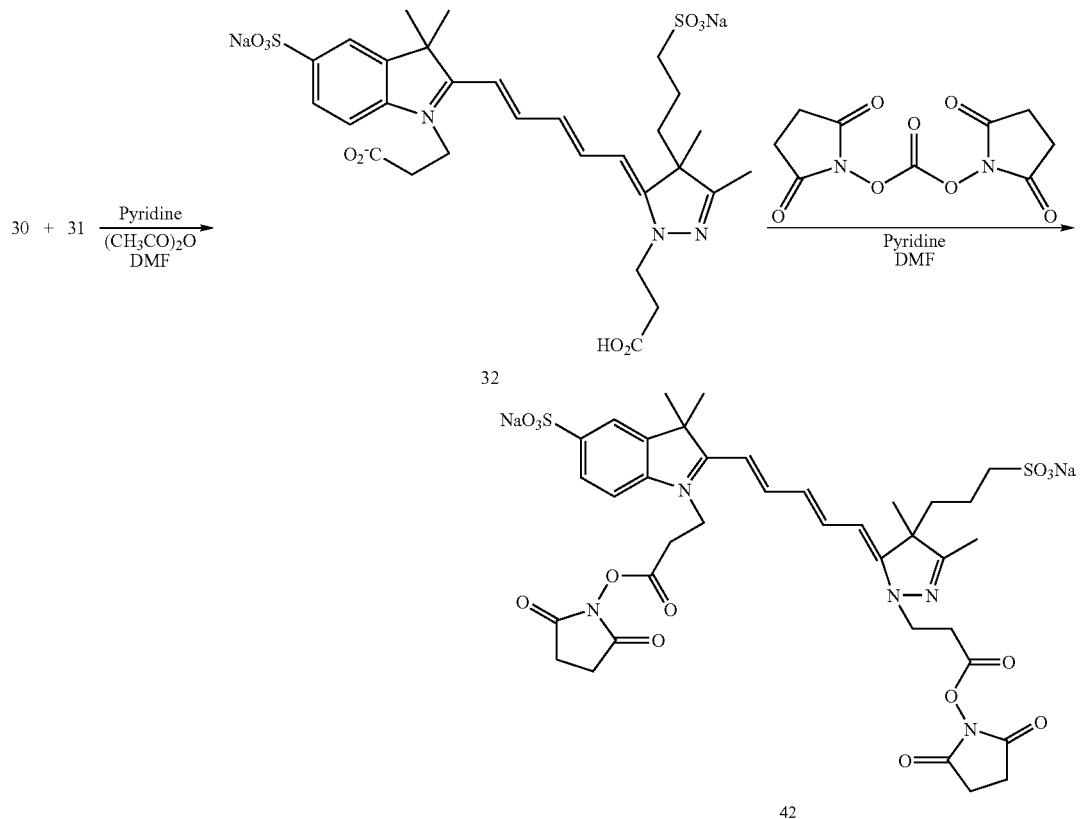

[Synthesis of the Compound (32)]

The resulting indolenine compound (30) in Example 4, (1) (70 mg, 0.139 mmol) and the resulting pyrazole compound (31) in Example 4, (2) (45 mg, 0.139 mmol) were dissolved in DMF (5 mL), and pyridine (1 mL) and acetic anhydride (0.5 mL) were further added thereto to be subjected to stirring at 80° C. for 1 hour. After completion of the reaction, the solvent was removed under reduced pressure to be subjected to purification by using reversed phase column chromatography (elution liquid: 10% aqueous solution of methanol) and Sephadex LH-20 (elution liquid: methanol) to give the compound (32) (11 mg, yield; 12%).

Property data: Mass (nega=649)

Fluorescence characteristics are shown below.

| Max. absorption wavelength (λmax) | 628 nm |
| Molar absorption coefficient (ε) | 211,000 $M^{-1}cm^{-1}$ |
| Max. excitation wavelength [Ex(max)] | 629 nm |
| Max. fluorescence wavelength [Em(max)] | 653 nm |

[Synthesis of the Compound (42)]

The compound (32) (10 mg, 0.019 mmol) was dissolved in DMF (1 mL), and disuccinimidyl carbonate (DSC) (113 mg, Example 5

Synthesis of the Compounds (33) to (34) of the Present Invention

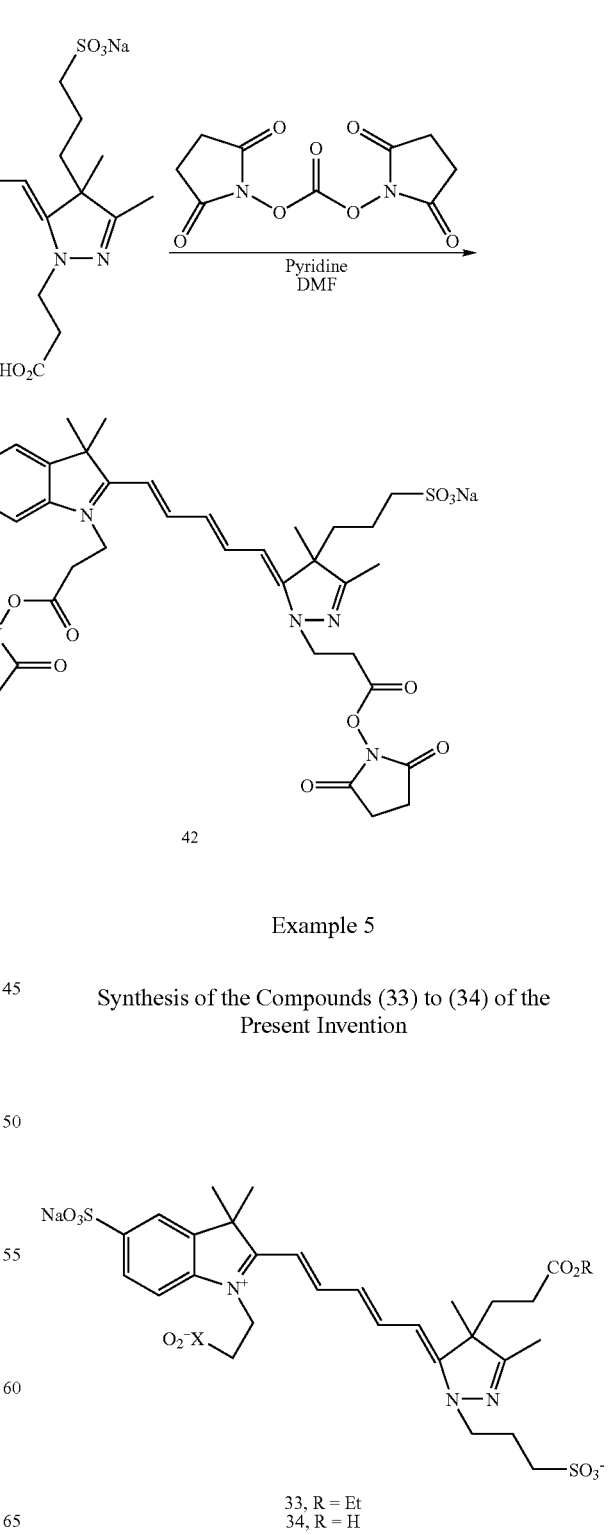

(1) Synthesis of Indolenine Compound—Pyrazole Compound Complexes (Compounds of the Present Invention)

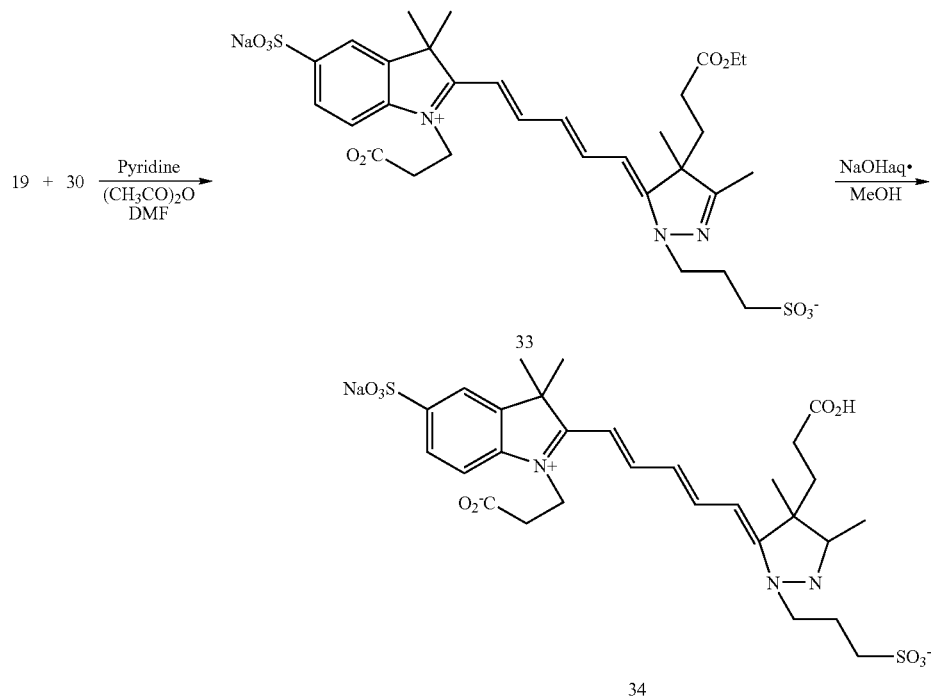

[Synthesis of the Compound (33)]

The resulting indolenine compound (19) in Example 2, (1) (47 mg, 0.139 mmol) and the resulting pyrazole compound (30) in Example 4, (1) (72 mg, 0.143 mmol) were dissolved in DMF (5 mL), and pyridine (1 mL) and acetic anhydride (0.5 mL) were further added thereto to be subjected to stirring at 80° C. for 1 hour. After completion of the reaction, the solvent was removed under reduced pressure to be subjected to purification by using reversed phase column chromatography (elution liquid: 10% aqueous solution of methanol) to give the compound (33) (15 mg, yield; 15%).

Property data: Mass (nega=677)

[Synthesis of the Compound (34)]

The compound (33) (10 mg, 0.014 mmol) was dissolved in methanol (1 mL), and a 1N aqueous solution of sodium hydroxide (0.5 mL) was added to stirring at 40° C. for 1 hour. After completion of the reaction, the solution was subjected to purification by using Sephadex LH-20 (elution liquid: methanol) to give the compound (34) (3.5 mg, yield; 37%).

Property data: Mass (nega=649)

Fluorescence characteristics are shown below.

| | |
|---|---|
| Max. absorption wavelength ($\lambda$max) | 630 nm |
| Max. excitation wavelength [Ex(max)] | 632 nm |
| Max. fluorescence wavelength [Em(max)] | 658 nm |

Example 6

Synthesis of the Compounds (37) to (39) of the Present Invention

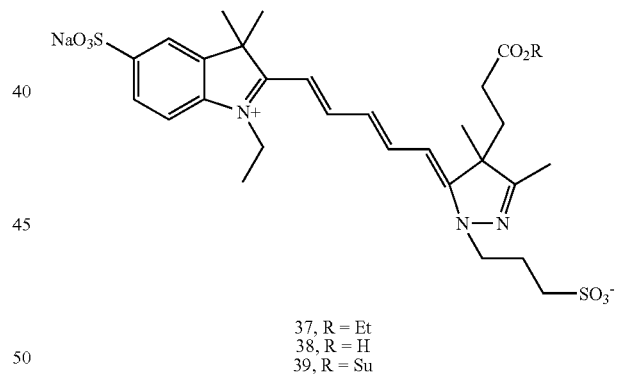

37, R = Et
38, R = H
39, R = Su (1) Synthesis of the Indolenine Compound (36)

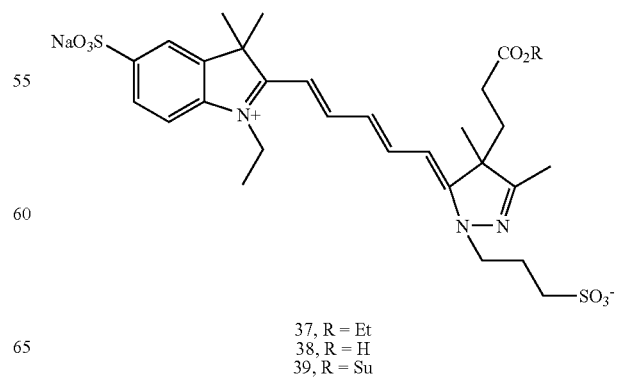

37, R = Et
38, R = H
39, R = Su

[Synthesis of the Compound (35)]

The resulting compound (28) in Example 4, (1) (4.9 g, 18.7 mmol) was dissolved in sulfolane (25 mL) and then ethyltoluenesulfonic acid (11.3 g, 56.1 mmol) was added to a reaction at 14° C. for 18 hours. After completion of the reaction, the reaction solution was added into ethyl acetate (100 mL) and a deposited substance was filtered off. The resulting crystal was washed with ethyl acetate and subjected to drying under reduced pressure to give the compound (35) (4.04 g, yield; 74.4%).

Property data: Mass (nega=267)

[Synthesis of the Compound (36)]

The compound (35) (3 g, 10 mmol) and malonaldehyde dianilide hydrochloride (2.67 g, 10 mmol) were dissolved in acetic anhydride (30 mL) to be subjected to stirring at 120° C. for 1 hour. After completion of the reaction, ethyl acetate (100 mL) was added and a deposited substance was filtered off. The resulting crystal was washed with ethyl acetate (100 mL) twice and subjected to drying under reduced pressure to give the indolenine compound (36) (2.4 g, yield; 52.1%).

Property data: Mass (nega=436)

(2) Synthesis of Indolenine Compound—Pyrazole Compound Complexes (Compounds of the Present Invention) (37) to (39)

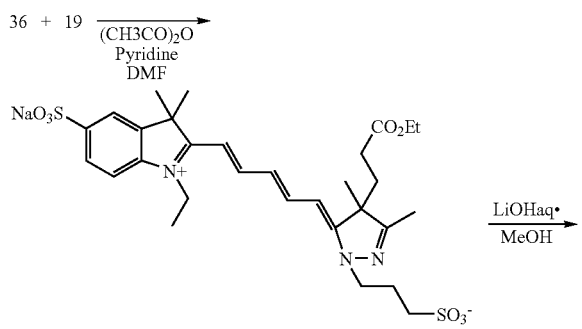

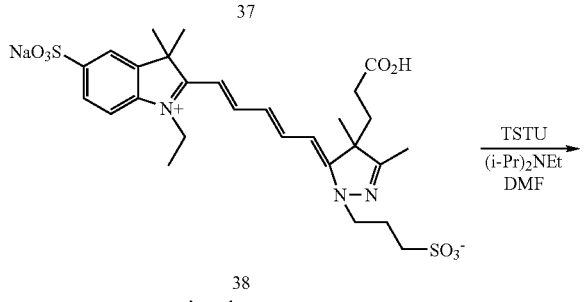

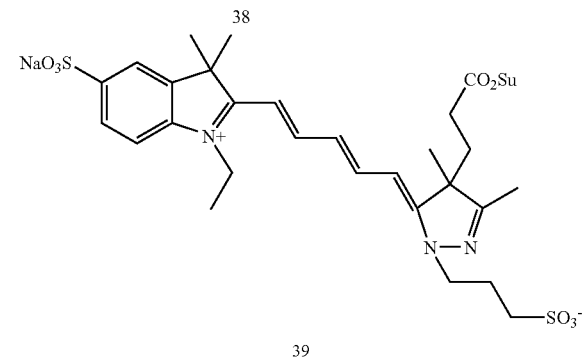

[Synthesis of the Compound (37)]

The resulting indolenine compound (36) in Example 6, (1) (1 g, 2.17 mmol) and the resulting pyrazole compound (19) in Example 2, (1) (1.8 g, 5.41 mmol) were dissolved in DMF (20 mL), and pyridine (8 mL) and acetic anhydride (4 mL) were further added thereto to be subjected to stirring at 80° C. for 1 hour. After completion of the reaction, the solvent was removed under reduced pressure to be subjected to purification by using reversed phase column chromatography (elution liquid: 20% aqueous solution of methanol) and Sephadex LH-20 (elution liquid: methanol) to give the compound (37) (130 mg, yield; 9.5%).

Property data: Mass (nega=634)

[Synthesis of the Compound (38)]

Methanol (15 mL) and an aqueous solution of 5% lithium hydroxide (5 mL) were added to the compound (37) (130 mg, 0.21 mmol) to be subjected to a reaction at 20° C. for 1 hour. After completion of the reaction, the solvent was removed under reduced pressure to be subjected to purification by using reversed phase column chromatography (elution liquid: water) to give the compound (38) (12 mg, yield; 9.7%).

Property data: Mass (nega=606)

Fluorescence characteristics are shown below.

| Max. absorption wavelength (λmax) | 631 nm |
| Molar absorption coefficient (ε) | 198,000 $M^{-1}cm^{-1}$ |
| Max. excitation wavelength [Ex(max)] | 631 nm |
| Max. fluorescence wavelength [Em(max)] | 652 nm |

[Synthesis of the Compound (39)]

The compound (38) (12 mg, 0.019 mmol) was dissolved in DMF (600 µL), and TSTU (57 mg, 0.19 mmol) and N-ethyldiisopropylamine (74 µL) were added to a reaction under stirring at room temperature for 3 hours. After completion of the reaction, ethyl acetate (40 mL) was added to deposit a crystal, which was subjected to centrifugal separation to give the compound (39) (10.7 mg, yield; 80%).

Property data: Mass (nega=703)

Example 7

Synthesis of a Labeled Compound of the Present Invention [a Fluorescent Labeling, 2'-deoxycytidine-5'-triphosphate Derivative]

Mononucleotide (2'-deoxycytidine-5'-triphosphate) labeled with the compound [1] of the present invention was synthesized as follows according to the above-described synthesis route.

(1) Synthesis of the Partial Linker (A)

(i) Trifluoroacetylation (Tfa) (the First Step)

To 21 g of propagylamine, [the compound (51) in the above synthesis route], (manufactured by Tokyo Chemical Industry Co., Ltd.), methyl trifluoroacetate (MeOTfa) (54 g) and triethylamine (Et₃N) (25 mL) were added, under ice-cooling, to be subjected to stirring at room temperature for 2 days. After completion of the reaction, purification was carried out under reduced pressure to give the compound (52), [the compound (52) in the above synthesis route], (56 g, yield; 98.1%).

(ii) To make tri(n-butyl)tin (Bu₃Sn) (the second step)

Into benzene (300 mL), 15 g of the compound (52) [the compound (52) in the above synthesis route] was dissolved, and after the addition of tri(n-butyl)tin hydride (Bu₃SnH) (35 mL) and azobisisobutyronitrile (AIBN) (2.1 g), the solution was subjected to stirring under refluxing for 1.5 hours. After completion of the reaction, the reaction solution was concentrated under reduced pressure. The residue was subjected to purification by using silica gel column chromatography (elution liquid: ethyl acetate/hexane=1/20) to give 11.4 g of the compound (53) (the partial linker A), [the compound (53) in the above synthesis route], (yield; 25.8%).

(2) Synthesis of the Partial Linker B (i) Trifluoroacetylation (Tfa) (the Third Step)

To a suspension of 10 g of 6-aminohexanoic acid [the compound (54) in the above synthesis route], (manufactured by Wako Pure Chemical Industries, Ltd.), methyl trifluoroacetate (25 g) and triethylamine ($Et_3N$) (25 mL) were added to stirring at room temperature for 2 days. After completion of the reaction, the solvent was removed to give 8.4 g of the compound (55) [the compound (55) in the above synthesis route] by crystallization from water (yield; 48.6%).

(ii) Active Esterification (the Fourth Step)

Into N,N-dimethylformamide (DMF) (50 mL), 2.3 g of the compound (55) [the compound (55) in the above synthesis route] was dissolved, and N-hydroxysuccinic acid (HO-Su) (1.4 g) and WSC (2.3 g) were added thereto and then it was subjected to stirring at room temperature overnight. After completion of the reaction, the reaction solution was concentrated under reduced pressure, and fractionated and washed with ethyl acetate. By subjecting the organic layer to concentration under reduced pressure, 3.6 g of the compound (56) (the partial linker B), [the compound (56) in the above synthesis route] was gave (yield; quantitative).

(3) Introduction of the Partial Linker (i) Introduction of the Partial Linker A (the Fifth Step)

Into acetonitrile (30 mL), 1.0 g of 5-iodo-2'-deoxycytidine [the compound (57) in the above synthesis route], (manufactured by Wako Pure Chemical Industries, Ltd.), was suspended, and after the addition of o-bis(trimethylsilyl)acetamide (TMS-Acetamide) (3 mL) by purging with Ar, the solution was subjected to stirring under refluxing for 2 hours. After cooling the reaction solution to room temperature, bis (acetonitrile)dichloropalladium (II) [$PdCl_2(CH_3CN)_2$] (40 mg) and 2 g of the partial linker A [the compound (53) in the above synthesis route] were added to further stirring at 50 to 60° C. for 20 hours. After completion of the reaction, the reaction solution was concentrated under reduced pressure. The residue was subjected to purification by using silica gel column (elution liquid: trichloromethane/methanol=9/1) to give 720 mg of a 2'-deoxycytidine derivative [the compound (58) in the above synthesis route] by crystallization from diethyl ether (yield; 67.3%).

(ii) De-trifluoroacetylation (Tfa) (the Sixth Step)

Into ethanol (EtOH, 10 mL), 500 mg of the 2'-deoxycytidine derivative, [the compound (58) in the above synthesis route] was dissolved, and after the addition of 25% ammonia water (25 mL), the solution was subjected to stirring at room temperature for 4 hours. After completion of the reaction, the reaction solution was concentrated under reduced pressure. The residue was subjected to purification by using ODS column chromatography (elution liquid: 5% methanol) to give 190 mg of the 2'-deoxycytidine derivative, [the compound (59) in the above synthesis route], (yield; 50.9%).

(iii) Introduction of the Partial Linker B (the Seventh Step)

Into N,N-dimethylformamide (DMF, 4 mL), 190 mg of the 2'-deoxycytidine derivative, [the compound (59) in the above synthesis route] was dissolved, and after the addition of 330 mg of the partial linker B, [the compound (56) in the above synthesis route], the reaction solution was subjected to stirring at room temperature overnight. After completion of the reaction, the reaction solution was concentrated under reduced pressure, and the residue was subjected to purification by using silica gel column (elution liquid: trichloromethane/methanol/acetic acid=80/20/5) and further by ODS column chromatography (elution liquid: 20% methanol) to give 169 mg of the 2'-deoxycytidine derivative, [the compound (60) in the above synthesis route], (yield; 51.2%).

(4) Triphosphorylation and De-trifluoroacetylation of Mononucleoside (the Eighth Step)

(i) Preparation of a Triphosphorylation Agent, 0.5 M-tris (TBAPP)

To a column with a diameter of 2.5 cm, 100 $cm^3$ of Dowex 50W×8 ($H^+$ Form), regenerated in advance, was charged and washed with ion-exchanged water. An aqueous solution of sodium pyrophosphate decahydrate (6.7 g/100 mL) was charged, and an elution liquid (a solution of pyrophosphoric acid) was directly dropped into an ethanol solution (50 mL) containing 10.6 mL of tributylamine. After the dropping till pH of the elution liquid became neutralized, it was subjected to stirring for 10 minutes. After the stirring, the solution was concentrated under reduced pressure, and ethanol (30 mL×twice), toluene (30 mL×3 times) and DMF (20 mL×twice) were added sequentially to the residue, and concentration under reduced pressure was repeated. After dilution to 30 mL with DMF, MS4A was added to dehydration overnight to give the 0.5 M tris(TBAPP) solution.

(ii) Triphosphorylation

Into triethyl phosphate [$(EtO)_3PO$] (1.4 mL), 147 mg (0.3 mmol) of a 2'-deoxycytidine derivative, [the compound (60) in the above synthesis route], was dissolved, and after the addition of phosphorus oxychloride (27 μL+24 μL), it was subjected to stirring in a low temperature chamber for 4 hours to convert to monophosphoric acid. Into this solution, 4 mL of 0.5 M-tris (TBAPP) was charged to be subjected to stirring in a low temperature chamber for 2 hours to convert to triphosphoric acid (HPLC process inspection; yield 37.8%). After the reaction, the reaction solution was neutralized with a 7% aqueous solution of triethylamine (7 mL), and subjected to further stirring overnight. After the reaction, the reaction solution was washed with diethyl ether, and the water layer was subjected to purification by using a DEAE-TOYOPEARL column (elution liquid; gradient from water to 0.2 M TEAB). The eluted fraction was concentrated under reduced pressure to give an intermediate substance. Then, the intermediate substance was dissolved in 25% ammonia water (30 mL) and subjected to stirring in a low temperature chamber overnight. After completion of the reaction, ammonia was removed under reduced pressure, and the residue was subjected to freeze-drying to give 130 mg of the 2'-dCTP-amino linker derivative, [the compound (61) in the above synthesis route].

As a result of process inspection on the present product, it was found that HPLC purity; 95.8% and content; 77.3%.

(5) Labeling of Mononucleotide (the Ninth Step)

Into ion-exchanged water (150 μL), 6.5 mg of the 2'-dCTP-amino linker derivative, [the compound (61) in the above synthesis route], was dissolved, and after 7 times of the addition of a DMF solution of the compound of the present invention (labeling compound), [the compound (25) in the above synthesis route] (1 mg/100 μL), it was subjected to stirring at room temperature overnight (HPLC process inspection; yield 60.0%). After completion of the reaction, the reaction solution was concentrated under reduced pressure, and subjected to purification by using a $Wakosil_{50}Cl_8$ column (elution solution; 5% methanol); and then a DEAE-TOYOPEARL 650 M column (Fr inspection; HPLC). The residue was subjected to freeze-drying to give 3.4 mg of the fluorescence labeled 2'-dCTP derivative, [the compound (25a) in the above synthesis route: Mononucleotide labeled with the compound (labeling substance) of the present invention].

Example 8

Measurement of Novel Fluorescence Intensity of a Compound of the Present Invention Relative fluorescence intensity of a compound of the present invention was roughly calculated relative to fluorescence intensity of Cy5, which is a conventional cyanine dye.

First, fluorescence intensity of Cy5 per 1 μM was measured from fluorescence intensity of Cy5, and relative fluorescence intensity of the compound of the present invention was roughly calculated relative to this fluorescence intensity value as 100. The result is shown in Table 29.

(1) Measurement of Fluorescence Intensity of Cy5

Into 1 mL of purified water, Cy5 for labeling 1 mg of protein (manufactured by GE Healthcare Bioscience Biohealth Co., Ltd.), was dissolved. This solution was diluted 200 times with a 50 mM phosphoric acid buffer solution (pH 7.5) to measure OD value (0.1020).

Concentration of a Cy5 solution was determined from this OD value and molar absorption coefficient ($\epsilon$=250,000), [described in a general product catalogue 2006 "7-4" of GE Healthcare Bioscience Co., Ltd.]), (0.408 μM). Then fluorescence was measured using the present solution.

Fluorescence characteristics are shown below.

| | |
|---|---|
| Max. excitation wavelength [Ex(max)] | 649 nm |
| Max. fluorescence wavelength [Em(max)] | 670 nm |
| Fluorescence intensity | 3,161 |
| Fluorescence intensity of Cy5/1 μM | 7,747 |

(2) Rough Calculation of Relative Fluorescence Intensity of a Compound of the Present Invention Relative fluorescence intensities of the compounds (13), (21), (32) and (38) of the present invention were roughly estimated relative to fluorescence intensity of Cy5 per 1 μM, obtained in Example 8, (1), as 100. The results were shown in Table 29.

TABLE 29

| Compound | (fluorescent dye) | Relative fluorescence intensity [relative to fluorescence intensity of Cy5 (1 μM) as 100] |
|---|---|---|
| Example 1 | Compound (13) | 145 |
| Example 2 | Compound (21) | 120 |
| Example 4 | Compound (32) | 106 |
| Example 6 | Compound (38) | 135 |
| Com. Exa. 1 | Cy5 | 100 |

As is clear from the result of Table 29, in comparing the compounds of the present invention and Cy5 (conventional cyanine dye), it was found that the compounds of the present invention exhibited fluorescence intensities equivalent or higher than that of Cy5.

Example 9

Practical Evaluation of a Novel Fluorescence Dye (1) Preparation of a Novel Fluorescence Labeled Anti-AFP-Fab' (a Labeled Compound of the Present Invention)

After pepsin digestion of anti α-fetoprotein antibody (AFP) (manufactured by Wako Pure Chemical Industries, Ltd.), this was reduced with 2-aminoethanethiol, and subjected to purification by using a gel permeation column (Superdex200, manufactured by GE Healthcare Bioscience Co., Ltd.), to give an anti-AFP-Fab'.

Into a 50 mM phosphoric acid buffer solution (PBS, pH 6.0, 0.892 mL) containing the anti-AFP-Fab' (2 mg as protein mass calculated by using absorption of 280 nm), a DMF solution of the compound (15) obtained in the above Example 1, [the compound of the present invention (a maleimide substance)], (4 mg/mL, 0.1 mL) was added to a reaction overnight in a low temperature chamber. The resulting reaction solution was subjected to purification by using an ion-exchange column (DEAE-5PW, manufactured by Tosoh Corp.) and a gel permeation column to give a 50 mM phosphoric acid buffer solution (pH 6.0, 0.2 mg as protein mass calculated by using absorption of 280 nm) of a novel fluorescence labeled anti-AFP-Fab', a labeled compound of the present invention.

(2) Measurement of Fluorescence Intensity of a Novel Fluorescence Labeled Anti-AFP-Fab' (a Labeled Compound of the Present Invention) with an HPLC Fluorescence Analysis Method Into 0.05 mL of the 50 mM phosphoric acid buffer solution (PBS, pH 6.0), [containing 1 mM of ethylenediamine tetraacetic acid (EDTA)], containing 150 nM of the fluorescence labeled anti-AFP-Fab', obtained in the above Example 9, (1), 0.05 mM of 50 mM trishydrochloric acid solutions (pH 8.0) containing each concentration of AFP (0, 0.625, 1.25, 2.5, 5, 10 and 20 nM) were added to a reaction for 2 hours. The resulting reaction solution was analyzed with HPLC (LC-10A, manufactured by Shimadzu Corp.) and a gel permeation column (Diol-200, manufactured by Wako Pure Chemical Industries, Ltd.), and peak area of a complex between a novel fluorescence labeled anti-AFP-Fab' and AFP (a labeled compound of the present invention) was calculated as fluorescence intensity (hereafter abbreviated as "a labeled complex of the present invention"). The results are shown in the following Table 30.

Comparative Example 2

Measurement of Fluorescence Intensity of Cy5 Fluorescence Labeled Anti-AFP-Fab'

A 50 mM phosphoric acid buffer solution (pH 6.0) of Cy5 fluorescence labeled anti-AFP-Fab' was obtained by executing operation similarly as in Example 9, (1) except that a Cy5 maleimidation reagent (Cy5 maleimide, manufactured by GE Healthcare Bioscience Co., Ltd.) was used, as a labeling substance, instead of the compound (15) of the present invention used in Example 9, (1).

Still more, fluorescence intensity of a complex between the resulting Cy5 fluorescence labeled anti-AFP-Fab' and AFP (hereafter abbreviated as "Cy5 labeled complex") was calculated, by executing operation similarly as in Example 9, (2). The above results are all shown in the following Table 30.

TABLE 30

| | Fluorescence intensity of labeled complex | | |
|---|---|---|---|
| AFP conc. (uM) | Labeled complex (B1) of the invention (EX: 636 nm, Em: 651 nm) | Cy5 Labeled complex (B2) (EX: 647 nm, Em: 671 nm) | (B1/B2) |
| 20 | 8713 | 6393 | 1.36 |
| 10 | 7878 | 5530 | 1.42 |
| 5 | 6194 | 4152 | 1.49 |
| 2.5 | 2920 | 1523 | 1.92 |
| 1.25 | 832 | 359 | 2.32 |

TABLE 30-continued

| | Fluorescence intensity of labeled complex | | |
|---|---|---|---|
| AFP conc. (uM) | Labeled complex (B1) of the invention (EX: 636 nm, Em: 651 nm) | Cy5 Labeled complex (B2) (EX: 647 nm, Em: 671 nm) | (B1/B2) |
| 0.625 | 244 | 188 | 1.30 |
| 0 | 0 | 0 | — |

As is clear from Table 30, in comparing the cases where a fluorescence reagent of the present invention and a conventional fluorescence reagent are used, it was found that the labeled complex of the present invention exhibited fluorescence intensities about 1.2 to 2.0 times higher.

Example 10

Practical Evaluation of a Novel Fluorescence Dye (Incorporation of Labeled Nucleotide)

(1) Incorporation of Fluorescence Labeled Nucleotide with a PCR Method

Reaction solutions were prepared by the following compositions.

| | Soln. 1 | Soln. 2 | Soln. 3 | Soln. 4 | Soln. 5 |
|---|---|---|---|---|---|
| Final concentration of WY-535 during reaction | 0 mM WY-535 | 0 mM WY-535 Addition of WY-535 after reaction (0.15 nM WY-535) | 0.100 mM WY-535 | 0.125 mM WY-535 | 0.150 mM WY-535 |
| 10 × ExTaq Buffer | 5 μl | 5 μl | 5 μl | 5 μl | 5 μl |
| Foward Primer 10 pmol/μl | 1.25 μl | 1.25 μl | 1.25 μl | 1.25 μl | 1.25 μl |
| Reverse Primer 10 pmol/μl | 1.25 μl | 1.25 μl | 1.25 μl | 1.25 μl | 1.25 μl |
| 2 mM dATP, dGTP, dTTP | 5 μl | 5 μl | 5 μl | 5 μl | 5 μl |
| 1 mM dCTP | 10 μl | 10 μl | 5 μl | 3.75 μl | 2.5 μl |
| EX Taq | 0.5 μl | 0.5 μl | 0.5 μl | 0.5 μl | 0.5 μl |
| 1 mM WY535-dCTP | 0 μl | 0 μl | 5 μl | 6.25 μl | 7.5 μl |
| Template 0.01 mg/ml | 5 μl | 5 μl | 5 μl | 5 μl | 5 μl |
| Sterilized Distilled Water | 22 μl | 22 μl | 22 μl | 22 μl | 22 μl |

In the above Table, "WY-535" is the compound (25) of the present invention obtained in Example 3.

"WY-535-dCTP" is mononucleotide labeled with the compound (25) of the present invention obtained in Example 3, [a fluorescent labeling, 2'-deoxycytidin-5'-triphosphate derivative].

"Template" was one purified by a phenol chloroform method, after bacteriolysis with lysozyme from *Escherichia coli* JCM 1649$^T$.

As "Primer", a sequence applying a part of 16S ribosome gene was used.

"Forward Primer": (AGAGTTTGATCMTGGCTCAG)
"Reverse Primer": (CCCACTGCTGCCTCCCGTAG)

As "Taq", ExTaq HS manufactured by TaKaRa Co., Ltd., was used.

PCR reaction condition: After a reaction at 95° C. for 5 minute, a reaction at 95° C. for 30 seconds, at 55° C. for 20 seconds, and at 70° C. for 30 seconds, was repeated 30 times, and then a reaction at 72° C. for 5 minute was carried out.

(2) Purification of a Labeled Genome DNA Fragment Using a Spinning Column

By using a PCR Purification Kit (manufactured by Qiagen Co., Ltd.), unreacted labeled nucleotide (WY535-dCTP) and Primer, dNTP, present in the reaction solution of the above (1), were removed. To an each tube after termination of the reaction, 275 μL of Binding Buffer (Buffer included in the PCR Purification Kit, manufactured by Qiagen Co., Ltd.) was added, and mixed by pipeting. Whole amount of the mixed solution was applied to a spin column (column included in the PCR Purification Kit, manufactured by Qiagen Co., Ltd.) and subjected to centrifugal separation treatment at 6,000 rpm (3,500×g) for 2 minutes. A flow through portion was discarded, and 750 μL of spin column Wash Buffer (Buffer included in the PCR Purification Kit, manufactured by Qiagen Co., Ltd.) was added to centrifugal separation treatment at 6,000 rpm (3,500×g) for 2 minutes. A flow through portion was discarded to be subjected to centrifugal separation treatment at 12,000 rpm (14,000×g) for 3 minutes. A new 1.5 mL micro tube was set in the spin column to add 50 μL of Elution Buffer (Buffer included in the PCR Purification Kit, manufactured by Qiagen Co., Ltd.) at the center of the column, stood still at room temperature for 5 minutes, under light shielding condition, to be subjected to centrifugal separation treatment at 12,000 rpm (14,000×g) for 3 minutes. After the addition of 30 μL of Elution Buffer (Buffer included in the PCR Purification Kit, manufactured by Qiagen Co., Ltd.) at the center of the column, the solution was stood still at room temperature for 5 minutes, under light shielding condition, and subjected to centrifugal separation treatment at 12,000 rpm (14,000×g) for 3 minutes to give 80 μL of purified DNA labeled with WY-535. Synthesized amount of nucleic acid and incorporation amount of the fluorescence dye were measured with a spectrometer. The results are shown in Table 31.

TABLE 31

| | Conc. of WY535 | Molar absorption coefficient of 260 nm (ε) [$M^{-1}cm^{-1}$] | Molar absorption coefficient of 635 nm (ε) [$M^{-1}cm^{-1}$] | Synthsis amount of nucleic acid (μg) | Incorp. amount of fluorescence substance (pmol) |
|---|---|---|---|---|---|
| Solution 1 | 0 mM | 0.615 | 0.0017 | 2.46 | Blank |
| Solution 2 | 0 mM Addtion of 0.15 mM after reaction | 0.6174 | 0.0035 | 2.47 | 0.96 |

TABLE 31-continued

|  | Conc. of WY535 | Molar absorption coefficient of 260 nm (ε) $[M^{-1}cm^{-1}]$ | Molar absorption coefficient of 635 nm (ε) $[M^{-1}cm^{-1}]$ | Synthsis amount of nucleic acid (μg) | Incorp. amount of fluorescence substance (pmol) |
|---|---|---|---|---|---|
| Solution 3 | 0.1 mM | 0.6041 | 0.0083 | 2.42 | 3.52 |
| Solution 4 | 0.125 mM | 0.5781 | 0.0122 | 2.31 | 5.60 |
| Solution 5 | 0.15 mM | 0.5718 | 0.0167 | 2.29 | 8.00 |

As is clear from Table 31, it was found that contamination level of an unreacted labeling substance with the PCR Purification Kit was about 1 μmol. From this fact, it was found that nearly complete removal of the unreacted labeling substance with the PCR Purification Kit was possible.

In addition, from the results of solutions 3 to 5, it was found that incorporation amount of the fluorescence substance was increased depending on concentration of fluorescence labeled nucleotide. From this fact, it was found that enzymatic incorporation of a DNA chain was possible by using the labeled nucleotide of the present invention.

As is clear from the above results, also by using nucleotide labeled with the compound of the present invention, detection of a measurement target (for example, nucleic acid or the like) is possible, similarly to in the case of using a known fluorescence dye.

Example 11

Synthesis of the Compound (40) of the Present Invention

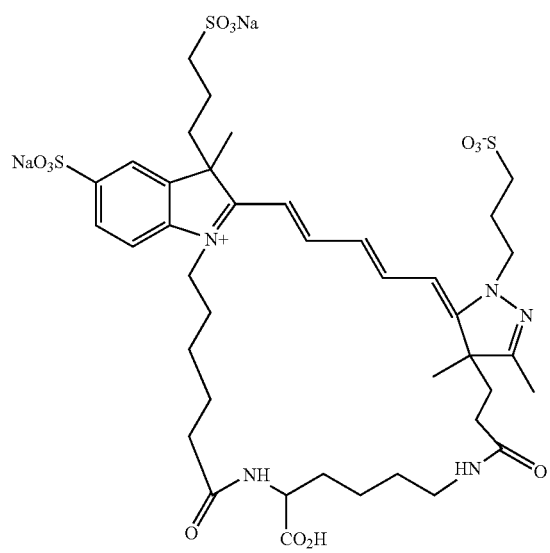

(1) Synthesis of the Indolenine Compound (8)

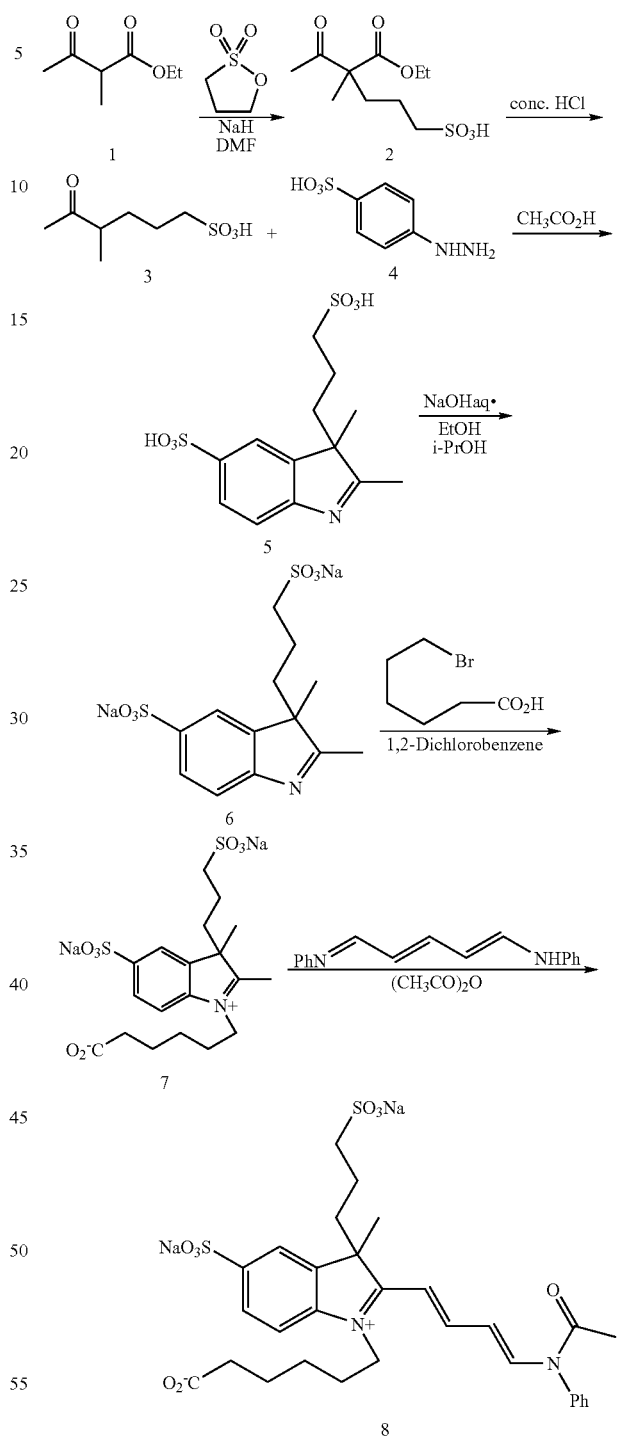

[Synthesis of the Compound (2)]

In N,N-dimethylformamide (DMF, 80 mL), ethyl 2-methylacetoacetate (1) (25.0 g, 0.173 mol), 1,3-propanesultone (23.3 g, 0.190 mol) and sodium hydride (8.5 g, 0.208 mol) were added to a reaction under stirring at 90° C. overnight. After completion of the reaction, the solvent was removed under reduced pressure to be subjected to washing twice by the addition of water (200 mL) and diethyl ether (200 mL).

After that, the water layer portion was removed under reduced pressure to give the compound (2) (42.1 g, yield; 91%).

[Synthesis of the Compound (3)]

In concentrated hydrochloric acid (60 mL), the compound (2) (40.5 g, 0.152 mol) was subjected to a reaction under stirring at 100° C. for 3 hours. After completion of the reaction, the solvent was removed under reduced pressure to be subjected to purification by using silica gel column chromatography (elution liquid: methanol) to give the compound (3) (16.6 g, yield; 56%).

[Synthesis of the Compound (5)]

In acetic acid (50 mL), the compound (3) (10.0 g, 0.051 mol) and the compound (4) (12.9 g, 0.066 mol) were subjected to refluxing under heating at 120° C. for 4 hours. After completion of the reaction, the solvent was removed under reduced pressure to be subjected to purification by using reversed phase column chromatography (elution liquid: water) to give the compound (5) (11.5 g, yield; 65%).

Property data: IR (KBr) (cm$^{-1}$): 3450, 1196

[Synthesis of the Compound (6)]

The compound (5) (11.5 g, 0.033 mol) was dissolved in water (50 mL) and ethanol (50 mL) to be subjected to a reaction under stirring at room temperature for 4 hours. After completion of the reaction, the solvent was removed under reduced pressure to be subjected to purification by using reversed phase column chromatography (elution liquid: water) to give the compound (6) (10.3 g, yield; 80%).

Property data: Mass (nega=346)

IR (KBr) (cm$^{-1}$): 3444, 1193

[Synthesis of the Compound (7)]

The compound (6) (10.0 g, 0.026 mol) and 6-bromohexanoic acid (9.97 g, 0.052 mol) were dissolved in 1,2-dichlorobenzene (100 mL) and subjected to a reaction under stirring at 120° C. overnight. After completion of the reaction, the solvent was removed under reduced pressure to be subjected to washing three times by using ethyl acetate to give the compound (7) (11.5 g, yield; 89%).

Property data: Mass (nega=460)

IR (KBr) (cm$^{-1}$): 3446, 1723, 1194

[Synthesis of the Compound (8)]

The compound (7) (1.5 g, 2.967 mmol) and malonaldehydedianilide hydrochloride (0.77 g, 2.967 mmol) were dissolved in acetic anhydride (20 mL) and subjected to a reaction under stirring at 120° C. for 1 hour. After completion of the reaction, the solvent was removed under reduced pressure to be subjected to purification by using reversed phase column chromatography (elution liquid: 10% aqueous solution of acetonitrile) to give the indolenine compound (8) (0.18 g, yield; 10%).

Property data: Mass (nega: posi=631:633)

IR (KBr) (cm$^{-1}$): 3443, 1716, 1574, 1465, 1189

(2) Synthesis of the Pyrazole Compound (19)

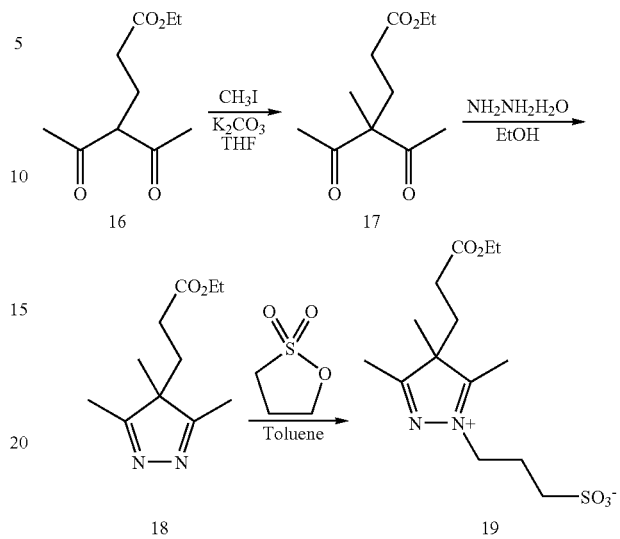

[Synthesis of the Compound (17)]

In tetrahydrofuran (THF, 100 mL), 4-acetyl-5-oxohexanoic acid ethyl ester (16) (10.0 g, 49.94 mmol), methyliodide (10.6 g, 74.91 mmol) and potassium carbonate (17.3 g, 0.125 mol) were added to stirring at room temperature overnight. After completion of the reaction, neutralization was carried out by using 1N hydrochloric acid, and subjected to washing twice by the addition of water (100 mL) and ethyl acetate (100 mL). After that, the ethyl acetate layer was washed twice with a saturated aqueous solution of sodium bicarbonate (100 mL) and a saturated aqueous solution of sodium chloride (100 mL). Then, the resulting ethyl acetate layer was removed under reduced pressure to be subjected to purification by using silica gel column chromatography (elution liquid: ethyl acetate/hexane=1/3) to give the compound (17) (10.0 g, yield; 93%).

[Synthesis of the Compound (18)]

The compound (17) (10.0 g, 46.7 mmol) and hydrazine monohydrate (2.6 g, 51.4 mmol) were dissolved in ethanol (EtOH, 150 mL), and were subjected to stirring at 80° C. for 2 hours. After completion of the reaction, the solvent was removed under reduced pressure to be subjected to purification by using silica gel column chromatography (elution liquid: methanol/chloroform=1/1) to give the compound (18) (9.3 g, yield; 95%).

[Synthesis of the Compound (19)]

The compound (18) (9.3 g, 44.2 mmol) and 1,3-propanesultone (5.9 g, 44.9 mmol) were dissolved in toluene (150 mL), and were subjected to stirring at 120° C. for 5 hours. After completion of the reaction, ethyl acetate (200 mL) was added to deposit a crystal, which was filtered to give the pyrazole compound (19) (10.6 g, yield; 72%).

Property data: Mass (nega=331)

IR (KBr) (cm$^{-1}$): 3436, 1726, 1211

(3) Synthesis of Indolenine Compound—Pyrazole Compound Complex (a Compound of the Present Invention) (40)

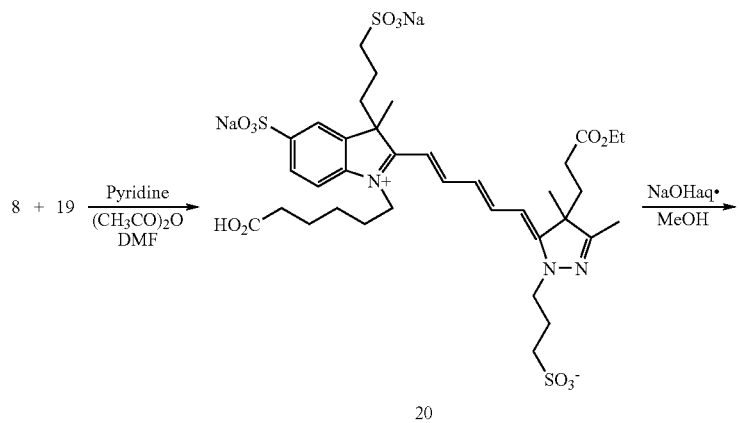
20
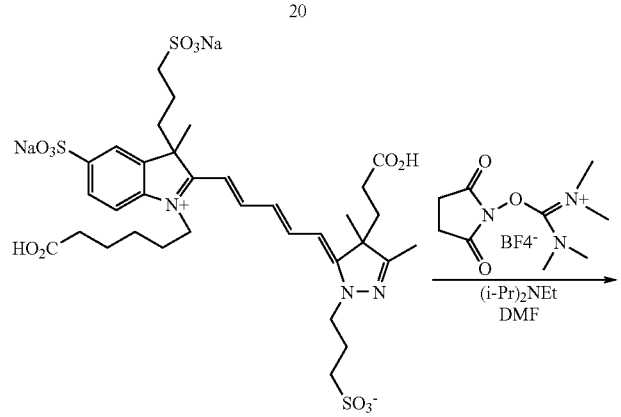
21
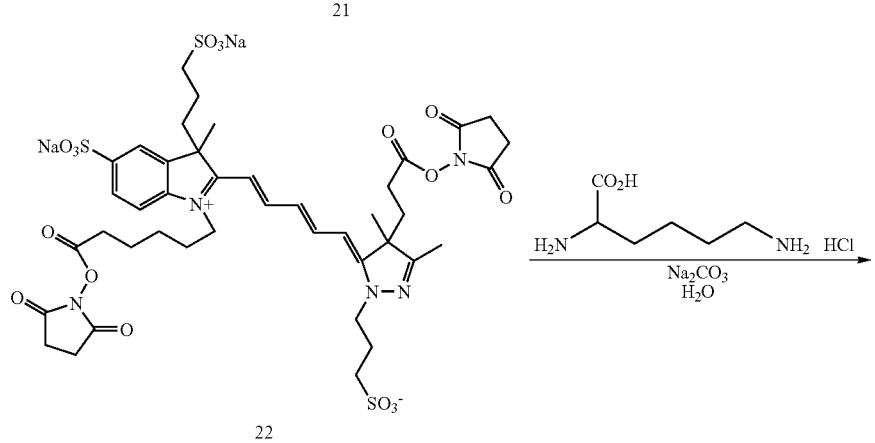
22
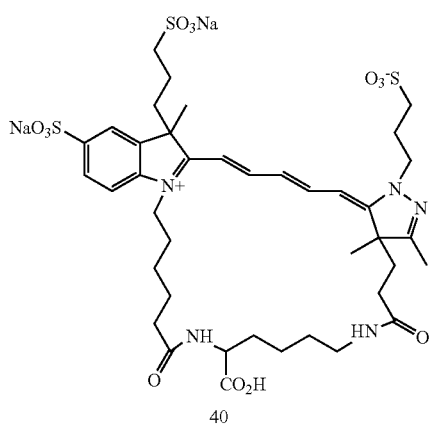
40

147

[Synthesis of the Compound (20)]

The resulting indolenine compound (8) in Example 11, (1) (0.15 g, 0.237=mol) and the resulting pyrazole compound (19) in Example 11, (2) (0.24 g, 0.711 mmol) were dissolved in DMF (2 mL), and pyridine (1 mL) and acetic anhydride (0.5 mL) were added to stirring at 80° C. for 1 hour. After completion of the reaction, the solvent was removed under reduced pressure, to be subjected to purification by using reversed phase column chromatography (elution liquid: 10% aqueous solution of methanol) and Sephadex LH-20 [manufactured by GE Healthcare Bioscience Co., Ltd.] (elution liquid: methanol) to give the compound (20) (52 mg, yield; 26%).

Property data: Mass (nega=828)

[Synthesis of the Compound (21)]

The compound (20) (53 mg, 0.064 mmol) was dissolved in methanol (3 mL), and a 1N aqueous solution of sodium hydroxide (1 mL) was added to stirring at 40° C. for 1 hour. After completion of the reaction, the solution was subjected to purification by using Sephadex LH-20 (elution liquid: methanol) to give the compound (21) (15 mg, yield; 29%).

Property data: Mass (nega=800)

[Synthesis of the Compound (22)]

The compound (21) (15 mg, 0.019 mmol) was dissolved in DMF (1 mL), 2-succinimide-1,1,3,3-tetramethyluronium tetrafluoroborate (TSTU) (113 mg, 0.337 mmol) and N-ethyl-diisopropylamine ((i-Pr)$_2$NEt) (120 μl) were added to stirring at room temperature for 3 hours. After completion of the reaction, ethyl acetate (15 mL) was added to deposit a crystal, which was subjected to centrifugal separation to give the compound (22) (15 mg, yield; 81%).

Property data: Mass (nega=995)

[Synthesis of the Compound (40)]

The compound (22) (6 mg, 0.006 mmol) was dissolved in water (12 mL) to be subjected to stirring for 10 minutes. Then, to the resulting reaction solution, a solution dissolved with lysine monohydrate (2.1 mg, 0.011 mmol) and sodium carbonate (0.6 mg, 0.006 mmol) in water (6 mL) was slowly added to stirring at room temperature overnight. After completion of the reaction, the solvent was removed under reduced pressure, to be subjected to purification by using fractionation reversed phase HPLC [elution liquid; A solution (5% acetonitrile-0.1% trifluoroacetic acid, aqueous solution): B solution (95% acetonitrile-0.1% trifluoroacetic acid, aqueous solution)=90:10] (trade name [Wakosil-II 5C18 RS Press (20.0 mm×250 mm)], manufactured by Wako Pure Chemical Industries, Ltd.) to give the compound (40) (1 mg, yield; 18%).

Property data: Mass (nega=955)

Fluorescence characteristics are shown below.

| | |
|---|---|
| Max. absorption wavelength (λmax) | 634 nm |
| Molar absorption coefficient (ε) | 235,000 M$^{-1}$cm$^{-1}$ |
| Max. excitation wavelength [Ex(max)] | 635 nm |
| Max. fluorescence wavelength [Em(max)] | 659 nm |

148

Example 12

Synthesis of the Compound (43) of the Present Invention

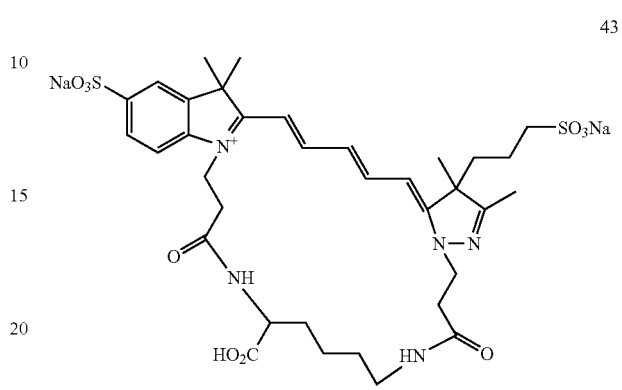

(1) Synthesis of Indolenine Compound (30)

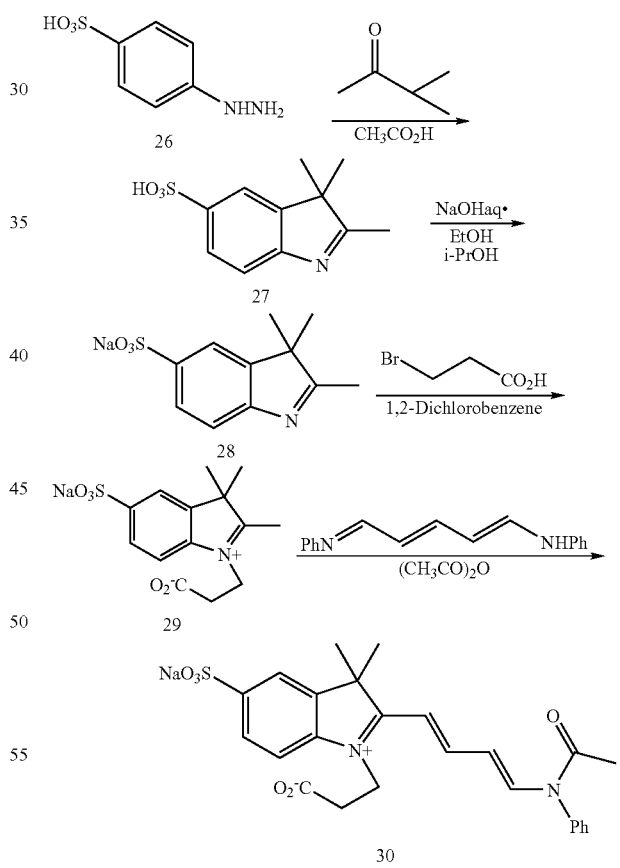

[Synthesis of the Compound (27)]

As starting raw materials, 4-hydrazinobenzene sulfonic acid 0.5 hydrate (26) (50.0 g, 0.253 mol) and 3-methyl-2-butanone (65.5 g, 0.759 mol) were used, which were subjected to stirring in acetic acid (200 mL) at 120° C. for 3 hours. After completion of the reaction, the solvent was cooled, to be subjected to washing twice by the addition of diethyl ether (300 mL) to give the compound (27) (52.0 g, yield; 86%).

Property data: Mass (nega=238)

[Synthesis of the Compound (28)]

The compound (27) (10.0 g, 0.042 mol) and sodium hydroxide (1.67 g, 0.042 mol) were subjected to stirring in a mixed solvent of ethanol (30 mL)/2-propanol (100 mL) at room temperature for 4 hours. After completion of the reaction, the solvent was removed under reduced pressure, and 2-propanol (100 mL) was added for washing twice to give the compound (28) (4.2 g, yield; 39%).

Property data: IR (KBr) (cm$^{-1}$): 3206, 1205

[Synthesis of the Compound (29)]

The compound (28) (3.5 g, 0.013 mol) and 3-bromopropionic acid (2.5 g, 0.016 mol) were subjected to refluxing under heating in toluene (50 mL) at 110° C. overnight. After completion of the reaction, ethyl acetate (100 mL) was added for washing three times to give the compound (29) (1.7 g, yield; 41%).

Property data: Mass (nega=310)

[Synthesis of the Compound (30)]

The compound (29) (1.5 g, 4.5 mmol) and malonaldehydedianilide hydrochloride (1.16 g, 4.50 mmol) were dissolved in acetic anhydride (20 mL) to be subjected to stirring at 120° C. for 1 hour. After completion of the reaction, ethyl acetate (50 mL) was added for washing twice to give the indolenine compound (30) (1.59 g, yield; 70%).

Property data: Mass (nega=481)

(2) Synthesis of pyrazole compound (31)

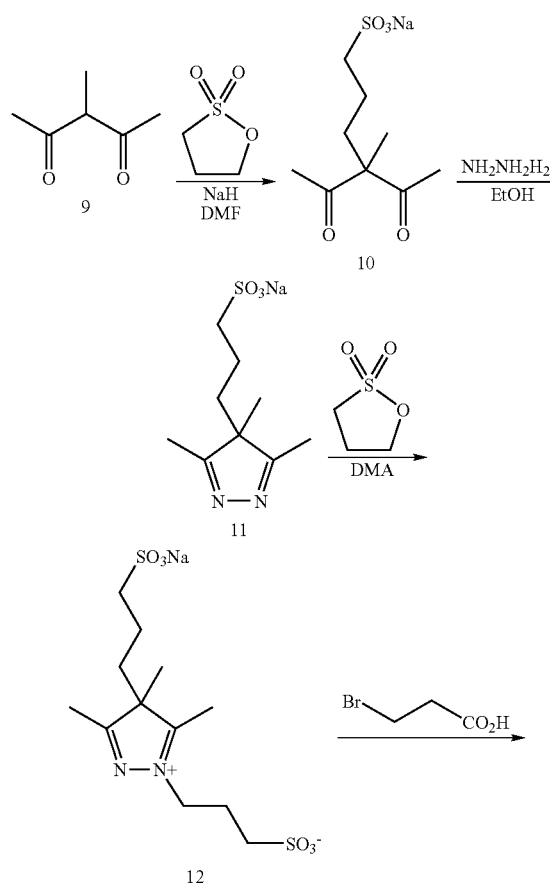

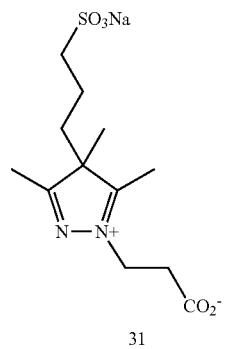

[Synthesis of the Compound (10)]

In DMF (100 mL), 3-methyl-2,4-pentanedione (9) (15.0 g, 0.13 mol), 1,3-propansultone (16.1 g, 0.13 mol) and sodium hydride (5.0 g, 0.208 mol) were used to a reaction under stirring at 50° C. for 16 hours. After completion of the reaction, neutralization was carried out by using 1N sodium hydroxide, and the solvent was removed under reduced pressure, to be subjected to washing twice by the addition of water (200 mL) and diethyl ether (200 mL). After that, the water layer portion was removed under reduced pressure to give the pyrazole compound (10) (32.2 g, yield; 96%).

Property data: IR (KBr) (cm$^{-1}$): 3474, 1695, 1665, 1191

[Synthesis of the Compound (11)]

The compound (10) (10.0 g, 0.042 mol) and hydrazine monohydrate (2.1 g, 0.042 mol) were dissolved in ethanol (150 mL), and were subjected to a reaction under stirring at 80° C. for 3 hours. After completion of the reaction, the solvent was removed under reduced pressure to be subjected to purification by using silica gel column chromatography (elution liquid: methanol/chloroform=1/1) to give the compound (11) (9.0 g, yield; 92%).

Property data: IR (KBr) (cm$^{-1}$): 3421, 1195

[Synthesis of the Compound (12)]

The compound (11) (4.8 g, 0.019 mol) and 1,3-propane sultone (2.5 g, 0.02 mol) were dissolved in dimethylacetoamide (DMA, 30 mL), and were subjected to stirring at 140° C. for 4 hours. After completion of the reaction, ethyl acetate (200 mL) was added to deposit a crystal, which was filtered to give the compound (12) (5.3 g, yield; 76%).

Property data: Mass (nega=352)

IR (KBr) (cm$^{-1}$): 3446, 1194

[Synthesis of the Compound (31)]

The compound (12) (0.59 g, 2.32 mmol) and 3-bromopropionic acid (0.39 g, 2.55 mmol) were subjected to stirring overnight in non-solvent. After completion of the reaction, ethyl acetate (30 mL) was added for washing twice to give the compound (31) (0.73 g, yield; 96%).

Property data: Mass (nega=303)

(3) Synthesis of Indolenine Compound—Pyrazole Compound Complex (a Compound of the Present Invention) (43)

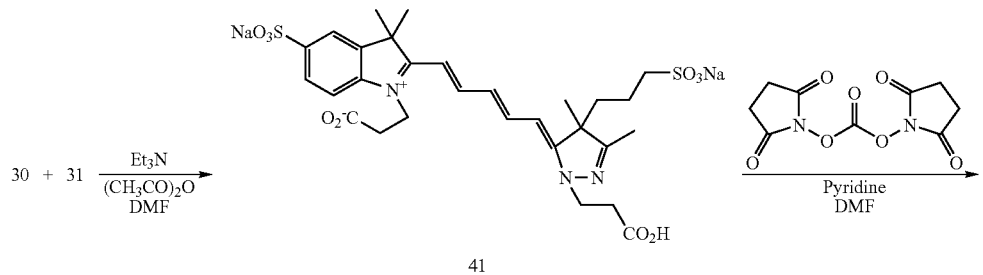

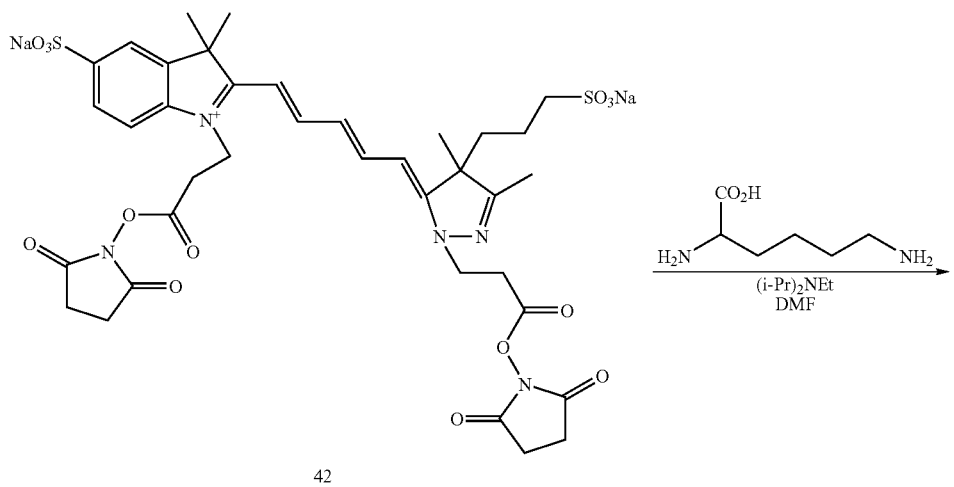

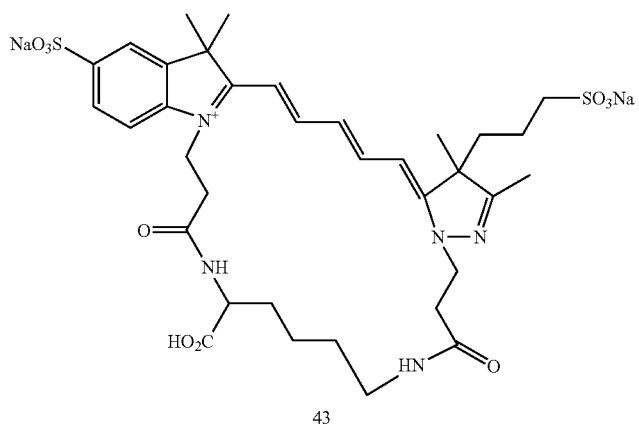

[Synthesis of the Compound (41)]

The resulting indolenine compound (30) in Example 12, (1) (70 mg, 0.139 mmol) and the resulting pyrazole compound (31) in Example 12, (2) (91 mg, 0.278 mmol) were dissolved in DMF (1 mL), and pyridine (0.1 mL) and acetic anhydride (0.1 mL) were added thereto to be subjected to stirring at 80° C. for 1 hour. After completion of the reaction, the solvent was removed under reduced pressure to be subjected to purification by using reversed phase column chromatography (elution liquid: 10% methanol) and Sephadex LH-20 (elution liquid: methanol) to give the compound (41) (11 mg, yield; 12%).

Property data: Mass (nega=649)

[Synthesis of the Compound (42)]

The compound (41) (10 mg, 0.019 mmol) was dissolved in DMF (1 mL), disuccinimidyl carbonate (DSC) (113 mg, 0.37 mmol) and pyridine (120 µl) were added to stirring at 40° C. for 4 hours. After completion of the reaction, ethyl acetate (15 mL) was added to deposit a crystal, which was subjected to washing to give the compound (42) (10 mg, yield; 79%).

Property data: Mass (nega=846)

[Synthesis of the Compound (43)]

The compound (42) (10 mg, 0.011 mmol) was dissolved in water (12 mL) to be subjected to stirring for 10 minutes. Then, to the resulting solution, a solution dissolved with lysin monohydrochloride (4 mg, 0.022 mmol) and sodium carbonate (1.1 mg, 0.011 mmol) in water (6 mL) was slowly added to stirring at room temperature overnight. After completion of the reaction, the solvent was removed under reduced pressure, to be subjected to purification by using fractionation reversed phase HPLC [elution liquid; A solution (5% acetonitrile-0.1% trifluoroacetic acid, aqueous solution): B solution (95% acetonitrile-0.1% trifluoroacetic acid, aqueous solution)=90:10] (trade name [Wakosil-II 5C18 RS Prep (20.0 mm×250 mm)]), manufactured by Wako Pure Chemical Industries, Ltd.) to give the compound (43) of the present invention (1.5 mg, yield; 17%).

Property data: Mass (nega=761)

Fluorescence characteristics are shown below.

| Max. absorption wavelength (λmax) | 632 nm |
| --- | --- |
| Molar absorption coefficient (ε) | 220,000 $M^{-1}cm^{-1}$ |
| Max. excitation wavelength [Ex(max)] | 632 nm |
| Max. fluorescence wavelength [Em(max)] | 657 nm |

Example 13

Synthesis of the Compounds (47) to (48) of the Present Invention

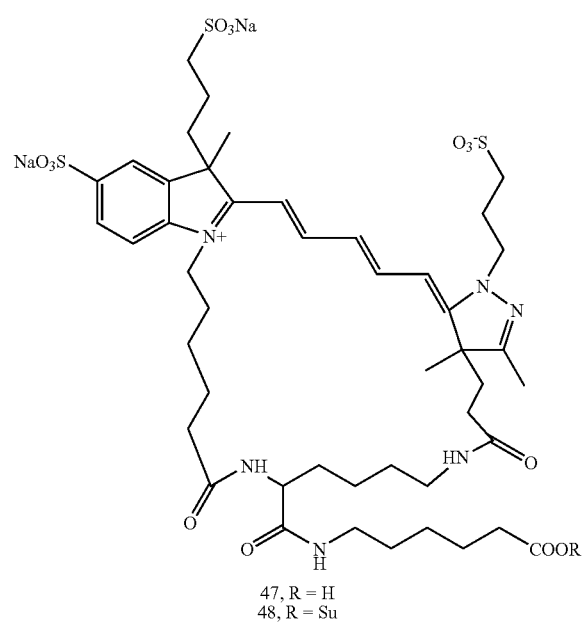

47, R = H
48, R = Su

[Synthesis of the Compound (46)]

(1) Synthesis of the Linker Compound (46)

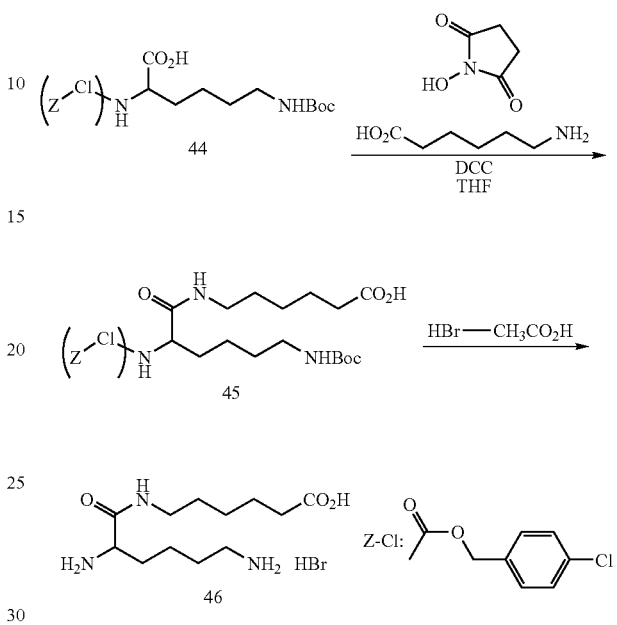

* Boc=tert-butoxycarbonyl group

[Synthesis of the Compound (45)]

In tetrahydrofuran (THF, 100 mL), dicyclohexylcarbodiimide (DCC) (2.6 g, 12.6 mmol), (Z—Cl)-Lys-Boc (compound (44)) (5.0 g, 12.1 mmol) and N-hydroxysuccinimide (1.4 g, 12.1 mmol) were added to stirring at room temperature overnight. After completion of the reaction, excess urea was filtered and 6-aminohexanoic acid (3.2 g 12.1 mmol) was added to stirring again at room temperature overnight. After completion of the reaction, neutralization was carried out with 1N hydrochloric acid, and subjected to washing twice by the addition of water (200 mL) and ethyl acetate (200 mL). After that, the ethyl acetate layer was washed twice with a saturated aqueous solution of sodium chloride (200 mL). Then, the resulting ethyl acetate layer was washed twice with a saturated aqueous solution of sodium chloride (200 mL), and the resulting ethyl acetate layer was removed under reduced pressure to give the compound (45) (6.6 g, yield; 52%).

Property data: Mass (nega:posi=526:528)

[Synthesis of the Compound (46)]

The compound (45) (1.0 g, 1.9 mmol) was dissolved in 25% hydrogen bromide-acetic acid (52 mL) to be subjected to stirring at room temperature overnight. After completion of the reaction, the reaction solution was concentrated and washed three times with ethyl acetate to give the compound (46) (0.61 g, yield 94%).

Property data: Mass (posi=260)

(2) Synthesis of Indolenine Compound—Pyrazole Compound Complex (a Compound of the Present Invention) (48)
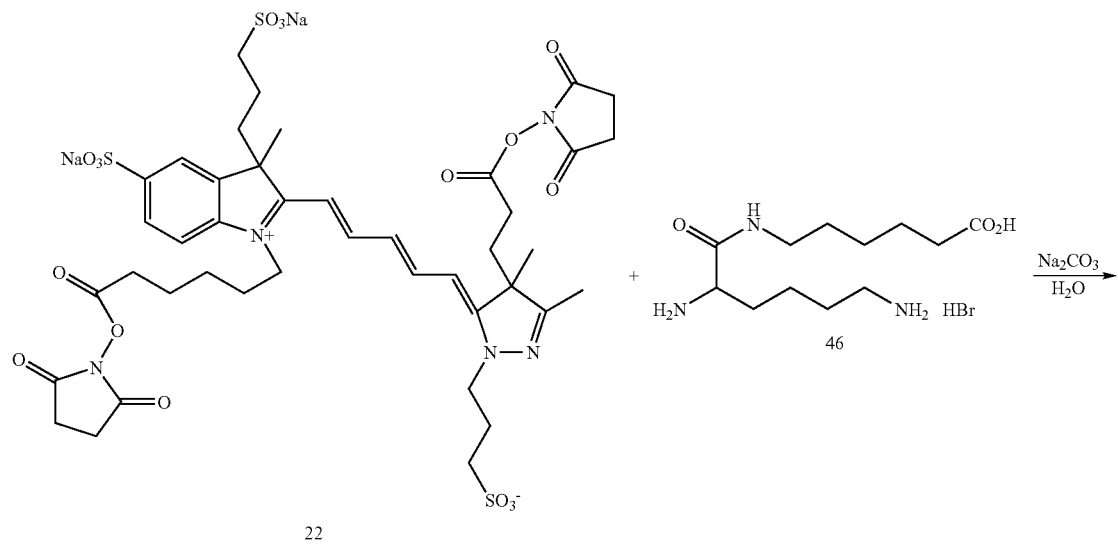
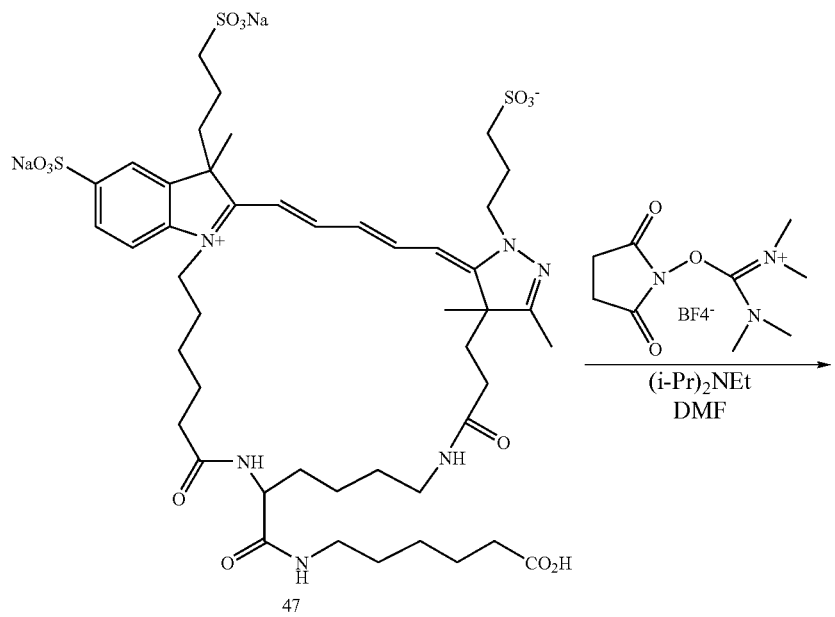

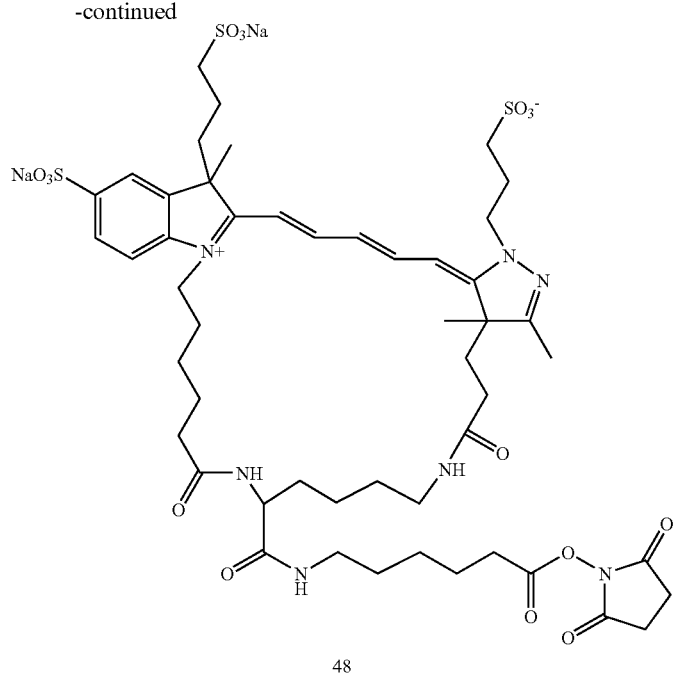

48

[Synthesis of the Compound (47)]

The resulting compound (22) (22 mg, 0.02 mmol) in Example 11 was dissolved in water (25 mL) to be subjected to stirring for 10 minutes. Then, to the resulting reaction solution, a solution dissolved with the lysin derivative (the compound (46), 11 mg, 0.04 mmol) and sodium carbonate ($Na_2CO_3$) (2.2 mg, 0.02 mmol), in water (10 mL), was slowly added to stirring at room temperature overnight. After completion of the reaction, the solvent was removed under reduced pressure, to be subjected to purification by using fractionation reversed phase HPLC [elution liquid; A solution (5% acetonitrile-0.1% trifluoroacetic acid, aqueous solution): B solution (95% acetonitrile-0.1% trifluoroacetic acid, aqueous solution)=90:10] (trade name [Wakosil-II 5C18 RS Prep (20.0 mm×250 mm)], manufactured by Wako Pure Chemical Industries, Ltd.) to give the compound (47) (5 mg, yield; 23%).

Property data: Mass (nega=1068, $2Na^+$)

[Synthesis of the Compound (48)]

The compound (47) (5 mg, 0.005 mmol) was dissolved in N,N-dimethylformamide (DMF) (300 μL), and 2-succinimide-1,1,3,3-tetramethyluronium tetrafluoroborate (TSTU) (14 mg, 0.046 mmol) and N-ethyldiisopropylamine (15 μl) were added to stirring at room temperature for 3 hours. After completion of the reaction, ethyl acetate (10 mL) was added to deposit a crystal, which was subjected to centrifugal separation to give the compound (48) (4 mg, yield; 75%).

Example 14

Measurement of Novel Fluorescence Intensity of a Compound of the Present Invention Relative fluorescence intensity of a compound of the present invention was roughly calculated based on fluorescence intensity of Cy5, which is a conventional cyanine dye derivative.

First, fluorescence intensity of Cy5 per 1 μM was measured from fluorescence intensity of Cy5, and relative fluorescence intensity of the compound of the present invention was roughly calculated based on this fluorescence intensity value as 100.

(1) Measurement of Fluorescence Intensity of Cy5

Into 1 mL of purified water, Cy5 (manufactured by GE Healthcare Bioscience Biohealth Co., Ltd.) for labeling 1 mg of protein, was dissolved. This solution was diluted 200 times with a 50 mM phosphoric acid buffer solution (pH 7.5) to measure OD value (0.1020).

Concentration of a Cy5 solution was determined from this OD value and molar absorption coefficient (E=250,000, [described in a general product catalogue 2006 "7-4" of GE Healthcare Bioscience Co., Ltd.]), (0.408 μM).

Then fluorescence of Cy5 was measured using the present solution.

Fluorescence characteristics are shown below.

| | |
|---|---|
| Max. excitation wavelength [Ex(max)] | 649 nm |
| Max. fluorescence wavelength [Em(max)] | 670 nm |
| Fluorescence intensity | 3,161 |
| Fluorescence intensity of Cy5/1 μM | 7,747 |

(2) Rough Calculation of Relative Fluorescence Intensity of a Compound of the Present Invention Relative fluorescence intensity of the compound (40) of the present invention, obtained in Example 11 and the compound (43) of the present invention, obtained in Example 12 were roughly calculated, relative to fluorescence intensity per 1 μM of Cy5, obtained in Example 14, (1), as 100. The results are shown in Table 32.

TABLE 32

| Compound (fluorescent dye) | | Relative fluorescence intensity [relative to fluorescence intensity of Cy5 (1 µM) as 100] |
| --- | --- | --- |
| Example 1 | Compound (16) | 155 |
| Example 2 | Compound (28) | 124 |
| Com. Exa. 1 | Cy5 | 100 |

As is clear from Table 32, in comparing the compounds of the present invention and Cy5 (conventional cyanine dye), it was found that the compounds of the present invention exhibited higher fluorescence intensities than that of Cy5.

Example 15

Practical Evaluation of a Novel Fluorescence Reagent (1) Preparation of a Novel Fluorescence Labeled Anti-AFP-Fab' (a Labeled Compound of the Present Invention)

After pepsin digestion of anti α-fetoprotein antibody (AFP) (manufactured by Wako Pure Chemical Industries, Ltd.), this was reduced with 2-aminoethanethiol, and the SH group was masked with N-ethylmaleimide to be subjected to purification by using a gel permeation column (Superdex200, manufactured by GE Healthcare Bioscience Co., Ltd.), an anti-AFP-Fab' was obtained.

Into a 0.43 mL of a 0.1 M sodium carbonate buffer solution (pH 8.5) containing the anti-AFP-Fab' (1.0 mg as protein mass calculated by using absorption of 280 nm), a dimethylsulfoxide (DMSO) solution of the compound (22) (1.0 mg/mL), obtained in the above Example 11 [a compound of the present invention (an active ester substance)], was added to a reaction overnight in a low temperature chamber. The resulting reaction solution was subjected to purification by using a gel permeation column to give a 50 mM phosphoric acid buffer solution (PBS, pH 6.0,) of the novel fluorescence labeled anti-AFP-Fab', a labeled compound of the present invention (0.23 mg as protein mass calculated by using absorption of 280 nm).

(2) Measurement of Fluorescence Intensity of the Novel Fluorescence Labeled Anti-AFP-Fab' (a Labeled Compound of the Present Invention) with an HPLC Fluorescence Analysis Method Into 0.05 mL of a 50 mM phosphoric acid buffer solution (PBS, pH 6.0), [containing 1 mM of ethylenediamine tetraacetic acid (EDTA)], containing 150 nM of the fluorescence labeled anti-AFP-Fab' obtained in the above Example 15, (1), 0.05 mM of 50 mM tris-hydrochloric acid solutions (pH 8.0) containing various concentrations of AFP (0, 0.625, 1.25, 2.5, 5, 10 and 20 nM) were added to a reaction for 2 hours. The resulting reaction solutions were analyzed with HPLC (LC-10A, manufactured by Shimadzu Corp.) and a gel permeation column (Diol-200, manufactured by Wako Pure Chemical Industries, Ltd.), and peak area of a complex between the novel fluorescence labeled anti-AFP-Fab' and AFP was calculated as fluorescence intensity. The resulting fluorescence intensities of various fluorescence labeled complexes are shown in the following Table 33.

Comparative Example 1

Synthesis of Cy5 Fluorescence Labeled Anti-AFP-Fab'

A 50 mM phosphoric acid buffer solution (PBS, pH 6.0) of Cy5 fluorescence labeled anti-AFP-Fab' was obtained by executing operation similarly as in Example 15, except that a Cy5 active ester reagent (Cy5 active ester, manufactured by GE Healthcare Bioscience Co., Ltd.) was used, as a labeling substance, instead of the compound (22) of the present invention used in Example 15. The results are all shown in Table 2.

TABLE 33

| | Fluorescence intensity of labeled complex | | |
| --- | --- | --- | --- |
| AFP conc. (uM) | Labeled complex (B1) of the invention (EX: 636 nm, Em: 651 nm) | Cy5 Labeled complex (B2) (EX: 647 nm, Em: 671 nm) | (B1/ B2) |
| 20 | 8366 | 6234 | 1.34 |
| 10 | 7457 | 5337 | 1.40 |
| 5 | 5814 | 3958 | 1.47 |
| 2.5 | 2727 | 1527 | 1.79 |
| 1.25 | 803 | 344 | 2.33 |
| 0.625 | 209 | 177 | 1.18 |
| 0 | 0 | 0 | — |

As is clear from Table 33, in comparing the cases where a fluorescence reagent of the present invention and a conventional fluorescence reagent are used, it was found that the labeled complex of the present invention exhibited about 1.1 to 2.0 times higher fluorescence intensity.

INDUSTRIAL APPLICABILITY

Because a pyrazole-based cyanine dye of the present invention has a structure where a pyrazole skeleton and an indole skeleton are bound to a polymethine chain, and has the fluorescence characteristics in shorter wavelength region as compared with a conventional light source, it becomes possible to use a light source of a short wavelength region with high energy efficiency. In addition, in the case where a measurement object is detected by using this as a labeling agent (a labeling substance), it becomes possible to detect the measurement object in high detection sensitivity, without having problems, for example, low water-solubility, reduced detection sensitivity by optical quenching caused by aggregation of dyes themselves and the like, which a conventional cyanine dye derivative had.

The invention claimed is:

1. A compound represented by the following general formula [50], and a salt thereof:

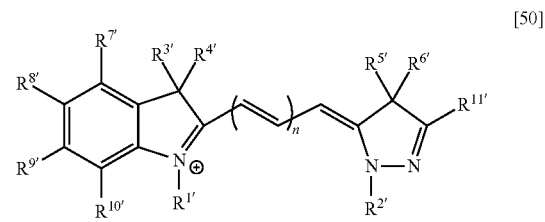

[50]

[wherein $R^{1'}$ to $R^{6'}$ each independently represent an alkyl group which may substitute a group represented by the general formula [2]:

—COOR$^{12}$      [2]

(wherein $R^{12}$ represents hydrogen atom, $C_1$ to $C_{10}$ alkyl group, alkali metal atom, organic ammonium ion, ammonium ion or anion) or a group represented by the general formula [3]:

—SO$_3$R$^{13}$      [3]

(wherein R¹³ represents hydrogen atom, alkali metal atom, organic ammonium ion, ammonium ion or anion); R⁷' to R¹⁰' each independently represent a hydrogen atom, the group represented by the general formula [2] or the group represented by the general formula [3]; R¹¹' represents hydrogen atom or alkyl group, being able to have substituents; and n represents an integer of from 0 to 3, provided that any of R¹' and R²', R⁴' and R⁵', R¹' and R⁶', and R²' and R⁴' may form a bivalent group with a group selected from groups represented by the general formulae [52] to [54]:

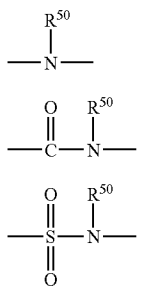

(wherein R⁵⁰ represents hydrogen atom or alkyl group being able to have substituents), and substituted or unsubstituted alkylene group; and in the case where said bivalent group is formed, at least one of R¹' to R¹¹', along with the bivalent group formed by any of R¹' and R²', R⁴' and R⁵', R¹' and R⁶', and R²' and R⁴', has the group represented by the general formula or the group represented by the general formula [3]; and in the case where said bivalent group is not formed, at least one of R¹' to R¹¹' has the group represented by the general formula or the group represented by the general formula [3]].

2. The compound according to claim 1, wherein the compound represented by the general formula [50] of claim 1 is one represented by the following general formula [1]:

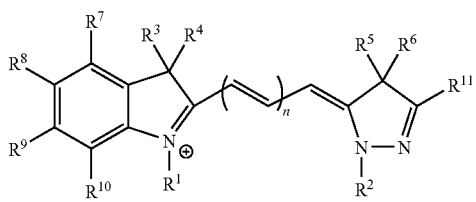

[wherein R¹ to R⁶ each independently represent an alkyl group which may substitute a group represented by the general formula [2]:

—COOR¹²      [2]

(wherein R¹² represents hydrogen atom, $C_1$ to $C_{10}$ alkyl group, alkali metal atom, organic ammonium ion, ammonium ion or anion) or a group represented by the general formula [3]:

—SO₃R¹³      [3]

(wherein R¹³ represents hydrogen atom, alkali metal atom, organic ammonium ion, ammonium ion or anion); R⁷ to R¹⁰ each independently represent a hydrogen atom, the group represented by the general formula [2] or the group represented by the general formula [3]; R¹¹ represents hydrogen atom or alkyl group being able to have substituents; and n represents an integer of from 0 to 3, provided that at least one of R¹ to R¹¹ has the group represented by the general formula [2] or the group represented by the general formula [3]].

3. The compound according to claim 2, wherein the compound represented by the general formula [1] of claim 2 is a compound represented by the following general formula [1-1]:

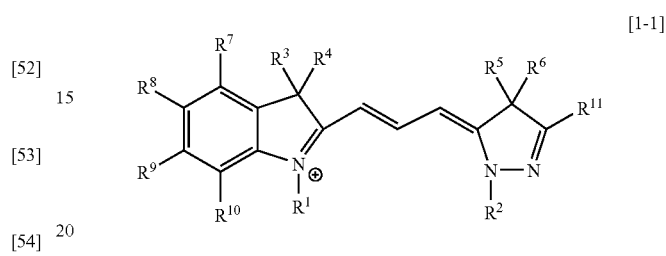

(wherein definitions of R¹ to R¹¹ and others are the same as above).

4. The compound according to claim 2, wherein the compound represented by the general formula [1] of claim 2 is a compound represented by the following general formula [1-2]:

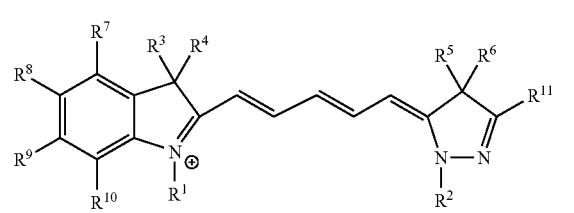

(wherein definitions of R¹ to R¹¹ and others are the same as above).

5. The compound according to claim 2, wherein the compound represented by the general formula [1] of claim 2 is one represented by the following general formula [1']:

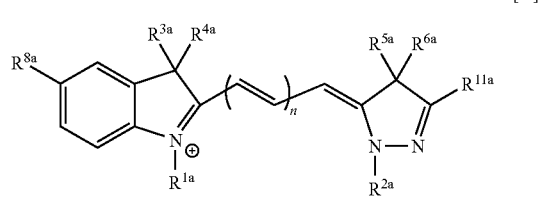

(wherein R¹ᵃ to R⁶ᵃ each independently represent the alkyl group which may have the group represented by the general formula [2] or [3] as a substituent; R⁸ᵃ represents the group represented by the general formula [3]; R¹¹ᵃ represents an alkyl group; and n is the same as above).

6. The compound according to claim 1, wherein the compound represented by the general formula [50] of claim 1 is one represented by the following general formula [51]:

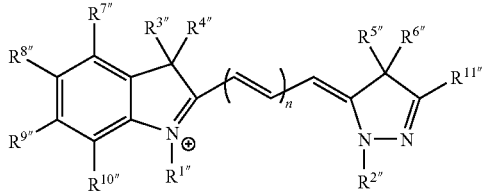
[51]

[wherein $R^{1''}$ to $R^{6''}$ each independently represent an alkyl group which may substitute a group represented by the general formula [2]:

—COOR$^{12}$ [2]

(wherein $R^{12}$ represents hydrogen atom, $C_1$ to $C_{10}$ alkyl group, alkali metal atom, organic ammonium ion, ammonium ion or anion) or a group represented by the general formula [3]:

—SO$_3$R$^{13}$ [3]

(wherein $R^{13}$ represents hydrogen atom, alkali metal atom, organic ammonium ion, ammonium ion or anion); $R^{7''}$ to $R^{10''}$ each independently represent a hydrogen atom, the group represented by the general formula [2] or the group represented by the general formula [3]; $R^{11''}$ represents hydrogen atom or alkyl group being able to have substituents; and n represents an integer of from 0 to 3, provided that any of $R^{1''}$ and $R^{2''}$, $R^{4''}$ and $R^{5''}$, $R^{1''}$ and $R^{6''}$, and $R^{2''}$ and $R^{4''}$ form a bivalent group with a group selected from the groups represented by the general formulae [52] to [54]:

[52]

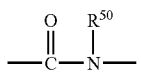
[53]

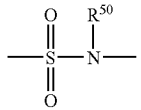
[54]

(wherein $R^{50}$ represents hydrogen atom or alkyl group being able to have substituents), and substituted or unsubstituted alkylene group, and at least one of $R^{1''}$ to $R^{11''}$, along with the bivalent group formed by any of $R^{1''}$ and $R^{2''}$, $R^{4''}$ and $R^{5''}$, $R^{1''}$ and $R^{6''}$, and $R^{2''}$ and $R^{4''}$, has the group represented by the general formula [2] or the group represented by the general formula [3]].

7. The compound according to claim 6, wherein the compound represented by the general formula [51] of claim 6 is one represented by the following general formula [51']:

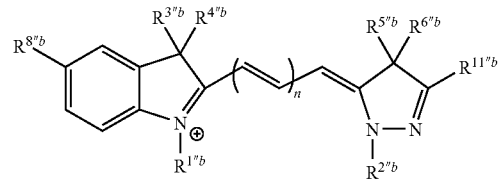
[51']

[wherein $R^{1''b}$ to $R^{6''b}$ each independently represent an alkyl group which may have the group represented by the general formula [2] or [3] as a substituent; $R^{8''b}$ represents the group represented by the general formula [3]; $R^{11''b}$ represents an alkyl group; and n represents an integer of from 0 to 3, provided that any of $R^{1''b}$ and $R^{2''b}$, $R^{4''b}$ and $R^{5''b}$, $R^{1''b}$ and $R^{6''b}$, and $R^{2''b}$ and $R^{4''b}$ form a bivalent group with a group selected from the groups represented by the general formulae [52] to [54], and substituted or unsubstituted alkylene group, and at least one of $R^{1''b}$ to $R^{11''b}$, along with the bivalent group formed by any of $R^{1''b}$ and $R^{2''b}$, $R^{4''b}$ and $R^{5''b}$, $R^{1''b}$ and $R^{6''b}$, and $R^{2''b}$ and $R^{4''b}$, has the group represented by the general formula [2] or the group represented by the general formula [3]].

8. The compound according to claim 6, wherein the compound represented by the general formula [51] of claim 6 is one represented by the following general formula [55]:

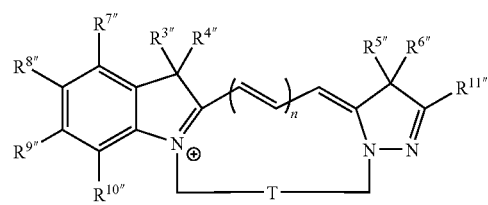
[55]

[wherein T forms a bivalent group with a group selected from the groups represented by the general formulae [52] to [54], and substituted or unsubstituted alkylene group; and $R^{3''}$ to $R^{11''}$ and n are the same as above, provided that at least one of $R^{3''}$ to $R^{11''}$ along with the bivalent group represented by T has the group represented by the general formula [2]].

9. The compound according to claim 6, wherein the compound represented by the general formula [51] of claim 6 is one represented by the following general formula [56]:

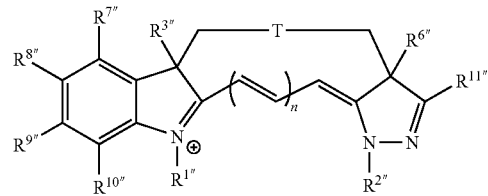
[56]

[wherein T forms a bivalent group with a group selected from the groups represented by the general formulae [52] to [54], and substituted or unsubstituted alkylene group; and $R^{1''}$ to $R^{3''}$, $R^{6''}$ to $R^{11''}$ and n are the same as above, provided that at least one of $R^{1''}$ to $R^{3''}$, $R^{6''}$ to $R^{11''}$ along with the bivalent group represented by T, has the group represented by the general formula [2] or the group represented by the general formula [3]].

10. The compound according to claim 6, wherein the compound represented by the general formula [51] of claim 6 is one represented by the following general formula [57]:

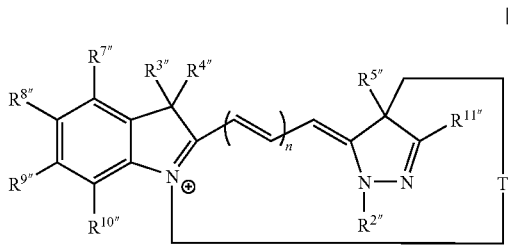

[57]

[wherein T forms a bivalent group with a group selected from the groups represented by the general formulae [52] to [54], and substituted or unsubstituted alkylene group; and $R^{2''}$ to $R^{5''}$, $R^{7''}$ to $R^{11''}$ and n are the same as above, provided that at least one of $R^{2''}$ to $R^{5''}$, $R^{7''}$ to $R^{11''}$ along the bivalent group represented by T, has the group represented by the general formula [2] or the group represented by the general formula [3]].

11. The compound according to claim 6, wherein the compound represented by the general formula [51] of claim 6 is one represented by the following general formula [58]:

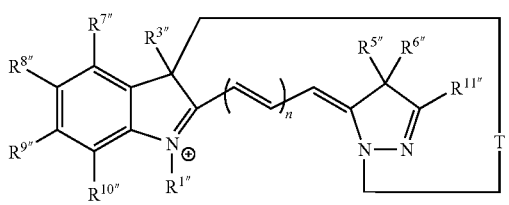

[58]

[wherein T forms a bivalent group with a group selected from the groups represented by the general formulae [52] to [54], and substituted or unsubstituted alkylene group; and $R^{1''}$, $R^{3''}$, $R^{5''}$ to $R^{11''}$ and n are the same as above, provided that at least one of $R^{1''}$, $R^{3''}$, $R^{5''}$ to $R^{11''}$ along with the bivalent group represented by T has the group represented by the general formula [2] or the group represented by the general formula [3]].

12. The compound according to claim 6 or 7, wherein the bivalent group formed by any of $R^{1''}$ and $R^{2''}$, $R^{4''}$ and $R^{5''}$, $R^{1''}$ and $R^{6''}$, and $R^{2''}$ and $R^{4''}$ is a group represented by the following general formula [60]:

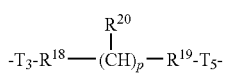

[60]

[wherein $R^{18}$ and $R^{19}$ each independently represent the groups represented by the general formulae [52] to [54]; and $R^{20}$ represents groups represented by the following general formulae [70] to [72]:

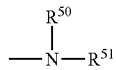

[70]

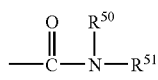

[71]

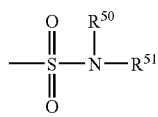

[72]

(wherein $R^{51}$ represents hydrogen atom or alkyl group being able to have substituents; $R^{50}$ is the same as above), hydrogen atom, the group represented by the general formula [2] or the group represented by the general formula [3]; $T_3$ and $T_5$ each independently represent alkylene group; and p represents an integer of from 1 to 20].

13. The compound according to any one of claims 8 to 11, wherein the bivalent group represented by T is a group represented by the following general formula [60]:

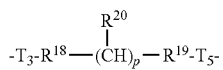

[60]

[wherein $R^{18}$ and $R^{19}$ each independently represent the groups represented by the general formulae [52] to [54]; and $R^{20}$ represents the groups represented by the following general formulae [70] to [72]:

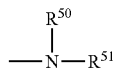

[70]

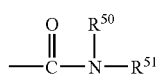

[71]

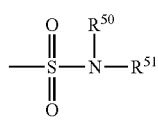

[72]

(wherein $R^{51}$ represents hydrogen atom or alkyl group being able to have substituents; $R^{50}$ is the same as above), hydrogen atom, the group represented by the general formula [2] or the group represented by the general formula [3]; $T_3$ and $T_5$ each independently represent alkylene group; and p represents an integer of from 1 to 20].

14. The compound according to claim 13, wherein $R^{20}$ represents the group represented by the general formula [2] or a group represented by the general formula [73]:

—CONH-$T_4$-COOR$^{12}$      [73]

(wherein T₄ represents an alkylene group; and $R^{12}$ is the same as above).

15. The compound according to any one of claims 6 to 11, wherein n is 2.

16. A labeled compound obtained by subjecting the compound represented by the following general formula [50] and a substance to be labeled to direct or indirect binding:

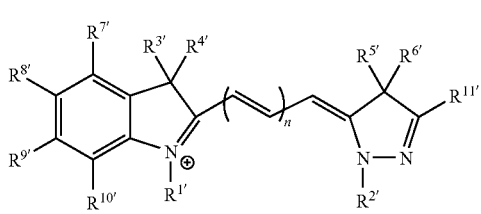

[wherein $R^{1'}$ to $R^{6'}$ each independently represent an alkyl group which may substitute a group represented by the general formula [2]:

—COOR¹²          [2]

(wherein $R^{12}$ represents hydrogen atom, $C_1$ to $C_{10}$ alkyl group, alkali metal atom, organic ammonium ion, ammonium ion or anion) or a group represented by the general formula [3]:

—SO₃R¹³          [3]

(wherein $R^{13}$ represents hydrogen atom, alkali metal atom, organic ammonium ion, ammonium ion or anion) $R^{7'}$ to $R^{10'}$ each independently represent a hydrogen atom, the group represented by the general formula [3];
$R^{11'}$ represents hydrogen atom or alkyl group being able to have substituents; and n represents an integer of from 0 to 3, provided that any of $R^{1'}$ and $R^{2'}$, $R^{4'}$ and $R^{5'}$, $R^{1'}$ and $R^{6'}$, and $R^{2'}$ and $R^{4'}$ may form a bivalent group with a group selected from the groups represented by the general formulae [52] to [54]:

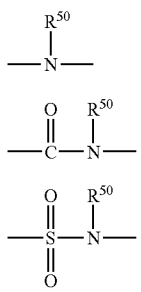

(wherein $R^{50}$ represents hydrogen atom or alkyl group being able to have substituents), and substituted or unsubstituted alkylene group; and in the case where said bivalent group is formed, at least one of $R^{1'}$ and $R^{11'}$, along with the bivalent group formed by any of $R^{1'}$ and $R^{2'}$, $R^{4'}$ and $R^{5'}$, $R^{1'}$ and $R^{6'}$, and $R^{2'}$ and $R^{4'}$, has the group represented by the general formula [2] or the group represented by the general formula [3]; and in the case where said bivalent group is not formed, at least one of $R^{1'}$ to $R^{11'}$ has the group represented by the general formula [2] or the group represented by the general formula [3]].

17. The labeled compound according to claim 16, wherein the substance to be labeled is nucleotide or an antibody.

18. The labeled compound according to claim 16, wherein the compound represented by the general formula [50] of claim 16 is one represented by the following general formula [1]:

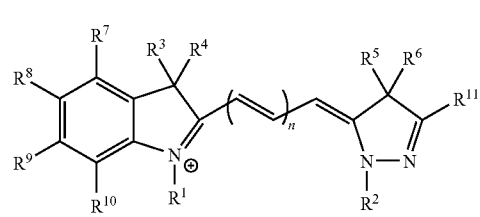

[wherein $R^1$ to $R^6$ each independently represent an alkyl group which may substitute a group represented by the general formula [2]:

—COOR¹²          [2]

(wherein $R^{12}$ represents hydrogen atom, $C_1$ to $C_{10}$ alkyl group, alkali metal atom, organic ammonium ion, ammonium ion or anion) or a group represented by the general formula [3]:

—SO₃R¹³          [3]

(wherein $R^{13}$ represents hydrogen atom, alkali metal atom, organic ammonium ion, ammonium ion or anion); $R^7$ to $R^{10}$ each independently represent a hydrogen atom, the group represented by the general formula [2] or the group represented by the general formula [3];
$R^{11}$ represents hydrogen atom or alkyl group being able to have substituents; and n represents an integer of from 0 to 3, provided that at least one of $R^1$ to $R^{11}$ has the group represented by the general formula [2] or the group represented by the general formula [3]].

19. The labeled compound according to claim 18, wherein carboxyl group or sulfo group, in the compound represented by the general formula [1], binds directly or indirectly to a substance to be labeled.

20. The labeled compound according to claim 18, wherein carboxyl group or sulfo group included in $R^1$ to $R^6$ in the general formula [1], binds directly or indirectly to a substance to be labeled.

21. The labeled compound according to claim 18, wherein carboxyl group or sulfo group included in $R^1$ or $R^6$ in the general formula [1], binds directly or indirectly to a substance to be labeled.

22. The compound according to claim 16, wherein the compound represented by the general formula [50] of claim 16 is one represented by the following general formula [51]:

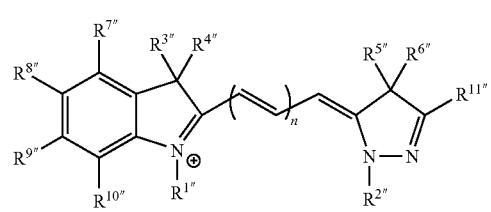

[wherein $R^{1'''}$ to $R^{6'''}$ each independently represent an alkyl group which may substitute a group represented by the general formula [2]:

  [2]

(wherein $R^{12}$ represents hydrogen atom, $C_1$ to $C_{10}$ alkyl group, alkali metal atom, organic ammonium ion, ammonium ion or anion) or a group represented by the general formula [3]:

  [3]

(wherein $R^{13}$ represents hydrogen atom, alkali metal atom, organic ammonium ion, ammonium ion or anion); $R^{7'''}$ to $R^{10'''}$ each independently represent a hydrogen atom, the group represented by the general formula [2] or the group represented by the general formula [3]; $R^{11'''}$ represents hydrogen atom or alkyl group being able to have substituents; and n represents an integer of from 0 to 3, provided that any of $R^{1'''}$ and $R^{2'''}$, $R^{4'''}$ and $R^{5'''}$, $R^{1'''}$ and $R^{6'''}$, and $R^{2'''}$ and $R^{4'''}$ forms a bivalent group with a group selected from the groups represented by the general formulae [52] to [54]:

  [52]

  [53]

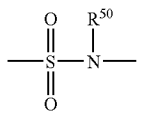  [54]

(wherein $R^{50}$ represents hydrogen atom or alkyl group being able to have substituents), and substituted or unsubstituted alkylene group; and at least one of $R^{1'''}$ to $R^{11'''}$ along with the bivalent group formed by any of $R^{1'''}$ and $R^{2'''}$, $R^{4'''}$ and $R^{5'''}$, $R^{1'''}$ and $R^{6'''}$, and $R^{2'''}$ and $R^{4'''}$, has the group represented by the general formula [2] or the group represented by the general formula [3]].

23. The labeled compound according to claim 22, wherein the group represented by the general formula [2] or the group represented by the general formula [3] in the compound represented by the general formula [51], binds directly or indirectly to a substance to be labeled.

24. The labeled compound according to claim 22, wherein the group represented by the general formula [2] or the group represented by the general formula [3], contained in $R^{1'''}$ to $R^{6'''}$, or the bivalent group formed by any of $R^{1'''}$ and $R^{2'''}$, $R^{4'''}$ and $R^{5'''}$, $R^{1'''}$ and $R^{6'''}$, and $R^{2'''}$ and $R^{4'''}$, in the general formula [51], binds directly or indirectly to a substance to be labeled.

25. The labeled compound according to claim 22, wherein the group represented by the general formula [2] or the group represented by the general formula [3] contained in the bivalent group formed by any of $R^{1'''}$ and $R^{2'''}$, $R^{4'''}$ and $R^{5'''}$, $R^{1'''}$ and $R^{6'''}$, and $R^{2'''}$ and $R^{4'''}$, in the general formula [51], binds directly or indirectly to a substance to be labeled.

26. A labeling method for a substance to be labeled, comprising subjecting the compound represented by the following general formula [50] or a salt thereof to direct or indirect binding to the substance to be labeled:

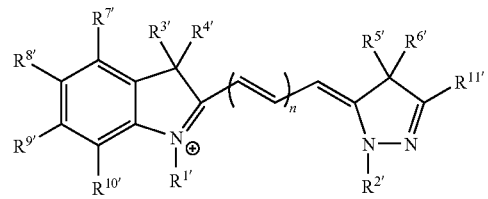  [50]

[wherein $R^{1'}$ to $R^{6'}$ each independently represent an alkyl group which may substitute a group represented by the general formula [2]:

  [2]

(wherein $R^{12}$ represents hydrogen atom, $C_1$ to $C_{10}$ alkyl group, alkali metal atom, organic ammonium ion, ammonium ion or anion) or a group represented by the general formula [3]:

  [3]

(wherein $R^{13}$ represents hydrogen atom, alkali metal atom, organic ammonium ion, ammonium ion or anion); $R^{7'}$ to $R^{10'}$ each independently represent a hydrogen atom, the group represented by the general formula [2] or the group represented by the general formula [3];

$R^{11'}$ represents hydrogen atom or alkyl group being able to have substituents; and n represents an integer of from 0 to 3, provided that any of $R^{1'}$ and $R^{2'}$, $R^{4'}$ and $R^{5'}$, $R^{1'}$ and $R^{6'}$, and $R^{2'}$ and $R^{4'}$ may form a bivalent group with a group selected from groups represented by the general formulae [52] to [54]:

  [52]

  [53]

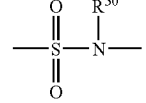  [54]

(wherein $R^{50}$ represents hydrogen atom or alkyl group being able to have substituents), and substituted or unsubstituted alkylene group; and in the case where said bivalent group is formed, at least one of $R^{1'}$ and $R^{11'}$ along with the bivalent group formed by any of $R^{1'}$ and $R^{2'}$, $R^{4'}$ and $R^{5'}$, $R^{1'}$ and $R^{6'}$, and $R^{2'}$ and $R^{4'}$, has the group represented by the general formula [2] or the group represented by the general formula [3]; and in the case where said bivalent group is not formed, at least one of $R^{1'}$ to $R^{11'}$ has the group represented by the general formula [2] or the group represented by the general formula [3]].

27. The labeling method according to claim 26, wherein the compound represented by the general formula [50] of claim 26 is the compound represented by the following general formula [1]:

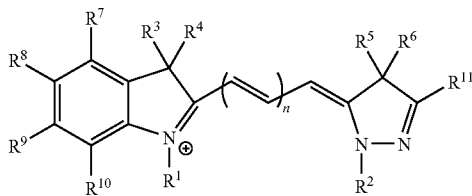

[1]

[wherein $R^1$ to $R^6$ each independently represent an alkyl group which may substitute a group represented by the general formula [2]:

—COOR$^{12}$ [2]

(wherein $R^{12}$ represents hydrogen atom, $C_1$ to $C_{10}$ alkyl group, alkali metal atom, organic ammonium ion, ammonium ion or anion) or a group represented by the general formula [3]:

—SO$_3$R$^{13}$ [3]

(wherein $R^{13}$ represents hydrogen atom, alkali metal atom, organic ammonium ion, ammonium ion or anion); $R^7$ to $R^{10}$ each independently represent a hydrogen atom, the group represented by the general formula [2] or the group represented by the general formula [3];

$R^{11}$ represents hydrogen atom or alkyl group being able to have substituents; and n represents an integer of from 0 to 3, provided that at least one of $R^1$ to $R^{11}$ has the group represented by the general formula [2] or the group represented by the general formula [3]].

28. The labeling method according to claim 26, wherein the compound represented by the general formula [50] of claim 26 is the compound represented by the following general formula [51]:

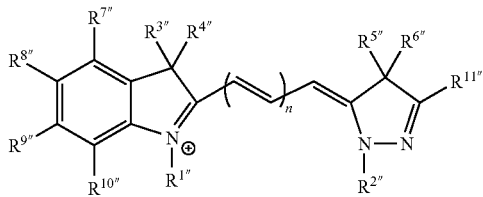

[51]

[wherein $R^{1''}$ to $R^{6''}$ each independently represent an alkyl group which may substitute a group represented by the general formula [2]:

—COOR$^{12}$ [2]

(wherein $R^{12}$ represents hydrogen atom, $C_1$ to $C_{10}$ alkyl group, alkali metal atom, organic ammonium ion, ammonium ion or anion) or a group represented by the general formula [3]:

—SO$_3$R$^{13}$ [3]

(wherein $R^{13}$ represents hydrogen atom, alkali metal atom, organic ammonium ion, ammonium ion or anion); $R^{7''}$ to $R^{10''}$ each independently represent a hydrogen atom, the group represented by the general formula [2] or the group represented by the general formula [3];

$R^{11''}$ represents hydrogen atom or alkyl group, being able to have substituents; and n represents an integer of from 0 to 3, provided that any of $R^{1''}$ and $R^{2''}$, $R^{4''}$ and $R^{5''}$, $R^{1''}$ and $R^{6''}$, and $R^{2''}$ and $R^{4''}$ forms a bivalent group with a group selected from the groups represented by the general formulae [52] to [54]:

$$\begin{array}{c} R^{50} \\ | \\ -N- \end{array}$$ [52]

$$\begin{array}{cc} O & R^{50} \\ \| & | \\ -C-N- \end{array}$$ [53]

$$\begin{array}{cc} O & R^{50} \\ \| & | \\ -S-N- \\ \| \\ O \end{array}$$ [54]

(wherein $R^{50}$ represents hydrogen atom or alkyl group being able to have substituents), and substituted or unsubstituted alkylene group; and at least one of $R^{1''}$ to $R^{11''}$, along with the bivalent group formed by any of $R^{1''}$ and $R^{2''}$, $R^{4''}$ and $R^{5''}$, $R^{1''}$ and $R^{6''}$, and $R^{2''}$ and $R^{4''}$, has the group represented by the general formula [2] or the group represented by the general formula [3]].

\* \* \* \* \*